US008980284B2

(12) United States Patent
Ichtchenko et al.

(10) Patent No.: US 8,980,284 B2
(45) Date of Patent: Mar. 17, 2015

(54) RECOMBINANT DERIVATIVES OF BOTULINUM NEUROTOXINS ENGINEERED FOR TRAFFICKING STUDIES AND NEURONAL DELIVERY

(75) Inventors: Konstantin Ichtchenko, Brooklyn, NY (US); Philip A. Band, West Orange, NJ (US)

(73) Assignee: New York University, New York, NY (US)

( * ) Notice: Subject to any disclaimer, the term of this patent is extended or adjusted under 35 U.S.C. 154(b) by 783 days.

(21) Appl. No.: 13/013,518

(22) Filed: Jan. 25, 2011

(65) Prior Publication Data

US 2011/0206616 A1 Aug. 25, 2011

Related U.S. Application Data

(60) Provisional application No. 61/298,078, filed on Jan. 25, 2010.

(51) Int. Cl.

| | |
|---|---|
| ***C07K 1/00*** | (2006.01) |
| ***C07K 14/00*** | (2006.01) |
| ***C07K 17/00*** | (2006.01) |
| ***A61K 39/08*** | (2006.01) |
| ***A61K 39/02*** | (2006.01) |
| ***C12N 9/52*** | (2006.01) |
| ***C07K 14/33*** | (2006.01) |
| ***G01N 33/50*** | (2006.01) |
| *A61K 38/00* | (2006.01) |

(52) U.S. Cl.

CPC . *C12N 9/52* (2013.01); *C07K 14/33* (2013.01); *G01N 33/5058* (2013.01); *A61K 38/00* (2013.01); *C07K 2319/02* (2013.01); *C07K 2319/036* (2013.01); *C07K 2319/50* (2013.01); *G01N 2333/33* (2013.01)

USPC .................. 424/247.1; 424/234.1; 424/239.1; 530/350

(58) Field of Classification Search

None

See application file for complete search history.

(56) References Cited

U.S. PATENT DOCUMENTS

| | | | | |
|---|---|---|---|---|
| 5,750,383 | A | 5/1998 | Blissard et al. | |
| 5,846,929 | A | 12/1998 | Johnson et al. | |
| 6,001,806 | A | 12/1999 | Hilbert et al. | |
| 6,022,950 | A | 2/2000 | Murphy | |
| 6,461,617 | B1 | 10/2002 | Shone et al. | |
| 6,967,088 | B1 | 11/2005 | Williams et al. | |
| 7,132,259 | B1 | 11/2006 | Dolly et al. | |
| 7,172,764 | B2 | 2/2007 | Li et al. | |
| 7,227,010 | B2 | 6/2007 | Smith | |
| 7,419,676 | B2 | 9/2008 | Dolly et al. | |
| 7,422,877 | B2 | 9/2008 | Dolly et al. | |
| 7,785,606 | B2 * | 8/2010 | Ichtchenko et al. | 424/234.1 |
| 8,044,188 | B2 * | 10/2011 | Ichtchenko et al. | 536/23.7 |
| 8,187,834 | B2 * | 5/2012 | Foster et al. | 435/69.1 |
| 8,865,186 | B2 * | 10/2014 | Ichtchenko et al. | 424/234.1 |
| 2001/0016199 | A1 | 8/2001 | Johnston et al. | |
| 2002/0137886 | A1 | 9/2002 | Lin et al. | |
| 2003/0027752 | A1 | 2/2003 | Steward et al. | |
| 2003/0100071 | A1 | 5/2003 | Apicella et al. | |
| 2003/0143651 | A1 | 7/2003 | Steward et al. | |
| 2003/0166238 | A1 | 9/2003 | Shone et al. | |
| 2004/0013687 | A1 | 1/2004 | Simpson et al. | |
| 2004/0052819 | A1 | 3/2004 | Kingsley et al. | |
| 2004/0101531 | A1 | 5/2004 | Curtiss, III et al. | |
| 2004/0220386 | A1 | 11/2004 | Steward et al. | |
| 2005/0106182 | A1 | 5/2005 | Li et al. | |
| 2005/0158323 | A1 | 7/2005 | Evans et al. | |
| 2005/0260230 | A1 | 11/2005 | Steward et al. | |
| 2006/0024331 | A1 | 2/2006 | Fernandez-Salas et al. | |
| 2006/0024794 | A1 | 2/2006 | Li et al. | |
| 2006/0039929 | A1 | 2/2006 | Fernandez-Salas et al. | |
| 2006/0204524 | A1 * | 9/2006 | Ichtchenko et al. | 424/239.1 |
| 2008/0057575 | A1 | 3/2008 | Fernandez-Salas et al. | |
| 2010/0196421 | A1 * | 8/2010 | Ichtchenko et al. | 424/239.1 |
| 2011/0206616 | A1 * | 8/2011 | Ichtchenko et al. | 424/9.6 |
| 2012/0021002 | A1 * | 1/2012 | Ichtchenko et al. | 424/239.1 |
| 2012/0207735 | A1 * | 8/2012 | Foster et al. | 424/94.3 |
| 2012/0276132 | A1 * | 11/2012 | Feng et al. | 424/192.1 |
| 2014/0212456 | A1 * | 7/2014 | Vazquez-Cintron et al. | 424/239.1 |

FOREIGN PATENT DOCUMENTS

| | | |
|---|---|---|
| EP | 0209281 | 1/1987 |
| WO | WO-98/07864 | 2/1998 |

OTHER PUBLICATIONS

Vazquez-Cintron et al, Abstracts Toxins 2011 / Toxicon 68 (2013): 77 Abstract only.*

Fischer et al, PNAS, Jun. 19, 2007, vol. 104/ No. 25 pp. 10447-10452.*

(Continued)

*Primary Examiner* — Nita M Minnifield

(74) *Attorney, Agent, or Firm* — LeClairRyan, a Professional Corporation

(57) ABSTRACT

This invention relates to isolated *Clostridium botulinum* propeptides and neurotoxins, isolated nucleic acid molecules encoding *Clostridium botulinum* propeptides and neurotoxins, methods of expression, treatment methods, and methods of detecting neurotoxin trafficking. The isolated *Clostridium botulinum* propeptides have a light chain region; a heavy chain region, where the light and heavy chain regions are linked by a disulfide bond; an intermediate region connecting the light and heavy chain regions and comprising a highly specific protease cleavage site; and an S6 peptide sequence according to SEQ ID NO:2 positioned upstream from, but not attached directly to, the N-terminus of the neurotoxin propeptide at the light chain region to enable site specific attachment of cargo.

34 Claims, 7 Drawing Sheets

(56) References Cited

OTHER PUBLICATIONS

Fischer et al, The Journal of Biological Chemistry vol. 282, No. 40, pp. 29604-29611, Oct. 5, 2007.*
Band et al, Protein Expression and Purification 71 (2010) 62-73.*
Vazquez-Cintron EJ, Vakulenko M, Band PA, Stanker LH, Johnson EA, et al. (2014) Atoxic Derivative of Botulinum Neurotoxin A as a Prototype Molecular Vehicle for Targeted Delivery to the Neuronal Cytoplasm. PLoS ONE 9(1): e85517. doi:10.1371/journal.pone.0085517.*
Zhou et al, ACS Chemical Biology, 2007, 2/5:337-346.*
Shone et al, "Inactivation of Clostridium botulinum type A Neurotoxin by Trypsin and Purification of Two Tryptic Fragments," *European Journal of Biochemistry* 151:75-82 (1985).
von Heijne, "Signals for Protein Targeting Into and Across Membranes," *Sub-Cellular Biochemistry* 22(1):1-19 (1994).
National Institute of Allergy and Infectious Diseases, "NIAID Biodefense Research Agenda for CDC Category A Agents. Progress Report," NIH Publication # 03-5432, pp. 1-37 (2003).
Abrams, P., "The Role of Neuromodulation in the Management of Urinary Urge Incontinence," *BJU Int.* 93(7):1116 (2004).
Achem, S.R., "Treatment of Spastic Esophageal Motility Disorders," *Gastroenterol Clin. North Am.* 33(1):107-124 (2004).
Adler et al., "Botulinum Toxin Type A for Treating Voice Tremor," *Arch. Neurol.* 61(9):1416-1420 (2004).
Agarwal et al., "Structural Analysis of Botulinum Neurotoxin Type E Catalytic Domain and Its Mutant Glu212→Gln Reveals the Pivotal Role of the Glu212 Carboxylate in the Catalytic Pathway," *Biochemistry* 43(21):6637-6644 (2004).
Ahn et al., "Botulinum Toxin for Masseter Reduction in Asian Patients," *Arch. Facial Plast. Surg.* 6(3):188-191 (2004).
Aoki, K.R., "Evidence for Antinociceptive Activity of Botulinum Toxin Type A in Pain Management," *Headache* 43(Suppl 1):S9-S15 (2003).
Aquilina et al., "Reduction of a Chronic Bilateral Temporomandibular Joint Dislocation with Intermaxillary Fixation and Botulinum Toxin A," *Br J. Oral Maxillofac. Surg.* 42(3):272-273 (2004).
Bach-Rojecky & Lacković, "Antinociceptive Effect of Botulinum Toxin Type A in Rat Model of Carrageenan and Capsaicin Induced Pain," *Croat. Med. J* 46(2):201-208 (2005).
Bade et al., "Botulinum Neurotoxin Type D Enables Cytosolic Delivery of Enzymatically Active Cargo Proteins to Neurons via Unfolded Translocation Intermediates," *J. Neurochem.* 91(6):1461-1472 (2004).
Bakheit, A.M., "Optimizing the Methods of Evaluation of the Effectiveness of Botulinum Toxin Treatment of Post-Stroke Muscle Spasticity," *J. Neurol. Neurosurg. Psychiatry* 75:665-666 (2004).
Balkrishnan et al., "Longitudinal Examination of Health Outcomes Associated with Botulinum Toxin Use in Children with Cerebral Palsy," *J. Surg. Orthop. Adv.* 13:76-80 (2004).
Bayles & Deschler, "Operative Prevention and Management of Voice-Limiting Pharyngoesophageal Spasm," *Otolaryngol Clin. North Am.* 37(3):547-558 (2004).
Bender et al., "Speech Intelligibility in Severe Adductor Spasmodic Dysphonia," *J. Speech Lang. Hear. Res.* 47(1):21-32 (2004).
Bentsianov et al., "Noncosmetic Uses of Botulinum Toxin," *Clin. Dermatol.* 22(1):82-88 (2004).
Berweck & Heinen, "Use of Botulinum Toxin in Pediatric Spasticity (Cerebral Palsy)," *Mov. Disord.* 19(Suppl 8)S162-S167 (2004).
Blersch et al., "Botulinum Toxin A and the Cutaneous Nociception in Humans: A Prospective, Double-Blind, Placebo-Controlled, Randomized Study," *J. Neurol. Sci.* 205(1):59-63 (2002).
Blumenfeld et al., "Botulinum Neurotoxin for the Treatment of Migraine and Other Primary Headache Disorders," *Dermatol. Clin.* 22(2):167-175 (2004).
Brandt & Boker, "Botulinum Toxin for the Treatment of Neck Lines and Neck Bands," *Dermatol. Clin.* 22(2):159-166 (2004).
Brisinda et al., "Botulinum Neurotoxin to Treat Chronic Anal Fissure: Results of a Randomized 'Botox vs. Dysport' Controlled Trial," *Aliment Pharmacol. Ther.*, 19(6):695-701 (2004).
Byrne et al., "Purification, Potency, and Efficacy of the Botulinum Neurotoxin Type A Binding Domain from *Pichia pastoris* as a Recombinant Vaccine Candidate," *Infect. Immun.* 66(10):4817-4822 (1998).
Caccin et al., "VAMP/Synaptobrevin Cleavage by Tetanus and Botulinum Neurotoxins is Strongly Enhanced by Acidic Liposomes," *FEBS Lett.* 542(1-3):132-136 (2003).
Capaccio et al., "Diagnosis and Therapeutic Management of Iatrogenic Parotid Sialocele," *Ann. Otol. Rhinol. Laryngol.* 113(7):562-564 (2004).
Carruthers & Carruthers, "Botox: Beyond Wrinkles," *Clin. Dermatol.* 22(1):89-93 (2004).
Carruthers & Carruthers, "Botulinum Toxin A in the Mid and Lower Face and Neck," *Dermatol. Clin.* 22(2):151-158 (2004).
Carruthers & Carruthers, "Botulinum Toxin Type A for the Treatment of Glabellar Rhytides," *Dermatol. Clin.* 22(2):137-144 (2004).
Chaddock et al., "Expression and Purification of Catalytically Active, Non-Toxic Endopeptidase Derivatives of *Clostridium botulinum* Toxin Type A," *Protein Expr. Purif.* 25(2):219-228 (2002).
Chaddock et al., "Retargeted Clostridial Endopeptidases: Inhibition of Nociceptive Neurotransmitter Release In Vitro, and Antinociceptive Activity in In Vivo Models of Pain," *Mov. Disord.* 19(Suppl 8):S42-S47 (2004).
Chao et al., "Management of Pharyngoesophageal Spasm with Botox," *Otolaryngol Clin. North Am.* 37(3):559-566 (2004).
Chen et al., "Altering Brow Contour with Botulinum Toxin," *Facial Plast. Surg. Clin. N. Am.* 11:457-464 (2003).
Cruz, F., "Mechanisms Involved in New Therapies for Overactive Bladder," *Urology* 63(Suppl 3A):65-73 (2004).
Cui et al., "Subcutaneous Administration of Botulinum Toxin A Reduces Formalin-Induced Pain," *Pain* 107:(1-2):125-133 (2004).
Defazio & Livrea, "Primary Blepharospasm: Diagnosis and Management," *Drugs* 64(3):237-244 (2004).
Dekleva & DAsGUPTA, "Nicking of Single Chain Clostridium Botulinum Type A Neurotoxin by an Endogenous Protease," *Biochem. Biophys. Res. Commun.* 162(2):767-772 (1989).
Derman et al., "Mutations That Allow Disulfide Bond Formation in the Cytoplasm of *Escherichia coli*," *Science* 262(5140):1744-1747 (1993).
Dolly et al., "Acceptors for Botulinum Neurotoxin Reside on Motor Nerve Terminals and Mediate Its Internalization," *Nature* 307(5950):457-460 (1984).
Dong et al., "Synaptotagmins I and II Mediate Entry of Botulinum Neurotoxin B Into Cells," *J. Cell. Biol.* 162(7):1293-1303 (2003).
Eleopra et al., "Different Types of Botulinum Toxin in Humans," *Mov. Disord.* 19(Suppl 8)S53-S59 (2004).
Emonard et al., "Regulation of Matrix Metalloproteinase (MMP) Activity by the Low-Density Lipoprotein Receptor-Related Protein (LRP). A New Function for an 'Old Friend'," *Biochimie* 87(3-4):369-376 (2005).
Finn, J.C., "Botulinum Toxin Type A: Fine-Tuning Treatment of Facial Nerve Injury," *J. Drugs Dermatol.* 3(2):133-137 (2004).
Flynn, T.C., "Myobloc," *Dermatol. Clin.* 22(2):207-211 (2004).
Giannantoni et al., "Intravesical Resiniferatoxin Versus Botulinum-A Toxin Injections for Neurogenic Detrusor Overactivity: A Prospective Randomized Study," *J. Urol.* 172(1):240-243 (2004).
Glogau, R.G., "Treatment of Hyperhidrosis with Botulinum Toxin," *Dermatol. Clin.* 22(2):177-185 (2004).
Goodnough et al., "Development of a Delivery Vehicle for Intracellular Transport of Botulinum Neurotoxin Antagonists," *FEBS Lett.* 513(2-3):163-168 (2002).
Haussermann et al., "Long-Term Follow-Up of Cervical Dystonia Patients Treated with Botulinum Toxin A," *Mov. Disord.* 19(3):303-308 (2004).
Hayden et al., "Discovery and Design of Novel Inhibitors of Botulinus Neurotoxin A: Targeted 'Hinge' Peptide Libraries," *J. Appl. Toxicol.* 23(1):1-7 (2003).

(56) References Cited

OTHER PUBLICATIONS

Hoch et al., "Channels Formed by Botulinum, Tetanus, and Diphtheria Toxins in Planar Lipid Bilayers: Relevance to Translocation of Proteins Across Membranes," *Proc. Natl. Acad. Sci. USA* 82(6):1692-1696 (1985).

Hojilla et al., "Matrix Metalloproteinases and Their Tissue Inhibitors Direct Cell Fate During Cancer Development," *Br. J. Cancer* 89(10):1817-1821 (2003).

Hyman et al., "Botulinum Toxin (*Dysport*®) Treatment of Hip Adductor Spasticity in Multiple Sclerosis: A Prospective, Randomised, Double Blind, Placebo Controlled, Dose Ranging Study," *J. Neurol. Neurosurg. Psychiatry* 68(6):707-712 (2000).

Jankovic, J., "Botulinum Toxin in Clinical Practice," *J. Neurol. Neurosurg. Psychiatry* 75(7):951-957 (2004).

Johnson, E.A., "Clostridial Toxins as Therapeutic Agents: Benefits of Nature's Most Toxic Proteins," *Annu. Rev. Microbiol.* 53:551-575 (1999).

Jost & Aoki, "Botulinum Toxin A in Anal Fissure: Why Does It Work?" *Dis. Colon Rectum.* 47(2):257-258 (2004).

Kadkhodayan et al., "Cloning, Expression, and One-Step Purification of the Minimal Essential Domain of the Light Chain of Botulinum Neurotoxin Type A," *Protein Expr. Purif.* 19(1):125-130 (2000).

Kern et al., "Effects of Botulinum Toxin Type B on Stump Pain and Involuntary Movements of the Stump," *Am. J. Phys. Med. Rehabil.* 83(5):396-399 (2004).

Kiyatkin et al., "Induction of an Immune Response by Oral Administration of Recombinant Botulinum Toxin," *Infect. Immun.* 65(11):4586-4591 (1997).

Klein, A.W., "The Therapeutic Potential of Botulinum Toxin," *Dermatol. Surg.* 30(3):452-455 (2004).

Koriazova & Montal., "Translocation of Botulinum Neurotoxin Light Chain Protease Through the Heavy Chain Channel," *Nat. Struct. Biol.* 10(1):13-18 (2003).

Krämer et al., "Botulinum Toxin A Reduces Neurogenic Flare But Has Almost No Effect on Pain and Hyperalgesia in Human Skin," *J. Neurol.* 250(2):188-193 (2003).

Kurazono et al., "Minimal Essential Domains Specifying Toxicity of the Light Chains of Tetanus Toxin and Botulinum Neurotoxin Type A," *J. Biol. Chem.* 267(21):14721-14729 (1992).

Kyrmizakis et al., "The Use of Botulinum Toxin Type A in the Treatment of Frey and Crocodile Tears Syndromes," *J. Oral Maxillofac. Surg.* 62(7):840-844 (2004).

Lacy et al., "Crystal Structure of Botulinum Neurotoxin Type A and Implications for Toxicity," *Nat. Struct. Biol.* 5(10):898-902 (1998).

Lacy & Stevens, "Recombinant Expression and Purification of the Botulinum Neurotoxin Type A Translocation Domain," *Protein Expr. Purif.* 11(2):195-200 (1997).

Lalli et al., "Functional Characterisation of Tetanus and Botulinum Neurotoxins Binding Domains," *J. Cell Sci.* 112(Pt 16):2715-2724 (1999).

Lang, A., "History and Uses of BOTOX (Botulinum Toxin Type A)," *Lippincott's Case Manag.* 9(2):109-112 (2004).

Layeeque et al., "Botulinum Toxin Infiltration for Pain Control After Mastectomy and Expander Reconstruction," *Ann. Surg.* 240(4):608-614 (2004).

Lee et al., "A Case of Foul Genital Odor Treated with Botulinum Toxin A," *Dermatol. Surg.* 30(9):1233-1235 (2004).

Leippold et al., "Botulinum Toxin as a New Therapy Option for Voiding Disorders: Current State of the Art," *Eur. Urol.* 44(2):165-174 (2003).

Levy et al., "Botulinum Toxin A: A 9-Month Clinical and 3D In Vivo Profilometric Crow's Feet Wrinkle Formation Study," *J. Cosmet. Laser Ther.* 6(1):16-20 (2004).

Li et al., "Recombinant Forms of Tetanus Toxin Engineered for Examining and Exploiting Neuronal Trafficking Pathways," *J. Biol. Chem.* 276(33):31394-31401 (2001).

Lozsadi et al., "Botulinum Toxin A Improves Involuntary Limb Movements in Rasmussen Syndrome," *Neurology* 62(7):1233-1234 (2004).

MacKINNON et al., "Corticospinal Excitability Accompanying Ballistic Wrist Movements in Primary Dystonia," *Mov. Disord.* 19(3):273-284 (2004).

Mahowald et al., "Long Term Effects of Intra-Articular Botulinum Toxin A for Refractory Joint Pain," *Annual Meeting of the American College of Rheumatology* (Oct. 19, 2004).

Mannello et al., "Matrix Metalloproteinase Inhibitors as Anticancer Therapeutics," *Curr. Cancer Drug Targets* 5:285-298 (2005).

Maskos, K., "Crystal Structures of MMPs in Complex with Physiological and Pharmacological Inhibitors," *Biochimie* 87(3-4):249-263 (2005).

Mazo et al., "Botulinic Toxin in Patients with Neurogenic Dysfunction of the Lower Urinary Tracts," *Urologia* Jul.-Aug. 44-48, (2004).

Matteoli et al., "Synaptic Vesicle Endocytosis Mediates the Entry of Tetanus Neurotoxin Into Hippocampal Neurons," *Proc. Natl. Acad. Sci. USA* 93(23):13310-13315 (1996).

Montecucco, C., "How Do Tetanus and Botulinum Toxins Bind to Neuronal Membranes?" *Trends Biochem. Sci.* 11(8):314-317 (1986).

Montecucco et al., "SNARE Complexes and Neuroexocytosis: How Many, How Close?" *Trends Biochem. Sci.* 30(7):367-372 (2005).

Montecucco et al., "Structure and Function of Tetanus and Botulinum Neurotoxins," *Q. Rev. Biophys.* 28(4):423-472 (1995).

Mukherjee et al., "Endocytosis," *Physiol. Rev.* 77(3):759-803 (1997).

Namazi & Majd, "Botulinum Toxin as a Novel Addition to Anti-Arthritis Armamentarium," *Am. J. Immun.* 1(2):92-93 (2005).

Naumann & Jankovic, "Safety of Botulinum Toxin Type A: A Systematic Review and Meta-Analysis," *Curr. Med. Res. Opin.* 20(7):981-990 (2004).

Nishiki et al., "The High-Affinity Binding of *Clostridium botulinum* Type B Neurotoxin to Synaptotagmin II Associated with Gangliosides $G_{T1b}/G_{D1a}$," *FEBS Lett.* 378(3):253-257 (1996).

Oost et al., "Design and Synthesis of Substrate-Based Inhibitors of Botulinum Neurotoxin Type B Metalloprotease," *Biopolymers* 71(6):602-619 (2003).

Özsoy et al., "Two-Plane Injection of Botulinum Exotoxin A in Glabellar Frown Lines," *Aesth. Plast. Surg.* 28(2):114-115 (2004).

Park & Simpson, "Inhalational Poisoning by Botulinum Toxin and Inhalation Vaccination with Its Heavy-Chain Component," *Infect. Immun.* 71(3):1147-1154 (2003).

Pidcock, F.S., "The Emerging Role of Therapeutic Botulinum Toxin in the Treatment of Cerebral Palsy," *J. Pediatr.* 145(2 Suppl):S33-S35 (2004).

Pless et al., "High-Affinity, Protective Antibodies to the Binding Domain of Botulinum Neurotoxin Type A," *Infect. Immun.* 69(1):570-574 (2001).

Porta et al., "Treatment of Phonic Tics in Patients with Tourette's Syndrome Using Botulinum Toxin Type A," *Neurol. Sci.* 24(6):420-423 (2003).

Prinz et al., "The Role of the Thioredoxin and Glutaredoxin Pathways in Reducing Protein Disulfide Bonds in the *Escherichia coli* Cytoplasm," *J. Biol. Chem.* 272(25):15661-15667 (1997).

Pucinelli et al., "Botulinic Toxin for the Rehabilitation of Osteoarthritis Fixed-Flexion Knee Deformity," *Annual Meeting of the Osteoarthitis Research Society International*, pp. S143, Abstract P346 (2004).

Rajkumar & Conn, "Botulinum Toxin: A New Dimension in the Treatment of Lower Urinary Tract Dysfunction," *Urology* 64(1):2-8 (2004).

Reitz & Schurch, "Intravesical Therapy Options for Neurogenic Detrusor Overactivity," *Spinal Cord* 42(5):267-272 (2004).

Rigoni et al., "Site-Directed Mutagenesis Identifies Active-Site Residues of the Light Chain of Botulinum Neurotoxin Type A," *Biochem. Biophys. Res. Commun.* 288(5):1231-1237 (2001).

Rossetto et al., "SNARE Motif and Neurotoxins," *Nature* 372(6505):415-416 (1994).

Rummel et al., "The $H_{cc}$-Domain of Botulinum Neurotoxins A and B Exhibits a Singular Ganglioside Binding Site Displaying Serotype Specific Carbohydrate Interaction," *Mol. Microbiol.* 51(3):631-643 (2004).

Rummel et al., "Synaptotagmins I and II Act as Nerve Cell Receptors for Botulinum Neurotoxin G," *J. Biol. Chem.* 279(29):30865-30870 (2004).

(56) References Cited

OTHER PUBLICATIONS

Russman et al., "Cerebral Palsy: A Rational Approach to a Treatment Protocol, and the Role of Botulinum Toxin in Treatment," *Muscle Nerve* 20(Suppl 6):S181-S193 (1997).
Sadick & Matarasso, "Comparison of Botulinum Toxins A and B in the Treatment of Facial Rhytides," *Dermatol. Clin.* 22(2):221-226 (2004).
Salmanpoor & Rahmanian, "Treatment of Axillary Hyperhidrosis with Botulinum-A Toxin," *Int. J. Dermatol.* 41(7):428-430 (2002).
Sampaio et al., "Clinical Comparability of Marketed Formulations of Botulinum Toxin," *Mov. Disord.* 19(Suppl 8):S129-S136 (2004).
Schmulson & Valdovinos, "Current and Future Treatment of Chest Pain of Presumed Esophageal Origin," *Gastroenterol Clin. North Am.* 33(1):93-105 (2004).
Schurch, "The Role of Botulinum Toxin in Neurology," *Drugs of Today* 40(3):205-212 (2004).
Segelke et al., "Crystal Structure of *Clostridium botulinum* Neurotoxin Protease in a Product-Bound State: Evidence for Noncanonical Zinc Protease Activity," *Proc. Natl. Acad. Sci. USA* 101(18):6888-6893 (2004).
Shapiro et al., "Identification of a Ganglioside Recognition Domain of Tetanus Toxin Using a Novel Ganglioside Photoaffinity Ligand," *J. Biol. Chem.* 272(48):30380-30386 (1997).
Simpson, L.L., "Identification of the Major Steps in Botulinum Toxin Action," *Annu. Rev. Pharmacol. Toxicol.* 44:167-193 (2004).
Sukonpan et al., "Synthesis of Substrates and Inhibitors of Botulinum Neurotoxin Type A Metalloprotease," *J. Pept. Res.* 63(2):181-193 (2004).
Sutton et al., "Crystal Structure of a SNARE Complex Involved in Synaptic Exocytosis at 2.4 Å Resolution," *Nature* 395(6700):347-353 (1998).
Swaminathan & Eswaramoorthy, "Structural Analysis of the Catalytic and Binding Sites of *Clostridium botulinum* Neurotoxin B," *Nat. Struct. Biol.* 7(8):693-699 (2000).
Van Heyningen & Miller, "The Fixation of Tetanus Toxin by Ganglioside," *J. Gen. Microbiol.* 24:107-119 (1961).
Vartanian & Dayan, "Facial Rejuvenation Using Botulinum Toxin A: Review and Updates," *Facial Plast. Surg.* 20(1):11-19 (2004).
Wissel & Entner, "Botulinum Toxin Typ A in der Behandlung der Adduktorenspastizität (Botulinum Toxin Treatment of Hip Adductor Spasticity in Multiple Sclerosis)," *Wien. Klin. Wochesnchr.* 113[Suppl 4]:20-24 (2001).
No Author, "Botulinum Toxin (*Botox*) for Axillary Hyperhidrosis," *Med. Lett. Drugs Ther.* 46(1191):76 (2004).
Marvaud et al., "Le Botulisme: Agent, Mode D'action des Neurotoxines Botuliques, Formes D'Acquisition, Traitement et Prevention," *C.R. Biologies* 325:863-878 (2002) (with English abstract).
Baldwin et al., "The C-Terminus of Botulinum Neurotoxin Type A Light Chain Contributes to Solubility, Catalysis, and Stability," *Protein Expression and Purification* 37:187-195 (2004).
Prabakaran et al., "Botulinum Neurotoxin Types B and E: Purification, Limited Proteolysis by Endoproteinase Glu-C and Pepsin, and Comparison of Their Identified Cleaved Sites Relative to the Three-Dimensional Structure of Type A Neurotoxin," *Toxicon* 39:1515-1531 (2001).
Band et al., "Recombinant Derivatives of Botulinum Neurotoxin A Engineered for Trafficking Studies and Neuronal Delivery," *Protein Expr. Purif.* 71:62-73 (2010).
Band et al., "Recombinant Derivatives of Botulinum Neurotoxin A Engineered to Dissect Toxin Uptake and Trafficking Pathways," Abstract, 46th Annual Meeting of the Interagency Botulism Research Coordinating Committee (Oct. 18-21, 2009).
Ichtchenko, "Recombinant Derivatives of Botulinum Neurotoxin A Engineered for Trafficking Studies and Neuronal Delivery," Presentation, 46th Annual Meeting of the Interagency Botulism Research Coordinating Committee (Oct. 21, 2009).
International Search Report for PCT/US05/43307 (Oct. 5, 2006).
International Search Report and Written Opinion for PCT/US2011/022408 (Dec. 26, 2011).

* cited by examiner

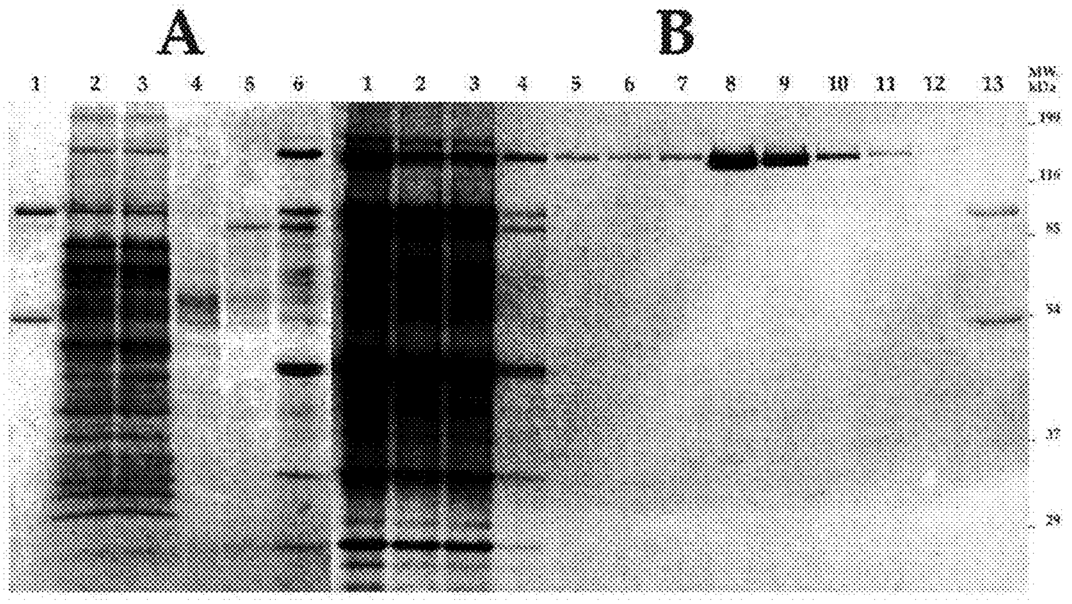
FIGS. 2A-B
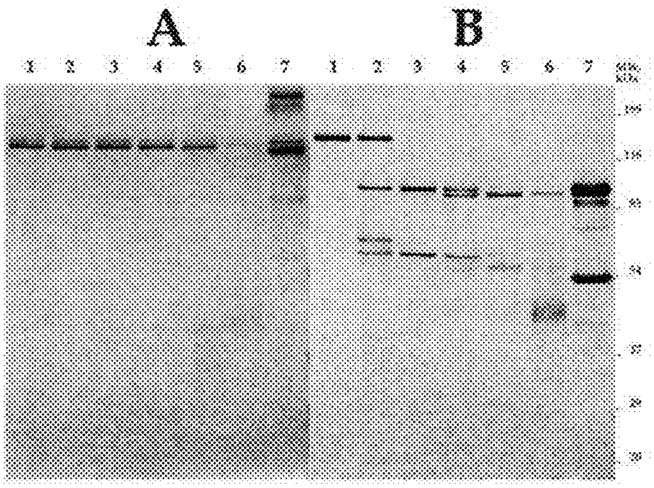
FIGS. 3A-B

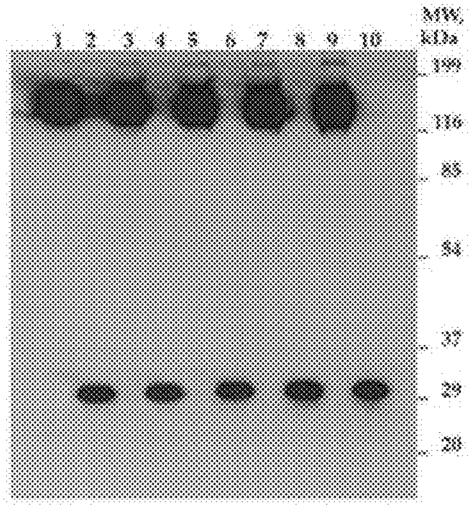
FIG. 4
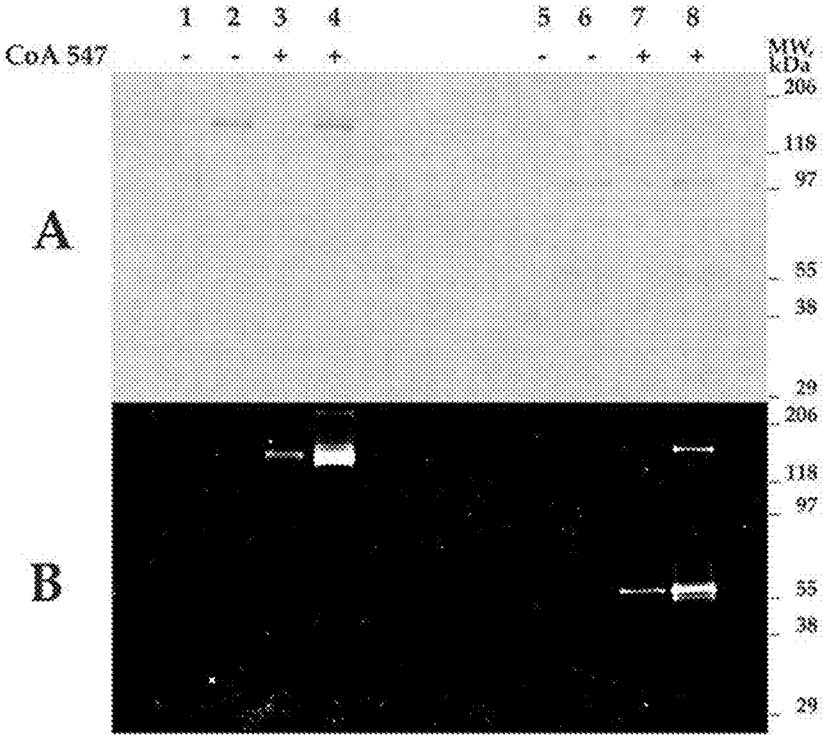
FIGS. 5A-B

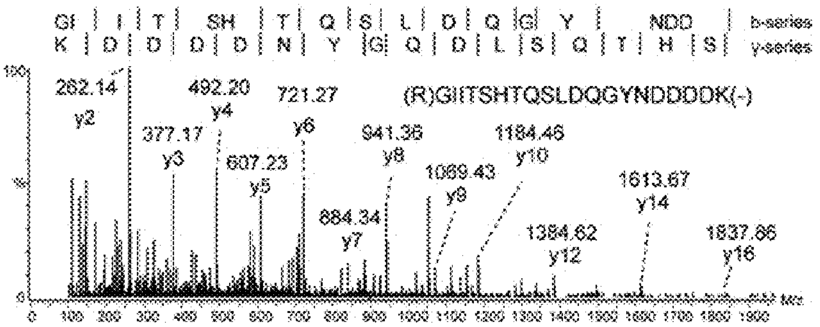
FIG. 6
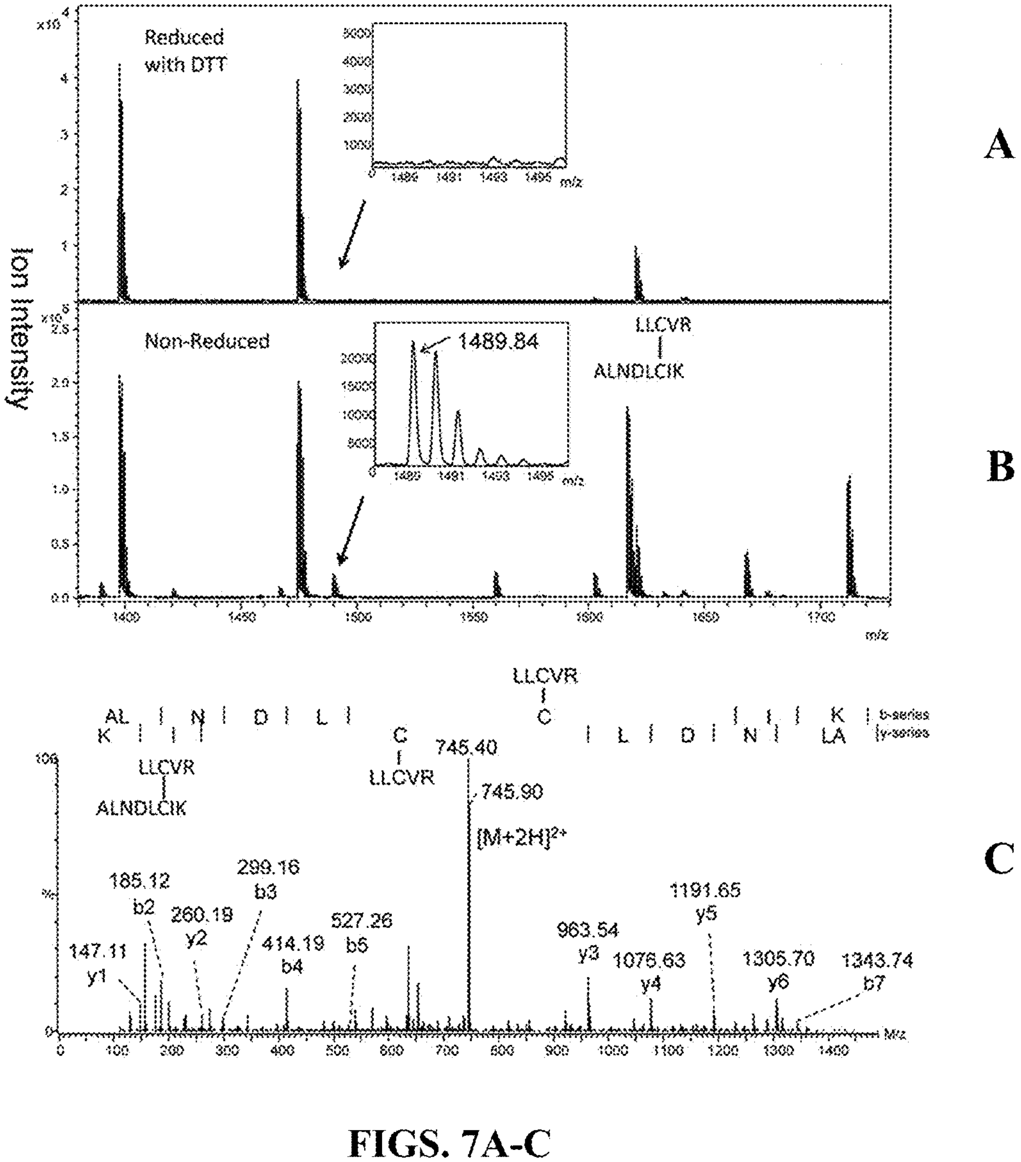
FIGS. 7A-C

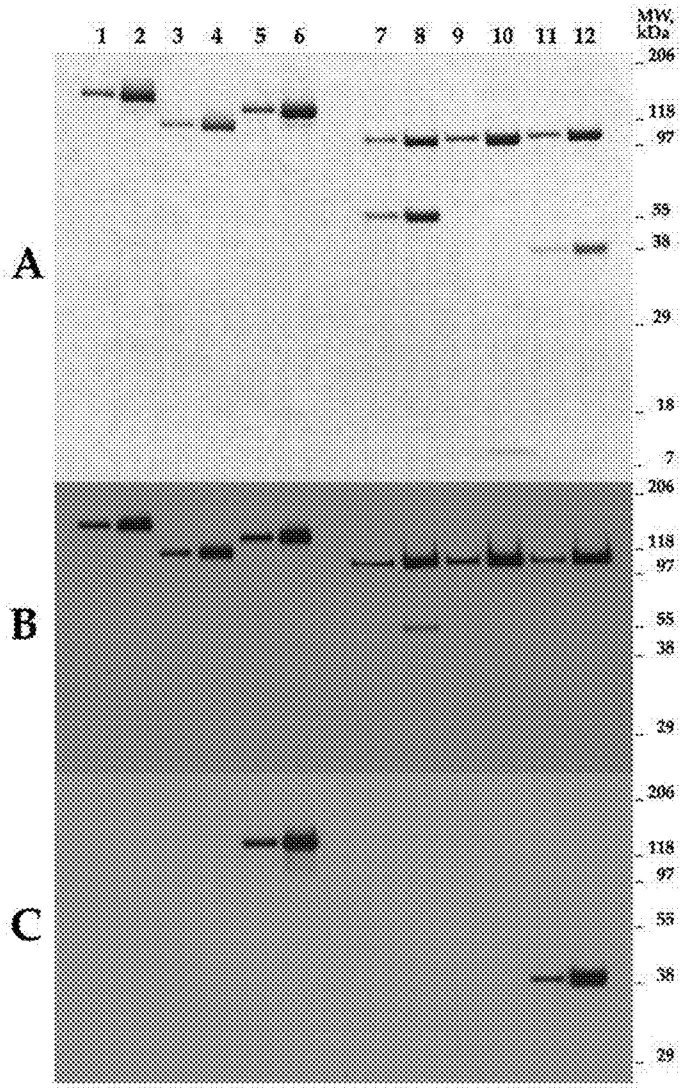
FIGS. 8A-C
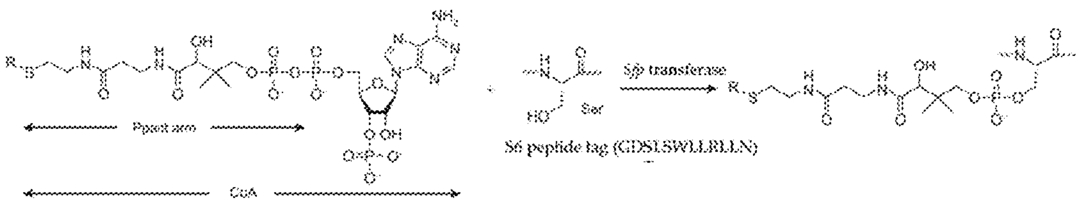
FIG. 9

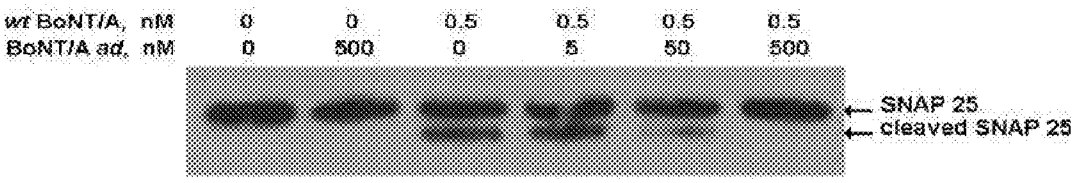
FIG. 10
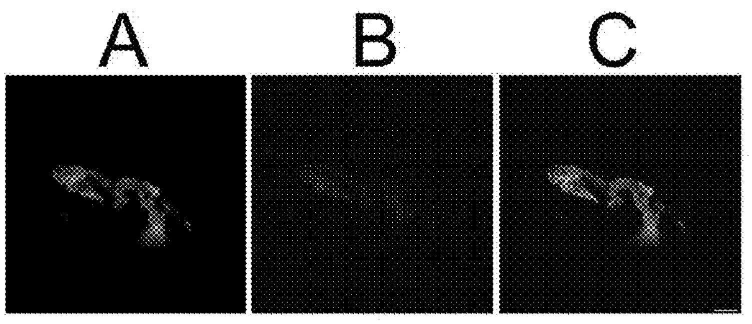
FIGS. 11A-C
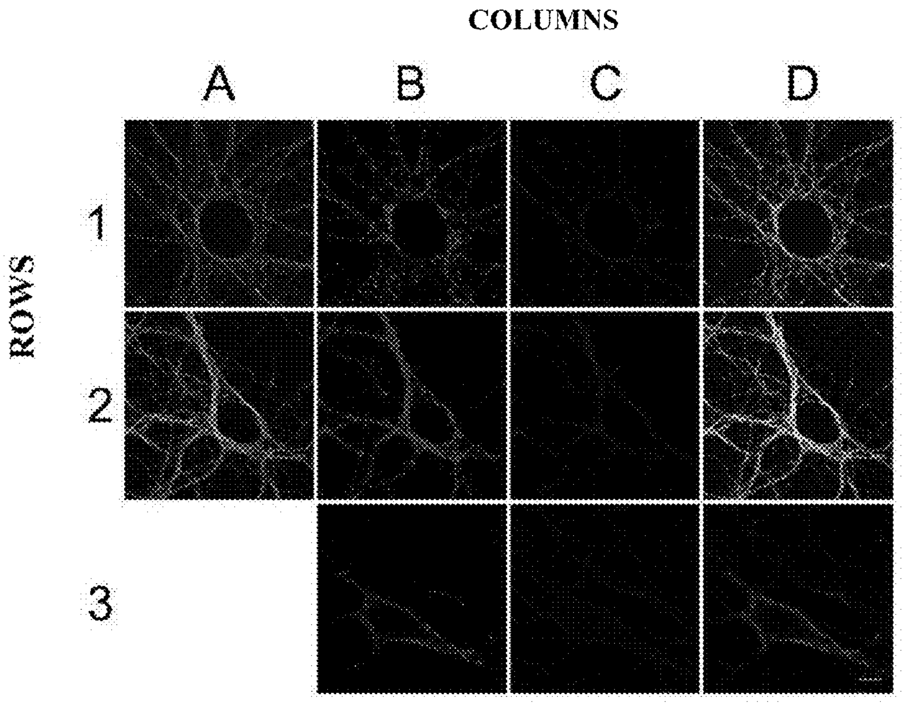
FIG. 12

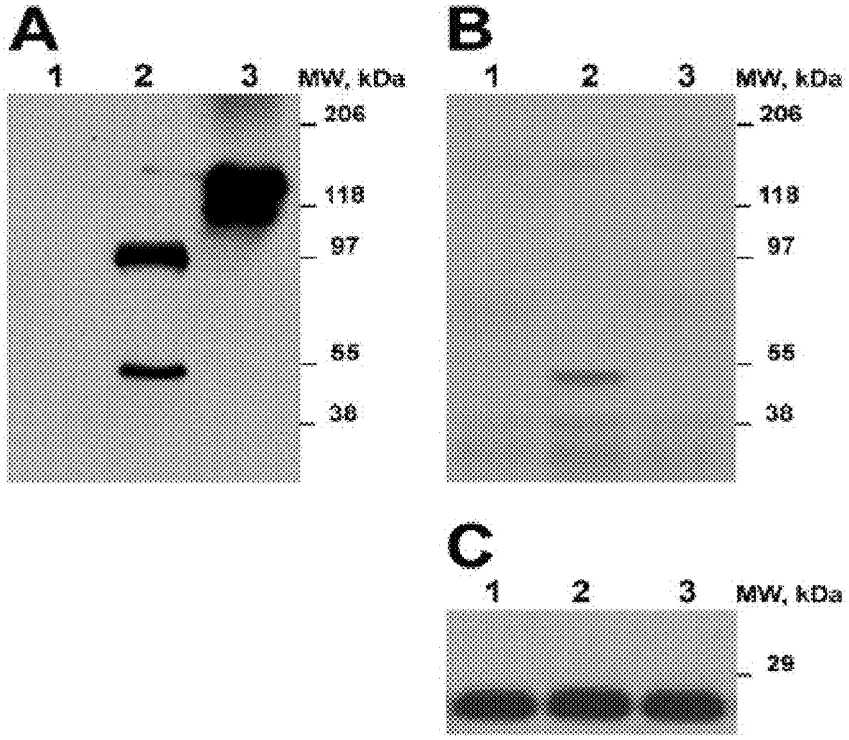
FIGS. 13A-C
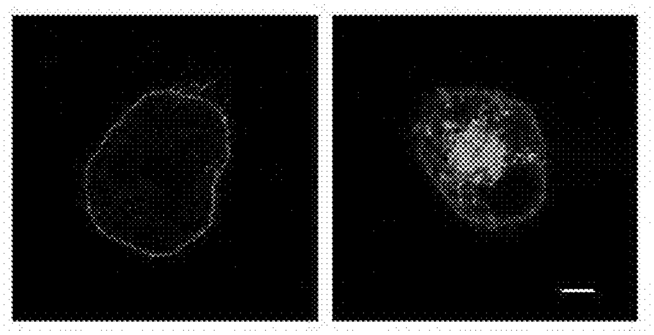
A B
FIGS. 14A-B

SEQUENCE LISTING

```
<160> NUMBER OF SEQ ID NOS: 49

<210> SEQ ID NO 1
<211> LENGTH: 8
<212> TYPE: PRT
<213> ORGANISM: Artificial
<220> FEATURE:
<223> OTHER INFORMATION: Botulinum Neurotoxin Light Chain Motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 1

His Glu Xaa Xaa His Xaa Xaa His
1               5


<210> SEQ ID NO 2
<211> LENGTH: 12
<212> TYPE: PRT
<213> ORGANISM: Artificial
<220> FEATURE:
<223> OTHER INFORMATION: S6 Peptide Sequence

<400> SEQUENCE: 2

Gly Asp Ser Leu Ser Trp Leu Leu Arg Leu Leu Asn
1               5                   10


<210> SEQ ID NO 3
<211> LENGTH: 1372
<212> TYPE: PRT
<213> ORGANISM: Artificial
<220> FEATURE:
<223> OTHER INFORMATION: BoNT/Aadek Neurotoxin

<400> SEQUENCE: 3

Met Lys Phe Leu Val Asn Val Ala Leu Val Phe Met Val Val Tyr Ile
1               5                   10                  15

Ser Tyr Ile Tyr Ala Ala Ala His His His His His His His His His
            20                  25                  30

His Thr Arg Glu Asn Leu Tyr Phe Gln Gly Ala Gly Asp Ser Leu Ser
        35                  40                  45

Trp Leu Leu Arg Leu Leu Asn Ala Arg Gly Gly Ala Ser Gly Pro Phe
    50                  55                  60

Val Asn Lys Gln Phe Asn Tyr Lys Asp Pro Val Asn Gly Val Asp Ile
65                  70                  75                  80

Ala Tyr Ile Lys Ile Pro Asn Ala Gly Gln Met Gln Pro Val Lys Ala
                85                  90                  95

Phe Lys Ile His Asn Lys Ile Trp Val Ile Pro Glu Arg Asp Thr Phe
            100                 105                 110

Thr Asn Pro Glu Glu Gly Asp Leu Asn Pro Pro Pro Glu Ala Lys Gln
```

```
        115                 120                 125

Val Pro Val Ser Tyr Tyr Asp Ser Thr Tyr Leu Ser Thr Asp Asn Glu
    130                 135                 140

Lys Asp Asn Tyr Leu Lys Gly Val Thr Lys Leu Phe Glu Arg Ile Tyr
145                 150                 155                 160

Ser Thr Asp Leu Gly Arg Met Leu Leu Thr Ser Ile Val Arg Gly Ile
                165                 170                 175

Pro Phe Trp Gly Gly Ser Thr Ile Asp Thr Glu Leu Lys Val Ile Asp
            180                 185                 190

Thr Asn Cys Ile Asn Val Ile Gln Pro Asp Gly Ser Tyr Arg Ser Glu
        195                 200                 205

Glu Leu Asn Leu Val Ile Ile Gly Pro Ser Ala Asp Ile Ile Gln Phe
    210                 215                 220

Glu Cys Lys Ser Phe Gly His Glu Val Leu Asn Leu Thr Arg Asn Gly
225                 230                 235                 240

Tyr Gly Ser Thr Gln Tyr Ile Arg Phe Ser Pro Asp Phe Thr Phe Gly
                245                 250                 255

Phe Glu Glu Ser Leu Glu Val Asp Thr Asn Pro Leu Leu Gly Ala Gly
            260                 265                 270

Lys Phe Ala Thr Asp Pro Ala Val Thr Leu Ala His Ala Leu Ile His
        275                 280                 285

Ala Gly His Arg Leu Tyr Gly Ile Ala Ile Asn Pro Asn Arg Val Phe
    290                 295                 300

Lys Val Asn Thr Asn Ala Tyr Tyr Glu Met Ser Gly Leu Glu Val Ser
305                 310                 315                 320

Phe Glu Glu Leu Arg Thr Phe Gly Gly His Asp Ala Lys Phe Ile Asp
                325                 330                 335

Ser Leu Gln Glu Asn Glu Phe Arg Leu Tyr Tyr Tyr Asn Lys Phe Lys
            340                 345                 350

Asp Ile Ala Ser Thr Leu Asn Lys Ala Lys Ser Ile Val Gly Thr Thr
        355                 360                 365

Ala Ser Leu Gln Tyr Met Lys Asn Val Phe Lys Glu Lys Tyr Leu Leu
    370                 375                 380

Ser Glu Asp Thr Ser Gly Lys Phe Ser Val Asp Lys Leu Lys Phe Asp
385                 390                 395                 400

Lys Leu Tyr Lys Met Leu Thr Glu Ile Tyr Thr Glu Asp Asn Phe Val
                405                 410                 415

Lys Phe Phe Lys Val Leu Asn Arg Lys Thr Ala Leu Asn Phe Asp Lys
            420                 425                 430

Ala Val Phe Lys Ile Asn Ile Val Pro Lys Val Asn Tyr Thr Ile Tyr
        435                 440                 445

Asp Gly Phe Asn Leu Arg Asn Thr Asn Leu Ala Ala Asn Phe Asn Gly
    450                 455                 460

Gln Asn Thr Glu Ile Asn Asn Met Asn Phe Thr Lys Leu Lys Asn Phe
465                 470                 475                 480

Thr Gly Leu Phe Glu Phe Tyr Lys Leu Leu Cys Val Arg Gly Ile Ile
                485                 490                 495

Thr Ser His Thr Gln Ser Leu Asp Gln Gly Tyr Asn Asp Asp Asp Asp
            500                 505                 510

Lys Ala Leu Asn Asp Leu Cys Ile Lys Val Asn Asn Trp Asp Leu Phe
        515                 520                 525

Phe Ser Pro Ser Glu Asp Asn Phe Thr Asn Asp Leu Asn Lys Gly Glu
    530                 535                 540
```

-continued

```
Glu Ile Thr Ser Asp Thr Asn Ile Glu Ala Ala Glu Glu Asn Ile Ser
545                 550                 555                 560

Leu Asp Leu Ile Gln Gln Tyr Tyr Leu Thr Phe Asn Phe Asp Asn Glu
                565                 570                 575

Pro Glu Asn Ile Ser Ile Glu Asn Leu Ser Ser Asp Ile Ile Gly Gln
            580                 585                 590

Leu Glu Leu Met Pro Asn Ile Glu Arg Phe Pro Asn Gly Lys Lys Tyr
        595                 600                 605

Glu Leu Asp Lys Tyr Thr Met Phe His Tyr Leu Arg Ala Gln Glu Phe
    610                 615                 620

Glu His Gly Lys Ser Arg Ile Ala Leu Thr Asn Ser Val Asn Glu Ala
625                 630                 635                 640

Leu Leu Asn Pro Ser Arg Val Tyr Thr Phe Phe Ser Ser Asp Tyr Val
                645                 650                 655

Lys Lys Val Asn Lys Ala Thr Glu Ala Ala Met Phe Leu Gly Trp Val
            660                 665                 670

Glu Gln Leu Val Tyr Asp Phe Thr Asp Glu Thr Ser Glu Val Ser Thr
        675                 680                 685

Thr Asp Lys Ile Ala Asp Ile Thr Ile Ile Ile Pro Tyr Ile Gly Pro
    690                 695                 700

Ala Leu Asn Ile Gly Asn Met Leu Tyr Lys Asp Asp Phe Val Gly Ala
705                 710                 715                 720

Leu Ile Phe Ser Gly Ala Val Ile Leu Leu Glu Phe Ile Pro Glu Ile
                725                 730                 735

Ala Ile Pro Val Leu Gly Thr Phe Ala Leu Val Ser Tyr Ile Ala Asn
            740                 745                 750

Lys Val Leu Thr Val Gln Thr Ile Asp Asn Ala Leu Ser Lys Arg Asn
        755                 760                 765

Glu Lys Trp Asp Glu Val Tyr Lys Tyr Ile Val Thr Asn Trp Leu Ala
    770                 775                 780

Lys Val Asn Thr Gln Ile Asp Leu Ile Arg Lys Lys Met Lys Glu Ala
785                 790                 795                 800

Leu Glu Asn Gln Ala Glu Ala Thr Lys Ala Ile Ile Asn Tyr Gln Tyr
                805                 810                 815

Asn Gln Tyr Thr Glu Glu Glu Lys Asn Asn Ile Asn Phe Asn Ile Asp
            820                 825                 830

Asp Leu Ser Ser Lys Leu Asn Glu Ser Ile Asn Lys Ala Met Ile Asn
        835                 840                 845

Ile Asn Lys Phe Leu Asn Gln Cys Ser Val Ser Tyr Leu Met Asn Ser
    850                 855                 860

Met Ile Pro Tyr Gly Val Lys Arg Leu Glu Asp Phe Asp Ala Ser Leu
865                 870                 875                 880

Lys Asp Ala Leu Leu Lys Tyr Ile Tyr Asp Asn Arg Gly Thr Leu Ile
                885                 890                 895

Gly Gln Val Asp Arg Leu Lys Asp Lys Val Asn Asn Thr Leu Ser Thr
            900                 905                 910

Asp Ile Pro Phe Gln Leu Ser Lys Tyr Val Asp Asn Gln Arg Leu Leu
        915                 920                 925

Ser Thr Phe Thr Glu Tyr Ile Asn Asn Ile Ile Asn Thr Ser Ile Leu
    930                 935                 940

Asn Leu Arg Tyr Glu Ser Asn His Leu Ile Asp Leu Ser Arg Tyr Ala
945                 950                 955                 960
```

-continued

Ser Lys Ile Asn Ile Gly Ser Lys Val Asn Phe Asp Pro Ile Asp Lys
965 970 975

Asn Gln Ile Gln Leu Phe Asn Leu Glu Ser Ser Lys Ile Glu Val Ile
980 985 990

Leu Lys Asn Ala Ile Val Tyr Asn Ser Met Tyr Glu Asn Phe Ser Thr
995 1000 1005

Ser Phe Trp Ile Arg Ile Pro Lys Tyr Phe Asn Ser Ile Ser Leu
1010 1015 1020

Asn Asn Glu Tyr Thr Ile Ile Asn Cys Met Glu Asn Asn Ser Gly
1025 1030 1035

Trp Lys Val Ser Leu Asn Tyr Gly Glu Ile Ile Trp Thr Leu Gln
1040 1045 1050

Asp Thr Gln Glu Ile Lys Gln Arg Val Val Phe Lys Tyr Ser Gln
1055 1060 1065

Met Ile Asn Ile Ser Asp Tyr Ile Asn Arg Trp Ile Phe Val Thr
1070 1075 1080

Ile Thr Asn Asn Arg Leu Asn Asn Ser Lys Ile Tyr Ile Asn Gly
1085 1090 1095

Arg Leu Ile Asp Gln Lys Pro Ile Ser Asn Leu Gly Asn Ile His
1100 1105 1110

Ala Ser Asn Asn Ile Met Phe Lys Leu Asp Gly Cys Arg Asp Thr
1115 1120 1125

His Arg Tyr Ile Trp Ile Lys Tyr Phe Asn Leu Phe Asp Lys Glu
1130 1135 1140

Leu Asn Glu Lys Glu Ile Lys Asp Leu Tyr Asp Asn Gln Ser Asn
1145 1150 1155

Ser Gly Ile Leu Lys Asp Phe Trp Gly Asp Tyr Leu Gln Tyr Asp
1160 1165 1170

Lys Pro Tyr Tyr Met Leu Asn Leu Tyr Asp Pro Asn Lys Tyr Val
1175 1180 1185

Asp Val Asn Asn Val Gly Ile Arg Gly Tyr Met Tyr Leu Lys Gly
1190 1195 1200

Pro Arg Gly Ser Val Met Thr Thr Asn Ile Tyr Leu Asn Ser Ser
1205 1210 1215

Leu Tyr Arg Gly Thr Lys Phe Ile Ile Lys Lys Tyr Ala Ser Gly
1220 1225 1230

Asn Lys Asp Asn Ile Val Arg Asn Asn Asp Arg Val Tyr Ile Asn
1235 1240 1245

Val Val Val Lys Asn Lys Glu Tyr Arg Leu Ala Thr Asn Ala Ser
1250 1255 1260

Gln Ala Gly Val Glu Lys Ile Leu Ser Ala Leu Glu Ile Pro Asp
1265 1270 1275

Val Gly Asn Leu Ser Gln Val Val Val Met Lys Ser Lys Asn Asp
1280 1285 1290

Gln Gly Ile Thr Asn Lys Cys Lys Met Asn Leu Gln Asp Asn Asn
1295 1300 1305

Gly Asn Asp Ile Gly Phe Ile Gly Phe His Gln Phe Asn Asn Ile
1310 1315 1320

Ala Lys Leu Val Ala Ser Asn Trp Tyr Asn Arg Gln Ile Glu Arg
1325 1330 1335

Ser Ser Arg Thr Leu Gly Cys Ser Trp Glu Phe Ile Pro Val Asp
1340 1345 1350

Asp Gly Trp Gly Glu Arg Pro Leu Gly Ala Gly Trp Ser His Pro

```
    1355                1360                1365

Gln Phe  Glu Lys
    1370


<210> SEQ ID NO 4
<211> LENGTH: 1373
<212> TYPE: PRT
<213> ORGANISM: Artificial
<220> FEATURE:
<223> OTHER INFORMATION: BoNT/Aadtev Neurotoxin

<400> SEQUENCE: 4

Met Lys Phe Leu Val Asn Val Ala Leu Val Phe Met Val Val Tyr Ile
1               5                   10                  15

Ser Tyr Ile Tyr Ala Ala Ala His His His His His His His His His
            20                  25                  30

His Thr Arg Glu Asn Leu Tyr Phe Gln Gly Ala Gly Asp Ser Leu Ser
        35                  40                  45

Trp Leu Leu Arg Leu Leu Asn Ala Arg Gly Gly Ala Ser Gly Pro Phe
    50                  55                  60

Val Asn Lys Gln Phe Asn Tyr Lys Asp Pro Val Asn Gly Val Asp Ile
65                  70                  75                  80

Ala Tyr Ile Lys Ile Pro Asn Ala Gly Gln Met Gln Pro Val Lys Ala
                85                  90                  95

Phe Lys Ile His Asn Lys Ile Trp Val Ile Pro Glu Arg Asp Thr Phe
            100                 105                 110

Thr Asn Pro Glu Glu Gly Asp Leu Asn Pro Pro Pro Glu Ala Lys Gln
        115                 120                 125

Val Pro Val Ser Tyr Tyr Asp Ser Thr Tyr Leu Ser Thr Asp Asn Glu
    130                 135                 140

Lys Asp Asn Tyr Leu Lys Gly Val Thr Lys Leu Phe Glu Arg Ile Tyr
145                 150                 155                 160

Ser Thr Asp Leu Gly Arg Met Leu Leu Thr Ser Ile Val Arg Gly Ile
                165                 170                 175

Pro Phe Trp Gly Gly Ser Thr Ile Asp Thr Glu Leu Lys Val Ile Asp
            180                 185                 190

Thr Asn Cys Ile Asn Val Ile Gln Pro Asp Gly Ser Tyr Arg Ser Glu
        195                 200                 205

Glu Leu Asn Leu Val Ile Ile Gly Pro Ser Ala Asp Ile Ile Gln Phe
    210                 215                 220

Glu Cys Lys Ser Phe Gly His Glu Val Leu Asn Leu Thr Arg Asn Gly
225                 230                 235                 240

Tyr Gly Ser Thr Gln Tyr Ile Arg Phe Ser Pro Asp Phe Thr Phe Gly
                245                 250                 255

Phe Glu Glu Ser Leu Glu Val Asp Thr Asn Pro Leu Leu Gly Ala Gly
            260                 265                 270

Lys Phe Ala Thr Asp Pro Ala Val Thr Leu Ala His Ala Leu Ile His
        275                 280                 285

Ala Gly His Arg Leu Tyr Gly Ile Ala Ile Asn Pro Asn Arg Val Phe
    290                 295                 300

Lys Val Asn Thr Asn Ala Tyr Tyr Glu Met Ser Gly Leu Glu Val Ser
305                 310                 315                 320

Phe Glu Glu Leu Arg Thr Phe Gly Gly His Asp Ala Lys Phe Ile Asp
                325                 330                 335

Ser Leu Gln Glu Asn Glu Phe Arg Leu Tyr Tyr Tyr Asn Lys Phe Lys
```

```
            340                 345                 350

Asp Ile Ala Ser Thr Leu Asn Lys Ala Lys Ser Ile Val Gly Thr Thr
        355                 360                 365

Ala Ser Leu Gln Tyr Met Lys Asn Val Phe Lys Glu Lys Tyr Leu Leu
    370                 375                 380

Ser Glu Asp Thr Ser Gly Lys Phe Ser Val Asp Lys Leu Lys Phe Asp
385                 390                 395                 400

Lys Leu Tyr Lys Met Leu Thr Glu Ile Tyr Thr Glu Asp Asn Phe Val
                405                 410                 415

Lys Phe Phe Lys Val Leu Asn Arg Lys Thr Ala Leu Asn Phe Asp Lys
            420                 425                 430

Ala Val Phe Lys Ile Asn Ile Val Pro Lys Val Asn Tyr Thr Ile Tyr
        435                 440                 445

Asp Gly Phe Asn Leu Arg Asn Thr Asn Leu Ala Ala Asn Phe Asn Gly
    450                 455                 460

Gln Asn Thr Glu Ile Asn Asn Met Asn Phe Thr Lys Leu Lys Asn Phe
465                 470                 475                 480

Thr Gly Leu Phe Glu Phe Tyr Lys Leu Leu Cys Val Arg Gly Ile Ile
                485                 490                 495

Thr Ser His Thr Gln Ser Leu Asp Gln Gly Gly Glu Asn Leu Tyr Phe
            500                 505                 510

Gln Gly Ala Leu Asn Asp Leu Cys Ile Lys Val Asn Asn Trp Asp Leu
        515                 520                 525

Phe Phe Ser Pro Ser Glu Asp Asn Phe Thr Asn Asp Leu Asn Lys Gly
    530                 535                 540

Glu Glu Ile Thr Ser Asp Thr Asn Ile Glu Ala Ala Glu Glu Asn Ile
545                 550                 555                 560

Ser Leu Asp Leu Ile Gln Gln Tyr Tyr Leu Thr Phe Asn Phe Asp Asn
                565                 570                 575

Glu Pro Glu Asn Ile Ser Ile Glu Asn Leu Ser Ser Asp Ile Ile Gly
            580                 585                 590

Gln Leu Glu Leu Met Pro Asn Ile Glu Arg Phe Pro Asn Gly Lys Lys
        595                 600                 605

Tyr Glu Leu Asp Lys Tyr Thr Met Phe His Tyr Leu Arg Ala Gln Glu
    610                 615                 620

Phe Glu His Gly Lys Ser Arg Ile Ala Leu Thr Asn Ser Val Asn Glu
625                 630                 635                 640

Ala Leu Leu Asn Pro Ser Arg Val Tyr Thr Phe Phe Ser Ser Asp Tyr
                645                 650                 655

Val Lys Lys Val Asn Lys Ala Thr Glu Ala Ala Met Phe Leu Gly Trp
            660                 665                 670

Val Glu Gln Leu Val Tyr Asp Phe Thr Asp Glu Thr Ser Glu Val Ser
        675                 680                 685

Thr Thr Asp Lys Ile Ala Asp Ile Thr Ile Ile Ile Pro Tyr Ile Gly
    690                 695                 700

Pro Ala Leu Asn Ile Gly Asn Met Leu Tyr Lys Asp Asp Phe Val Gly
705                 710                 715                 720

Ala Leu Ile Phe Ser Gly Ala Val Ile Leu Leu Glu Phe Ile Pro Glu
                725                 730                 735

Ile Ala Ile Pro Val Leu Gly Thr Phe Ala Leu Val Ser Tyr Ile Ala
            740                 745                 750

Asn Lys Val Leu Thr Val Gln Thr Ile Asp Asn Ala Leu Ser Lys Arg
        755                 760                 765
```

```
Asn Glu Lys Trp Asp Glu Val Tyr Lys Tyr Ile Val Thr Asn Trp Leu
    770                 775                 780

Ala Lys Val Asn Thr Gln Ile Asp Leu Ile Arg Lys Lys Met Lys Glu
785                 790                 795                 800

Ala Leu Glu Asn Gln Ala Glu Ala Thr Lys Ala Ile Ile Asn Tyr Gln
                805                 810                 815

Tyr Asn Gln Tyr Thr Glu Glu Glu Lys Asn Asn Ile Asn Phe Asn Ile
            820                 825                 830

Asp Asp Leu Ser Ser Lys Leu Asn Glu Ser Ile Asn Lys Ala Met Ile
        835                 840                 845

Asn Ile Asn Lys Phe Leu Asn Gln Cys Ser Val Ser Tyr Leu Met Asn
    850                 855                 860

Ser Met Ile Pro Tyr Gly Val Lys Arg Leu Glu Asp Phe Asp Ala Ser
865                 870                 875                 880

Leu Lys Asp Ala Leu Leu Lys Tyr Ile Tyr Asp Asn Arg Gly Thr Leu
                885                 890                 895

Ile Gly Gln Val Asp Arg Leu Lys Asp Lys Val Asn Asn Thr Leu Ser
            900                 905                 910

Thr Asp Ile Pro Phe Gln Leu Ser Lys Tyr Val Asp Asn Gln Arg Leu
        915                 920                 925

Leu Ser Thr Phe Thr Glu Tyr Ile Asn Asn Ile Ile Asn Thr Ser Ile
    930                 935                 940

Leu Asn Leu Arg Tyr Glu Ser Asn His Leu Ile Asp Leu Ser Arg Tyr
945                 950                 955                 960

Ala Ser Lys Ile Asn Ile Gly Ser Lys Val Asn Phe Asp Pro Ile Asp
                965                 970                 975

Lys Asn Gln Ile Gln Leu Phe Asn Leu Glu Ser Ser Lys Ile Glu Val
            980                 985                 990

Ile Leu Lys Asn Ala Ile Val Tyr  Asn Ser Met Tyr Glu  Asn Phe Ser
        995                 1000                1005

Thr Ser  Phe Trp Ile Arg Ile  Pro Lys Tyr Phe Asn  Ser Ile Ser
    1010                1015                1020

Leu Asn  Asn Glu Tyr Thr Ile  Ile Asn Cys Met Glu  Asn Asn Ser
    1025                1030                1035

Gly Trp  Lys Val Ser Leu Asn  Tyr Gly Glu Ile Ile  Trp Thr Leu
    1040                1045                1050

Gln Asp  Thr Gln Glu Ile Lys  Gln Arg Val Val Phe  Lys Tyr Ser
    1055                1060                1065

Gln Met  Ile Asn Ile Ser Asp  Tyr Ile Asn Arg Trp  Ile Phe Val
    1070                1075                1080

Thr Ile  Thr Asn Asn Arg Leu  Asn Asn Ser Lys Ile  Tyr Ile Asn
    1085                1090                1095

Gly Arg  Leu Ile Asp Gln Lys  Pro Ile Ser Asn Leu  Gly Asn Ile
    1100                1105                1110

His Ala  Ser Asn Asn Ile Met  Phe Lys Leu Asp Gly  Cys Arg Asp
    1115                1120                1125

Thr His  Arg Tyr Ile Trp Ile  Lys Tyr Phe Asn Leu  Phe Asp Lys
    1130                1135                1140

Glu Leu  Asn Glu Lys Glu Ile  Lys Asp Leu Tyr Asp  Asn Gln Ser
    1145                1150                1155

Asn Ser  Gly Ile Leu Lys Asp  Phe Trp Gly Asp Tyr  Leu Gln Tyr
    1160                1165                1170
```

```
Asp Lys  Pro Tyr Tyr Met Leu  Asn Leu Tyr Asp Pro  Asn Lys Tyr
    1175                 1180                 1185

Val Asp  Val Asn Asn Val Gly  Ile Arg Gly Tyr Met  Tyr Leu Lys
    1190                 1195                 1200

Gly Pro  Arg Gly Ser Val Met  Thr Thr Asn Ile Tyr  Leu Asn Ser
    1205                 1210                 1215

Ser Leu  Tyr Arg Gly Thr Lys  Phe Ile Ile Lys Lys  Tyr Ala Ser
    1220                 1225                 1230

Gly Asn  Lys Asp Asn Ile Val  Arg Asn Asn Asp Arg  Val Tyr Ile
    1235                 1240                 1245

Asn Val  Val Val Lys Asn Lys  Glu Tyr Arg Leu Ala  Thr Asn Ala
    1250                 1255                 1260

Ser Gln  Ala Gly Val Glu Lys  Ile Leu Ser Ala Leu  Glu Ile Pro
    1265                 1270                 1275

Asp Val  Gly Asn Leu Ser Gln  Val Val Val Met Lys  Ser Lys Asn
    1280                 1285                 1290

Asp Gln  Gly Ile Thr Asn Lys  Cys Lys Met Asn Leu  Gln Asp Asn
    1295                 1300                 1305

Asn Gly  Asn Asp Ile Gly Phe  Ile Gly Phe His Gln  Phe Asn Asn
    1310                 1315                 1320

Ile Ala  Lys Leu Val Ala Ser  Asn Trp Tyr Asn Arg  Gln Ile Glu
    1325                 1330                 1335

Arg Ser  Ser Arg Thr Leu Gly  Cys Ser Trp Glu Phe  Ile Pro Val
    1340                 1345                 1350

Asp Asp  Gly Trp Gly Glu Arg  Pro Leu Gly Ala Gly  Trp Ser His
    1355                 1360                 1365

Pro Gln  Phe Glu Lys
    1370
```

```
<210> SEQ ID NO 5
<211> LENGTH: 993
<212> TYPE: PRT
<213> ORGANISM: Artificial
<220> FEATURE:
<223> OTHER INFORMATION: Delta LC-Peptide-BoNT/Atev Neurotoxin

<400> SEQUENCE: 5

Met Lys Phe Leu Val Asn Val Ala Leu Val Phe Met Val Val Tyr Ile
1               5                   10                  15

Ser Tyr Ile Tyr Ala Ala Ala His His His His His His His His His
            20                  25                  30

His Thr Arg Glu Asn Leu Tyr Phe Gln Gly Ala Gly Asp Ser Leu Ser
        35                  40                  45

Trp Leu Leu Arg Leu Leu Asn Ala Arg Gly Gly Ala Ser Gly Gly Thr
    50                  55                  60

Asn Gly Asn Gly Asn Gly Gly Asn Leu Arg Asn Thr Asn Leu Ala Ala
65                  70                  75                  80

Asn Phe Asn Gly Gln Asn Thr Glu Ile Asn Asn Met Asn Phe Thr Lys
                85                  90                  95

Leu Lys Asn Phe Thr Gly Leu Phe Glu Phe Tyr Lys Leu Leu Cys Val
            100                 105                 110

Arg Gly Ile Ile Thr Ser His Thr Gln Ser Leu Asp Gln Gly Gly Glu
        115                 120                 125

Asn Leu Tyr Phe Gln Gly Ala Leu Asn Asp Leu Cys Ile Lys Val Asn
    130                 135                 140
```

-continued

Asn Trp Asp Leu Phe Phe Ser Pro Ser Glu Asp Asn Phe Thr Asn Asp
145 150 155 160

Leu Asn Lys Gly Glu Glu Ile Thr Ser Asp Thr Asn Ile Glu Ala Ala
165 170 175

Glu Glu Asn Ile Ser Leu Asp Leu Ile Gln Gln Tyr Tyr Leu Thr Phe
180 185 190

Asn Phe Asp Asn Glu Pro Glu Asn Ile Ser Ile Glu Asn Leu Ser Ser
195 200 205

Asp Ile Ile Gly Gln Leu Glu Leu Met Pro Asn Ile Glu Arg Phe Pro
210 215 220

Asn Gly Lys Lys Tyr Glu Leu Asp Lys Tyr Thr Met Phe His Tyr Leu
225 230 235 240

Arg Ala Gln Glu Phe Glu His Gly Lys Ser Arg Ile Ala Leu Thr Asn
245 250 255

Ser Val Asn Glu Ala Leu Leu Asn Pro Ser Arg Val Tyr Thr Phe Phe
260 265 270

Ser Ser Asp Tyr Val Lys Lys Val Asn Lys Ala Thr Glu Ala Ala Met
275 280 285

Phe Leu Gly Trp Val Glu Gln Leu Val Tyr Asp Phe Thr Asp Glu Thr
290 295 300

Ser Glu Val Ser Thr Thr Asp Lys Ile Ala Asp Ile Thr Ile Ile Ile
305 310 315 320

Pro Tyr Ile Gly Pro Ala Leu Asn Ile Gly Asn Met Leu Tyr Lys Asp
325 330 335

Asp Phe Val Gly Ala Leu Ile Phe Ser Gly Ala Val Ile Leu Leu Glu
340 345 350

Phe Ile Pro Glu Ile Ala Ile Pro Val Leu Gly Thr Phe Ala Leu Val
355 360 365

Ser Tyr Ile Ala Asn Lys Val Leu Thr Val Gln Thr Ile Asp Asn Ala
370 375 380

Leu Ser Lys Arg Asn Glu Lys Trp Asp Glu Val Tyr Lys Tyr Ile Val
385 390 395 400

Thr Asn Trp Leu Ala Lys Val Asn Thr Gln Ile Asp Leu Ile Arg Lys
405 410 415

Lys Met Lys Glu Ala Leu Glu Asn Gln Ala Glu Ala Thr Lys Ala Ile
420 425 430

Ile Asn Tyr Gln Tyr Asn Gln Tyr Thr Glu Glu Glu Lys Asn Asn Ile
435 440 445

Asn Phe Asn Ile Asp Asp Leu Ser Ser Lys Leu Asn Glu Ser Ile Asn
450 455 460

Lys Ala Met Ile Asn Ile Asn Lys Phe Leu Asn Gln Cys Ser Val Ser
465 470 475 480

Tyr Leu Met Asn Ser Met Ile Pro Tyr Gly Val Lys Arg Leu Glu Asp
485 490 495

Phe Asp Ala Ser Leu Lys Asp Ala Leu Leu Lys Tyr Ile Tyr Asp Asn
500 505 510

Arg Gly Thr Leu Ile Gly Gln Val Asp Arg Leu Lys Asp Lys Val Asn
515 520 525

Asn Thr Leu Ser Thr Asp Ile Pro Phe Gln Leu Ser Lys Tyr Val Asp
530 535 540

Asn Gln Arg Leu Leu Ser Thr Phe Thr Glu Tyr Ile Asn Asn Ile Ile
545 550 555 560

Asn Thr Ser Ile Leu Asn Leu Arg Tyr Glu Ser Asn His Leu Ile Asp

```
                565                 570                 575

Leu Ser Arg Tyr Ala Ser Lys Ile Asn Ile Gly Ser Lys Val Asn Phe
            580                 585                 590

Asp Pro Ile Asp Lys Asn Gln Ile Gln Leu Phe Asn Leu Glu Ser Ser
        595                 600                 605

Lys Ile Glu Val Ile Leu Lys Asn Ala Ile Val Tyr Asn Ser Met Tyr
    610                 615                 620

Glu Asn Phe Ser Thr Ser Phe Trp Ile Arg Ile Pro Lys Tyr Phe Asn
625                 630                 635                 640

Ser Ile Ser Leu Asn Asn Glu Tyr Thr Ile Ile Asn Cys Met Glu Asn
                645                 650                 655

Asn Ser Gly Trp Lys Val Ser Leu Asn Tyr Gly Glu Ile Ile Trp Thr
            660                 665                 670

Leu Gln Asp Thr Gln Glu Ile Lys Gln Arg Val Val Phe Lys Tyr Ser
        675                 680                 685

Gln Met Ile Asn Ile Ser Asp Tyr Ile Asn Arg Trp Ile Phe Val Thr
    690                 695                 700

Ile Thr Asn Asn Arg Leu Asn Asn Ser Lys Ile Tyr Ile Asn Gly Arg
705                 710                 715                 720

Leu Ile Asp Gln Lys Pro Ile Ser Asn Leu Gly Asn Ile His Ala Ser
                725                 730                 735

Asn Asn Ile Met Phe Lys Leu Asp Gly Cys Arg Asp Thr His Arg Tyr
            740                 745                 750

Ile Trp Ile Lys Tyr Phe Asn Leu Phe Asp Lys Glu Leu Asn Glu Lys
        755                 760                 765

Glu Ile Lys Asp Leu Tyr Asp Asn Gln Ser Asn Ser Gly Ile Leu Lys
    770                 775                 780

Asp Phe Trp Gly Asp Tyr Leu Gln Tyr Asp Lys Pro Tyr Tyr Met Leu
785                 790                 795                 800

Asn Leu Tyr Asp Pro Asn Lys Tyr Val Asp Val Asn Asn Val Gly Ile
                805                 810                 815

Arg Gly Tyr Met Tyr Leu Lys Gly Pro Arg Gly Ser Val Met Thr Thr
            820                 825                 830

Asn Ile Tyr Leu Asn Ser Ser Leu Tyr Arg Gly Thr Lys Phe Ile Ile
        835                 840                 845

Lys Lys Tyr Ala Ser Gly Asn Lys Asp Asn Ile Val Arg Asn Asn Asp
    850                 855                 860

Arg Val Tyr Ile Asn Val Val Val Lys Asn Lys Glu Tyr Arg Leu Ala
865                 870                 875                 880

Thr Asn Ala Ser Gln Ala Gly Val Glu Lys Ile Leu Ser Ala Leu Glu
                885                 890                 895

Ile Pro Asp Val Gly Asn Leu Ser Gln Val Val Val Met Lys Ser Lys
            900                 905                 910

Asn Asp Gln Gly Ile Thr Asn Lys Cys Lys Met Asn Leu Gln Asp Asn
        915                 920                 925

Asn Gly Asn Asp Ile Gly Phe Ile Gly Phe His Gln Phe Asn Asn Ile
    930                 935                 940

Ala Lys Leu Val Ala Ser Asn Trp Tyr Asn Arg Gln Ile Glu Arg Ser
945                 950                 955                 960

Ser Arg Thr Leu Gly Cys Ser Trp Glu Phe Ile Pro Val Asp Asp Gly
                965                 970                 975

Trp Gly Glu Arg Pro Leu Gly Ala Gly Trp Ser His Pro Gln Phe Glu
            980                 985                 990
```

Lys

<210> SEQ ID NO 6
<211> LENGTH: 1230
<212> TYPE: PRT
<213> ORGANISM: Artificial
<220> FEATURE:
<223> OTHER INFORMATION: Delta LC-GFP-BoNT/Atev Neurotoxin

<400> SEQUENCE: 6

Met Lys Phe Leu Val Asn Val Ala Leu Val Phe Met Val Val Tyr Ile
1 5 10 15

Ser Tyr Ile Tyr Ala Ala Ala His His His His His His His His His
20 25 30

His Thr Arg Glu Asn Leu Tyr Phe Gln Gly Ala Gly Asp Ser Leu Ser
35 40 45

Trp Leu Leu Arg Leu Leu Asn Ala Arg Gly Gly Ala Ser Val Ser Lys
50 55 60

Gly Ala Glu Leu Phe Thr Gly Ile Val Pro Ile Leu Ile Glu Leu Asn
65 70 75 80

Gly Asp Val Asn Gly His Lys Phe Ser Val Ser Gly Glu Gly Glu Gly
85 90 95

Asp Ala Thr Tyr Gly Lys Leu Thr Leu Lys Phe Ile Cys Thr Thr Gly
100 105 110

Lys Leu Pro Val Pro Trp Pro Thr Leu Val Thr Thr Leu Ser Tyr Gly
115 120 125

Val Gln Cys Phe Ser Arg Tyr Pro Asp His Met Lys Gln His Asp Phe
130 135 140

Phe Lys Ser Ala Met Pro Glu Gly Tyr Ile Gln Glu Arg Thr Ile Phe
145 150 155 160

Phe Glu Asp Asp Gly Asn Tyr Lys Ser Arg Ala Glu Val Lys Phe Glu
165 170 175

Gly Asp Thr Leu Val Asn Arg Ile Glu Leu Thr Gly Thr Asp Phe Lys
180 185 190

Glu Asp Gly Asn Ile Leu Gly Asn Lys Met Glu Tyr Asn Tyr Asn Ala
195 200 205

His Asn Val Tyr Ile Met Thr Asp Lys Ala Lys Asn Gly Ile Lys Val
210 215 220

Asn Phe Lys Ile Arg His Asn Ile Glu Asp Gly Ser Val Gln Leu Ala
225 230 235 240

Asp His Tyr Gln Gln Asn Thr Pro Ile Gly Asp Gly Pro Val Leu Leu
245 250 255

Pro Asp Asn His Tyr Leu Ser Thr Gln Ser Ala Leu Ser Lys Asp Pro
260 265 270

Asn Glu Lys Arg Asp His Met Ile Tyr Phe Gly Phe Val Thr Ala Ala
275 280 285

Ala Ile Thr His Gly Met Asp Glu Leu Tyr Lys Gly Thr Asn Gly Asn
290 295 300

Gly Asn Gly Gly Asn Leu Arg Asn Thr Asn Leu Ala Ala Asn Phe Asn
305 310 315 320

Gly Gln Asn Thr Glu Ile Asn Asn Met Asn Phe Thr Lys Leu Lys Asn
325 330 335

Phe Thr Gly Leu Phe Glu Phe Tyr Lys Leu Leu Cys Val Arg Gly Ile
340 345 350

-continued

```
Ile Thr Ser His Thr Gln Ser Leu Asp Gln Gly Gly Glu Asn Leu Tyr
        355                 360                 365

Phe Gln Gly Ala Leu Asn Asp Leu Cys Ile Lys Val Asn Asn Trp Asp
    370                 375                 380

Leu Phe Phe Ser Pro Ser Glu Asp Asn Phe Thr Asn Asp Leu Asn Lys
385                 390                 395                 400

Gly Glu Glu Ile Thr Ser Asp Thr Asn Ile Glu Ala Ala Glu Glu Asn
                405                 410                 415

Ile Ser Leu Asp Leu Ile Gln Gln Tyr Tyr Leu Thr Phe Asn Phe Asp
            420                 425                 430

Asn Glu Pro Glu Asn Ile Ser Ile Glu Asn Leu Ser Ser Asp Ile Ile
        435                 440                 445

Gly Gln Leu Glu Leu Met Pro Asn Ile Glu Arg Phe Pro Asn Gly Lys
    450                 455                 460

Lys Tyr Glu Leu Asp Lys Tyr Thr Met Phe His Tyr Leu Arg Ala Gln
465                 470                 475                 480

Glu Phe Glu His Gly Lys Ser Arg Ile Ala Leu Thr Asn Ser Val Asn
                485                 490                 495

Glu Ala Leu Leu Asn Pro Ser Arg Val Tyr Thr Phe Phe Ser Ser Asp
            500                 505                 510

Tyr Val Lys Lys Val Asn Lys Ala Thr Glu Ala Ala Met Phe Leu Gly
        515                 520                 525

Trp Val Glu Gln Leu Val Tyr Asp Phe Thr Asp Glu Thr Ser Glu Val
    530                 535                 540

Ser Thr Thr Asp Lys Ile Ala Asp Ile Thr Ile Ile Ile Pro Tyr Ile
545                 550                 555                 560

Gly Pro Ala Leu Asn Ile Gly Asn Met Leu Tyr Lys Asp Asp Phe Val
                565                 570                 575

Gly Ala Leu Ile Phe Ser Gly Ala Val Ile Leu Leu Glu Phe Ile Pro
            580                 585                 590

Glu Ile Ala Ile Pro Val Leu Gly Thr Phe Ala Leu Val Ser Tyr Ile
        595                 600                 605

Ala Asn Lys Val Leu Thr Val Gln Thr Ile Asp Asn Ala Leu Ser Lys
    610                 615                 620

Arg Asn Glu Lys Trp Asp Glu Val Tyr Lys Tyr Ile Val Thr Asn Trp
625                 630                 635                 640

Leu Ala Lys Val Asn Thr Gln Ile Asp Leu Ile Arg Lys Lys Met Lys
                645                 650                 655

Glu Ala Leu Glu Asn Gln Ala Glu Ala Thr Lys Ala Ile Ile Asn Tyr
            660                 665                 670

Gln Tyr Asn Gln Tyr Thr Glu Glu Glu Lys Asn Asn Ile Asn Phe Asn
        675                 680                 685

Ile Asp Asp Leu Ser Ser Lys Leu Asn Glu Ser Ile Asn Lys Ala Met
    690                 695                 700

Ile Asn Ile Asn Lys Phe Leu Asn Gln Cys Ser Val Ser Tyr Leu Met
705                 710                 715                 720

Asn Ser Met Ile Pro Tyr Gly Val Lys Arg Leu Glu Asp Phe Asp Ala
                725                 730                 735

Ser Leu Lys Asp Ala Leu Leu Lys Tyr Ile Tyr Asp Asn Arg Gly Thr
            740                 745                 750

Leu Ile Gly Gln Val Asp Arg Leu Lys Asp Lys Val Asn Asn Thr Leu
        755                 760                 765

Ser Thr Asp Ile Pro Phe Gln Leu Ser Lys Tyr Val Asp Asn Gln Arg
```

-continued

```
    770                 775                 780

Leu Leu Ser Thr Phe Thr Glu Tyr Ile Asn Asn Ile Ile Asn Thr Ser
785                 790                 795                 800

Ile Leu Asn Leu Arg Tyr Glu Ser Asn His Leu Ile Asp Leu Ser Arg
                805                 810                 815

Tyr Ala Ser Lys Ile Asn Ile Gly Ser Lys Val Asn Phe Asp Pro Ile
            820                 825                 830

Asp Lys Asn Gln Ile Gln Leu Phe Asn Leu Glu Ser Ser Lys Ile Glu
        835                 840                 845

Val Ile Leu Lys Asn Ala Ile Val Tyr Asn Ser Met Tyr Glu Asn Phe
    850                 855                 860

Ser Thr Ser Phe Trp Ile Arg Ile Pro Lys Tyr Phe Asn Ser Ile Ser
865                 870                 875                 880

Leu Asn Asn Glu Tyr Thr Ile Ile Asn Cys Met Glu Asn Asn Ser Gly
                885                 890                 895

Trp Lys Val Ser Leu Asn Tyr Gly Glu Ile Ile Trp Thr Leu Gln Asp
            900                 905                 910

Thr Gln Glu Ile Lys Gln Arg Val Val Phe Lys Tyr Ser Gln Met Ile
        915                 920                 925

Asn Ile Ser Asp Tyr Ile Asn Arg Trp Ile Phe Val Thr Ile Thr Asn
    930                 935                 940

Asn Arg Leu Asn Asn Ser Lys Ile Tyr Ile Asn Gly Arg Leu Ile Asp
945                 950                 955                 960

Gln Lys Pro Ile Ser Asn Leu Gly Asn Ile His Ala Ser Asn Asn Ile
                965                 970                 975

Met Phe Lys Leu Asp Gly Cys Arg Asp Thr His Arg Tyr Ile Trp Ile
            980                 985                 990

Lys Tyr Phe Asn Leu Phe Asp Lys  Glu Leu Asn Glu Lys  Glu Ile Lys
        995                 1000                1005

Asp Leu  Tyr Asp Asn Gln Ser  Asn Ser Gly Ile Leu  Lys Asp Phe
    1010                1015                1020

Trp Gly  Asp Tyr Leu Gln Tyr  Asp Lys Pro Tyr Tyr  Met Leu Asn
    1025                1030                1035

Leu Tyr  Asp Pro Asn Lys Tyr  Val Asp Val Asn Asn  Val Gly Ile
    1040                1045                1050

Arg Gly  Tyr Met Tyr Leu Lys  Gly Pro Arg Gly Ser  Val Met Thr
    1055                1060                1065

Thr Asn  Ile Tyr Leu Asn Ser  Ser Leu Tyr Arg Gly  Thr Lys Phe
    1070                1075                1080

Ile Ile  Lys Lys Tyr Ala Ser  Gly Asn Lys Asp Asn  Ile Val Arg
    1085                1090                1095

Asn Asn  Asp Arg Val Tyr Ile  Asn Val Val Val Lys  Asn Lys Glu
    1100                1105                1110

Tyr Arg  Leu Ala Thr Asn Ala  Ser Gln Ala Gly Val  Glu Lys Ile
    1115                1120                1125

Leu Ser  Ala Leu Glu Ile Pro  Asp Val Gly Asn Leu  Ser Gln Val
    1130                1135                1140

Val Val  Met Lys Ser Lys Asn  Asp Gln Gly Ile Thr  Asn Lys Cys
    1145                1150                1155

Lys Met  Asn Leu Gln Asp Asn  Asn Gly Asn Asp Ile  Gly Phe Ile
    1160                1165                1170

Gly Phe  His Gln Phe Asn Asn  Ile Ala Lys Leu Val  Ala Ser Asn
    1175                1180                1185
```

-continued

```
Trp Tyr  Asn Arg Gln Ile Glu  Arg Ser Ser Arg Thr  Leu Gly Cys
    1190                 1195                 1200

Ser Trp  Glu Phe Ile Pro Val  Asp Asp Gly Trp Gly  Glu Arg Pro
    1205                 1210                 1215

Leu Gly  Ala Gly Trp Ser His  Pro Gln Phe Glu Lys
    1220                 1225                 1230


<210> SEQ ID NO 7
<211> LENGTH: 1296
<212> TYPE: PRT
<213> ORGANISM: Clostridium Botulinum

<400> SEQUENCE: 7

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
```

-continued

```
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750
```

Gln Tyr Thr Glu Glu Glu Lys Asn Asn Ile Asn Phe Asn Ile Asp Asp
755 760 765

Leu Ser Ser Lys Leu Asn Glu Ser Ile Asn Lys Ala Met Ile Asn Ile
770 775 780

Asn Lys Phe Leu Asn Gln Cys Ser Val Ser Tyr Leu Met Asn Ser Met
785 790 795 800

Ile Pro Tyr Gly Val Lys Arg Leu Glu Asp Phe Asp Ala Ser Leu Lys
805 810 815

Asp Ala Leu Leu Lys Tyr Ile Tyr Asp Asn Arg Gly Thr Leu Ile Gly
820 825 830

Gln Val Asp Arg Leu Lys Asp Lys Val Asn Asn Thr Leu Ser Thr Asp
835 840 845

Ile Pro Phe Gln Leu Ser Lys Tyr Val Asp Asn Gln Arg Leu Leu Ser
850 855 860

Thr Phe Thr Glu Tyr Ile Lys Asn Ile Ile Asn Thr Ser Ile Leu Asn
865 870 875 880

Leu Arg Tyr Glu Ser Asn His Leu Ile Asp Leu Ser Arg Tyr Ala Ser
885 890 895

Lys Ile Asn Ile Gly Ser Lys Val Asn Phe Asp Pro Ile Asp Lys Asn
900 905 910

Gln Ile Gln Leu Phe Asn Leu Glu Ser Ser Lys Ile Glu Val Ile Leu
915 920 925

Lys Asn Ala Ile Val Tyr Asn Ser Met Tyr Glu Asn Phe Ser Thr Ser
930 935 940

Phe Trp Ile Arg Ile Pro Lys Tyr Phe Asn Ser Ile Ser Leu Asn Asn
945 950 955 960

Glu Tyr Thr Ile Ile Asn Cys Met Glu Asn Asn Ser Gly Trp Lys Val
965 970 975

Ser Leu Asn Tyr Gly Glu Ile Ile Trp Thr Leu Gln Asp Thr Gln Glu
980 985 990

Ile Lys Gln Arg Val Val Phe Lys Tyr Ser Gln Met Ile Asn Ile Ser
995 1000 1005

Asp Tyr Ile Asn Arg Trp Ile Phe Val Thr Ile Thr Asn Asn Arg
1010 1015 1020

Leu Asn Asn Ser Lys Ile Tyr Ile Asn Gly Arg Leu Ile Asp Gln
1025 1030 1035

Lys Pro Ile Ser Asn Leu Gly Asn Ile His Ala Ser Asn Asn Ile
1040 1045 1050

Met Phe Lys Leu Asp Gly Cys Arg Asp Thr His Arg Tyr Ile Trp
1055 1060 1065

Ile Lys Tyr Phe Asn Leu Phe Asp Lys Glu Leu Asn Glu Lys Glu
1070 1075 1080

Ile Lys Asp Leu Tyr Asp Asn Gln Ser Asn Ser Gly Ile Leu Lys
1085 1090 1095

Asp Phe Trp Gly Asp Tyr Leu Gln Tyr Asp Lys Pro Tyr Tyr Met
1100 1105 1110

Leu Asn Leu Tyr Asp Pro Asn Lys Tyr Val Asp Val Asn Asn Val
1115 1120 1125

Gly Ile Arg Gly Tyr Met Tyr Leu Lys Gly Pro Arg Gly Ser Val
1130 1135 1140

Met Thr Thr Asn Ile Tyr Leu Asn Ser Ser Leu Tyr Arg Gly Thr
1145 1150 1155

```
Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Gln Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295


<210> SEQ ID NO 8
<211> LENGTH: 5
<212> TYPE: PRT
<213> ORGANISM: Artificial
<220> FEATURE:
<223> OTHER INFORMATION: Enterokinase cleavage site

<400> SEQUENCE: 8

Asp Asp Asp Asp Lys
1               5


<210> SEQ ID NO 9
<211> LENGTH: 7
<212> TYPE: PRT
<213> ORGANISM: Artificial
<220> FEATURE:
<223> OTHER INFORMATION: Spacer or linker sequence

<400> SEQUENCE: 9

Ala Arg Gly Gly Ala Ser Gly
1               5


<210> SEQ ID NO 10
<211> LENGTH: 8971
<212> TYPE: DNA
<213> ORGANISM: Artificial
<220> FEATURE:
<223> OTHER INFORMATION: BoNT/Aadtev vector pFB1SB3ATEV

<400> SEQUENCE: 10

gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420
```

-continued

```
aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440

cattggtaac tgtcagacca agtttactca tatatacttt agattgattt aaaacttcat   1500

ttttaattta aaaggatcta ggtgaagatc ctttttgata atctcatgac caaaatccct   1560

taacgtgagt tttcgttcca ctgagcgtca gaccccgtag aaaagatcaa aggatcttct   1620

tgagatcctt tttttctgcg cgtaatctgc tgcttgcaaa caaaaaaacc accgctacca   1680

gcggtggttt gtttgccgga tcaagagcta ccaactcttt ttccgaaggt aactggcttc   1740

agcagagcgc agataccaaa tactgtcctt ctagtgtagc cgtagttagg ccaccacttc   1800

aagaactctg tagcaccgcc tacatacctc gctctgctaa tcctgttacc agtggctgct   1860

gccagtggcg ataagtcgtg tcttaccggg ttggactcaa gacgatagtt accggataag   1920

gcgcagcggt cgggctgaac ggggggttcg tgcacacagc ccagcttgga gcgaacgacc   1980

tacaccgaac tgagatacct acagcgtgag cattgagaaa gcgccacgct tcccgaaggg   2040

agaaaggcgg acaggtatcc ggtaagcggc agggtcggaa caggagagcg cacgagggag   2100

cttccagggg gaaacgcctg gtatctttat agtcctgtcg ggtttcgcca cctctgactt   2160

gagcgtcgat ttttgtgatg ctcgtcaggg gggcggagcc tatggaaaaa cgccagcaac   2220

gcggcctttt tacggttcct ggccttttgc tggccttttg ctcacatgtt ctttcctgcg   2280

ttatcccctg attctgtgga taaccgtatt accgcctttg agtgagctga taccgctcgc   2340

cgcagccgaa cgaccgagcg cagcgagtca gtgagcgagg aagcggaaga gcgcctgatg   2400

cggtattttc tccttacgca tctgtgcggt atttcacacc gcagaccagc cgcgtaacct   2460

ggcaaaatcg gttacggttg agtaataaat ggatgccctg cgtaagcggg tgtgggcgga   2520

caataaagtc ttaaactgaa caaaatagat ctaaactatg acaataaagt cttaaactag   2580

acagaatagt tgtaaactga aatcagtcca gttatgctgt gaaaaagcat actggacttt   2640

tgttatggct aaagcaaact cttcattttc tgaagtgcaa attgcccgtc gtattaaaga   2700

ggggcgtggc caagggcatg gtaaagacta tattcgcggc gttgtgacaa tttaccgaac   2760
```

-continued

```
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcccgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccgctca tcaccaccat catcaccatc accaccacac gcgtgaaaac   4200
ctgtattttc agggcgccgg tgactccctg tcttggctgc tccgtctgct caacgcgcgc   4260
ggtggagcta gcggcccgtt cgttaacaaa caatttaact acaaggatcc tgtcaatggt   4320
gtggacattg cctatattaa gatcccgaat gcgggtcaga tgcaacccgt gaaagcattc   4380
aagatccaca acaaaatctg ggtcatccct gaacgtgaca ctttcacaaa ccctgaagag   4440
ggcgacctca accctccccc agaagccaaa caggttccgg tgtcttacta cgatagcacg   4500
tacttgtcca ccgataacga gaaggacaac tacctgaagg gagtgaccaa gttgtttgag   4560
aggatctact ctaccgatct cggacgtatg ctgctcacga gcattgtgcg cggtatccca   4620
ttctggggcg gttcaaccat tgatacagaa ctgaaagtca ttgacactaa ttgtatcaac   4680
gttattcaac cagatggcag ctaccgttcc gaggaattga acttggtcat cattggtcca   4740
tccgcagaca tcattcagtt tgaatgcaaa tccttcggtc acgaagtgct caacctgacg   4800
cgcaacggtt acggctccac ccagtacatc cgtttcagcc ctgatttcac atttggcttc   4860
gaggaaagcc tggaggttga caccaacccg ctcctgggtg ctggcaagtt tgcaaccgat   4920
cccgcggtga ctctcgctca tgctctgatc cacgccggac accgcctcta tggcatcgct   4980
atcaatccga accgcgtgtt caaagtgaat acgaacgcct actatgagat gagcggtctg   5040
gaggtttcct ttgaggaact gagaaccttc ggcggtcacg atgccaagtt catcgacagc   5100
ttgcaggaaa atgagtttcg cctgtactat tacaacaagt ttaaagacat cgcttccaca   5160
```

ttgaacaaag ccaagtcaat cgtgggtacg acagcttcat tgcagtatat gaagaatgtt 5220
ttcaaggaga aatacttgct gtcagaggat acctctggca agttctctgt ggacaaactg 5280
aaattcgaca aactgtacaa gatgctgacc gagatttata cggaagataa ctttgtgaaa 5340
ttcttcaaag tcctcaacag gaaaactgct ctgaactttg acaaggctgt gttcaagatc 5400
aacatcgtcc ccaaagttaa ctacacaatc tatgatggat tcaatctgag aaacaccaac 5460
ttggccgcca acttcaacgg ccaaaatacc gaaattaata acatgaattt caccaaactg 5520
aagaacttta ctggactgtt cgagttctac aagctgctct gcgtgcgtgg catcatcacc 5580
tcacatactc agtctctaga ccagggtggc gagaacctgt acttccaggg tgctctgaac 5640
gatctgtgta tcaaggtgaa taactgggat ctgttcttta gcccaagcga ggataacttc 5700
acgaacgatc tcaacaaagg tgaagagatc acgtctgata ccaatatcga agcggctgaa 5760
gagaatatct ccttggatct catccagcaa tattacctga cctttaactt cgataacgag 5820
cccgaaaaca tctccatcga gaacctcagc tcagacatca ttggtcagtt ggagctgatg 5880
ccaaacattg aacgcttccc caacggcaag aaatacgaac tcgacaagta tacgatgttt 5940
cattacttaa gagcgcagga gtttgaacac ggcaagagcc gcattgctct cactaactcc 6000
gtgaatgaag ccctgctcaa tccgtcaagg gtgtacacat tctttagctc cgactatgtc 6060
aagaaagtga acaaagccac cgaagcggca atgttcctgg gatgggttga acaactggtc 6120
tacgacttca ccgacgagac ctctgaggtg agcacaacgg acaagattgc tgacatcact 6180
atcattatcc cgtatattgg acctgccttg aatattggca acatgctcta caaagacgat 6240
ttcgttggtg ccctgatctt cagcggtgcc gtgatcctgt tggagttcat tcctgaaatc 6300
gccatccctg tgctgggcac gttcgctctg gtctcataca ttgcgaataa ggtcttgacc 6360
gtgcagacaa tcgataatgc cctctccaaa cgtaacgaaa aatgggacga ggtctacaaa 6420
tacatcgtga ccaactggct ggcaaaggtt aacacccaaa ttgatctgat ccgtaagaaa 6480
atgaaggagg ctttggagaa ccaggctgaa gctactaaag ccattatcaa ctaccagtat 6540
aatcagtata cagaagagga aaagaataac atcaatttca acatcgatga cttgtcctca 6600
aagctgaacg agtccatcaa caaagctatg atcaacatca acaaattcct gaatcagtgc 6660
tccgtgtctt acctgatgaa ctctatgatc ccatacggtg tgaagcgcct ggaggacttc 6720
gatgccagcc tgaaagacgc actgctcaaa tacatttacg ataatcgcgg cactttgatt 6780
ggccaagttg accgtctgaa ggacaaggtt aacaatacct tgtcaaccga tatccccttt 6840
caactgtcca aatacgttga taaccagcgc ttgctctcta ctttcaccga atacattaac 6900
aacattatca atacatcaat tctcaacctg cgctatgagt ccaatcatct gatcgatctg 6960
tctcgttacg ccagcaagat caacattggc agcaaagtga acttcgatcc gattgacaag 7020
aaccaaatcc agttgttcaa cctcgaaagc tccaaaatcg aagtgatcct gaagaatgcc 7080
atcgtctaca actccatgta tgaaaatttc tcaacttcat tctggattag aatcccgaaa 7140
tacttcaact caatctctct gaataacgaa tacacgatca ttaactgtat ggagaataac 7200
tctggttgga aggtttcctt gaactatgga gaaattatct ggactctgca agatacgcaa 7260
gagatcaaac agcgtgtggt ctttaaatac agccagatga ttaacatctc tgactacatc 7320
aacagatgga tctttgtcac cattacaaac aatcgcctga ataactccaa aatctacatc 7380
aacggtcgtc tgatcgacca gaaacctatt tcaaacctcg gcaacattca tgcttccaat 7440
aacatcatgt ttaagttgga tggttgccgc gatacccacc gttacatctg gatcaagtat 7500

-continued

```
ttcaatctgt tcgacaaaga actcaatgag aaagagatca aagacttgta tgataatcag   7560
tcaaactccg gcattctgaa agacttctgg ggcgattacc tccagtacga taagccatat   7620
tacatgctga atctctatga ccctaacaaa tatgtggacg tgaacaatgt cggtatccgt   7680
ggctacatgt acctcaaagg accacgtggt agcgttatga caaccaacat ctacctgaat   7740
agctccttgt atcgcggtac gaagttcatt atcaagaagt acgcttcagg caacaaggac   7800
aacatcgtga ggaacaatga tcgcgtgtac atcaacgtcg tggtgaagaa taaggaatac   7860
cgcttggcga ccaacgcttc tcaggctgga gttgagaaga tcctgagcgc cttggagatc   7920
ccagacgttg gcaacctgag ccaagtggtt gtgatgaaaa gcaagaatga ccagggaatc   7980
accaacaaat gcaaaatgaa cctgcaagac aacaacggca atgacatcgg tttcatcggt   8040
ttccaccagt ttaacaatat tgcgaagctg gtcgccagca actggtacaa caggcagatt   8100
gagaggtcat cccgtacctt aggatgctct tgggaattta tccccgtgga cgatggttgg   8160
ggcgagagac ccctgggcgc aggttggtcc caccctcagt tcgagaagta atagttaata   8220
gataataata gctcgaggca tgcgagctcc ctcaggaggc ctacgtcgac gagctcacta   8280
gtcgcggccg ctttcgaatc tagagcctgc agtctcgagg catgcggtac caagcttgtc   8340
gagaagtact agaggatcat aatcagccat accacatttg tagaggtttt acttgcttta   8400
aaaaacctcc cacacctccc cctgaacctg aaacataaaa tgaatgcaat tgttgttgtt   8460
aacttgttta ttgcagctta taatggttac aaataaagca atagcatcac aaatttcaca   8520
aataaagcat ttttttcact gcattctagt tgtggtttgt ccaaactcat caatgtatct   8580
tatcatgtct ggatctgatc actgcttgag cctaggagat ccgaaccaga taagtgaaat   8640
ctagttccaa actattttgt catttttaat tttcgtatta gcttacgacg ctacacccag   8700
ttcccatcta ttttgtcact cttccctaaa taatccttaa aaactccatt tccacccctc   8760
ccagttccca actattttgt ccgcccacag cggggcattt ttcttcctgt tatgttttta   8820
atcaaacatc ctgccaactc catgtgacaa accgtcatct tcggctactt tttctctgtc   8880
acagaatgaa aatttttctg tcatctcttc gttattaatg tttgtaattg actgaatatc   8940
aacgcttatt tgcagcctga atggcgaatg g                                  8971
```

<210> SEQ ID NO 11
<211> LENGTH: 7831
<212> TYPE: DNA
<213> ORGANISM: Artificial
<220> FEATURE:
<223> OTHER INFORMATION: Delta LC-Peptide-BoNT/Atev Vector pFB1SPepB2ATEV

<400> SEQUENCE: 11

```
gacgcgccct gtagcggcgc attaagcgcg gcgggtgtgg tggttacgcg cagcgtgacc     60
gctacacttg ccagcgccct agcgcccgct cctttcgctt tcttcccttc ctttctcgcc    120
acgttcgccg gctttccccg tcaagctcta aatcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
```

-continued

```
agacaataac cctgataaat gcttcaataa tattgaaaaa ggaagagtat gagtattcaa    600
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
```

-continued

```
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcccgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccgctca tcaccaccat catcaccatc accaccacac gcgtgaaaac   4200
ctgtattttc agggcgccgg tgactccctg tcttggctgc tccgtctgct caacgcgcgc   4260
ggtggagcta gcggcggtac caatggcaac ggtaacggtg gtaatctgag aaacaccaac   4320
ttggccgcca acttcaacgg ccaaaatacc gaaattaata acatgaattt caccaaactg   4380
aagaacttta ctggactgtt cgagttctac aagctgctct gcgtgcgtgg catcatcacc   4440
tcacatactc agtctctaga ccagggtggc gagaacctgt acttccaggg tgctctgaac   4500
gatctgtgta tcaaggtgaa taactgggat ctgttcttta gcccaagcga ggataacttc   4560
acgaacgatc tcaacaaagg tgaagagatc acgtctgata ccaatatcga agcggctgaa   4620
gagaatatct ccttggatct catccagcaa tattacctga cctttaactt cgataacgag   4680
cccgaaaaca tctccatcga gaacctcagc tcagacatca ttggtcagtt ggagctgatg   4740
ccaaacattg aacgcttccc caacggcaag aaatacgaac tcgacaagta tacgatgttt   4800
cattacttaa gagcgcagga gtttgaacac ggcaagagcc gcattgctct cactaactcc   4860
gtgaatgaag ccctgctcaa tccgtcaagg gtgtacacat tctttagctc cgactatgtc   4920
aagaaagtga acaaagccac cgaagcggca atgttcctgg gatgggttga acaactggtc   4980
tacgacttca ccgacgagac ctctgaggtg agcacaacgg acaagattgc tgacatcact   5040
atcattatcc cgtatattgg acctgccttg aatattggca acatgctcta caaagacgat   5100
ttcgttggtg ccctgatctt cagcggtgcc gtgatcctgt tggagttcat tcctgaaatc   5160
gccatccctg tgctgggcac gttcgctctg gtctcataca ttgcgaataa ggtcttgacc   5220
gtgcagacaa tcgataatgc cctctccaaa cgtaacgaaa aatgggacga ggtctacaaa   5280
```

-continued

```
tacatcgtga ccaactggct ggcaaaggtt aacacccaaa ttgatctgat ccgtaagaaa   5340
atgaaggagg ctttggagaa ccaggctgaa gctactaaag ccattatcaa ctaccagtat   5400
aatcagtata cagaagagga aaagaataac atcaatttca acatcgatga cttgtcctca   5460
aagctgaacg agtccatcaa caaagctatg atcaacatca acaaattcct gaatcagtgc   5520
tccgtgtctt acctgatgaa ctctatgatc ccatacggtg tgaagcgcct ggaggacttc   5580
gatgccagcc tgaaagacgc actgctcaaa tacatttacg ataatcgcgg cactttgatt   5640
ggccaagttg accgtctgaa ggacaaggtt aacaatacct tgtcaaccga tatccccttt   5700
caactgtcca aatacgttga taaccagcgc ttgctctcta ctttcaccga atacattaac   5760
aacattatca atacatcaat tctcaacctg cgctatgagt ccaatcatct gatcgatctg   5820
tctcgttacg ccagcaagat caacattggc agcaaagtga acttcgatcc gattgacaag   5880
aaccaaatcc agttgttcaa cctcgaaagc tccaaaatcg aagtgatcct gaagaatgcc   5940
atcgtctaca actccatgta tgaaaatttc tcaacttcat tctggattag aatcccgaaa   6000
tacttcaact caatctctct gaataacgaa tacacgatca ttaactgtat ggagaataac   6060
tctggttgga aggtttcctt gaactatgga gaaattatct ggactctgca agatacgcaa   6120
gagatcaaac agcgtgtggt ctttaaatac agccagatga ttaacatctc tgactacatc   6180
aacagatgga tctttgtcac cattacaaac aatcgcctga ataactccaa aatctacatc   6240
aacggtcgtc tgatcgacca gaaacctatt tcaaacctcg gcaacattca tgcttccaat   6300
aacatcatgt ttaagttgga tggttgccgc gatacccacc gttacatctg gatcaagtat   6360
ttcaatctgt tcgacaaaga actcaatgag aaagagatca aagacttgta tgataatcag   6420
tcaaactccg gcattctgaa agacttctgg ggcgattacc tccagtacga taagccatat   6480
tacatgctga atctctatga ccctaacaaa tatgtggacg tgaacaatgt cggtatccgt   6540
ggctacatgt acctcaaagg accacgtggt agcgttatga caaccaacat ctacctgaat   6600
agctccttgt atcgcggtac gaagttcatt atcaagaagt acgcttcagg caacaaggac   6660
aacatcgtga ggaacaatga tcgcgtgtac atcaacgtcg tggtgaagaa taaggaatac   6720
cgcttggcga ccaacgcttc tcaggctgga gttgagaaga tcctgagcgc cttggagatc   6780
ccagacgttg gcaacctgag ccaagtggtt gtgatgaaaa gcaagaatga ccagggaatc   6840
accaacaaat gcaaaatgaa cctgcaagac aacaacggca atgacatcgg tttcatcggt   6900
ttccaccagt ttaacaatat tgcgaagctg gtcgccagca actggtacaa caggcagatt   6960
gagaggtcat cccgtacctt aggatgctct tgggaattta tccccgtgga cgatggttgg   7020
ggcgagagac ccctgggcgc aggttggtcc caccctcagt tcgagaagta atagttaata   7080
gataataata gctcgaggca tgcgagctcc ctcaggaggc ctacgtcgac gagctcacta   7140
gtcgcggccg ctttcgaatc tagagcctgc agtctcgagg catgcggtac caagcttgtc   7200
gagaagtact agaggatcat aatcagccat accacatttg tagaggtttt acttgcttta   7260
aaaaacctcc cacacctccc cctgaacctg aaacataaaa tgaatgcaat tgttgttgtt   7320
aacttgttta ttgcagctta taatggttac aaataaagca atagcatcac aaatttcaca   7380
aataaagcat ttttttcact gcattctagt tgtggtttgt ccaaactcat caatgtatct   7440
tatcatgtct ggatctgatc actgcttgag cctaggagat ccgaaccaga taagtgaaat   7500
ctagttccaa actattttgt catttttaat tttcgtatta gcttacgacg ctacacccag   7560
ttcccatcta ttttgtcact cttccctaaa taatccttaa aaactccatt tccacccctc   7620
ccagttccca actattttgt ccgcccacag cggggcattt ttcttcctgt tatgttttta   7680
```

```
atcaaacatc ctgccaactc catgtgacaa accgtcatct tcggctactt tttctctgtc   7740

acagaatgaa aatttttctg tcatctcttc gttattaatg tttgtaattg actgaatatc   7800

aacgcttatt tgcagcctga atggcgaatg g                                  7831
```

<210> SEQ ID NO 12
<211> LENGTH: 8542
<212> TYPE: DNA
<213> ORGANISM: Artificial
<220> FEATURE:
<223> OTHER INFORMATION: Delta LC-GFP-BoNT/Atev Vector pFB1SGFPB2ATEV

<400> SEQUENCE: 12

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440

cattggtaac tgtcagacca agtttactca tatatacttt agattgattt aaaacttcat   1500

ttttaattta aaaggatcta ggtgaagatc ctttttgata atctcatgac caaaatccct   1560

taacgtgagt tttcgttcca ctgagcgtca gaccccgtag aaaagatcaa aggatcttct   1620

tgagatcctt tttttctgcg cgtaatctgc tgcttgcaaa caaaaaaacc accgctacca   1680

gcggtggttt gtttgccgga tcaagagcta ccaactcttt ttccgaaggt aactggcttc   1740

agcagagcgc agataccaaa tactgtcctt ctagtgtagc cgtagttagg ccaccacttc   1800

aagaactctg tagcaccgcc tacatacctc gctctgctaa tcctgttacc agtggctgct   1860
```

-continued

```
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcccgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccgctca tcaccaccat catcaccatc accaccacac gcgtgaaaac   4200
ctgtattttc agggcgccgg tgactccctg tcttggctgc tccgtctgct caacgcgcgc   4260
```

```
ggtggagcta gcgtgagcaa gggcgccgag ctgttcaccg gcatcgtgcc catcctgatc   4320
gagctgaatg gcgatgtgaa tggccacaag ttcagcgtga gcggcgaggg cgagggcgat   4380
gccacctacg gcaagctgac cctgaagttc atctgcacca ccggcaagct gcctgtgccc   4440
tggcccaccc tggtgaccac cctgagctac ggcgtgcagt gcttctcacg ctaccccgat   4500
cacatgaagc agcacgactt cttcaagagc gccatgcctg agggctacat ccaggagcgc   4560
accatcttct tcgaggatga cggcaactac aagtcgcgcg ccgaggtgaa gttcgagggc   4620
gataccctgg tgaatcgcat cgagctgacc ggcaccgatt tcaaggagga tggcaacatc   4680
ctgggcaata agatggagta caactacaac gcccacaatg tgtacatcat gaccgacaag   4740
gccaagaatg gcatcaaggt gaacttcaag atccgccaca acatcgagga tggcagcgtg   4800
cagctggccg accactacca gcagaatacc cccatcggcg atggccctgt gctgctgccc   4860
gataaccact acctgtccac ccagagcgcc ctgtccaagg accccaacga gaagcgcgat   4920
cacatgatct acttcggctt cgtgaccgcc gccgccatca cccacggcat ggatgagctg   4980
tacaagggta ccaatggcaa cggtaacggt ggtaatctga gaaacaccaa cttggccgcc   5040
aacttcaacg gccaaaatac cgaaattaat aacatgaatt tcaccaaact gaagaacttt   5100
actggactgt tcgagttcta caagctgctc tgcgtgcgtg gcatcatcac ctcacatact   5160
cagtctctag accagggtgg cgagaacctg tacttccagg gtgctctgaa cgatctgtgt   5220
atcaaggtga ataactggga tctgttcttt agcccaagcg aggataactt cacgaacgat   5280
ctcaacaaag gtgaagagat cacgtctgat accaatatcg aagcggctga agagaatatc   5340
tccttggatc tcatccagca atattacctg acctttaact tcgataacga gcccgaaaac   5400
atctccatcg agaacctcag ctcagacatc attggtcagt tggagctgat gccaaacatt   5460
gaacgcttcc ccaacggcaa gaaatacgaa ctcgacaagt atacgatgtt tcattactta   5520
agagcgcagg agtttgaaca cggcaagagc cgcattgctc tcactaactc cgtgaatgaa   5580
gccctgctca atccgtcaag ggtgtacaca ttctttagct ccgactatgt caagaaagtg   5640
aacaaagcca ccgaagcggc aatgttcctg ggatgggttg aacaactggt ctacgacttc   5700
accgacgaga cctctgaggt gagcacaacg gacaagattg ctgacatcac tatcattatc   5760
ccgtatattg gacctgcctt gaatattggc aacatgctct acaaagacga tttcgttggt   5820
gccctgatct tcagcggtgc cgtgatcctg ttggagttca ttcctgaaat cgccatccct   5880
gtgctgggca cgttcgctct ggtctcatac attgcgaata aggtcttgac cgtgcagaca   5940
atcgataatg ccctctccaa acgtaacgaa aaatgggacg aggtctacaa atacatcgtg   6000
accaactggc tggcaaaggt taacacccaa attgatctga tccgtaagaa aatgaaggag   6060
gctttggaga accaggctga agctactaaa gccattatca actaccagta taatcagtat   6120
acagaagagg aaaagaataa catcaatttc aacatcgatg acttgtcctc aaagctgaac   6180
gagtccatca acaaagctat gatcaacatc aacaaattcc tgaatcagtg ctccgtgtct   6240
tacctgatga actctatgat cccatacggt gtgaagcgcc tggaggactt cgatgccagc   6300
ctgaaagacg cactgctcaa atacatttac gataatcgcg gcactttgat tggccaagtt   6360
gaccgtctga aggacaaggt taacaatacc ttgtcaaccg atatccccct tcaactgtcc   6420
aaatacgttg ataaccagcg cttgctctct actttcaccg aatacattaa caacattatc   6480
aatacatcaa ttctcaacct gcgctatgag tccaatcatc tgatcgatct gtctcgttac   6540
gccagcaaga tcaacattgg cagcaaagtg aacttcgatc cgattgacaa gaaccaaatc   6600
```

```
cagttgttca acctcgaaag ctccaaaatc gaagtgatcc tgaagaatgc catcgtctac   6660
aactccatgt atgaaaattt ctcaacttca ttctggatta gaatcccgaa atacttcaac   6720
tcaatctctc tgaataacga atacacgatc attaactgta tggagaataa ctctggttgg   6780
aaggtttcct tgaactatgg agaaattatc tggactctgc aagatacgca agagatcaaa   6840
cagcgtgtgg tctttaaata cagccagatg attaacatct ctgactacat caacagatgg   6900
atctttgtca ccattacaaa caatcgcctg aataactcca aaatctacat caacggtcgt   6960
ctgatcgacc agaaacctat ttcaaacctc ggcaacattc atgcttccaa taacatcatg   7020
tttaagttgg atggttgccg cgatacccac cgttacatct ggatcaagta tttcaatctg   7080
ttcgacaaag aactcaatga gaaagagatc aaagacttgt atgataatca gtcaaactcc   7140
ggcattctga aagacttctg gggcgattac ctccagtacg ataagccata ttacatgctg   7200
aatctctatg accctaacaa atatgtggac gtgaacaatg tcggtatccg tggctacatg   7260
tacctcaaag gaccacgtgg tagcgttatg acaaccaaca tctacctgaa tagctccttg   7320
tatcgcggta cgaagttcat tatcaagaag tacgcttcag gcaacaagga caacatcgtg   7380
aggaacaatg atcgcgtgta catcaacgtc gtggtgaaga ataaggaata ccgcttggcg   7440
accaacgctt ctcaggctgg agttgagaag atcctgagcg ccttggagat cccagacgtt   7500
ggcaacctga gccaagtggt tgtgatgaaa agcaagaatg accagggaat caccaacaaa   7560
tgcaaaatga acctgcaaga caacaacggc aatgacatcg gtttcatcgg tttccaccag   7620
tttaacaata ttgcgaagct ggtcgccagc aactggtaca acaggcagat tgagaggtca   7680
tcccgtacct taggatgctc ttgggaattt atccccgtgg acgatggttg gggcgagaga   7740
cccctgggcg caggttggtc ccaccctcag ttcgagaagt aatagttaat agataataat   7800
agctcgaggc atgcgagctc cctcaggagg cctacgtcga cgagctcact agtcgcggcc   7860
gctttcgaat ctagagcctg cagtctcgag gcatgcggta ccaagcttgt cgagaagtac   7920
tagaggatca taatcagcca taccacattt gtagaggttt tacttgcttt aaaaaacctc   7980
ccacacctcc ccctgaacct gaaacataaa atgaatgcaa ttgttgttgt taacttgttt   8040
attgcagctt ataatggtta caaataaagc aatagcatca caaatttcac aaataaagca   8100
tttttttcac tgcattctag ttgtggtttg tccaaactca tcaatgtatc ttatcatgtc   8160
tggatctgat cactgcttga gcctaggaga tccgaaccag ataagtgaaa tctagttcca   8220
aactattttg tcatttttaa ttttcgtatt agcttacgac gctacaccca gttcccatct   8280
attttgtcac tcttccctaa ataatcctta aaaactccat ttccacccct cccagttccc   8340
aactattttg tccgcccaca gcggggcatt tttcttcctg ttatgttttt aatcaaacat   8400
cctgccaact ccatgtgaca aaccgtcatc ttcggctact tttctctgt cacagaatga   8460
aaatttttct gtcatctctt cgttattaat gtttgtaatt gactgaatat caacgcttat   8520
ttgcagcctg aatggcgaat gg                                            8542
```

<210> SEQ ID NO 13
<211> LENGTH: 2890
<212> TYPE: DNA
<213> ORGANISM: Artificial
<220> FEATURE:
<223> OTHER INFORMATION: Vector pLitmus28C1

<400> SEQUENCE: 13

```
gttaactacg tcaggtggca cttttcgggg aaatgtgcgc ggaaccccta tttgtttatt     60
tttctaaata cattcaaata tgtatccgct catgagacaa taaccctgat aaatgcttca    120
```

```
ataatattga aaaaggaaga gtatgagtat tcaacatttc cgtgtcgccc ttattccctt    180
ttttgcggca ttttgccttc ctgtttttgc tcacccagaa acgctggtga aagtaaaaga    240
tgctgaagat cagttgggtg cacgagtggg ttacatcgaa ctggatctca acagcggtaa    300
gatccttgag agttttcgcc ccgaagaacg ttctccaatg atgagcactt ttaaagttct    360
gctatgtggc gcggtattat cccgtgttga cgccgggcaa gagcaactcg gtcgccgcat    420
acactattct cagaatgact tggttgagta ctcaccagtc acagaaaagc atcttacgga    480
tggcatgaca gtaagagaat tatgcagtgc tgccataacc atgagtgata acactgcggc    540
caacttactt ctgacaacga tcggaggacc gaaggagcta accgcttttt tgcacaacat    600
gggggatcat gtaactcgcc ttgatcgttg ggaaccggag ctgaatgaag ccataccaaa    660
cgacgagcgt gacaccacga tgcctgtagc aatggcaaca acgttgcgca aactattaac    720
tggcgaacta cttactctag cttcccggca acaattaata gactggatgg aggcggataa    780
agttgcagga ccacttctgc gctcggccct tccggctggc tggtttattg ctgataaatc    840
tggagccggt gagcgtgggt ctcgcggtat cattgcagca ctggggccag atggtaagcc    900
ctcccgtatc gtagttatct acacgacggg gagtcaggca actatggatg aacgaaatag    960
acagatcgct gagataggtg cctcactgat taagcattgg taactgtcag accaagttta   1020
ctcatatata ctttagattg atttaccccg gttgataatc agaaaagccc caaaaacagg   1080
aagattgtat aagcaaatat ttaaattgta aacgttaata ttttgttaaa attcgcgtta   1140
aatttttgtt aaatcagctc atttttaac caataggccg aaatcggcaa aatcccttat   1200
aaatcaaaag aatagcccga gatagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc caaatcaagt tttttggggt cgaggtgccg taaagcacta   1380
aatcggaacc ctaaagggag cccccgattt agagcttgac ggggaaagcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtaaaagg   1560
atctaggtga agatcctttt tgataatctc atgaccaaaa tcccttaacg tgagttttcg   1620
ttccactgag cgtcagaccc cgtagaaaag atcaaaggat cttcttgaga tcctttttt    1680
ctgcgcgtaa tctgctgctt gcaaacaaaa aaaccaccgc taccagcggt ggtttgtttg   1740
ccggatcaag agctaccaac tctttttccg aaggtaactg gcttcagcag agcgcagata   1800
ccaaatactg ttcttctagt gtagccgtag ttaggccacc acttcaagaa ctctgtagca   1860
ccgcctacat acctcgctct gctaatcctg ttaccagtgg ctgctgccag tggcgataag   1920
tcgtgtctta ccgggttgga ctcaagacga tagttaccgg ataaggcgca gcggtcgggc   1980
tgaacggggg gttcgtgcac acagcccagc ttggagcgaa cgacctacac cgaactgaga   2040
tacctacagc gtgagctatg agaaagcgcc acgcttcccg aagggagaaa ggcggacagg   2100
tatccggtaa gcggcagggt cggaacagga gagcgcacga gggagcttcc agggggaaac   2160
gcctggtatc tttatagtcc tgtcgggttt cgccacctct gacttgagcg tcgatttttg   2220
tgatgctcgt caggggggcg gagcctatgg aaaaacgcca gcaacgcggc ctttttacgg   2280
ttcctggcct tttgctggcc ttttgctcac atgtaatgtg agttagctca ctcattaggc   2340
accccaggct ttacacttta tgcttccggc tcgtatgttg tgtggaattg tgagcggata   2400
acaatttcac acaggaaaca gctatgacca tgattacgcc aagctacgta atacgactca   2460
```

```
ctatagggca gatctgaaga cataagtcgg tccgttcgaa ccagaactct ggaagcttga   2520

cgcggccgct atccatggca cacgcgttca gctagcttag gcgcctatgc gcgctaaccg   2580

cggtcactta agtatgatat ctctctgcag ttacccgggc atgacgtcta tatgcatatt   2640

ctcgaggcat gcgagctccc tcaggaggcc tatagtgagt cgtattacgg actggccgtc   2700

gttttacaac gtcgtgactg ggaaaaccct ggcgttaccc aacttaatcg ccttgcagca   2760

catccccctt tcgccagctg gcgtaatagc gaagaggccc gcaccgatcg cccttcccaa   2820

cagttgcgca gcctgaatgg cgaatggcgc ttcgcttggt aataaagccc gcttcggcgg   2880

gctttttttt                                                          2890
```

<210> SEQ ID NO 14
<211> LENGTH: 6925
<212> TYPE: DNA
<213> ORGANISM: Artificial
<220> FEATURE:
<223> OTHER INFORMATION: Vector pLitSB3A

<400> SEQUENCE: 14

```
gttaactacg tcaggtggca cttttcgggg aaatgtgcgc ggaaccccta tttgtttatt     60

tttctaaata cattcaaata tgtatccgct catgagacaa taaccctgat aaatgcttca    120

ataatattga aaaaggaaga gtatgagtat tcaacatttc cgtgtcgccc ttattccctt    180

ttttgcggca ttttgccttc ctgtttttgc tcacccagaa acgctggtga aagtaaaaga    240

tgctgaagat cagttgggtg cacgagtggg ttacatcgaa ctggatctca acagcggtaa    300

gatccttgag agttttcgcc ccgaagaacg ttctccaatg atgagcactt ttaaagttct    360

gctatgtggc gcggtattat cccgtgttga cgccgggcaa gagcaactcg gtcgccgcat    420

acactattct cagaatgact tggttgagta ctcaccagtc acagaaaagc atcttacgga    480

tggcatgaca gtaagagaat tatgcagtgc tgccataacc atgagtgata acactgcggc    540

caacttactt ctgacaacga tcggaggacc gaaggagcta accgcttttt tgcacaacat    600

gggggatcat gtaactcgcc ttgatcgttg ggaaccggag ctgaatgaag ccataccaaa    660

cgacgagcgt gacaccacga tgcctgtagc aatggcaaca acgttgcgca aactattaac    720

tggcgaacta cttactctag cttcccggca acaattaata gactggatgg aggcggataa    780

agttgcagga ccacttctgc gctcggccct tccggctggc tggtttattg ctgataaatc    840

tggagccggt gagcgtgggt ctcgcggtat cattgcagca ctggggccag atggtaagcc    900

ctcccgtatc gtagttatct acacgacggg gagtcaggca actatggatg aacgaaatag    960

acagatcgct gagataggtg cctcactgat taagcattgg taactgtcag accaagttta   1020

ctcatatata ctttagattg atttaccccg gttgataatc agaaaagccc caaaaacagg   1080

aagattgtat aagcaaatat ttaaattgta aacgttaata ttttgttaaa attcgcgtta   1140

aatttttgtt aaatcagctc atttttaac caataggccg aaatcggcaa aatcccttat   1200

aaatcaaaag aatagcccga gatagggttg agtgttgttc cagtttggaa caagagtcca   1260

ctattaaaga acgtggactc caacgtcaaa gggcgaaaaa ccgtctatca gggcgatggc   1320

ccactacgtg aaccatcacc caaatcaagt tttttggggt cgaggtgccg taaagcacta   1380

aatcggaacc ctaaagggag cccccgattt agagcttgac ggggaaagcg aacgtggcga   1440

gaaaggaagg gaagaaagcg aaaggagcgg gcgctagggc gctggcaagt gtagcggtca   1500

cgctgcgcgt aaccaccaca cccgccgcgc ttaatgcgcc gctacagggc gcgtaaaagg   1560

atctaggtga agatcctttt tgataatctc atgaccaaaa tcccttaacg tgagttttcg   1620
```

```
ttccactgag cgtcagaccc cgtagaaaag atcaaaggat cttcttgaga tcctttttt   1680
ctgcgcgtaa tctgctgctt gcaaacaaaa aaaccaccgc taccagcggt ggtttgtttg  1740
ccggatcaag agctaccaac tctttttccg aaggtaactg gcttcagcag agcgcagata  1800
ccaaatactg ttcttctagt gtagccgtag ttaggccacc acttcaagaa ctctgtagca  1860
ccgcctacat acctcgctct gctaatcctg ttaccagtgg ctgctgccag tggcgataag  1920
tcgtgtctta ccgggttgga ctcaagacga tagttaccgg ataaggcgca gcggtcgggc  1980
tgaacggggg gttcgtgcac acagcccagc ttggagcgaa cgacctacac cgaactgaga  2040
tacctacagc gtgagctatg agaaagcgcc acgcttcccg aagggagaaa ggcggacagg  2100
tatccggtaa gcggcagggt cggaacagga gagcgcacga gggagcttcc agggggaaac  2160
gcctggtatc tttatagtcc tgtcgggttt cgccacctct gacttgagcg tcgatttttg  2220
tgatgctcgt caggggggcg gagcctatgg aaaaacgcca gcaacgcggc ctttttacgg  2280
ttcctggcct tttgctggcc ttttgctcac atgtaatgtg agttagctca ctcattaggc  2340
accccaggct ttacacttta tgcttccggc tcgtatgttg tgtggaattg tgagcggata  2400
acaatttcac acaggaaaca gctatgacca tgattacgcc aagctacgta atacgactca  2460
ctatagggca gatctgaaga cataagtcgg tccgttcgaa ccagaactct ggaagcttaa  2520
ctcctaaaaa accgccacca tgaaattctt agtcaacgtt gcccttgttt ttatggtcgt  2580
atacatttct tacatctatg cggccgctca tcaccaccat catcaccatc accaccacac  2640
gcgtgaaaac ctgtattttc agggcgccgg tgactccctg tcttggctgc tccgtctgct  2700
caacgcgcgc ggtggagcta gcggcccgtt cgttaacaaa caatttaact acaaggatcc  2760
tgtcaatggt gtggacattg cctatattaa gatcccgaat gcgggtcaga tgcaacccgt  2820
gaaagcattc aagatccaca acaaaatctg ggtcatccct gaacgtgaca ctttcacaaa  2880
ccctgaagag ggcgacctca accctccccc agaagccaaa caggttccgg tgtcttacta  2940
cgatagcacg tacttgtcca ccgataacga gaaggacaac tacctgaagg gagtgaccaa  3000
gttgtttgag aggatctact ctaccgatct cggacgtatg ctgctcacga gcattgtgcg  3060
cggtatccca ttctggggcg gttcaaccat tgatacagaa ctgaaagtca ttgacactaa  3120
ttgtatcaac gttattcaac cagatggcag ctaccgttcc gaggaattga acttggtcat  3180
cattggtcca tccgcagaca tcattcagtt tgaatgcaaa tccttcggtc acgaagtgct  3240
caacctgacg cgcaacggtt acggctccac ccagtacatc cgtttcagcc ctgatttcac  3300
atttggcttc gaggaaagcc tggaggttga caccaacccg ctcctgggtg ctggcaagtt  3360
tgcaaccgat cccgcggtga ctctcgctca tgctctgatc cacgccggac accgcctcta  3420
tggcatcgct atcaatccga accgcgtgtt caaagtgaat acgaacgcct actatgagat  3480
gagcggtctg gaggtttcct ttgaggaact gagaaccttc ggcggtcacg atgccaagtt  3540
catcgacagc ttgcaggaaa atgagtttcg cctgtactat tacaacaagt ttaaagacat  3600
cgcttccaca ttgaacaaag ccaagtcaat cgtgggtacg acagcttcat tgcagtatat  3660
gaagaatgtt ttcaaggaga aatacttgct gtcagaggat acctctggca agttctctgt  3720
ggacaaactg aaattcgaca aactgtacaa gatgctgacc gagatttata cggaagataa  3780
ctttgtgaaa ttcttcaaag tcctcaacag gaaaactgct ctgaactttg acaaggctgt  3840
gttcaagatc aacatcgtcc ccaaagttaa ctacacaatc tatgatggat tcaatctgag  3900
aaacaccaac ttggccgcca acttcaacgg ccaaaatacc gaaattaata acatgaattt  3960
```

-continued

```
caccaaactg aagaacttta ctggactgtt cgagttctac aagctgctct gcgtgcgtgg   4020
catcatcacc tcacatactc agtctctaga ccagggttat aacgacgatg acgataaagc   4080
tctgaacgat ctgtgtatca aggtgaataa ctgggatctg ttctttagcc caagcgagga   4140
taacttcacg aacgatctca acaaaggtga agagatcacg tctgatacca atatcgaagc   4200
ggctgaagag aatatctcct tggatctcat ccagcaatat tacctgacct ttaacttcga   4260
taacgagccc gaaaacatct ccatcgagaa cctcagctca gacatcattg gtcagttgga   4320
gctgatgcca aacattgaac gcttccccaa cggcaagaaa tacgaactcg acaagtatac   4380
gatgtttcat tacttaagag cgcaggagtt tgaacacggc aagagccgca ttgctctcac   4440
taactccgtg aatgaagccc tgctcaatcc gtcaagggtg tacacattct ttagctccga   4500
ctatgtcaag aaagtgaaca aagccaccga agcggcaatg ttcctgggat gggttgaaca   4560
actggtctac gacttcaccg acgagacctc tgaggtgagc acaacggaca agattgctga   4620
catcactatc attatcccgt atattggacc tgccttgaat attggcaaca tgctctacaa   4680
agacgatttc gttggtgccc tgatcttcag cggtgccgtg atcctgttgg agttcattcc   4740
tgaaatcgcc atccctgtgc tgggcacgtt cgctctggtc tcatacattg cgaataaggt   4800
cttgaccgtg cagacaatcg ataatgccct ctccaaacgt aacgaaaaat gggacgaggt   4860
ctacaaatac atcgtgacca actggctggc aaaggttaac acccaaattg atctgatccg   4920
taagaaaatg aaggaggctt tggagaacca ggctgaagct actaaagcca ttatcaacta   4980
ccagtataat cagtatacag aagaggaaaa gaataacatc aatttcaaca tcgatgactt   5040
gtcctcaaag ctgaacgagt ccatcaacaa agctatgatc aacatcaaca aattcctgaa   5100
tcagtgctcc gtgtcttacc tgatgaactc tatgatccca tacggtgtga agcgcctgga   5160
ggacttcgat gccagcctga aagacgcact gctcaaatac atttacgata atcgcggcac   5220
tttgattggc caagttgacc gtctgaagga caaggttaac aataccttgt caaccgatat   5280
ccccttttcaa ctgtccaaat acgttgataa ccagcgcttg ctctctactt tcaccgaata   5340
cattaacaac attatcaata catcaattct caacctgcgc tatgagtcca atcatctgat   5400
cgatctgtct cgttacgcca gcaagatcaa cattggcagc aaagtgaact tcgatccgat   5460
tgacaagaac caaatccagt tgttcaacct cgaaagctcc aaaatcgaag tgatcctgaa   5520
gaatgccatc gtctacaact ccatgtatga aaatttctca acttcattct ggattagaat   5580
cccgaaatac ttcaactcaa tctctctgaa taacgaatac acgatcatta actgtatgga   5640
gaataactct ggttggaagg tttccttgaa ctatggagaa attatctgga ctctgcaaga   5700
tacgcaagag atcaaacagc gtgtggtctt taaatacagc cagatgatta acatctctga   5760
ctacatcaac agatggatct ttgtcaccat tacaaacaat cgcctgaata actccaaaat   5820
ctacatcaac ggtcgtctga tcgaccagaa acctatttca aacctcggca acattcatgc   5880
ttccaataac atcatgttta agttggatgg ttgccgcgat acccaccgtt acatctggat   5940
caagtatttc aatctgttcg acaaagaact caatgagaaa gagatcaaag acttgtatga   6000
taatcagtca aactccggca ttctgaaaga cttctggggc gattacctcc agtacgataa   6060
gccatattac atgctgaatc tctatgaccc taacaaatat gtggacgtga acaatgtcgg   6120
tatccgtggc tacatgtacc tcaaaggacc acgtggtagc gttatgacaa ccaacatcta   6180
cctgaatagc tccttgtatc gcggtacgaa gttcattatc aagaagtacg cttcaggcaa   6240
caaggacaac atcgtgagga acaatgatcg cgtgtacatc aacgtcgtgg tgaagaataa   6300
ggaataccgc ttggcgacca acgcttctca ggctggagtt gagaagatcc tgagcgcctt   6360
```

```
ggagatccca gacgttggca acctgagcca agtggttgtg atgaaaagca agaatgacca   6420

gggaatcacc aacaaatgca aaatgaacct gcaagacaac aacggcaatg acatcggttt   6480

catcggtttc caccagttta acaatattgc gaagctggtc gccagcaact ggtacaacag   6540

gcagattgag aggtcatccc gtaccttagg atgctcttgg gaatttatcc ccgtggacga   6600

tggttggggc gagagacccc tgggcgcagg ttggtcccac cctcagttcg agaagtaata   6660

gttaatagat aataatagct cgaggcatgc gagctccctc aggaggatag tgagtcgtat   6720

tacggactgg ccgtcgtttt acaacgtcgt gactgggaaa accctggcgt tacccaactt   6780

aatcgccttg cagcacatcc ccctttcgcc agctggcgta atagcgaaga ggcccgcacc   6840

gatcgccctt cccaacagtt gcgcagcctg aatggcgaat ggcgcttcgc ttggtaataa   6900

agcccgcttc ggcgggcttt ttttt                                       6925
```

<210> SEQ ID NO 15
<211> LENGTH: 8968
<212> TYPE: DNA
<213> ORGANISM: Artificial
<220> FEATURE:
<223> OTHER INFORMATION: BoNT/Aadek vector pFB1SB3AEK

<400> SEQUENCE: 15

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440
```

-continued

```
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
```

-continued

```
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcccgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccgctca tcaccaccat catcaccatc accaccacac gcgtgaaaac   4200
ctgtattttc agggcgccgg tgactccctg tcttggctgc tccgtctgct caacgcgcgc   4260
ggtggagcta gcggcccgtt cgttaacaaa caatttaact acaaggatcc tgtcaatggt   4320
gtggacattg cctatattaa gatcccgaat gcgggtcaga tgcaacccgt gaaagcattc   4380
aagatccaca acaaaatctg ggtcatccct gaacgtgaca ctttcacaaa ccctgaagag   4440
ggcgacctca accctccccc agaagccaaa caggttccgg tgtcttacta cgatagcacg   4500
tacttgtcca ccgataacga gaaggacaac tacctgaagg gagtgaccaa gttgtttgag   4560
aggatctact ctaccgatct cggacgtatg ctgctcacga gcattgtgcg cggtatccca   4620
ttctggggcg gttcaaccat tgatacagaa ctgaaagtca ttgacactaa ttgtatcaac   4680
gttattcaac cagatggcag ctaccgttcc gaggaattga acttggtcat cattggtcca   4740
tccgcagaca tcattcagtt tgaatgcaaa tccttcggtc acgaagtgct caacctgacg   4800
cgcaacggtt acggctccac ccagtacatc cgtttcagcc ctgatttcac atttggcttc   4860
gaggaaagcc tggaggttga caccaacccg ctcctgggtg ctggcaagtt tgcaaccgat   4920
cccgcggtga ctctcgctca tgctctgatc cacgccggac accgcctcta tggcatcgct   4980
atcaatccga accgcgtgtt caaagtgaat acgaacgcct actatgagat gagcggtctg   5040
gaggtttcct ttgaggaact gagaaccttc ggcggtcacg atgccaagtt catcgacagc   5100
ttgcaggaaa atgagtttcg cctgtactat tacaacaagt ttaaagacat cgcttccaca   5160
ttgaacaaag ccaagtcaat cgtgggtacg acagcttcat tgcagtatat gaagaatgtt   5220
ttcaaggaga aatacttgct gtcagaggat acctctggca agttctctgt ggacaaactg   5280
aaattcgaca aactgtacaa gatgctgacc gagatttata cggaagataa ctttgtgaaa   5340
ttcttcaaag tcctcaacag gaaaactgct ctgaactttg acaaggctgt gttcaagatc   5400
aacatcgtcc ccaaagttaa ctacacaatc tatgatggat tcaatctgag aaacaccaac   5460
ttggccgcca acttcaacgg ccaaaatacc gaaattaata acatgaattt caccaaactg   5520
aagaacttta ctggactgtt cgagttctac aagctgctct gcgtgcgtgg catcatcacc   5580
tcacatactc agtctctaga ccagggttat aacgacgatg acgataaagc tctgaacgat   5640
ctgtgtatca aggtgaataa ctgggatctg ttctttagcc caagcgagga taacttcacg   5700
aacgatctca acaaaggtga agagatcacg tctgatacca atatcgaagc ggctgaagag   5760
aatatctcct tggatctcat ccagcaatat tacctgacct ttaacttcga taacgagccc   5820
gaaaacatct ccatcgagaa cctcagctca gacatcattg gtcagttgga gctgatgcca   5880
aacattgaac gcttccccaa cggcaagaaa tacgaactcg acaagtatac gatgtttcat   5940
tacttaagag cgcaggagtt tgaacacggc aagagccgca ttgctctcac taactccgtg   6000
aatgaagccc tgctcaatcc gtcaagggtg tacacattct ttagctccga ctatgtcaag   6060
aaagtgaaca aagccaccga agcggcaatg ttcctgggat gggttgaaca actggtctac   6120
gacttcaccg acgagacctc tgaggtgagc acaacggaca agattgctga catcactatc   6180
```

-continued

```
attatcccgt atattggacc tgccttgaat attggcaaca tgctctacaa agacgatttc   6240
gttggtgccc tgatcttcag cggtgccgtg atcctgttgg agttcattcc tgaaatcgcc   6300
atccctgtgc tgggcacgtt cgctctggtc tcatacattg cgaataaggt cttgaccgtg   6360
cagacaatcg ataatgccct ctccaaacgt aacgaaaaat gggacgaggt ctacaaatac   6420
atcgtgacca actggctggc aaaggttaac acccaaattg atctgatccg taagaaaatg   6480
aaggaggctt tggagaacca ggctgaagct actaaagcca ttatcaacta ccagtataat   6540
cagtatacag aagaggaaaa gaataacatc aatttcaaca tcgatgactt gtcctcaaag   6600
ctgaacgagt ccatcaacaa agctatgatc aacatcaaca aattcctgaa tcagtgctcc   6660
gtgtcttacc tgatgaactc tatgatccca tacggtgtga agcgcctgga ggacttcgat   6720
gccagcctga aagacgcact gctcaaatac atttacgata atcgcggcac tttgattggc   6780
caagttgacc gtctgaagga caaggttaac aataccttgt caaccgatat cccctttcaa   6840
ctgtccaaat acgttgataa ccagcgcttg ctctctactt tcaccgaata cattaacaac   6900
attatcaata catcaattct caacctgcgc tatgagtcca atcatctgat cgatctgtct   6960
cgttacgcca gcaagatcaa cattggcagc aaagtgaact tcgatccgat tgacaagaac   7020
caaatccagt tgttcaacct cgaaagctcc aaaatcgaag tgatcctgaa gaatgccatc   7080
gtctacaact ccatgtatga aaatttctca acttcattct ggattagaat cccgaaatac   7140
ttcaactcaa tctctctgaa taacgaatac acgatcatta actgtatgga gaataactct   7200
ggttggaagg tttccttgaa ctatggagaa attatctgga ctctgcaaga tacgcaagag   7260
atcaaacagc gtgtggtctt taaatacagc cagatgatta acatctctga ctacatcaac   7320
agatggatct ttgtcaccat tacaaacaat cgcctgaata actccaaaat ctacatcaac   7380
ggtcgtctga tcgaccagaa acctatttca aacctcggca acattcatgc ttccaataac   7440
atcatgttta agttggatgg ttgccgcgat acccaccgtt acatctggat caagtatttc   7500
aatctgttcg acaaagaact caatgagaaa gagatcaaag acttgtatga taatcagtca   7560
aactccggca ttctgaaaga cttctggggc gattacctcc agtacgataa gccatattac   7620
atgctgaatc tctatgaccc taacaaatat gtggacgtga acaatgtcgg tatccgtggc   7680
tacatgtacc tcaaaggacc acgtggtagc gttatgacaa ccaacatcta cctgaatagc   7740
tccttgtatc gcggtacgaa gttcattatc aagaagtacg cttcaggcaa caaggacaac   7800
atcgtgagga acaatgatcg cgtgtacatc aacgtcgtgg tgaagaataa ggaataccgc   7860
ttggcgacca acgcttctca ggctggagtt gagaagatcc tgagcgcctt ggagatccca   7920
gacgttggca acctgagcca agtggttgtg atgaaaagca agaatgacca gggaatcacc   7980
aacaaatgca aaatgaacct gcaagacaac aacggcaatg acatcggttt catcggtttc   8040
caccagttta acaatattgc gaagctggtc gccagcaact ggtacaacag gcagattgag   8100
aggtcatccc gtaccttagg atgctcttgg gaatttatcc ccgtggacga tggttggggc   8160
gagagacccc tgggcgcagg ttggtcccac cctcagttcg agaagtaata gttaatagat   8220
aataatagct cgaggcatgc gagctccctc aggaggccta cgtcgacgag ctcactagtc   8280
gcggccgctt tcgaatctag agcctgcagt ctcgaggcat gcggtaccaa gcttgtcgag   8340
aagtactaga ggatcataat cagccatacc acatttgtag aggttttact tgctttaaaa   8400
aacctcccac acctccccct gaacctgaaa cataaaatga atgcaattgt tgttgttaac   8460
ttgtttattg cagcttataa tggttacaaa taaagcaata gcatcacaaa tttcacaaat   8520
aaagcatttt tttcactgca ttctagttgt ggtttgtcca aactcatcaa tgtatcttat   8580
```

catgtctgga tctgatcact gcttgagcct aggagatccg aaccagataa gtgaaatcta 8640
gttccaaact attttgtcat ttttaatttt cgtattagct tacgacgcta cacccagttc 8700
ccatctattt tgtcactctt ccctaaataa tccttaaaaa ctccatttcc acccctccca 8760
gttcccaact attttgtccg cccacagcgg ggcatttttc ttcctgttat gtttttaatc 8820
aaacatcctg ccaactccat gtgacaaacc gtcatcttcg gctacttttt ctctgtcaca 8880
gaatgaaaat tttctgtca tctcttcgtt attaatgttt gtaattgact gaatatcaac 8940
gcttatttgc agcctgaatg gcgaatgg 8968

<210> SEQ ID NO 16
<211> LENGTH: 103
<212> TYPE: DNA
<213> ORGANISM: Artificial
<220> FEATURE:
<223> OTHER INFORMATION: Oligonucleotide C1-1S

<400> SEQUENCE: 16
gatctgaaga cataagtcgg tccgttcgaa ccagaactct ggaagcttga cgcggccgct 60
atccatggca cacgcgttca gctagcttag gcgcctatga cgt 103

<210> SEQ ID NO 17
<211> LENGTH: 95
<212> TYPE: DNA
<213> ORGANISM: Artificial
<220> FEATURE:
<223> OTHER INFORMATION: Oligonucleotide C1-1A

<400> SEQUENCE: 17
cataggcgcc taagctagct gaacgcgtgt gccatggata gcggccgcgt caagcttcca 60
gagttctggt tcgaacggac cgacttatgt cttca 95

<210> SEQ ID NO 18
<211> LENGTH: 108
<212> TYPE: DNA
<213> ORGANISM: Artificial
<220> FEATURE:
<223> OTHER INFORMATION: Oligonucleotide C1-2S

<400> SEQUENCE: 18
gcgcctatgc gcgctaaccg cggtcactta agtatgatat ctctctgcag ttacccgggc 60
atgacgtcta tatgcatatt ctcgaggcat gcgagctccc tcaggagg 108

<210> SEQ ID NO 19
<211> LENGTH: 104
<212> TYPE: DNA
<213> ORGANISM: Artificial
<220> FEATURE:
<223> OTHER INFORMATION: Oligonucleotide C1-2A

<400> SEQUENCE: 19
cctcctgagg gagctcgcat gcctcgagaa tatgcatata gacgtcatgc ccgggtaact 60
gcagagagat atcatactta agtgaccgcg gttagcgcgc atag 104

<210> SEQ ID NO 20
<211> LENGTH: 88
<212> TYPE: DNA
<213> ORGANISM: Artificial
<220> FEATURE:
<223> OTHER INFORMATION: Oligonucleotide CP1S

<400> SEQUENCE: 20
agcttaactc ctaaaaaacc gccaccatga aattcttagt caacgttgcc cttgttttta 60
tggtcgtata catttcttac atctatgc 88

<210> SEQ ID NO 21
<211> LENGTH: 88
<212> TYPE: DNA
<213> ORGANISM: Artificial
<220> FEATURE:
<223> OTHER INFORMATION: Oligonucleotide CP1A

<400> SEQUENCE: 21
ggccgcatag atgtaagaaa tgtatacgac cataaaaaca agggcaacgt tgactaagaa 60
tttcatggtg gcggtttttt aggagtta 88

<210> SEQ ID NO 22
<211> LENGTH: 38
<212> TYPE: DNA
<213> ORGANISM: Artificial
<220> FEATURE:
<223> OTHER INFORMATION: Oligonucleotide CP2S

<400> SEQUENCE: 22
ggccgctcat caccaccatc atcaccatca ccaccaca 38

<210> SEQ ID NO 23
<211> LENGTH: 38
<212> TYPE: DNA
<213> ORGANISM: Artificial
<220> FEATURE:
<223> OTHER INFORMATION: Oligonucleotide CP2A

<400> SEQUENCE: 23
cgcgtgtggt ggtgatggtg atgatggtgg tgatgagc 38

<210> SEQ ID NO 24
<211> LENGTH: 78
<212> TYPE: DNA
<213> ORGANISM: Artificial
<220> FEATURE:
<223> OTHER INFORMATION: Oligonucleotide CP3S

<400> SEQUENCE: 24
cgcgtgaaaa cctgtatttt cagggcgccg gtgactccct gtcttggctg ctccgtctgc 60
tcaacgcgcg cggtggcg 78

<210> SEQ ID NO 25
<211> LENGTH: 78
<212> TYPE: DNA
<213> ORGANISM: Artificial
<220> FEATURE:
<223> OTHER INFORMATION: Oligonucleotide CP3A

<400> SEQUENCE: 25
ctagcgccac cgcgcgcgtt gagcagacgg agcagccaag acagggagtc accggcgccc 60
tgaaaataca ggttttca 78

<210> SEQ ID NO 26
<211> LENGTH: 45
<212> TYPE: DNA
<213> ORGANISM: Artificial
<220> FEATURE:
<223> OTHER INFORMATION: Oligonucleotide CP4S

<400> SEQUENCE: 26
agcttaccat gggtcatcac caccatcatc accatcacca ccaca 45

<210> SEQ ID NO 27
<211> LENGTH: 45
<212> TYPE: DNA
<213> ORGANISM: Artificial
<220> FEATURE:
<223> OTHER INFORMATION: Oligonucleotide CP4A

<400> SEQUENCE: 27
cgcgtgtggt ggtgatggtg atgatggtgg tgatgaccca tggta 45

<210> SEQ ID NO 28
<211> LENGTH: 45
<212> TYPE: DNA
<213> ORGANISM: Artificial
<220> FEATURE:
<223> OTHER INFORMATION: Oligonucleotide CP5S

<400> SEQUENCE: 28
agcttacgct gctccatcac caccatcatc accatcacca ccaca 45

<210> SEQ ID NO 29
<211> LENGTH: 45
<212> TYPE: DNA
<213> ORGANISM: Artificial
<220> FEATURE:
<223> OTHER INFORMATION: Oligonucleotide CP5A

<400> SEQUENCE: 29
cgcgtgtggt ggtgatggtg atgatggtgg tgatggagca tgcta 45

<210> SEQ ID NO 30
<211> LENGTH: 10
<212> TYPE: DNA
<213> ORGANISM: Artificial
<220> FEATURE:
<223> OTHER INFORMATION: Oligonucleotide CP6

<400> SEQUENCE: 30
taccctaggg 10

<210> SEQ ID NO 31
<211> LENGTH: 31
<212> TYPE: DNA
<213> ORGANISM: Artificial
<220> FEATURE:
<223> OTHER INFORMATION: Oligonucleotide CP7S

<400> SEQUENCE: 31
tcatgctagc gtgagcaagg gcgccgagct g 31

<210> SEQ ID NO 32
<211> LENGTH: 32
<212> TYPE: DNA
<213> ORGANISM: Artificial
<220> FEATURE:
<223> OTHER INFORMATION: Oligonucleotide CP7A

<400> SEQUENCE: 32
tataggtacc cttgtacagc tcatccatgc cg 32

<210> SEQ ID NO 33

<211> LENGTH: 21
<212> TYPE: DNA
<213> ORGANISM: Artificial
<220> FEATURE:
<223> OTHER INFORMATION: Enhancer sequence

<400> SEQUENCE: 33
aactcctaaa aaaccgccac c 21

<210> SEQ ID NO 34
<211> LENGTH: 8
<212> TYPE: PRT
<213> ORGANISM: Artificial
<220> FEATURE:
<223> OTHER INFORMATION: Strep Tag II Sequence

<400> SEQUENCE: 34

Trp Ser His Pro Gln Phe Glu Lys
1 5

<210> SEQ ID NO 35
<211> LENGTH: 21
<212> TYPE: DNA
<213> ORGANISM: Artificial
<220> FEATURE:
<223> OTHER INFORMATION: cis-DNA sequence

<400> SEQUENCE: 35
aactcctaaa aaaccgccac c 21

<210> SEQ ID NO 36
<211> LENGTH: 22
<212> TYPE: PRT
<213> ORGANISM: Artificial
<220> FEATURE:
<223> OTHER INFORMATION: Honeybee mellitin signal peptide

<400> SEQUENCE: 36

Met Lys Phe Leu Val Asn Val Ala Leu Val Phe Met Val Val Tyr Ile
1 5 10 15

Ser Tyr Ile Tyr Ala Ala
20

<210> SEQ ID NO 37
<211> LENGTH: 6
<212> TYPE: PRT
<213> ORGANISM: Artificial
<220> FEATURE:
<223> OTHER INFORMATION: BoNT/Aadek Light Chain N-Terminus

<400> SEQUENCE: 37

Gly Ala Gly Asp Ser Leu
1 5

<210> SEQ ID NO 38
<211> LENGTH: 6
<212> TYPE: PRT
<213> ORGANISM: Artificial
<220> FEATURE:
<223> OTHER INFORMATION: BoNT/Aadek Heavy Chain N-Terminus

<400> SEQUENCE: 38

Ala Leu Asn Asp Leu Cys
1 5

<210> SEQ ID NO 39

<211> LENGTH: 5
<212> TYPE: PRT
<213> ORGANISM: Artificial
<220> FEATURE:
<223> OTHER INFORMATION: BoNT/Aadek Light Chain Tryptic Peptide Sequence

<400> SEQUENCE: 39

Leu Leu Cys Val Arg
1 5

<210> SEQ ID NO 40
<211> LENGTH: 8
<212> TYPE: PRT
<213> ORGANISM: Artificial
<220> FEATURE:
<223> OTHER INFORMATION: BoNT/Aadek Heavy Chain Tryptic Peptide Sequence

<400> SEQUENCE: 40

Ala Leu Asn Asp Leu Cys Ile Lys
1 5

<210> SEQ ID NO 41
<211> LENGTH: 4
<212> TYPE: PRT
<213> ORGANISM: Artificial
<220> FEATURE:
<223> OTHER INFORMATION: Cleavage Product of BoNT/A Propeptide

<400> SEQUENCE: 41

Gly Tyr Asn Lys
1

<210> SEQ ID NO 42
<211> LENGTH: 10
<212> TYPE: PRT
<213> ORGANISM: Artificial
<220> FEATURE:
<223> OTHER INFORMATION: Excision Product of BoNT/A Precursor

<400> SEQUENCE: 42

Thr Lys Ser Leu Asp Lys Gly Tyr Asn Lys
1 5 10

<210> SEQ ID NO 43
<211> LENGTH: 13
<212> TYPE: PRT
<213> ORGANISM: Artificial
<220> FEATURE:
<223> OTHER INFORMATION: Peptide Insert With Substrate Sequence for BACE1

<400> SEQUENCE: 43

Ser Glu Ile Ser Tyr Glu Val Glu Phe Arg Trp Lys Lys
1 5 10

<210> SEQ ID NO 44
<211> LENGTH: 4
<212> TYPE: PRT
<213> ORGANISM: Artificial
<220> FEATURE:
<223> OTHER INFORMATION: Insert Between N447 and K448 of BoNT/Aadek Construct

<400> SEQUENCE: 44

Asp Asp Asp Asp
1

-continued

```
<210> SEQ ID NO 45
<211> LENGTH: 12
<212> TYPE: PRT
<213> ORGANISM: Artificial
<220> FEATURE:
<223> OTHER INFORMATION: Cargo Attachment Peptide

<400> SEQUENCE: 45

Gly Asp Ser Leu Asp Met Leu Glu Trp Ser Leu Met
1               5                   10


<210> SEQ ID NO 46
<211> LENGTH: 8
<212> TYPE: PRT
<213> ORGANISM: Artificial
<220> FEATURE:
<223> OTHER INFORMATION: Cargo Attachment Peptide

<400> SEQUENCE: 46

Asp Ser Leu Asp Met Leu Glu Trp
1               5


<210> SEQ ID NO 47
<211> LENGTH: 16
<212> TYPE: PRT
<213> ORGANISM: Artificial
<220> FEATURE:
<223> OTHER INFORMATION: Cargo Attachment Peptide

<400> SEQUENCE: 47

Met Ser Gly Leu Val Asp Ile Phe Glu Ala Gln Lys Ile Glu Trp His
1               5                   10                  15


<210> SEQ ID NO 48
<211> LENGTH: 7
<212> TYPE: PRT
<213> ORGANISM: Artificial
<220> FEATURE:
<223> OTHER INFORMATION: Cargo Attachment Peptide

<400> SEQUENCE: 48

Pro Lys Pro Gln Gln Phe Met
1               5


<210> SEQ ID NO 49
<211> LENGTH: 5
<212> TYPE: PRT
<213> ORGANISM: Artificial
<220> FEATURE:
<223> OTHER INFORMATION: Cargo Attachment Peptide

<400> SEQUENCE: 49

Gly Gly Gly Gly Gly
1               5
```

RECOMBINANT DERIVATIVES OF BOTULINUM NEUROTOXINS ENGINEERED FOR TRAFFICKING STUDIES AND NEURONAL DELIVERY

This application claims benefit of U.S. Provisional Patent Application Ser. No. 61/298,078, filed Jan. 25, 2010, which is hereby incorporated by reference in its entirety.

This invention was made with government support under NIH-NIAID AI072466, NIH NINDS NS050276, NIH-NCRR RR017990, and NIH Office of the Director DP2-OD004631. The government has certain rights in the invention.

FIELD OF THE INVENTION

This invention relates to isolated *Clostridium botulinum* propeptides and neurotoxins, isolated nucleic acid molecules encoding *Clostridium botulinum* propeptides and neurotoxins, methods of expression, treatment methods, methods of detecting neurotoxin trafficking, and methods of detecting levels of neuronal activity.

BACKGROUND OF THE INVENTION

*Botulinum* neurotoxins ("BoNTs") are a family of structurally similar proteins that cause peripheral neuromuscular blockade and respiratory paralysis. BoNTs are exceedingly toxic, possessing an extremely low $LD_{50}$ (1-50 ng/kg) (National Institute of Occupational Safety and Health, *Registry of Toxic Effects of Chemical Substances* (*R-TECS*), Cincinnati, Ohio: National Institute of Occupational Safety and Health, 1996). There are seven major BoNT serotypes (BoNT A-G) and multiple subtypes (Smith et al., "Sequence Variation Within *Botulinum* Neurotoxin Serotypes Impacts Antibody Binding and Neutralization," *Infect. Immun.* 73(9):5450-5457 (2005)), but all have common structural features and a similar mechanism of action. BoNTs are synthesized as single chain propeptides with intramolecular disulfide bonds (Mr approximately 150,000; approximately 1,300 amino acids) with extensive areas of sequence homology. The majority are activated by proteolytic cleavage to generate a disulfide-bonded heterodimer containing light (approximately 50 kDa) and heavy (approximately 100 kDa) chains ("LC" and "HC" respectively).

*Botulinum* neurotoxin serotype A ("BoNT/A") heterodimer has been extensively studied and has been found to contain three functional domains. Toxicity is associated with metalloprotease activity confined to the LC, neuron binding activity is associated with the C-terminal half of the HC ($HC_C$), and translocation activity responsible for delivering the LC protease to the neuronal cytosol is associated with the N-terminal half of the HC ($HC_N$) (Johnson, "Clostridial Toxins as Therapeutic Agents: Benefits of Nature's Most Toxic Proteins," *Annu. Rev. Microbiol.* 53:551-575 (1999); Montecucco et al., "Structure and Function of Tetanus and *Botulinum* Neurotoxins," *Q. Rev. Biophys.* 28(4):423-472 (1995)).

The toxicity of BoNTs is a consequence of a multi-step mechanism culminating in a LC-mediated proteolytic event that disrupts the neuronal machinery for synaptic vesicle exocytosis. During BoNT poisoning, BoNTs must first cross epithelial barriers by transcytosis (Simpson, "Identification of the Major Steps in *Botulinum* Toxin Action," *Annu. Rev. Pharmacol. Toxicol.* 44:167-193 (2004)). The BoNT then passes into the circulation by an unknown pathway, from which it selectively targets the presynaptic membrane of motor neurons at neuromuscular junctions. Toxicity at the neuromuscular junction involves (i) binding to the plasma membrane, (ii) internalization into endocytic vesicles, (iii) activation within an acidic endosomal compartment that enables HC-mediated translocation of the LC into the neuronal cytoplasm, and (iv) catalytic cleavage by the LC zinc-endopeptidase of protein components in the neuronal machinery required for synaptic vesicle exocytosis.

The endopeptidase activity responsible for toxicity is associated with a HExxHxxH (SEQ ID NO:1) motif in the LC which is characteristic of the thermolysin family of metalloproteases. Mutagenesis experiments with the BoNT/A light chain have identified the minimal essential domain for toxicity (Kurazono et al., "Minimal Essential Domains Specifying Toxicity of the Light Chains of Tetanus Toxin and *Botulinum* Neurotoxin Type A," *J. Biol. Chem.* 267(21):14721-14729 (1992)), and have pinpointed the amino acids involved in $Zn^{2+}$ coordination at the metalloprotease active site (Rigoni et al., "Site-Directed Mutagenesis Identifies Active-Site Residues of the Light Chain of *Botulinum* Neurotoxin Type A," *Biochem. Biophys. Res. Commun.* 288(5):1231-1237 (2001)). These data are corroborated by crystallography-based structures currently available for the majority of BoNT serotypes, and by crystallographic data for LC/LC mutants expressed as single entities, or co-crystallized with the substrate or inhibitors (Lacy et al., "Crystal Structure of *Botulinum* Neurotoxin Type A and Implications for Toxicity," *Nat. Struct. Biol.* 5(10):898-902 (1998); Breidenbach et al., "Substrate Recognition Strategy for *Botulinum* Neurotoxin Serotype A," *Nature* 432:925-929 (2004); Fu et al., "Light Chain of *Botulinum* Neurotoxin Serotype A: Structural Resolution of a Catalytic Intermediate," *Biochemistry* 45:8903-8911 (2006); Garcia-Rodriguez et al., "Molecular Evolution of Antibody Cross-Reactivity for Two Subtypes of Type A *Botulinum* Neurotoxin," *Nat. Biotechnol.* 25:107-116 (2007); Burnett et al., "Inhibition of Metalloprotease *Botulinum* Serotype A From a Pseudo-Peptide Binding Mode to a Small Molecule That is Active in Primary Neurons," *J. Biol. Chem.* 282:5004-5014 (2007); Silvaggi et al., "Structures of *Clostridium botulinum* Neurotoxin Serotype A Light Chain Complexed with Small-Molecule Inhibitors Highlight Active-Site Flexibility," *Chem. Biol.* 14(5):533-542 (2007); Silvaggi et al., "Catalytic Features of the *Botulinum* Neurotoxin A Light Chain Revealed by High Resolution Structure of an Inhibitory Peptide Complex," *Biochemistry* 47(21):5736-5745 (2008); Zuniga et al., "A Potent Peptidomimetic Inhibitor of *Botulinum* Neurotoxin Serotype A Has a Very Different Conformation than SNAP-25 Substrate," *Structure* 16:588-1597 (2008); Kumaran et al., "Structure- and Substrate-Based Inhibitor Design for *Clostridium botulinum* Neurotoxin Serotype A," *J. Biol. Chem.* 283:18883-18891 (2008); Kumaran et al., "Substrate Binding Mode and Its Implication on Drug Design for *Botulinum* Neurotoxin A," *PloS Pathog.* 4(9): e1000165 (2008); Swaminathan et al., "Structural Analysis of the Catalytic and Binding Sites of *Clostridium botulinum* Neurotoxin B," *Nat. Struct. Biol.* 7(8):693-699 (2000); Hanson et al., "Cocrystal Structure of Synaptobrevin-II Bound to *Botulinum* Neurotoxin Type B at 2.0 Å Resolution," *Nat. Struct. Biol.* 7(8):687-692 (2000); Eswaramoorthy et al., "Novel Mechanism for *Clostridium botulinum* Neurotoxin Inhibition," *Biochemistry* 41:9795-9802 (2002); Eswaramoorthy et al., "Role of Metals In the Biological Activity of *Clostridium botulinum* Neurotoxins," *Biochemistry* 43(8): 2209-2216 (2004); Jin et al., "Structural and Biochemical Studies of *Botulinum* Neurotoxin Serotype C1 Light Chain Protease: Implications for Dual Substrate Specificity," *Biochemistry* 46:10685-10693 (2007); Arndt et al., "Structure of *Botulinum* Neurotoxin Type D Light Chain at 1.65 Å Resolution: Repercussions for VAMP-2 Substrate Specificity," *Biochemistry* 45:3255-3262 (2006); Agarwal et al., "Structural Analysis of *Botulinum* Neurotoxin Type E Catalytic Domain and Its Mutant $Glu_{212}$>Gln Reveals the Pivotal Role of the $Glu_{212}$ Carboxylate in the Catalytic Pathway," *Biochemistry* 43:6637-6644 (2004); Agarwal et al., "Analysis of Active Site Residues of *Botulinum* Neurotoxin E By Mutational, Functional, and Structural Studies: $Glu_{335}$>Gln is an Apoenzyme," *Biochemistry* 44:8291-8302 (2005); Agarwal et al., "SNAP-25 Substrate Peptide (Residues 180-183) Binds to But Bypasses Cleavage by Catalytically Active *Clostridium botulinum* Neurotoxin E," *J. Biol. Chem.* 283: 25944-25951 (2008); Agarwal et al., "Structural Analysis of *Botulinum* Neurotoxin Serotype F Light Chain: Implications on Substrate Binding and Inhibitor Design," *Biochemistry* 44:11758-11765 (2005); Agarwal et al., "Mode of VAMP Substrate Recognition and Inhibition of *Clostridium botulinum* Neurotoxin F," *Nat. Struct. Mol. Biol.* 16:789-794 (2009); Arndt et al., "Crystal Structure of *Botulinum* Neurotoxin Type G Light Chain: Serotype Divergence In Substrate Recognition," *Biochemistry* 44:9574-9580 (2005)).

Recombinant BoNT proteins or peptides have been reported for several serotypes, primarily as part of efforts aimed at developing a vaccine against BoNT poisoning. The receptor-binding HC domain ($HC_C$) has been produced in a variety of expression systems. These recombinant HC preparations were effective immunogens and protected animals challenged with wt BoNTs (Byrne et al., "Development of Vaccines for Prevention of Botulism," *Biochimie* 82:955-966 (2000); Ravichandran et al., "Trivalent Vaccine Against *Botulinum* Toxin Serotypes A, B, and E That Can Be Administered By the Mucosal Route," *Infect. Immun.* 75(6):3043-3054 (2007); Baldwin et al., "Subunit Vaccine Against the Seven Serotypes of Botulism," *Infect. Immun.* 76(3):1314-131 (2008); Smith, "Development of Recombinant Vaccines for *Botulinum* Neurotoxin," *Toxicon* 36:1539-1548 (1998); Baldwin et al., "Characterization of the Antibody Response to the Receptor Binding Domain of *Botulinum* Neurotoxin Serotypes A and E," *Infect Immun.* 73(10):6998-7005 (2005); Woodward et al., "Expression of HC Subunits from *Clostridium botulinum* Types C and D and Their Evaluation as Candidate Vaccine Antigens In Mice," *Infect. Immun.* 71(5):2941-2944 (2003); Webb et al., "Protection with Recombinant *Clostridium botulinum* C1 and D Binding Domain Subunit (Hc) Vaccines Against C and D Neurotoxins," *Vaccine* 25(21):4273-4282 (2007); Lee et al., "C-Terminal Half Fragment (50 kDa) of Heavy Chain Components of *Clostridium botulinum* Type C and D Neurotoxins Can Be Used As an Effective Vaccine," *Microbiol. Immunol.* 51(4): 445-455 (2007); LaPenotiere et al., "Expression of a Large, Nontoxic Fragment of *Botulinum* Neurotoxin Serotype A and Its Use As an Immunogen," *Toxicon* 33(10):1383-1386 (1995); Clayton et al., "Protective Vaccination with a Recombinant Fragment of *Clostridium botulinum* Neurotoxin Serotype A Expressed From A Synthetic Gene In *Escherichia coli*," *Infect. Immun.* 63(7):2738-2742 (1995); Byrne et al., "Purification, Potency, and Efficacy of the *Botulinum* Neurotoxin Type A Binding Domain from *Pichia pastoris* As a Recombinant Vaccine Candidate," *Infect Immun.* 66(10): 4817-4822 (1998); Lee et al., "Candidate Vaccine Against *Botulinum* Neurotoxin Serotype A Derived From a Venezuelan Equine Encephalitis Virus Vector System," *Infect. Immun.* 69(9):5709-5715 (2001); Maddaloni et al., "Mucosal Vaccine Targeting Improves Onset of Mucosal and Systemic Immunity to *Botulinum* Neurotoxin A," *J. Immunol.* 177(8): 5524-5532 (2006); Yu et al., "The Recombinant He Subunit of *Clostridium botulinum* Neurotoxin Serotype A Is an Effective Botulism Vaccine Candidate," *Vaccine* 27(21):2816-2822 (2009); Boles et al., "Recombinant C Fragment of *Botulinum* Neurotoxin B Serotype (rBoNTB (HC)) Immune Response and Protection In the Rhesus Monkey," *Toxicon* 47(8):877-884 (2006); Zeng et al., "Protective Immunity Against Botulism Provided By a Single Dose Vaccination With an Adenovirus-Vectored Vaccine," *Vaccine* 25(43): 7540-7548 (2007); Xu et al., "An Adenoviral Vector-Based Mucosal Vaccine Is Effective In Protection Against Botulism," *Gene Ther.* 16(3):367-375 (2009); Byrne et al., "Fermentation, Purification, and Efficacy of a Recombinant Vaccine Candidate Against *Botulinum* Neurotoxin Type F From *Pichia pastoris*," *Protein Expr. Purif.* 18(3):327-337 (2000); Holley et al., "Cloning, Expression and Evaluation of a Recombinant Sub-Unit Vaccine Against *Clostridium botulinum* Type F Toxin," *Vaccine* 19(2-3):288-297 (2000); Foynes et al., "Vaccination Against Type F *Botulinum* Toxin using Attenuated *Salmonella enterica* var *typhimurium* Strains Expressing the BoNT/F H(C) Fragment," *Vaccine* 21(11-12): 1052-1059 (2003); Yu et al., "Evaluation of a Recombinant He of *Clostridium botulinum* Neurotoxin Serotype F As an Effective Subunit Vaccine," *Clin. Vaccine Immunol.* 15(12): 1819-1823 (2008)). Recombinant $HC_C$ was additionally demonstrated to retain the ability to transcytose epithelia, thereby providing effective immunogen delivery by inhalation (Baldwin et al., "Subunit Vaccine Against the Seven Serotypes of Botulism," *Infect. Immun.* 76(3):1314-131 (2008)). Enzymatically active and inactive recombinant LC derivatives have also been expressed (Kurazono et al., "Minimal Essential Domains Specifying Toxicity of the Light Chains of Tetanus Toxin and *Botulinum* Neurotoxin Type A," *J. Biol. Chem.* 267(21):14721-14729 (1992); Rigoni et al., "Site-Directed Mutagenesis Identifies Active-Site Residues of the Light Chain of *Botulinum* Neurotoxin Type A," *Biochem. Biophys. Res. Commun.* 288(5):1231-1237 (2001); Breidenbach et al., "Substrate Recognition Strategy for *Botulinum* Neurotoxin Serotype A," *Nature* 432:925-929 (2004); Fu et al., "Light Chain of *Botulinum* Neurotoxin Serotype A: Structural Resolution of a Catalytic Intermediate," *Biochemistry* 45:8903-8911 (2006); Silvaggi et al., "Structures of *Clostridium botulinum* Neurotoxin Serotype A Light Chain Complexed with Small-Molecule Inhibitors Highlight Active-Site Flexibility," *Chem. Biol.* 14(5):533-542 (2007); Kumaran et al., "Structure- and Substrate-Based Inhibitor Design for *Clostridium botulinum* Neurotoxin Serotype A," *J. Biol. Chem.* 283:18883-18891 (2008); Zhou et al., "Expression and Purification of the Light Chain of *Botulinum* Neurotoxin A: A Single Mutation Abolishes Its Cleavage of SNAP-25 and Neurotoxicity After Reconstitution With the Heavy Chain," *Biochemistry* 34(46):15175-15181 (1995); Li et al., "High-Level Expression, Purification, and Characterization of Recombinant Type A *Botulinum* Neurotoxin Light Chain," *Protein Expr. Purif.* 17(3):339-344 (1999); Kadkhodayan et al., "Cloning, Expression, and One-Step Purification of the Minimal Essential Domain of the Light Chain of *Botulinum* Neurotoxin Type A," *Protein Expr. Purif.* 19(1):125-130 (2000); Ahmed et al., "Light Chain of *Botulinum* A Neurotoxin Expressed As an Inclusion Body From a Synthetic Gene Is Catalytically and Functionally Active," *J. Protein Chem.* 19(6):475-487 (2000); Li et al., "Probing the Mechanistic Role of Glutamate Residue In the Zinc-Binding Motif of Type A *Botulinum* Neurotoxin Light Chain," *Biochemistry* 39(9):2399-2405 (2000); Ahmed et al., "Enzymatic Autocatalysis of *Botulinum* A Neurotoxin Light Chain," *J. Protein Chem.* 20(3):221-231 (2001); Ahmed et al., "Factors Affecting Autocatalysis of *Botulinum* A Neurotoxin Light Chain," *Protein J.* 23(7):445-451 (2004); Segelke et al., "Crystal Structure of *Clostridium botulinum* Neurotoxin Protease In a Product-Bound State: Evidence for Noncanonical Zinc Protease Activity," *Proc. Natl. Acad. Sci.* (*USA*) 101(18): 6888-6893 (2004); Baldwin et al., "The C-Terminus of *Botulinum* Neurotoxin Type A Light Chain Contributes to Solubility, Catalysis, and Stability," *Protein Expr. Purif.* 37(1): 187-195 (2004); Ahmed et al., "Identification of Residues Surrounding the Active Site of Type A *Botulinum* Neurotoxin Important for Substrate Recognition and Catalytic Activity," *Protein J.* 27(3):151-162 (2008)). These have been found to be non-toxic in vivo even when LC enzymatic activity was preserved, because the presence of disulfide-bonded HC is required for BoNT targeting. The LC expressed as a separate entity, or as part of a holotoxoid, is less immunogenic than HC (Smith et al., "Sequence Variation Within *Botulinum* Neurotoxin Serotypes Impacts Antibody Binding and Neutralization," *Infect. Immun.* 73(9):5450-5457 (2005)).

To achieve LC conformations that more closely resemble the native toxin, and to generate a greater variety of antigens for vaccine design, the enzymatically active endopeptidase constructs representing LC fused to the full and C-terminally truncated version of $HC_N$ were also expressed in *E. coli* (Chaddock et al., "Expression and Purification of Catalytically Active, Non-Toxic Endopeptidase Derivatives of *Clostridium botulinum* Toxin Type A," *Protein Expr. Purif.* 25(2):219-228 (2002); Jensen et al., "Expression, Purification, and Efficacy of the Type A *Botulinum* Neurotoxin Catalytic Domain Fused to Two Translocation Domain Variants," *Toxicon* 41(6):691-701 (2003); Sutton et al., "Preparation of Specifically Activatable Endopeptidase Derivatives of *Clostridium botulinum* Toxins Type A, B, and C and Their Applications," *Protein Expr. Purif.* 40(1):31-41 (2005)). With subsequent improvements in the constructs and the expression system, these derivatives were used as building blocks to re-target specificity of *botulinum* neurotoxin A through substitution of native $HC_C$ with wheat germ agglutinin (WGA), NGF, and EGF (Chaddock et al., "Inhibition of Vesicular Secretion In Both Neuronal and Nonneuronal Cells By a Retargeted Endopeptidase Derivative of *Clostridium botulinum* Neurotoxin Type A," *Infect. Immun.* 68(5):2587-2593 (2000); Chaddock et al., "A Conjugate Composed of Nerve Growth Factor Coupled to a Non-Toxic Derivative of *Clostridium botulinum* Neurotoxin Type A Can Inhibit Neurotransmitter Release In vitro," *Growth Factors* 18(2):147-155 (2000); Duggan et al., "Inhibition of Release of Neurotransmitters From Rat Dorsal Root Ganglia By a Novel Conjugate of a *Clostridium botulinum* Toxin A Endopeptidase Fragment and *Erythrina cristagalli* Lectin," *J. Biol. Chem.* 277(38):34846-34852 (2002); Chaddock et al., "Retargeted Clostridial Endopeptidases: Inhibition of Nociceptive Neurotransmitter Release In vitro, and Antinociceptive Activity In In vivo Models of Pain," *Mov. Disord.* Suppl 8:S42-S47 (2004); Foster et al., "Re-Engineering the Target Specificity of Clostridial Neurotoxins—A Route to Novel Therapeutics," *Neurotox. Res.* 9(2-3):101-107 (2006)).

Several laboratories have reported expressing recombinant, full-length BoNTs in *E. coli*. Rummel et al., "Two Carbohydrate Binding Sites in the $HC_C$-Domain of Tetanus Neurotoxin Are Required for Toxicity," *J. Mol. Biol.* 326(3): 835-847 (2003); Rummel et al., "The $HC_C$-Domain of *Botulinum* Neurotoxins A and B Exhibits a Singular Ganglioside Binding Site Displaying Serotype Specific Carbohydrate Interaction," *Mol. Microbiol.* 51(3):631-643 (2004); Rummel et al., "Synaptotagmins I and II Act as Nerve Cell Receptors for *Botulinum* Neurotoxin G," *J. Biol. Chem.* 279(29):30865-30870 (2004); and Bade et al., "*Botulinum* Neurotoxin Type D Enables Cytosolic Delivery of Enzymatically Active Cargo Proteins to Neurons Via Unfolded Translocation Intermediates," *J. Neurochem.* 91(6):1461-1472 (2004), described the expression of full-length single chain BoNT/G, /D, /B, and /A in *E. coli*, either as the wt, or with a thrombin-specific cleavage site inserted between the HC and LC, or with the LC protease inactivated by a point mutation. Kiyatkin et al., "Induction of an Immune Response by Oral Administration of Recombinant *Botulinum* Toxin," *Infect. Immun.* 65:4586-4591 (1997), reported the expression of BoNT/C in *E. coli*, with three inactivating point mutations ($H_{229}$>G; $E_{230}$>T; $H_{233}$>N) in the LC protease, without the insertion of any specific proteolytic cleavage site between the LC and HC. There was no evidence that this BoNT/C single chain was processed into a disulfide-bonded heterodimer in vivo, but it was effective as an immunogen when orally administered. In all reports, the single chain holotoxin expressed in *E. coli* was not secreted into the culture medium or periplasm and had to be recovered from whole cell lysates. Expression problems in *E. coli* are associated with improper protein folding stemming from the reducing environment in the *E. coli* cytosol, the tendency of *E. coli* to segregate unfolded recombinant proteins within aggregates of inclusion bodies, proteolytic degradation, and a strong codon bias against AT-rich clostridial genes.

Recently, a recombinant, atoxic BoNT/A holotoxoid was expressed in the non-toxic strain of *Clostridium botulinum*, LNT01, with a yield of approximately 1 mg/L (Pier et al., "Recombinant Holotoxoid Vaccine Against Botulism," *Infect. Immun.* 76(1):437-442 (2008)). This recombinant holotoxoid had the mutations $R_{364}$>A and $Y_{366}$>F introduced into the LC (BoNT/$A^{RYM}$), and lacked the ability to cleave the substrate SNAP 25 in vitro. Mice were challenged with up to 1 μg of this derivative (approximately $3.3\times10^4$ mouse $LD_{50}$) and monitored for 96 hours. All mice survived challenge with 1 μg of single-chain or trypsin-nicked dichain of BoNT/$A^{RYM}$. Immunization with this holotoxoid effectively protected mice against lethal BoNT/A challenge. Although this report is encouraging, no information has yet been provided regarding the physiological trafficking of BoNT/$A^{RYM}$ in comparison with wt BoNT/A.

The most recent report describes the production of catalytically inactive BoNT/A holoprotein ($H_{223}$>A; $E_{224}$>A; $H_{227}$>A) in *P. pastoris* (ciBoNT/A HP) (Webb et al., "Production of Catalytically Inactive BoNT/A1 Holoprotein and Comparison With BoNT/A1 Subunit Vaccines Against Toxin Subtypes A1, A2, and A3," *Vaccine* 27(33):4490-4497 (2009)). The protein expressed from the synthetic gene, which was optimized for codon bias in the host, accumulated intracellularly. There was no introduction of an artificial cleavage site into the loop between LC and HC in the propeptide. The protein was purified in several steps with conventional ion exchange chromatographies. The yield of highly purified product was reported to be approximately 1 milligram from four grams of the frozen methylotrophic yeast. ciBoNT/A HP provided excellent protective immunity, not only against the homologous toxin, but also against two distinct toxin subtypes with significant amino acid divergence. Mice challenged with 50 μg of this derivative (approximately $1.7\times10^6$ mouse $LD_{50}$) and monitored for 240 hours did not display discernible signs of BoNT intoxication.

The selectivity of BoNT targeting to neurons has led several laboratories to consider using BoNT-based molecular vehicles for delivering therapeutic agents. Early work reported that the HC and LC of wt BoNTs could be separated, and that the wt HC could be reconstituted in vitro with either wt LC, or with recombinant LC which could carry point mutations, such as $His_{227}$>Tyr, which rendered the LC atoxic (Zhou et al., "Expression and Purification of the Light Chain of *Botulinum* Neurotoxin A: A Single Mutation Abolishes Its Cleavage of SNAP-25 and Neurotoxicity After Reconstitution With the Heavy Chain," *Biochemistry* 34(46):15175-15181 (1995); Maisey et al., "Involvement of the Constituent Chains of *Botulinum* Neurotoxins A and B In the Blockade of Neurotransmitter Release," *Eur. J. Biochem.* 177(3):683-691 (1988); Sathyamoorthy et al., "Separation, Purification, Partial Characterization and Comparison of the Heavy and Light Chains of *Botulinum* Neurotoxin Types A, B, and E," *J. Biol. Chem.* 260(19):10461-10466 (1985)). The reconstituted BoNT holotoxin derivatives had a severely reduced ability to transport LC into the neuronal cytosol, probably resulting from the harsh conditions required for HC-LC separation and the difficulty of renaturing the protein and reconstituting native disulfide bonds. Attempts have also been made to use isolated wt HC for targeted delivery, by chemically coupling dextran to the HC to provide sites for attaching fluorescent markers or therapeutic agents (Goodnough et al., "Development of a Delivery Vehicle for Intracellular Transport of *Botulinum* Neurotoxin Antagonists," *FEBS Lett.* 513:163-168 (2002)). Although this "semi-synthetic" BoNT derivative was internalized by neurons, the dextran remained localized to the endosomal compartment and the specificity of the uptake was uncertain. Direct chemical or biochemical attachment of cargo molecules to the HC of BoNTs may not be sufficient for achieving cytosolic delivery, because structural features associated with the toxin LC are required for translocation to the cytosol (Baldwin et al., "The C-Terminus of *Botulinum* Neurotoxin Type A Light Chain Contributes to Solubility, Catalysis, and Stability," *Protein Expr. Purif.* 37(1):187-195 (2004); Brunger et al., "*Botulinum* Neurotoxin Heavy Chain Belt as an Intramolecular Chaperone for the Light Chain," *PLoS Pathog.* 3(9):e113 (2007)). Moreover, when chemical methods are used to attach cargo to BoNT toxoids, cargo attachment is not sufficiently selective and, consequently, produces a heterogeneous population of derivatives. These problems limit the utility of chemically labeled BoNTs as probes for definitive demonstration of BoNT trafficking pathways.

Bade et al., "*Botulinum* Neurotoxin Type D Enables Cytosolic Delivery of Enzymatically Active Cargo Proteins to Neurons Via Unfolded Translocation Intermediates," *J. Neurochem.* 91(6):1461-1472 (2004), described recombinant full-length derivatives of BoNT/D as effective delivery vehicles which were expressed in *E. coli* with or without an inactivating mutation ($E_{230}$>A) to the LC protease. To evaluate the delivery of prototypic cargo proteins in neuronal cultures, green fluorescent protein ("GFP"), dihydrofolate reductase, firefly luciferase, or BoNT/A LC were fused to the amino terminus of the recombinant BoNT/D holotoxin. Delivery to the cytosol was evaluated by measuring cleavage of the BoNT/D cytoplasmic substrate, synaptobrevin. Dihydrofolate reductase and BoNT/A LC were reported to be effectively delivered. When luciferase or GFP were the cargo, delivery of the corresponding BoNT/D LC catalytic activity to the cytosol was significantly reduced, presumably due to the large size of the cargo (luciferase) or its rigidity (GFP) (Brejc et al., "Structural Basis for Dual Excitation and Photoisomerization of the *Aequorea victoria* Green Fluorescent Protein," *Proc. Natl. Acad. Sci.* (*USA*) 94(6):2306-1231 (1997); Palm et al., "The Structural Basis for Spectral Variations in Green Fluorescent Protein," *Nat. Struct. Biol.* 4(5): 361-365 (1997)).

It has proven particularly difficult to successfully engineer translocation of recombinant toxin LCs from an endosomal compartment to the cytosol. This translocation requires acidification of the lumenal milieu, either to trigger a conformational change in the BoNT heterodimer or to enable its interaction with a translocation mediator (Brunger et al., "*Botulinum* Neurotoxin Heavy Chain Belt as an Intramolecular Chaperone for the Light Chain," *PLoS Pathog.* 3(9):e113 (2007); Kamata et al., "Involvement of Phospholipids In the Intoxication Mechanism of *Botulinum* Neurotoxin," *Biochim. Biophys. Acta.* 1199(1):65-68 (1994); Tortorella et al., "Immunochemical Analysis of the Structure of Diphtheria Toxin Shows all Three Domains Undergo Structural Changes at Low pH," *J. Biol. Chem.* 270(46):27439-27445 (1995); Tortorella et al., "Immunochemical Analysis Shows All Three Domains of Diphtheria Toxin Penetrate Across Model Membranes," *J. Biol. Chem.* 270(46):27446-27452 (1995)). A requirement for cooperation between the BoNT LC and the translocation domain of the HC is supported by evidence demonstrating that a decapeptide motif, common to the $HC_N$ of several BoNT serotypes as well as to diphtheria and anthrax toxins, is required for successful translocation of the LC to the cytosol (Ratts et al., "A Conserved Motif in Transmembrane Helix 1 of Diphtheria Toxin Mediates Catalytic Domain Delivery to the Cytosol," *Proc. Natl. Acad. Sci.* (*USA*) 102(43):15635-15640 (2005)). Future development of BoNTs as carrier vehicles will require a deeper understanding of how the LC itself, and its interaction with $HC_N$, contributes to this mechanism.

Although efforts to express recombinant BoNTs have succeeded in producing effective immunogens, which in some cases are competent for epithelial transcytosis, these efforts have not produced recombinant proteins with the structural features required for targeting the neuronal cytosol with the efficiency of wt toxins. These limitations emphasize the importance of selecting an expression system capable of producing full-length BoNT derivatives that retain native toxin structure, disulfide bonding, and physiological trafficking. Also, work from multiple laboratories has clarified how the structural domains of wt *botulinum* neurotoxin A (BoNT/A) disable neuronal exocytosis, but important questions remain unanswered. Because BoNT/A intoxication disables its own uptake, wt light chain does not accumulate in neurons at detectable levels.

The present invention is directed to overcoming these and other limitations in the art.

SUMMARY OF THE INVENTION

One aspect of the present invention relates to an isolated *Clostridium botulinum* neurotoxin propeptide. The propeptide has a light chain region; a heavy chain region, where the light and heavy chain regions are linked by a disulfide bond; an intermediate region connecting the light and heavy chain regions and comprising a highly specific protease cleavage site which has three or more specific adjacent amino acid residues that are recognized by the highly specific protease in order to enable cleavage; and a peptide sequence to enable site-specific attachment of cargo, where the peptide sequence is positioned upstream of the light chain region and is separated from the N-terminus of the light chain region by an amino acid spacer sequence.

Another aspect of the present invention relates to an isolated nucleic acid molecule encoding the *Clostridium botulinum* neurotoxin propeptide of the present invention as well as expression systems and host cells containing this nucleic acid molecule.

A further aspect of the present invention relates to an isolated, physiologically active *Clostridium botulinum* neurotoxin produced by cleaving the *Clostridium botulinum* neurotoxin propeptide of the present invention. The propeptide is cleaved at the highly specific protease cleavage site. The light and heavy chain regions are linked by a disulfide bond.

Yet another aspect of the present invention relates to a method of expressing a recombinant physiologically active *Clostridium botulinum* neurotoxin. This method involves providing a nucleic acid construct having a nucleic acid molecule encoding a *Clostridium botulinum* neurotoxin propeptide of the present invention. The nucleic acid construct has a heterologous promoter operably linked to the nucleic acid molecule and a 3' regulatory region operably linked to the nucleic acid molecule. The nucleic acid construct is introduced into a host cell under conditions effective to express the physiologically active *Clostridium botulinum* neurotoxin.

A further aspect of the present invention relates to a treatment method. This method involves providing the isolated *Clostridium botulinum* neurotoxin of the present invention, where the cargo comprises a therapeutic agent and administering the isolated *Clostridium botulinum* neurotoxin to an individual in need of treatment under conditions effective to provide treatment to the individual.

Another aspect of the present invention relates to a method of detecting *Clostridium botulinum* neurotoxin trafficking. This method involves expressing a recombinant physiologically active *Clostridium botulinum* neurotoxin as described herein. A fluorophore is coupled to the neurotoxin. Trafficking of the neurotoxin is then detected by detecting one or more locations of the fluorophore.

A further aspect of the present invention relates to a method of detecting levels of neuronal activity. This method involves providing the isolated *Clostridium botulinum* neurotoxin of the present invention and administering the neurotoxin to an individual or a tissue sample. The method further involves detecting location of the neurotoxin, where detection of the neurotoxin at a specific site in the individual or tissue sample indicates an increased level of activity of neurons at that site.

The invention described herein relates to the design, expression, and purification of recombinant, full length, BoNT heterodimers that retain all key structural elements required for native BoNT trafficking. Moreover, the expression constructs have been designed to contain a short peptide sequence that enables site selective attachment of cargo molecules using mild enzymatic conditions that do not contribute to protein denaturation. Because the BoNT derivatives of the present invention contain point mutations that inactivate the LC protease, they will be capable of accumulating in neurons at higher levels than wt BoNT, which will improve their efficiency for trafficking studies, cargo delivery, detection of neuronal activity, and therapeutic use. Using small molecule fluorophores as prototypic cargo, these derivatives provide unique molecular tools for studying the sequential steps in BoNT translocation and targeting events, and for defining the limits of the potential cargo that can be delivered to the neuronal cytoplasm with the use of this system for site-specific cargo attachment.

A series of BoNT/A derivatives have been designed, expressed, and purified that retain the wild type features required for native trafficking. For example, BoNT/A1ad$^{ek}$ and BoNT/A1ad$^{tev}$ are full length derivatives rendered atoxic through double point mutations in the LC protease ($E_{224}$>A and $Y_{366}$>A). ΔLC-peptide -BoNT/A$^{tev}$ and ΔLC-GFP-BoNT/A$^{tev}$ are derivatives where the catalytic portion of the LC is replaced with a short peptide or with GFP plus the peptide. In all four of these derivatives, the S6 peptide sequence GDSLSWLLRLLN (SEQ ID NO:2) has been fused to the N-terminus of the proteins to enable site-specific attachment of cargo using Sfp phosphopantetheinyl transferase. Cargo can be attached in a manner that provides a homogeneous derivative population rather than a polydisperse mixture of singly and multiply-labeled molecular species. All four of these exemplary derivatives contain an introduced cleavage site for conversion into disulfide-bonded heterodimers. These constructs were expressed in a baculovirus system and the proteins were secreted into culture medium and purified to homogeneity in yields ranging from 1 to 30 mg per liter. Derivatives of the present invention provide unique tools to study toxin trafficking in vivo, and to assess how the structure of cargo linked to the heavy chain influences delivery to the neuronal cytosol. Moreover, they enable engineering of BoNT-based molecular vehicles that can target therapeutic agents to the neuronal cytoplasm.

BRIEF DESCRIPTION OF THE DRAWINGS

FIGS. 2A-B show BoNT/Aad$^{ek}$ propeptide purification. A reduced 12% SDS PAGE was stained with Coomassie BB R-250. FIG. 2A: TALON® chromatography purification: lane 1, wt BoNT/A, control; lane 2, unfractionated sample of concentrated and dialyzed Sf-900 II medium containing secreted propeptide BoNT/Aad$^{ek}$ prior to loading on column; lane 3, column flow through; lane 4, wash 1, loading buffer; lane 5, wash 2, loading buffer with 20 mM imidazole; lane 6, elution, loading buffer with 200 mM imidazole. FIG. 2B: StrepTactin agarose chromatography: lane 1, sample of concentrated and dialyzed fraction from FIG. 2A, lane 6 prior to loading on column; lane 2, flow through; lanes 3-7, washes with loading buffer; lanes 8-12, elutions with loading buffer and 3 mM desthiobiotin; lane 13, wt BoNT/A, control.

FIGS. 3A-B show processing of BoNT/Aad$^{ek}$ propeptide to heterodimer by proteolytic cleavage with recombinant enterokinase (rEK). One microgram of BoNT/Aad$^{ek}$ propeptide per lane was treated with 0-5 U rEK at 16° C. for 12 hours, separated by 12% SDS PAGE, and stained with Coomassie BB R-250. FIG. 3A: non-reduced samples. FIG. 3B: samples reduced by addition of β-mercaptoethanol. Lane 1, no rEK;

Figure 1:
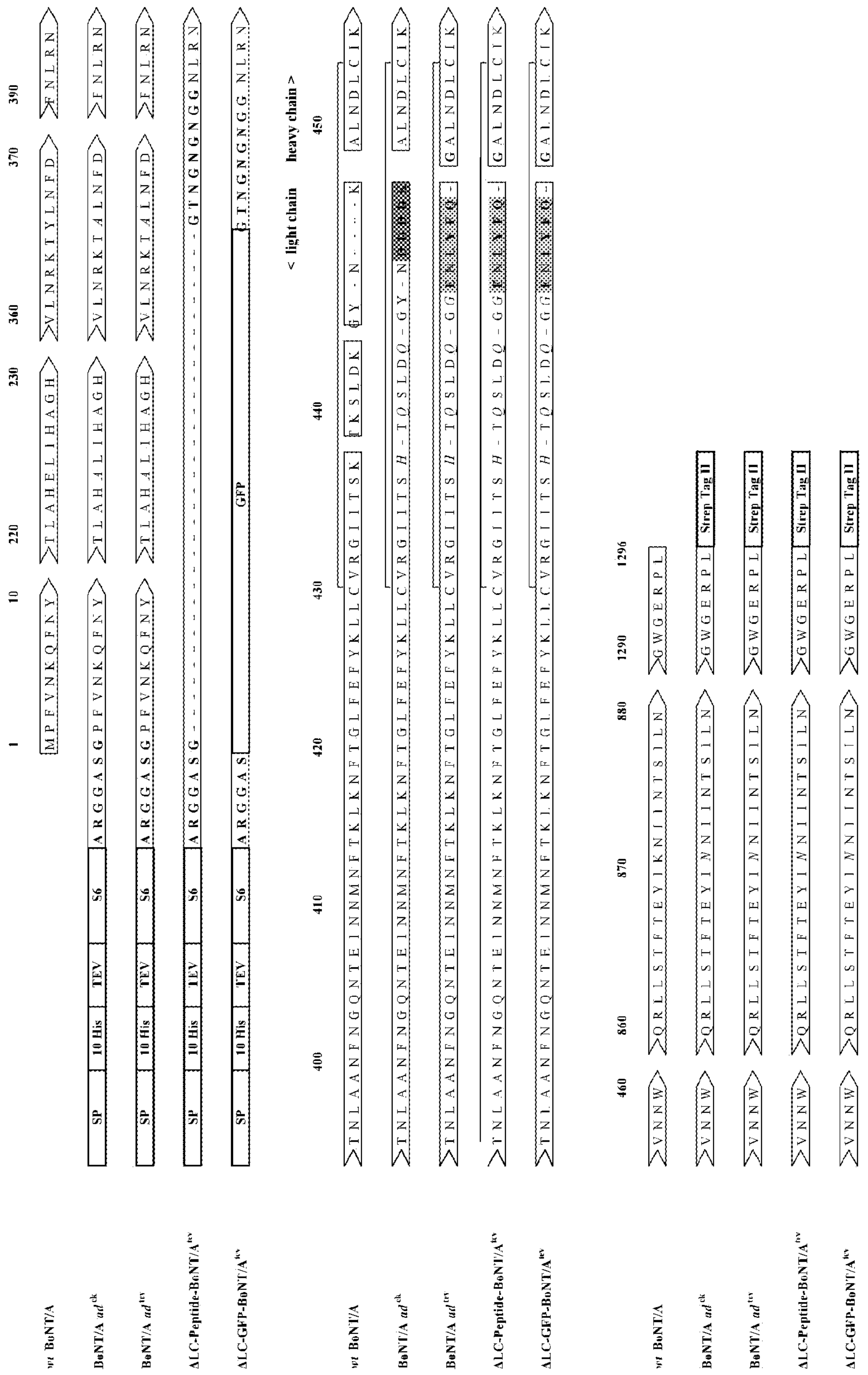
FIG. 1 is an amino acid sequence alignment showing features of expressed BoNT/A derivatives, including BoNT/Aad$^{ek}$ (SEQ ID NO:3), BoNT/Aad$^{tev}$ (SEQ ID NO:4), ΔLC-Peptide-BoNT/A$^{tev}$ (SEQ ID NO:5), and ΔLC-GFP-BoNT/A$^{tev}$ (SEQ ID NO:6), according to several embodiments of the present invention, in comparison with wild type BoNT A (GenBank Accession No. ABP48106 (SEQ ID NO:7)). Space between arrowheads and arrow tails represent regions of sequence identity omitted for simplicity. Numbers in the upper row correspond to amino acid residues in wt BoNT/A. Residues that are identical in all proteins are shown in regular type. Introduced mutations are shown in italics. Added amino acids are shown in bold. A signal peptide for insect cell secretion of the expressed derivatives into medium is indicated by "SP". Tags used for affinity chromatography are indicated: polyhistidine tag is indicated by "10 His"; StrepTag II is indicated by "StrepTag II". "TEV" and the amino acid sequence on light shading represent tobacco etch virus protease recognition (TEV) sequence. Amino acids on dark shading represent an enterokinase recognition sequence. "S6" identifies a peptide tag used for site-specific attachment of cargo to the expressed proteins. "GFP" represents a portion of green fluorescent protein. The five proteins are aligned to illustrate homology between respective structural domains. Gaps have been introduced to facilitate the alignment. Spaces between rectangle-enclosed sequences represent sites of proteolytic cleavage. The disulfide bridge between residues of the light and heavy chains are shown as long horizontal brackets.

lane 2, 0.001 U rEK; lane 3, 0.01 U rEK; lane 4, 0.1 U rEK; lane 5, 1 U rEK; lane 6, 5 U rEK; lane 7, wt BoNT/A, control.

FIG. 4 shows removal of 10-His tag from BoNT/Aad$^{ek}$ propeptide by treatment with AcTEV. BoNT/Aad$^{ek}$ was either treated with buffer (odd lane numbers) or AcTEV protease (even lane numbers; 1 U per microgram, 30° C.; see Examples infra for details) for the times indicated: lanes 1 and 2, one hour; lanes 3 and 4, two hours; lanes 5 and 6, three hours; lanes 7 and 8, four hours; lanes 9 and 10, six hours. Samples were loaded on the 12% SDS PAGE in the presence of β-mercaptoethanol, separated, and transferred to nitrocellulose. Western blot was probed with HRP-coupled anti-His MAb (Santa Cruz, H-3 His probe, Cat #sc-8036 HRP). The low MW band (approximately 30 kDa) in even lanes represents AcTEV protease which was supplied by Invitrogen as a 6-His tagged recombinant enzyme.

FIGS. 5A-B show in vitro fluorescent labeling of AcTEV-treated and rEK-treated BoNT/Aad$^{ek}$ with Sfp phosphopantetheinyl transferase and CoA 547. Lanes 1-4, unreduced samples; lanes 5-8, samples reduced by addition of β-mercaptoethanol. Lanes 1, 3, 5, 7: 0.02 μg BoNT/Aad$^{ek}$; lanes 2, 4, 6, 8: 0.1 μg BoNT/Aad$^{ek}$. FIG. 5A: 10.5-14% Criterion gel (Bio-Rad) stained with Bio-Safe Coomassie (Bio-Rad). FIG. 5B: Western blot of gel shown in FIG. 5A scanned on a Typhoon 9500 scanner (GE Healthcare) using 300V PMT, 532/580 nm excitation/emission filter set (green).

FIG. 6 is an ESI Q-TOF MS/MS spectrum of the C-terminal tryptic peptide isolated from enterokinase-processed BoNT/Aad$^{ek}$ LC under reducing conditions. The b and y ion series have been included at the top of FIG. 6 to identify the peptide fragment peaks found in the spectrum, where the position of vertical bars separating each amino acid(s) correspond to position of the respective ion m/z within the spectrum. Only the most intense peaks from y series have been labeled for simplicity.

FIGS. 7A-C are MALDI mass spectra and ESI Q-TOF MS/MS spectra of the tryptic dipeptide with internal disulfide bridge linking light and heavy chains of enterokinase-processed BoNT/Aad$^{ek}$. FIG. 7A is a MALDI-TOF mass spectrum of an in-gel tryptic digest of the enterokinase-processed BoNT/Aad$^{ek}$ LC, separated and isolated from SDS PAGE run in the presence of DTT. FIG. 7B is a MALDI-TOF mass spectrum of an in-gel tryptic digest of the enterokinase-processed BoNT/Aad$^{ek}$ separated and isolated from SDS PAGE run without reducing agent. A peak at m/z 1489.84 matched the predicted m/z of the dipeptide with internal disulfide bridge. FIG. 7C is an ESI Q-TOF MS/MS spectrum of the dipeptide with m/z 1489.8 shown in FIG. 7B, confirming presence of the S—S bond in the dipeptide. The b and y ion series have been included at the top of the panel to identify the peptide fragment peaks found in the spectrum, where the position of vertical bars separating each amino acid(s) correspond to position of the respective ion m/z within the spectrum. Only the most intense peaks have been labeled for clarity.

FIGS. 8A-C show BoNT/Aad$^{tev}$, ΔLC-Peptide-BoNT/A$^{tev}$, and ΔLC -GFP-BoNT/A$^{tev}$ expressed in the baculovirus system, purified by metal chelate and StrepTactin affinity chromatography, and processed with AcTEV. Lanes 1-6: unreduced samples; lanes 7-12: samples reduced by addition of β-mercaptoethanol. Lanes 1, 2, 7, 8: BoNT/Aad$^{tev}$; lanes 3, 4, 9, 10: ΔLC-Peptide-BoNT/A$^{tev}$; lanes 5, 6, 11, 12: ΔLC-GFP-BoNT/A$^{tev}$. FIG. 8A: 10.5-14% Criterion gel (Bio-Rad) stained with Bio-Safe Coomassie (Bio-Rad); odd lanes: 0.3 μg samples; even lanes: 1.0 μg samples. FIG. 8B: Western blot probed with polyclonal antibody Pol001 raised against BoNT/A holotoxoid (Staten Serum Institut, Denmark); odd lanes: 3 ng samples; even lanes: 10 ng samples. FIG. 8C, Western blot probed with monoclonal antibody against GFP (Clontech); odd lanes: 3 ng samples; even lanes: 10 ng samples.

FIG. 9 is an illustration of the chemical synthesis of cargo attachment to *Clostridium botulinum* propeptides using the S6 peptide of SEQ ID NO:2 (i.e., GDSLSWLLRLLN).

FIG. 10 is a Western blot illustrating that BoNT/A ad competes with wt BoNT/A for binding to receptors and protects SNAP 25 from cleavage. Rat spinal cord cells were exposed to the indicated concentration of BoNT/A ad in ice-cold culture medium supplemented with 56 mM KCl and 0.5 mM $CaCl_2$ for 15 min. wt BoNT/A in the same ice-cold culture medium was then added and incubation was continued on ice for an additional 15 min. Cells were then washed twice with ice-cold culture medium, fresh culture medium was added, and cells were incubated at 37° C. for 3 hours. Cells were harvested in SDS sample buffer, and lysates were analyzed by Western blot using anti-SNAP 25 antibody (Synaptic Systems).

FIGS. 11A-C are images of immunostaining that show symptoms of BoNT/A ad poisoning are concurrent with BoNT/A ad LC accumulation at the neuromuscular junction in vivo. 6 week old mice were injected ip with 1 μg of BoNT/A ad. The first signs of physiological effect of BoNT/A ad were observed ~4 hours after injection (low movement activity, ruffled fur, heavy breathing), and were pronounced at the time of animal euthanasia 12 hours after injection. *Triangularis sterni* nerve-muscle preparations were stained with primary antibody and probed with AlexaFluor 555-conjugated secondary antibody and Alexa-Fluor 488-conjugated α-bungarotoxin. FIG. 11A illustrates the postsynaptic acetylcholine receptors; FIG. 11B is the BoNT/A LC (Mab F1-40); FIG. 11C is a merge of images shown in FIGS. 11A and B. The scale bar is 5 μm.

FIG. 12 is a series of images of immunostaining showing continuous uptake of BoNT/A ad in the primary culture of rat hippocampal neurons. Row 1 shows results after culture was incubated with 15 nM BoNT/A ad for 30 mins. Row 2 shows results after culture was incubated with the same concentration of BoNT/A ad for 90 minutes, followed by 30 min chase with the BoNT/A ad-free medium. Row 3 shows results after culture was incubated with the same concentration of BoNT/A ad for 90 minutes, followed by 90 minute chase with BoNT/A ad-free medium. At the end of incubation time, cells were washed and processed for immunocytochemical staining. The staining was as follows: Column A: Primary—tau mouse monoclonal IgG2b; secondary—AlexaFluor 488 conjugated donkey-anti-IgG2b-mouse; Column B: Primary—mouse-anti-BoNT/A LC monoclonal IgG1 (F1-40), secondary—AlexaFluor 555 conjugated goat-anti-IgG1-mouse; Column C: Primary rabbit-anti -SNAP 25 polyclonal antibodies, secondary—AlexaFluor 647 conjugated goatanti -rabbit IgG. Column D is a merged image of the staining from three (Row 1 and 2), or two (Row 3) channels. Tau from Row 3 is omitted to better visualize the co-staining pattern with internalized LC ad and SNAP 25. The scale bar is equal to 10 μm.

FIGS. 13A-C are images of Western blots showing that LC ad binds SNAP 25 when BoNT/A ad is internalized by rat spinal cord cells. Cultured E18 rat spinal cord cells were either (1) untreated; (2) treated with 30 nM BoNT/A ad; or (3) treated with cross-linked/inactivated 30 nM BoNT/A ad. Following 8 h treatment, cells were washed and fractionated according to Bernocco et al., "Sequential Detergent Fractionation of Primary Neurons for Proteomics Studies," *Proteomics* 8 (5):930-938 (2008), which is hereby incorporated by reference in its entirety. Cytosolic extracts were immunoprecipitated with anti-SNAP 25 antibodies, and protein A and Protein G magnetic beads and separated by reduced SDS PAGE. FIG. 13A shows results from input proteins probed with anti-BoNT/A polyclonal antibodies (Staten Serum Institut, Denmark). FIGS. 13B and C show the Western blot of immunoprecipitates. FIG. 13B shows results from probe with mouse monoclonal anti-LC; FIG. 13C shows results from probe with rabbit anti-SNAP 25.

FIGS. 14A and B are images showing internalization of palmitoylated ΔLC-GFP-BoNT/A in COS7 cells. Palmitoylated derivative (25 nM) was added to COS7 cells and cells were incubated for 5 minutes (FIG. 14A), or for 1 hour (FIG. 14B). Image scanning was performed on a Nikon LSM 510 confocal microscope equipped with argon laser, producing an excitation line of 488 nm. The scale bar is equal to 25 μm.

DETAILED DESCRIPTION OF THE INVENTION

One aspect of the present invention relates to an isolated *Clostridium botulinum* neurotoxin propeptide. The propeptide has a light chain region; a heavy chain region, where the light and heavy chain regions are linked by a disulfide bond; an intermediate region connecting the light and heavy chain regions and comprising a highly specific protease cleavage site which has three or more specific adjacent amino acid residues that are recognized by the highly specific protease in order to enable cleavage; and a peptide sequence to enable site-specific attachment of cargo, where the peptide sequence is positioned upstream of the light chain region and is separated from the N-terminus of the light chain region by an amino acid spacer sequence.

BoNT/A propeptide has two chains, a light chain of Mr ~50,000 and a heavy chain of Mr ~100,000, linked by a disulfide bond between $Cys_{429}$ and $Cys_{453}$. All seven BoNT serotype propeptides have a light chain region and a heavy chain region linked by a disulfide bond. Two essential Cys residues, one adjacent to the C-terminus of the light chain, and a second adjacent to the N-terminus of the heavy chain are present in all seven BoNT serotypes. These two Cys residues form the single disulfide bond holding the HC and LC polypeptides together in the mature neurotoxin. This disulfide bond enables the mature neurotoxin to accomplish its native physiological activities by permitting the HC and LC to carry out their respective biological roles in concert. The intermediate region (i.e., $Lys_{438}$-$Lys_{448}$ of BoNT/A) identifies the amino acids eliminated during maturation of wild-type BoNT/A, and believed to be excised by a protease endogenous to the host microorganism. This cleavage event generates the biologically active BoNT HC-LC dimer.

All seven BoNT serotypes contain Lys or Arg residues in the intermediate region, which make the propeptides susceptible to activation by trypsin. Native BoNT/A propeptide recovered from young bacterial cultures can be activated by trypsinolysis, with production of intact, S—S bound light and heavy chain. Though multiple additional trypsin-susceptible sites are present in the propeptides, they are resistant to proteolysis due to their spatial positions within the native toxin molecule (Dekleva et al., "Nicking of Single Chain *Clostridium botulinum* Type A Neurotoxin by an Endogenous Protease," *Biochem. Biophys. Res. Commun.* 162:767-772 (1989); Lacy et al., "Crystal Structure of *Botulinum* Neurotoxin Type A and Implications for Toxicity," *Nat. Struct. Biol.* 5:898-902 (1998), which are hereby incorporated by reference in their entirety). A second site in the native propeptide of several BoNT serotypes can be susceptible to trypsin cleavage when subjected to higher enzyme concentrations or incubation times (Chaddock et al., "Expression and Purification of Catalytically Active, Non-Toxic Endopeptidase Derivatives of *Clostridium botulinum* Toxin Type A," *Protein Expr. Purif.* 25:219-228 (2002), which is hereby incorporated by reference in its entirety). This trypsin-susceptible site is located in the region adjacent to the toxin receptor binding domain. This region of the HC peptide is found to be exposed to solvent in BoNT serotypes for which information is available on their 3-D crystal structure (Lacy et al., "Crystal Structure of *Botulinum* Neurotoxin Type A and Implications for Toxicity," *Nat. Struct. Biol.* 5:898-902 (1998); Swaminathan et al., "Structural Analysis of the Catalytic and Binding Sites of *Clostridium botulinum* Neurotoxin B," *Nat. Struct. Biol.* 7:693-699 (2000), which are hereby incorporated by reference in their entirety).

Propeptides of the present invention have an intermediate region connecting the light and heavy chain regions which has a highly specific protease cleavage site and no low-specificity protease cleavage sites. For purposes of the present invention, a highly specific protease cleavage site has three or more specific adjacent amino acid residues that are recognized by the highly specific protease in order to permit cleavage (e.g., an enterokinase cleavage site or a TEV recognition sequence). In contrast, a low-specificity protease cleavage site has two or less adjacent amino acid residues that are recognized by a protease in order to enable cleavage (e.g., a trypsin cleavage site).

In all seven BoNT serotypes, the amino acid preceding the N-terminus of the heavy chain is a Lys or Arg residue which is susceptible to proteolysis with trypsin. This trypsin-susceptible site can be replaced with a five amino acid enterokinase cleavage site (i.e., DDDDK (SEQ ID NO:8)) upstream of the heavy chain's N-terminus, as illustrated by the amino acids on the dark shading in FIG. 1. Alternatively, the trypsin-susceptible site can be replaced with a TEV recognition sequence, as shown by the amino acid sequence on light shading in FIG. 1. Either of these modifications enables standardization activation with specific enzymes. In serotypes A and C, additional Lys residues within this region may be mutated to either Gln or His, thereby eliminating additional trypsin-susceptible sites which might result in undesirable non-specific activation of the toxin. Trypsin-susceptible recognition sequences also occur upstream of the heavy chain's receptor-binding domain in serotypes A, E, and F. This region's susceptibility to proteolysis is consistent with its exposure to solvent in the toxin's 3-D structure, as shown by X-ray crystallography analysis. Therefore, in serotypes A, E, and F, the susceptible residues are modified to Asn.

Propeptides of the present invention also include a cargo attachment peptide sequence to enable site-specific attachment of cargo (i.e., a cargo attachment peptide sequence or cargo attachment peptide). Examples of cargo attachment peptides include an S6 sequence having a sequence according to SEQ ID NO:2. The S6 sequence enables site specific attachment of cargo using Sfp phosphopantetheinyl transferase from *B. subtilis*, which targets the $S_3$ amino acid of SEQ ID NO:2 as a substrate. Zhou et al., "Genetically Encoded Short Peptide Tags for Orthogonal Protein Labeling by Sfp and AcpS Phosphopantetheinyl Transferases," *ACS Chem. Biol.* 2(5): 337-346 (2007), which is hereby incorporated by reference in its entirety. In addition, an N-terminally placed 12 aa sequence GDSLDMLEWSLM ("A1") (SEQ ID NO:45) enables site specific attachment of cargo using AcpS phosphopantetheinyl transferase from *E. coli*, which targets the $S_3$ amino acid of SEQ ID NO:45. Zhou et al., "Genetically Encoded Short Peptide Tags for Orthogonal Protein Labeling by Sfp and AcpS Phosphopantetheinyl Transferases," *ACS*

*Chem. Biol.* 2(5): 337-346 (2007), which is hereby incorporated by reference in its entirety. Another example of a cargo attachment peptide sequence is the N-terminally placed 8 amino acid sequence DSLDMLEW ("A4") (SEQ ID NO:46) that enables site specific attachment of cargo using AcpS phosphopantetheinyl transferase from *E. coli*, which targets the $S_2$ amino acid SEQ ID NO:46 as a substrate. Zhou et al., "An Eight Residue Fragment of an Acyl Carrier Protein Suffices for Post-translational Introduction of Fluorescent Pantetheinyl Arms in Protein Modification in vitro and in vivo," *J. Am. Chem. Soc.* 130(30): 9925-9930 (2008), which is hereby incorporated by reference in its entirety. Yet another example is an N-terminally placed amino acid sequence (e.g., MSGLVDIFEAQKIEWH (SEQ ID NO:47)) that enables site-specific attachment of cargo using biotin ligase, which targets the $K_{12}$ amino acid of SEQ ID NO:47 as a substrate. The N-terminally placed 7 amino acid sequence PKPQQFM ("Q tag") (SEQ ID NO:48) enables site-specific attachment of cargo using transglutaminase, which targets the QQ amino acids of SEQ ID NO:48 as a substrate. Lin et al., "Transglutaminase-catalyzed Site-specific Conjugation of Small-molecule Probes to Proteins in vitro and on the Surface of Living Cells," *J Am Chem Soc.* 128 (14): 4542-4543 (2006), which is hereby incorporated by reference in its entirety. The N-terminally placed 5 amino acid sequence GGGGG (SEQ ID NO:49) enables site specific attachment of cargo using sortase A from *S. aureus*, which targets the N-terminus of the $G_1$ amino acid of SEQ ID NO:49 as a substrate. Antos et al., "Site-specific N- and C-terminal Labeling of a Single Polypeptide Using Sortases of Different Specificity," *J. Am. Chem. Soc.* 131(31):10800-10801 (2009), which is hereby incorporated by reference in its entirety.

Propeptides of the present invention may include a signal peptide coupled to the cargo attachment peptide sequence, suitable to permit secreation of the neurotoxin propeptide from a eukaryotic cell to a medium. Coupling of a signal peptide sequence to the S6 peptide sequence is illustrated in the propeptides shown in FIG. 1 by the "SP" designation.

Propeptides of the present invention may additionally include a 10-His affinity tag positioned between and connecting the signal peptide to the peptide sequence. The designation "10 His" in FIG. 1 illustrates the placement of the polyhistidine tag.

Propeptides of the present invention may additionally include a TEV recognition sequence positioned between and connecting the 10-His affinity tag to the cargo attachment peptide. For example, as shown in FIG. 1 by the designation "TEV", a TEV sequence is positioned upstream of the S6 peptide sequence and downstream from the signal peptide.

Propeptides of the present invention may additionally include an 8 amino acid StrepTag II connected to the propeptide at the C-terminus (see FIG. 1, "StrepTag II").

In one embodiment, the entire catalytic domain of the light chain region has been removed from the isolated propeptide. According to this embodiment, the propeptide may have a fluorophore connected to the N-terminus of the light chain region.

Attachment of cargo to the propeptides of the present invention can be facilitated by the cargo attachment peptide sequence, an amino acid sequence that allows site-selective enzyme-specific attachment of cargo to the propeptide. For example, the chemistry involved in attaching cargo to the propeptide via the S6 peptide is illustrated in FIG. 9. Specifically, CoA derivatives, having the structure

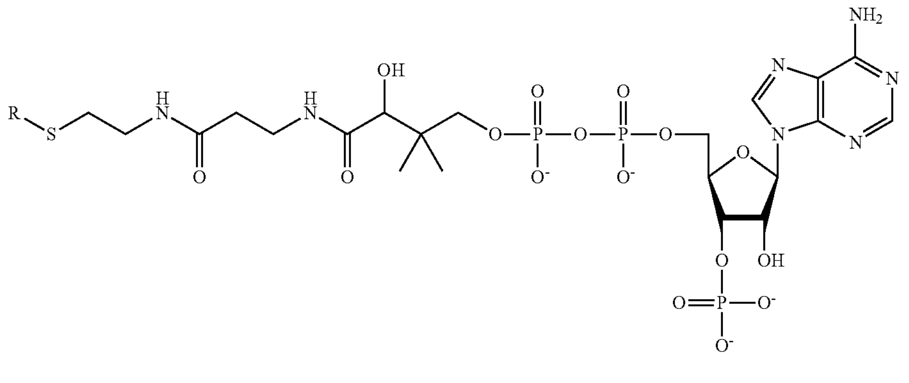

CoA Derivatives where R (i.e., the cargo) is any prosthetic group, can be biochemically coupled to CoA, with the resulting CoA adduct recognized as a substrate for Sfp phosphopantetheinyl transferase used for enzymatic labeling, as described in Zhou et al., "Genetically Encoded Short Peptide Tags for Orthogonal Protein Labeling by Sfp and AcpS Phosphopantetheinyl Transferases," *ACS Chemical Biology* 2(5):337-346 (2007), which is hereby incorporated by reference in its entirety.

Suitable cargo for attachment to propeptides of the present invention may include, without limitation, lipid moieties, therapeutic agents, marker molecules, and targeting agents.

Exemplary lipid moieties include fatty acids (e.g., saturated, unsaturated, greater than four carbon chain length, prostanoids, leukotienes, ecosanoids, etc.), neutral lipids (e.g., cholesterol and esters thereof, triglycerides, steroids, spermaceti (cetyl palmitate), waxes, fatty alcohols, etc.), phospholipids (e.g., phosphatidyl choline, phosphatidyl serine, ethanolamine, phosphatidyl inositol, platelet activating factor, fatty acid glycerol ethers, cardiolipids, etc.), and complex lipids (e.g., sphingolipids, ceramides, glycolipids, gangliosides, sulfolipids, etc.). In one particular embodiment, the lipid is selected from a group consisting of palmitoyl-CoA, C-22 aliphatic CoA, or cholesterol CoA. Incorporation of lipid moieties into the propeptide of the present invention anchors the propeptides to plasma membranes at the injection site and restricts its diffusion away from the site of intended action.

Exemplary therapeutic agents may include, without limitation, the peptide described in Zuniga et al., "A Potent Peptidomimetic Inhibitor of *Botulinum* Neurotoxin Serotype A Has a Very Different Conformation than SNAP-25 Substrate," *Structure* 16:1588-1597 (2008) (which is hereby incorporated by reference in its entirety), which is an effective BoNT inhibitor. Other therapeutic agents include any agent with a therapeutic target in, e.g., the neural cytosol including, without limitation, agents for treating neuropathic pain, Alzheimer's Disease, and virus inhibitors (e.g., HSV2 inhibitors).

Exemplary marker molecules include, without limitation, fluorophores having a photoluminescent property that can be detected and easily identified with appropriate detection equipment to permit neurotoxin trafficking studies. Exemplary fluorescent labels include, without limitation, fluorescent dyes, semiconductor quantum dots, lanthanide atom-containing complexes, and fluorescent proteins. The fluorophore used in the present invention is characterized by a fluorescent emission maxima that is detectable either visually or using optical detectors of the type known in the art.

Exemplary dyes include, without limitation, Cy2™, YO-PRO™-1, YOYO™-1, Calcein, FITC, FluorX™, Alexa™, Rhodamine 110, 5-FAM, Oregon Green™ 500, Oregon Green™ 488, RiboGreen™, Rhodamine Green™, Rhodamine 123, Magnesium Green™, Calcium Green™, TO-PRO™-1, TOTO®-1, JOE, BODIPY® 530/550, Dil, BODIPY® TMR, BODIPY® 558/568, BODIPY® 564/570, Cy3™, Alexa™ 546, TRITC, Magnesium Orange™, Phycoerythrin R&B, Rhodamine Phalloidin, Calcium Orange™, Pyronin Y, Rhodamine B, TAMRA, Rhodamine Red™, Cy3.5™, ROX, Calcium Crimson™, Alexa™ 594, TEXAS RED®, Nile Red, YO-PRO™-3, YOYO™-3, R-phycocyanin, C-Phycocyanin, TO -PRO™-3, TOTO®-3, DiD DilC(5), CyS™, Thiadicarbocyanine, and Cy5.5™. Other dyes now known or hereafter developed can similarly be used as long as their excitation and emission characteristics are compatible with a light source and non-interfering with other fluorophores that may be present.

Exemplary proteins include, without limitation, both naturally occurring and modified (i.e., mutant) green fluorescent proteins (Prasher et al., *Gene* 111:229-233 (1992); PCT Application WO 95/07463, which are hereby incorporated by reference in their entirety) from various sources such as *Aequorea* and *Renilla;* both naturally occurring and modified blue fluorescent proteins (Karatani et al., *Photochem. Photobiol.* 55(2):293-299 (1992); Lee et al., *Methods Enzymol.* (*Biolumin. Chemilumin.*) 57:226-234 (1978); Gast et al., *Biochem. Biophys. Res. Commun.* 80(1):14-21 (1978), which are hereby incorporated by reference in their entirety) from various sources such as *Vibrio* and *Photobacterium;* and phycobiliproteins of the type derived from cyanobacteria and eukaryotic algae (Apt et al., *J. Mol. Biol.* 238:79-96 (1995); Glazer, *Ann. Rev. Microbiol.* 36:173-198 (1982); Fairchild et al., *J. Biol. Chem.* 269:8686-8694 (1994); Pilot et al., *Proc. Natl. Acad. Sci. USA* 81:6983-6987 (1984); Lui et al., *Plant Physiol.* 103:293-294 (1993); Houmard et al., *J. Bacteriol.* 170:5512-5521 (1988), which are hereby incorporated by reference in their entirety), several of which are commercially available from ProZyme, Inc. (San Leandro, Calif.). Other fluorescent proteins now known or hereafter developed can similarly be used as long as their excitation and emission characteristics are compatible with the light source and non-interfering with other fluorophores that may be present.

Exemplary lanthanide atoms include, without limitation, Ce, Pr, Nd, Pm, Sm, Eu, Gd, Tb, Dy, Ho, Er, Tm, Yb, and Lv. Of these, Nd, Er, and Tb are preferred because they are commonly used in imaging applications.

Exemplary targeting agents may include, without limitation, agents that direct trafficking of *Botulinum* neurotoxins to specific neurons and other cell types. Ligands for cell receptors (e.g., NGF, EGF, and others) and antibodies against receptors may also be used as targeting agents. Selectively incorporating lipid moieties into recombinant BoNT/A derivatives by enzymatic coupling to the S6 peptide tag, in order to restrict the diffusion of the protein adduct from the site of injection, is described herein in the Examples.

Propeptides of the present invention may include a disabling mutation in an active metalloprotease site of the propeptide.

As noted supra, propeptides of the present invention may have a cargo attachment peptide sequence to enable site-specific attachment of cargo. The cargo attachment peptide is positioned upstream of the light chain region and is separated from the N-terminus of the light chain region by an amino acid spacer sequence. The amino acid spacer (or linker) sequence may comprise at least 2, 3, 4, 5, 6, 7, 8, 9, 10, 11, 12, 13, 14, 15, 16, 17, 18, 19, 20, 21-25, 26-30, 31-35, or 36-40, or more, amino acid residues. The amino acid spacer (or linker) sequence serves to preserve and protect conformational independence of the cargo attachment peptide and the *botulinum* neurotoxin. An exemplary amino acid spacer (or linker) sequence is shown in FIG. 1 (bold type) as the 7 amino acid spacer ARGGASG (SEQ ID NO:9).

Propeptides of the present invention may further include a neuron-specific protease cleavage site. In one embodiment, the cargo is attached at the N-terminus of the propeptide's light chain via a peptide linker carrying a neuron-specific protease cleavage site (e.g., a BACE1 cleavage site). In one embodiment, the neuron-specific cleavage site may be positioned between the cargo attachment peptide and the linker or spacer sequence. In one embodiment in which the cargo is a lipid moiety, the lipidated propeptide will remain anchored to the membrane until it is released by endogenous neuron-specific protease and will be internalized by interaction with endogenous neuronal receptors, leading to release of the active light chain into the neuronal cytoplasm. In non-neuronal cells, which are neuron-specific protease deficient, lipidated propeptide can only be internalized through a non-specific mechanism and directed into a degradation pathway, thereby contributing to removal of excess propeptide from the circulation.

Propeptides of the present invention may also possess a non-native motif in the light chain region that is capable of inactivating light chain metalloprotease activity in a toxic *Botulinum* neurotoxin, as described in U.S. Patent Application Publication No. 2006/0204524 to Ichtchenko et al., which is hereby incorporated by reference in its entirety.

In one embodiment, propeptides of the present invention have light and heavy chains that are not truncated. In another embodiment, the entire catalytic domain of the light chain has been removed.

Another aspect of the present invention relates to isolated nucleic acid molecules encoding propeptides of the present invention.

Wildtype BoNT/A has an amino acid sequence as set forth in GenBank Accession No. ABP48106 (SEQ ID NO:7), as follows:

MPFVNKQFNY KDPVNGVDIA YIKIPNAGQM QPVKAFKIHN KIWVIPERDT FTNPEEGDLN 60
PPPEAKQVPV SYYDSTYLST DNEKDNYLKG VTKLFERIYS TDLGRMLLTS IVRGIPFWGG 120
STIDTELKVI DTNCINVIQP DGSYRSEELN LVIIGPSADI IQFECKSFGH EVLNLTRNGY 180
GSTQYIRFSP DFTFGFEESL EVDTNPLLGA GKFATDPAVT LAHELIHAGH RLYGIAINPN 240
RVFKVNTNAY YEMSGLEVSF EELRTFGGHD AKFIDSLQEN EFRLYYYNKF KDIASTLNKA 300
KSIVGTTASL QYMKNVFKEK YLLSEDTSGK FSVDKLKFDK LYKMLTEIYT EDNFVKFFKV 360
LNRKTYLNFD KAVFKINIVP KVNYTIYDGF NLRNTNLAAN FNGQNTEINN MNFTKLKNFT 420
GLFEFYKLLC VRGIITSKTK SLDKGYNKAL NDLCIKVNNW DLFFSPSEDN FTNDLNKGEE 480
ITSDTNIEAA EENISLDLIQ QYYLTFNFDN EPENISIENL SSDIIGQLEL MPNIERFPNG 540
KKYELDKYTM FHYLRAQEFE HGKSRIALTN SVNEALLNPS RVYTFFSSDY VKKVNKATEA 600
AMFLGWVEQL VYDFTDETSE VSTTDKIADI TIIIPYIGPA LNIGNMLYKD DFVGALIFSG 660
AVILLEFIPE IAIPVLGTFA LVSYIANKVL TVQTIDNALS KRNEKWDEVY KYIVTNWLAK 720
VNTQIDLIRK KMKEALENQA EATKAIINYQ YNQYTEEEKN NINFNIDDLS SKLNESINKA 780
MININKFLNQ CSVSYLMNSM IPYGVKRLED FDASLKDALL KYIYDNRGTL IGQVDRLKDK 840
VNNTLSTDIP FQLSKYVDNQ RLLSTFTEYI KNIINTSILN LRYESNHLID LSRYASKINI 900
GSKVNFDPID KNQIQLFNLE SSKIEVILKN AIVYNSMYEN FSTSFWIRIP KYFNSISLNN 960
EYTIINCMEN NSGWKVSLNY GEIIWTLQDT QEIKQRVVFK YSQMINISDY INRWIFVTIT 1020
NNRLNNSKIY INGRLIDQKP ISNLGNIHAS NNIMFKLDGC RDTHRYIWIK YFNLFDKELN 1080
EKEIKDLYDN QSNSGILKDF WGDYLQYDKP YYMLNLYDPN KYVDVNNVGI RGYMYLKGPR 1140
GSVMTTNIYL NSSLYRGTKF IIKKYASGNK DNIVRNNDRV YINVVVKNKE YRLATNASQA 1200
GVEKILSALE IPDVGNLSQV VVMKSKNDQG ITNKCKMNLQ DNNGNDIGFI GFHQFNNIAK 1260
LVASNWYNRQ IERSSRTLGC SWEFIPVDDG WGERPL

An exemplary nucleic acid molecule of the present invention is set forth in GenBank Accession No. GQ855201 (SEQ ID NO:15), as follows:

gacgcgccct gtagcggcgc attaagcgcg gcgggtgtgg tggttacgcg cagcgtgacc 60
gctacacttg ccagcgccct agcgcccgct cctttcgctt tcttcccttc ctttctcgcc 120
acgttcgccg gctttccccg tcaagctcta aatcgggggc tccctttagg gttccgattt 180
agtgctttac ggcacctcga ccccaaaaaa cttgattagg gtgatggttc acgtagtggg 240
ccatcgccct gatagacggt ttttcgccct ttgacgttgg agtccacgtt ctttaatagt 300
ggactcttgt tccaaactgg aacaacactc aaccctatct cggtctattc ttttgattta 360
taagggattt tgccgatttc ggcctattgg ttaaaaaatg agctgattta acaaaaattt 420
aacgcgaatt ttaacaaaat attaacgttt acaatttcag gtggcacttt tcggggaaat 480
gtgcgcggaa cccctatttg tttatttttc taaatacatt caaatatgta tccgctcatg 540
agacaataac cctgataaat gcttcaataa tattgaaaaa ggaagagtat gagtattcaa 600
catttccgtg tcgcccttat tccctttttt gcggcatttt gccttcctgt ttttgctcac 660
ccagaaacgc tggtgaaagt aaaagatgct gaagatcagt tgggtgcacg agtgggttac 720
atcgaactgg atctcaacag cggtaagatc cttgagagtt ttcgccccga agaacgtttt 780
ccaatgatga gcacttttaa agttctgcta tgtggcgcgg tattatcccg tattgacgcc 840
gggcaagagc aactcggtcg ccgcatacac tattctcaga atgacttggt tgagtactca 900

-continued

```
ccagtcacag aaaagcatct tacggatggc atgacagtaa gagaattatg cagtgctgcc   960
ataaccatga gtgataacac tgcggccaac ttacttctga caacgatcgg aggaccgaag  1020
gagctaaccg cttttttgca caacatgggg gatcatgtaa ctcgccttga tcgttgggaa  1080
ccggagctga atgaagccat accaaacgac gagcgtgaca ccacgatgcc tgtagcaatg  1140
gcaacaacgt tgcgcaaact attaactggc gaactactta ctctagcttc ccggcaacaa  1200
ttaatagact ggatggaggc ggataaagtt gcaggaccac ttctgcgctc ggcccttccg  1260
gctggctggt ttattgctga taaatctgga gccggtgagc gtgggtctcg cggtatcatt  1320
gcagcactgg ggccagatgg taagccctcc cgtatcgtag ttatctacac gacggggagt  1380
caggcaacta tggatgaacg aaatagacag atcgctgaga taggtgcctc actgattaag  1440
cattggtaac tgtcagacca agtttactca tatatacttt agattgattt aaaacttcat  1500
ttttaattta aaaggatcta ggtgaagatc ctttttgata atctcatgac caaaatccct  1560
taacgtgagt tttcgttcca ctgagcgtca gaccccgtag aaaagatcaa aggatcttct  1620
tgagatcctt tttttctgcg cgtaatctgc tgcttgcaaa caaaaaaacc accgctacca  1680
gcggtggttt gtttgccgga tcaagagcta ccaactcttt ttccgaaggt aactggcttc  1740
agcagagcgc agataccaaa tactgtcctt ctagtgtagc cgtagttagg ccaccacttc  1800
aagaactctg tagcaccgcc tacatacctc gctctgctaa tcctgttacc agtggctgct  1860
gccagtggcg ataagtcgtg tcttaccggg ttggactcaa gacgatagtt accggataag  1920
gcgcagcggt cgggctgaac ggggggttcg tgcacacagc ccagcttgga gcgaacgacc  1980
tacaccgaac tgagatacct acagcgtgag cattgagaaa gcgccacgct tcccgaaggg  2040
agaaaggcgg acaggtatcc ggtaagcggc agggtcggaa caggagagcg cacgagggag  2100
cttccagggg gaaacgcctg gtatctttat agtcctgtcg ggtttcgcca cctctgactt  2160
gagcgtcgat ttttgtgatg ctcgtcaggg gggcggagcc tatggaaaaa cgccagcaac  2220
gcggcctttt tacggttcct ggccttttgc tggccttttg ctcacatgtt ctttcctgcg  2280
ttatcccctg attctgtgga taaccgtatt accgcctttg agtgagctga taccgctcgc  2340
cgcagccgaa cgaccgagcg cagcgagtca gtgagcgagg aagcggaaga gcgcctgatg  2400
cggtattttc tccttacgca tctgtgcggt atttcacacc gcagaccagc cgcgtaacct  2460
ggcaaaatcg gttacggttg agtaataaat ggatgccctg cgtaagcggg tgtgggcgga  2520
caataaagtc ttaaactgaa caaaatagat ctaaactatg acaataaagt cttaaactag  2580
acagaatagt tgtaaactga aatcagtcca gttatgctgt gaaaaagcat actggacttt  2640
tgttatggct aaagcaaact cttcattttc tgaagtgcaa attgcccgtc gtattaaaga  2700
ggggcgtggc caagggcatg gtaaagacta tattcgcggc gttgtgacaa tttaccgaac  2760
aactccgcgg ccgggaagcc gatctcggct tgaacgaatt gttaggtggc ggtacttggg  2820
tcgatatcaa agtgcatcac ttcttcccgt atgcccaact ttgtatagag agccactgcg  2880
ggatcgtcac cgtaatctgc ttgcacgtag atcacataag caccaagcgc gttggcctca  2940
tgcttgagga gattgatgag cgcggtggca atgccctgcc tccggtgctc gccggagact  3000
gcgagatcat agatatagat ctcactacgc ggctgctcaa acctgggcag aacgtaagcc  3060
gcgagagcgc caacaaccgc ttcttggtcg aaggcagcaa gcgcgatgaa tgtcttacta  3120
cggagcaagt tcccgaggta atcggagtcc ggctgatgtt gggagtaggt ggctacgtct  3180
ccgaactcac gaccgaaaag atcaagagca gcccgcatgg atttgacttg gtcagggccg  3240
agcctacatg tgcgaatgat gcccatactt gagccaccta actttgtttt agggcgactg  3300
ccctgctgcg taacatcgtt gctgctgcgt aacatcgttg ctgctccata acatcaaaca  3360
```

-continued

```
tcgacccacg gcgtaacgcg cttgctgctt ggatgcccga ggcatagact gtacaaaaaa  3420
acagtcataa caagccatga aaaccgccac tgcgccgtta ccaccgctgc gttcggtcaa  3480
ggttctggac cagttgcgtg agcgcatacg ctacttgcat tacagtttac gaaccgaaca  3540
ggcttatgtc aactgggttc gtgccttcat ccgtttccac ggtgtgcgtc acccggcaac  3600
cttgggcagc agcgaagtcg aggcatttct gtcctggctg gcgaacgagc gcaaggtttc  3660
ggtctccacg catcgtcagg cattggcggc cttgctgttc ttctacggca aggtgctgtg  3720
cacggatctg ccctggcttc aggagatcgg aagacctcgg ccgtcgcggc gcttgccggt  3780
ggtgctgacc ccggatgaag tggttcgcat cctcggtttt ctggaaggcg agcatcgttt  3840
gttcgcccag gactctagct atagttctag tggttggcta cgtatactcc ggaatattaa  3900
tagatcatgg agataattaa aatgataacc atctcgcaaa taaataagta ttttactgtt  3960
ttcgtaacag ttttgtaata aaaaaaccta taaatattcc ggattattca taccgtccca  4020
ccatcgggcg cggatcccgg tccgttcgaa ccagaactct ggaagcttaa ctcctaaaaa  4080
accgccacca tgaaattctt agtcaacgtt gcccttgttt ttatggtcgt atacatttct  4140
tacatctatg cggccgctca tcaccaccat catcaccatc accaccacac gcgtgaaaac  4200
ctgtattttc agggcgccgg tgactccctg tcttggctgc tccgtctgct caacgcgcgc  4260
ggtggagcta gcggcccgtt cgttaacaaa caatttaact acaaggatcc tgtcaatggt  4320
gtggacattg cctatattaa gatcccgaat gcgggtcaga tgcaacccgt gaaagcattc  4380
aagatccaca acaaaatctg ggtcatccct gaacgtgaca ctttcacaaa ccctgaagag  4440
ggcgacctca accctccccc agaagccaaa caggttccgg tgtcttacta cgatagcacg  4500
tacttgtcca ccgataacga gaaggacaac tacctgaagg gagtgaccaa gttgtttgag  4560
aggatctact ctaccgatct cggacgtatg ctgctcacga gcattgtgcg cggtatccca  4620
ttctggggcg gttcaaccat tgatacagaa ctgaaagtca ttgacactaa ttgtatcaac  4680
gttattcaac cagatggcag ctaccgttcc gaggaattga acttggtcat cattggtcca  4740
tccgcagaca tcattcagtt tgaatgcaaa tccttcggtc acgaagtgct caacctgacg  4800
cgcaacggtt acggctccac ccagtacatc cgtttcagcc ctgatttcac atttggcttc  4860
gaggaaagcc tggaggttga caccaacccg ctcctgggtg ctggcaagtt tgcaaccgat  4920
cccgcggtga ctctcgctca tgctctgatc cacgccggac accgcctcta tggcatcgct  4980
atcaatccga accgcgtgtt caaagtgaat acgaacgcct actatgagat gagcggtctg  5040
gaggtttcct ttgaggaact gagaaccttc ggcggtcacg atgccaagtt catcgacagc  5100
ttgcaggaaa atgagtttcg cctgtactat tacaacaagt ttaaagacat cgcttccaca  5160
ttgaacaaag ccaagtcaat cgtgggtacg acagcttcat tgcagtatat gaagaatgtt  5220
ttcaaggaga aatacttgct gtcagaggat acctctggca agttctctgt ggacaaactg  5280
aaattcgaca aactgtacaa gatgctgacc gagatttata cggaagataa ctttgtgaaa  5340
ttcttcaaag tcctcaacag gaaaactgct ctgaactttg acaaggctgt gttcaagatc  5400
aacatcgtcc ccaaagttaa ctacacaatc tatgatggat tcaatctgag aaacaccaac  5460
ttggccgcca acttcaacgg ccaaaatacc gaaattaata acatgaattt caccaaactg  5520
aagaacttta ctggactgtt cgagttctac aagctgctct gcgtgcgtgg catcatcacc  5580
tcacatactc agtctctaga ccagggttat aacgacgatg acgataaagc tctgaacgat  5640
ctgtgtatca aggtgaataa ctgggatctg ttctttagcc caagcgagga taacttcacg  5700
aacgatctca acaaaggtga agagatcacg tctgatacca atatcgaagc ggctgaagag  5760
```

-continued

```
aatatctcct tggatctcat ccagcaatat tacctgacct ttaacttcga taacgagccc  5820
gaaaacatct ccatcgagaa cctcagctca gacatcattg gtcagttgga gctgatgcca  5880
aacattgaac gcttccccaa cggcaagaaa tacgaactcg acaagtatac gatgtttcat  5940
tacttaagag cgcaggagtt tgaacacggc aagagccgca ttgctctcac taactccgtg  6000
aatgaagccc tgctcaatcc gtcaagggtg tacacattct ttagctccga ctatgtcaag  6060
aaagtgaaca aagccaccga agcggcaatg ttcctgggat gggttgaaca actggtctac  6120
gacttcaccg acgagacctc tgaggtgagc acaacggaca agattgctga catcactatc  6180
attatcccgt atattggacc tgccttgaat attggcaaca tgctctacaa agacgatttc  6240
gttggtgccc tgatcttcag cggtgccgtg atcctgttgg agttcattcc tgaaatcgcc  6300
atccctgtgc tgggcacgtt cgctctggtc tcatacattg cgaataaggt cttgaccgtg  6360
cagacaatcg ataatgccct ctccaaacgt aacgaaaaat gggacgaggt ctacaaatac  6420
atcgtgacca actggctggc aaaggttaac acccaaattg atctgatccg taagaaaatg  6480
aaggaggctt tggagaacca ggctgaagct actaaagcca ttatcaacta ccagtataat  6540
cagtatacag aagaggaaaa gaataacatc aatttcaaca tcgatgactt gtcctcaaag  6600
ctgaacgagt ccatcaacaa agctatgatc aacatcaaca aattcctgaa tcagtgctcc  6660
gtgtcttacc tgatgaactc tatgatccca tacggtgtga agcgcctgga ggacttcgat  6720
gccagcctga aagacgcact gctcaaatac atttacgata atcgcggcac tttgattggc  6780
caagttgacc gtctgaagga caaggttaac aataccttgt caaccgatat cccctttcaa  6840
ctgtccaaat acgttgataa ccagcgcttg ctctctactt tcaccgaata cattaacaac  6900
attatcaata catcaattct caacctgcgc tatgagtcca atcatctgat cgatctgtct  6960
cgttacgcca gcaagatcaa cattggcagc aaagtgaact tcgatccgat tgacaagaac  7020
caaatccagt tgttcaacct cgaaagctcc aaaatcgaag tgatcctgaa gaatgccatc  7080
gtctacaact ccatgtatga aaatttctca acttcattct ggattagaat cccgaaatac  7140
ttcaactcaa tctctctgaa taacgaatac acgatcatta actgtatgga gaataactct  7200
ggttggaagg tttccttgaa ctatggagaa attatctgga ctctgcaaga tacgcaagag  7260
atcaaacagc gtgtggtctt taaatacagc cagatgatta acatctctga ctacatcaac  7320
agatggatct ttgtcaccat tacaaacaat cgcctgaata actccaaaat ctacatcaac  7380
ggtcgtctga tcgaccagaa acctatttca aacctcggca acattcatgc ttccaataac  7440
atcatgttta agttggatgg ttgccgcgat acccaccgtt acatctggat caagtatttc  7500
aatctgttcg acaaagaact caatgagaaa gagatcaaag acttgtatga taatcagtca  7560
aactccggca ttctgaaaga cttctggggc gattacctcc agtacgataa gccatattac  7620
atgctgaatc tctatgaccc taacaaatat gtggacgtga acaatgtcgg tatccgtggc  7680
tacatgtacc tcaaaggacc acgtggtagc gttatgacaa ccaacatcta cctgaatagc  7740
tccttgtatc gcggtacgaa gttcattatc aagaagtacg cttcaggcaa caaggacaac  7800
atcgtgagga acaatgatcg cgtgtacatc aacgtcgtgg tgaagaataa ggaataccgc  7860
ttggcgacca acgcttctca ggctggagtt gagaagatcc tgagcgcctt ggagatccca  7920
gacgttggca acctgagcca agtggttgtg atgaaaagca agaatgacca gggaatcacc  7980
aacaaatgca aaatgaacct gcaagacaac aacggcaatg acatcggttt catcggtttc  8040
caccagttta acaatattgc gaagctggtc gccagcaact ggtacaacag gcagattgag  8100
aggtcatccc gtaccttagg atgctcttgg gaatttatcc ccgtggacga tggttggggc  8160
gagagacccc tgggcgcagg ttggtcccac cctcagttcg agaagtaata gttaatagat  8220
```

-continued

```
aataatagct cgaggcatgc gagctccctc aggaggccta cgtcgacgag ctcactagtc  8280
gcggccgctt tcgaatctag agcctgcagt ctcgaggcat gcggtaccaa gcttgtcgag  8340
aagtactaga ggatcataat cagccatacc acatttgtag aggttttact tgctttaaaa  8400
aacctcccac acctccccct gaacctgaaa cataaaatga atgcaattgt tgttgttaac  8460
ttgtttattg cagcttataa tggttacaaa taaagcaata gcatcacaaa tttcacaaat  8520
aaagcatttt tttcactgca ttctagttgt ggtttgtcca aactcatcaa tgtatcttat  8580
catgtctgga tctgatcact gcttgagcct aggagatccg aaccagataa gtgaaatcta  8640
gttccaaact attttgtcat ttttaatttt cgtattagct tacgacgcta cacccagttc  8700
ccatctattt tgtcactctt ccctaaataa tccttaaaaa ctccatttcc acccctccca  8760
gttcccaact attttgtccg cccacagcgg ggcatttttc ttcctgttat gtttttaatc  8820
aaacatcctg ccaactccat gtgacaaacc gtcatcttcg gctacttttt ctctgtcaca  8880
gaatgaaaat ttttctgtca tctcttcgtt attaatgttt gtaattgact gaatatcaac  8940
gcttatttgc agcctgaatg gcgaatgg
```

This nucleotide sequence encodes the neurotoxin BoNT/Aad$^{ek}$.

Another exemplary nucleic acid molecule of the present invention is set forth in GenBank Accession No. GQ855202 (SEQ ID NO:10), as follows:

```
gacgcgccct gtagcggcgc attaagcgcg gcgggtgtgg tggttacgcg cagcgtgacc    60
gctacacttg ccagcgccct agcgcccgct cctttcgctt tcttcccttc ctttctcgcc   120
acgttcgccg gctttccccg tcaagctcta aatcgggggc tccctttagg gttccgattt   180
agtgctttac ggcacctcga ccccaaaaaa cttgattagg gtgatggttc acgtagtggg   240
ccatcgccct gatagacggt ttttcgccct ttgacgttgg agtccacgtt ctttaatagt   300
ggactcttgt tccaaactgg aacaacactc aaccctatct cggtctattc ttttgattta   360
taagggattt tgccgatttc ggcctattgg ttaaaaaatg agctgattta acaaaaattt   420
aacgcgaatt ttaacaaaat attaacgttt acaatttcag gtggcacttt tcggggaaat   480
gtgcgcggaa cccctatttg tttatttttc taaatacatt caaatatgta tccgctcatg   540
agacaataac cctgataaat gcttcaataa tattgaaaaa ggaagagtat gagtattcaa   600
catttccgtg tcgcccttat tccctttttt gcggcatttt gccttcctgt ttttgctcac   660
ccagaaacgc tggtgaaagt aaaagatgct gaagatcagt tgggtgcacg agtgggttac   720
atcgaactgg atctcaacag cggtaagatc cttgagagtt ttcgccccga agaacgtttt   780
ccaatgatga gcacttttaa agttctgcta tgtggcgcgg tattatcccg tattgacgcc   840
gggcaagagc aactcggtcg ccgcatacac tattctcaga atgacttggt tgagtactca   900
ccagtcacag aaaagcatct tacggatggc atgacagtaa gagaattatg cagtgctgcc   960
ataaccatga gtgataacac tgcggccaac ttacttctga caacgatcgg aggaccgaag  1020
gagctaaccg cttttttgca caacatgggg gatcatgtaa ctcgccttga tcgttgggaa  1080
ccggagctga atgaagccat accaaacgac gagcgtgaca ccacgatgcc tgtagcaatg  1140
gcaacaacgt tgcgcaaact attaactggc gaactactta ctctagcttc ccggcaacaa  1200
ttaatagact ggatggaggc ggataaagtt gcaggaccac ttctgcgctc ggcccttccg  1260
gctggctggt ttattgctga taaatctgga gccggtgagc gtgggtctcg cggtatcatt  1320
gcagcactgg ggccagatgg taagccctcc cgtatcgtag ttatctacac gacggggagt  1380
```

-continued

```
caggcaacta tggatgaacg aaatagacag atcgctgaga taggtgcctc actgattaag  1440
cattggtaac tgtcagacca agtttactca tatatacttt agattgattt aaaacttcat  1500
ttttaattta aaaggatcta ggtgaagatc ctttttgata atctcatgac caaaatccct  1560
taacgtgagt tttcgttcca ctgagcgtca gaccccgtag aaaagatcaa aggatcttct  1620
tgagatcctt tttttctgcg cgtaatctgc tgcttgcaaa caaaaaaacc accgctacca  1680
gcggtggttt gtttgccgga tcaagagcta ccaactcttt ttccgaaggt aactggcttc  1740
agcagagcgc agataccaaa tactgtcctt ctagtgtagc cgtagttagg ccaccacttc  1800
aagaactctg tagcaccgcc tacatacctc gctctgctaa tcctgttacc agtggctgct  1860
gccagtggcg ataagtcgtg tcttaccggg ttggactcaa gacgatagtt accggataag  1920
gcgcagcggt cgggctgaac ggggggttcg tgcacacagc ccagcttgga gcgaacgacc  1980
tacaccgaac tgagatacct acagcgtgag cattgagaaa gcgccacgct tcccgaaggg  2040
agaaaggcgg acaggtatcc ggtaagcggc agggtcggaa caggagagcg cacgagggag  2100
cttccagggg gaaacgcctg gtatctttat agtcctgtcg ggtttcgcca cctctgactt  2160
gagcgtcgat ttttgtgatg ctcgtcaggg gggcggagcc tatggaaaaa cgccagcaac  2220
gcggcctttt tacggttcct ggccttttgc tggccttttg ctcacatgtt ctttcctgcg  2280
ttatcccctg attctgtgga taaccgtatt accgcctttg agtgagctga taccgctcgc  2340
cgcagccgaa cgaccgagcg cagcgagtca gtgagcgagg aagcggaaga gcgcctgatg  2400
cggtattttc tccttacgca tctgtgcggt atttcacacc gcagaccagc cgcgtaacct  2460
ggcaaaatcg gttacggttg agtaataaat ggatgccctg cgtaagcggg tgtgggcgga  2520
caataaagtc ttaaactgaa caaaatagat ctaaactatg acaataaagt cttaaactag  2580
acagaatagt tgtaaactga aatcagtcca gttatgctgt gaaaaagcat actggacttt  2640
tgttatggct aaagcaaact cttcattttc tgaagtgcaa attgcccgtc gtattaaaga  2700
ggggcgtggc caagggcatg gtaaagacta tattcgcggc gttgtgacaa tttaccgaac  2760
aactccgcgg ccgggaagcc gatctcggct tgaacgaatt gttaggtggc ggtacttggg  2820
tcgatatcaa agtgcatcac ttcttcccgt atgcccaact ttgtatagag agccactgcg  2880
ggatcgtcac cgtaatctgc ttgcacgtag atcacataag caccaagcgc gttggcctca  2940
tgcttgagga gattgatgag cgcggtggca atgccctgcc tccggtgctc gccggagact  3000
gcgagatcat agatatagat ctcactacgc ggctgctcaa acctgggcag aacgtaagcc  3060
gcgagagcgc caacaaccgc ttcttggtcg aaggcagcaa gcgcgatgaa tgtcttacta  3120
cggagcaagt tcccgaggta atcggagtcc ggctgatgtt gggagtaggt ggctacgtct  3180
ccgaactcac gaccgaaaag atcaagagca gcccgcatgg atttgacttg gtcagggccg  3240
agcctacatg tgcgaatgat gcccatactt gagccaccta actttgtttt agggcgactg  3300
ccctgctgcg taacatcgtt gctgctgcgt aacatcgttg ctgctccata acatcaaaca  3360
tcgacccacg gcgtaacgcg cttgctgctt ggatgcccga ggcatagact gtacaaaaaa  3420
acagtcataa caagccatga aaaccgccac tgcgccgtta ccaccgctgc gttcggtcaa  3480
ggttctggac cagttgcgtg agcgcatacg ctacttgcat tacagtttac gaaccgaaca  3540
ggcttatgtc aactgggttc gtgccttcat ccgtttccac ggtgtgcgtc acccggcaac  3600
cttgggcagc agcgaagtcg aggcatttct gtcctggctg gcgaacgagc gcaaggtttc  3660
ggtctccacg catcgtcagg cattggcggc cttgctgttc ttctacggca aggtgctgtg  3720
cacggatctg ccctggcttc aggagatcgg aagacctcgg ccgtcgcggc gcttgccggt  3780
```

-continued

```
ggtgctgacc ccggatgaag tggttcgcat cctcggtttt ctggaaggcg agcatcgttt  3840
gttcgcccag gactctagct atagttctag tggttggcta cgtatactcc ggaatattaa  3900
tagatcatgg agataattaa aatgataacc atctcgcaaa taaataagta ttttactgtt  3960
ttcgtaacag ttttgtaata aaaaaaccta taaatattcc ggattattca taccgtccca  4020
ccatcgggcg cggatcccgg tccgttcgaa ccagaactct ggaagcttaa ctcctaaaaa  4080
accgccacca tgaaattctt agtcaacgtt gcccttgttt ttatggtcgt atacatttct  4140
tacatctatg cggccgctca tcaccaccat catcaccatc accaccacac gcgtgaaaac  4200
ctgtattttc agggcgccgg tgactccctg tcttggctgc tccgtctgct caacgcgcgc  4260
ggtggagcta gcggcccgtt cgttaacaaa caatttaact acaaggatcc tgtcaatggt  4320
gtggacattg cctatattaa gatcccgaat gcgggtcaga tgcaacccgt gaaagcattc  4380
aagatccaca acaaaatctg ggtcatccct gaacgtgaca ctttcacaaa ccctgaagag  4440
ggcgacctca accctccccc agaagccaaa caggttccgg tgtcttacta cgatagcacg  4500
tacttgtcca ccgataacga gaaggacaac tacctgaagg gagtgaccaa gttgtttgag  4560
aggatctact ctaccgatct cggacgtatg ctgctcacga gcattgtgcg cggtatccca  4620
ttctggggcg gttcaaccat tgatacagaa ctgaaagtca ttgacactaa ttgtatcaac  4680
gttattcaac cagatggcag ctaccgttcc gaggaattga acttggtcat cattggtcca  4740
tccgcagaca tcattcagtt tgaatgcaaa tccttcggtc acgaagtgct caacctgacg  4800
cgcaacggtt acggctccac ccagtacatc cgtttcagcc ctgatttcac atttggcttc  4860
gaggaaagcc tggaggttga caccaacccg ctcctgggtg ctggcaagtt tgcaaccgat  4920
cccgcggtga ctctcgctca tgctctgatc cacgccggac accgcctcta tggcatcgct  4980
atcaatccga accgcgtgtt caaagtgaat acgaacgcct actatgagat gagcggtctg  5040
gaggtttcct ttgaggaact gagaaccttc ggcggtcacg atgccaagtt catcgacagc  5100
ttgcaggaaa atgagtttcg cctgtactat tacaacaagt ttaaagacat cgcttccaca  5160
ttgaacaaag ccaagtcaat cgtgggtacg acagcttcat tgcagtatat gaagaatgtt  5220
ttcaaggaga aatacttgct gtcagaggat acctctggca agttctctgt ggacaaactg  5280
aaattcgaca aactgtacaa gatgctgacc gagatttata cggaagataa ctttgtgaaa  5340
ttcttcaaag tcctcaacag gaaaactgct ctgaactttg acaaggctgt gttcaagatc  5400
aacatcgtcc ccaaagttaa ctacacaatc tatgatggat tcaatctgag aaacaccaac  5460
ttggccgcca acttcaacgg ccaaaatacc gaaattaata acatgaattt caccaaactg  5520
aagaacttta ctggactgtt cgagttctac aagctgctct gcgtgcgtgg catcatcacc  5580
tcacatactc agtctctaga ccagggtggc gagaacctgt acttccaggg tgctctgaac  5640
gatctgtgta tcaaggtgaa taactgggat ctgttcttta gcccaagcga ggataacttc  5700
acgaacgatc tcaacaaagg tgaagagatc acgtctgata ccaatatcga agcggctgaa  5760
gagaatatct ccttggatct catccagcaa tattacctga cctttaactt cgataacgag  5820
cccgaaaaca tctccatcga gaacctcagc tcagacatca ttggtcagtt ggagctgatg  5880
ccaaacattg aacgcttccc caacggcaag aaatacgaac tcgacaagta tacgatgttt  5940
cattacttaa gagcgcagga gtttgaacac ggcaagagcc gcattgctct cactaactcc  6000
gtgaatgaag ccctgctcaa tccgtcaagg gtgtacacat tctttagctc cgactatgtc  6060
aagaaagtga acaaagccac cgaagcggca atgttcctgg gatgggttga acaactggtc  6120
tacgacttca ccgacgagac ctctgaggtg agcacaacgg acaagattgc tgacatcact  6180
atcattatcc cgtatattgg acctgccttg aatattggca acatgctcta caaagacgat  6240
```

-continued

```
ttcgttggtg ccctgatctt cagcggtgcc gtgatcctgt tggagttcat tcctgaaatc  6300
gccatccctg tgctgggcac gttcgctctg gtctcataca ttgcgaataa ggtcttgacc  6360
gtgcagacaa tcgataatgc cctctccaaa cgtaacgaaa aatgggacga ggtctacaaa  6420
tacatcgtga ccaactggct ggcaaaggtt aacacccaaa ttgatctgat ccgtaagaaa  6480
atgaaggagg ctttggagaa ccaggctgaa gctactaaag ccattatcaa ctaccagtat  6540
aatcagtata cagaagagga aaagaataac atcaatttca acatcgatga cttgtcctca  6600
aagctgaacg agtccatcaa caaagctatg atcaacatca acaaattcct gaatcagtgc  6660
tccgtgtctt acctgatgaa ctctatgatc ccatacggtg tgaagcgcct ggaggacttc  6720
gatgccagcc tgaaagacgc actgctcaaa tacatttacg ataatcgcgg cactttgatt  6780
ggccaagttg accgtctgaa ggacaaggtt aacaatacct tgtcaaccga tatccccttt  6840
caactgtcca aatacgttga taaccagcgc ttgctctcta ctttcaccga atacattaac  6900
aacattatca atacatcaat tctcaacctg cgctatgagt ccaatcatct gatcgatctg  6960
tctcgttacg ccagcaagat caacattggc agcaaagtga acttcgatcc gattgacaag  7020
aaccaaatcc agttgttcaa cctcgaaagc tccaaaatcg aagtgatcct gaagaatgcc  7080
atcgtctaca actccatgta tgaaaatttc tcaacttcat tctggattag aatcccgaaa  7140
tacttcaact caatctctct gaataacgaa tacacgatca ttaactgtat ggagaataac  7200
tctggttgga aggtttcctt gaactatgga gaaattatct ggactctgca agatacgcaa  7260
gagatcaaac agcgtgtggt ctttaaatac agccagatga ttaacatctc tgactacatc  7320
aacagatgga tctttgtcac cattacaaac aatcgcctga ataactccaa aatctacatc  7380
aacggtcgtc tgatcgacca gaaacctatt tcaaacctcg gcaacattca tgcttccaat  7440
aacatcatgt ttaagttgga tggttgccgc gatacccacc gttacatctg gatcaagtat  7500
ttcaatctgt tcgacaaaga actcaatgag aaagagatca aagacttgta tgataatcag  7560
tcaaactccg gcattctgaa agacttctgg ggcgattacc tccagtacga taagccatat  7620
tacatgctga atctctatga ccctaacaaa tatgtggacg tgaacaatgt cggtatccgt  7680
ggctacatgt acctcaaagg accacgtggt agcgttatga caaccaacat ctacctgaat  7740
agctccttgt atcgcggtac gaagttcatt atcaagaagt acgcttcagg caacaaggac  7800
aacatcgtga ggaacaatga tcgcgtgtac atcaacgtcg tggtgaagaa taaggaatac  7860
cgcttggcga ccaacgcttc tcaggctgga gttgagaaga tcctgagcgc cttggagatc  7920
ccagacgttg gcaacctgag ccaagtggtt gtgatgaaaa gcaagaatga ccagggaatc  7980
accaacaaat gcaaaatgaa cctgcaagac aacaacggca atgacatcgg tttcatcggt  8040
ttccaccagt ttaacaatat tgcgaagctg gtcgccagca actggtacaa caggcagatt  8100
gagaggtcat cccgtacctt aggatgctct tgggaattta tccccgtgga cgatggttgg  8160
ggcgagagac ccctgggcgc aggttggtcc caccctcagt tcgagaagta atagttaata  8220
gataataata gctcgaggca tgcgagctcc ctcaggaggc ctacgtcgac gagctcacta  8280
gtcgcggccg ctttcgaatc tagagcctgc agtctcgagg catgcggtac caagcttgtc  8340
gagaagtact agaggatcat aatcagccat accacatttg tagaggtttt acttgcttta  8400
aaaaacctcc cacacctccc cctgaacctg aaacataaaa tgaatgcaat tgttgttgtt  8460
aacttgttta ttgcagctta taatggttac aaataaagca atagcatcac aaatttcaca  8520
aataaagcat ttttttcact gcattctagt tgtggtttgt ccaaactcat caatgtatct  8580
tatcatgtct ggatctgatc actgcttgag cctaggagat ccgaaccaga taagtgaaat  8640
```

-continued

```
ctagttccaa actattttgt catttttaat tttcgtatta gcttacgacg ctacacccag  8700

ttcccatcta ttttgtcact cttccctaaa taatccttaa aaactccatt tccacccctc  8760

ccagttccca actattttgt ccgcccacag cggggcattt ttcttcctgt tatgttttta  8820

atcaaacatc ctgccaactc catgtgacaa accgtcatct tcggctactt tttctctgtc  8880

acagaatgaa aatttttctg tcatctcttc gttattaatg tttgtaattg actgaatatc  8940

aacgcttatt tgcagcctga atggcgaatg g
```

This nucleotide sequence encodes the neurotoxin BoNT/Aad$^{tev}$.

Another exemplary nucleic acid molecule of the present invention is set forth in GenBank Accession No. GQ855203 (SEQ ID NO:11), as follows:

```
gacgcgccct gtagcggcgc attaagcgcg gcgggtgtgg tggttacgcg cagcgtgacc    60

gctacacttg ccagcgccct agcgcccgct cctttcgctt tcttcccttc ctttctcgcc   120

acgttcgccg gctttccccg tcaagctcta aatcgggggc tccctttagg gttccgattt   180

agtgctttac ggcacctcga ccccaaaaaa cttgattagg gtgatggttc acgtagtggg   240

ccatcgccct gatagacggt ttttcgccct ttgacgttgg agtccacgtt ctttaatagt   300

ggactcttgt tccaaactgg aacaacactc aaccctatct cggtctattc ttttgattta   360

taagggattt tgccgatttc ggcctattgg ttaaaaaatg agctgattta acaaaaattt   420

aacgcgaatt ttaacaaaat attaacgttt acaatttcag gtggcacttt tcggggaaat   480

gtgcgcggaa cccctatttg tttatttttc taaatacatt caaatatgta tccgctcatg   540

agacaataac cctgataaat gcttcaataa tattgaaaaa ggaagagtat gagtattcaa   600

catttccgtg tcgcccttat tccctttttt gcggcatttt gccttcctgt ttttgctcac   660

ccagaaacgc tggtgaaagt aaaagatgct gaagatcagt tgggtgcacg agtgggttac   720

atcgaactgg atctcaacag cggtaagatc cttgagagtt ttcgccccga agaacgtttt   780

ccaatgatga gcacttttaa agttctgcta tgtggcgcgg tattatcccg tattgacgcc   840

gggcaagagc aactcggtcg ccgcatacac tattctcaga atgacttggt tgagtactca   900

ccagtcacag aaaagcatct tacggatggc atgacagtaa gagaattatg cagtgctgcc   960

ataaccatga gtgataacac tgcggccaac ttacttctga caacgatcgg aggaccgaag  1020

gagctaaccg cttttttgca caacatgggg gatcatgtaa ctcgccttga tcgttgggaa  1080

ccggagctga atgaagccat accaaacgac gagcgtgaca ccacgatgcc tgtagcaatg  1140

gcaacaacgt tgcgcaaact attaactggc gaactactta ctctagcttc ccggcaacaa  1200

ttaatagact ggatggaggc ggataaagtt gcaggaccac ttctgcgctc ggcccttccg  1260

gctggctggt ttattgctga taaatctgga gccggtgagc gtgggtctcg cggtatcatt  1320

gcagcactgg ggccagatgg taagccctcc cgtatcgtag ttatctacac gacggggagt  1380

caggcaacta tggatgaacg aaatagacag atcgctgaga taggtgcctc actgattaag  1440

cattggtaac tgtcagacca agtttactca tatatacttt agattgattt aaaacttcat  1500

ttttaattta aaaggatcta ggtgaagatc ctttttgata atctcatgac caaaatccct  1560

taacgtgagt tttcgttcca ctgagcgtca gaccccgtag aaaagatcaa aggatcttct  1620

tgagatcctt tttttctgcg cgtaatctgc tgcttgcaaa caaaaaaacc accgctacca  1680

gcggtggttt gtttgccgga tcaagagcta ccaactcttt ttccgaaggt aactggcttc  1740

agcagagcgc agataccaaa tactgtcctt ctagtgtagc cgtagttagg ccaccacttc  1800
```

-continued

```
aagaactctg tagcaccgcc tacatacctc gctctgctaa tcctgttacc agtggctgct  1860
gccagtggcg ataagtcgtg tcttaccggg ttggactcaa gacgatagtt accggataag  1920
gcgcagcggt cgggctgaac ggggggttcg tgcacacagc ccagcttgga gcgaacgacc  1980
tacaccgaac tgagatacct acagcgtgag cattgagaaa gcgccacgct tcccgaaggg  2040
agaaaggcgg acaggtatcc ggtaagcggc agggtcggaa caggagagcg cacgagggag  2100
cttccagggg gaaacgcctg gtatctttat agtcctgtcg ggtttcgcca cctctgactt  2160
gagcgtcgat ttttgtgatg ctcgtcaggg gggcggagcc tatggaaaaa cgccagcaac  2220
gcggcctttt tacggttcct ggccttttgc tggccttttg ctcacatgtt ctttcctgcg  2280
ttatcccctg attctgtgga taaccgtatt accgcctttg agtgagctga taccgctcgc  2340
cgcagccgaa cgaccgagcg cagcgagtca gtgagcgagg aagcggaaga gcgcctgatg  2400
cggtattttc tccttacgca tctgtgcggt atttcacacc gcagaccagc cgcgtaacct  2460
ggcaaaatcg gttacggttg agtaataaat ggatgccctg cgtaagcggg tgtgggcgga  2520
caataaagtc ttaaactgaa caaaatagat ctaaactatg acaataaagt cttaaactag  2580
acagaatagt tgtaaactga aatcagtcca gttatgctgt gaaaaagcat actggacttt  2640
tgttatggct aaagcaaact cttcattttc tgaagtgcaa attgcccgtc gtattaaaga  2700
ggggcgtggc caagggcatg gtaaagacta tattcgcggc gttgtgacaa tttaccgaac  2760
aactccgcgg ccgggaagcc gatctcggct tgaacgaatt gttaggtggc ggtacttggg  2820
tcgatatcaa agtgcatcac ttcttcccgt atgcccaact ttgtatagag agccactgcg  2880
ggatcgtcac cgtaatctgc ttgcacgtag atcacataag caccaagcgc gttggcctca  2940
tgcttgagga gattgatgag cgcggtggca atgccctgcc tccggtgctc gccggagact  3000
gcgagatcat agatatagat ctcactacgc ggctgctcaa acctgggcag aacgtaagcc  3060
gcgagagcgc caacaaccgc ttcttggtcg aaggcagcaa gcgcgatgaa tgtcttacta  3120
cggagcaagt tcccgaggta atcggagtcc ggctgatgtt gggagtaggt ggctacgtct  3180
ccgaactcac gaccgaaaag atcaagagca gcccgcatgg atttgacttg gtcagggccg  3240
agcctacatg tgcgaatgat gcccatactt gagccaccta actttgtttt agggcgactg  3300
ccctgctgcg taacatcgtt gctgctgcgt aacatcgttg ctgctccata acatcaaaca  3360
tcgacccacg gcgtaacgcg cttgctgctt ggatgcccga ggcatagact gtacaaaaaa  3420
acagtcataa caagccatga aaaccgccac tgcgccgtta ccaccgctgc gttcggtcaa  3480
ggttctggac cagttgcgtg agcgcatacg ctacttgcat tacagtttac gaaccgaaca  3540
ggcttatgtc aactgggttc gtgccttcat ccgtttccac ggtgtgcgtc acccggcaac  3600
cttgggcagc agcgaagtcg aggcatttct gtcctggctg gcgaacgagc gcaaggtttc  3660
ggtctccacg catcgtcagg cattggcggc cttgctgttc ttctacggca aggtgctgtg  3720
cacggatctg ccctggcttc aggagatcgg aagacctcgg ccgtcgcggc gcttgccggt  3780
ggtgctgacc ccggatgaag tggttcgcat cctcggtttt ctggaaggcg agcatcgttt  3840
gttcgcccag gactctagct atagttctag tggttggcta cgtatactcc ggaatattaa  3900
tagatcatgg agataattaa aatgataacc atctcgcaaa taaataagta ttttactgtt  3960
ttcgtaacag ttttgtaata aaaaaaccta taaatattcc ggattattca taccgtccca  4020
ccatcgggcg cggatcccgg tccgttcgaa ccagaactct ggaagcttaa ctcctaaaaa  4080
accgccacca tgaaattctt agtcaacgtt gcccttgttt ttatggtcgt atacatttct  4140
tacatctatg cggccgctca tcaccaccat catcaccatc accaccacac gcgtgaaaac  4200
ctgtattttc agggcgccgg tgactccctg tcttggctgc tccgtctgct caacgcgcgc  4260
```

-continued

```
ggtggagcta gcggcggtac caatggcaac ggtaacggtg gtaatctgag aaacaccaac  4320
ttggccgcca acttcaacgg ccaaaatacc gaaattaata acatgaattt caccaaactg  4380
aagaacttta ctggactgtt cgagttctac aagctgctct gcgtgcgtgg catcatcacc  4440
tcacatactc agtctctaga ccagggtggc gagaacctgt acttccaggg tgctctgaac  4500
gatctgtgta tcaaggtgaa taactgggat ctgttcttta gcccaagcga ggataacttc  4560
acgaacgatc tcaacaaagg tgaagagatc acgtctgata ccaatatcga agcggctgaa  4620
gagaatatct ccttggatct catccagcaa tattacctga cctttaactt cgataacgag  4680
cccgaaaaca tctccatcga gaacctcagc tcagacatca ttggtcagtt ggagctgatg  4740
ccaaacattg aacgcttccc caacggcaag aaatacgaac tcgacaagta tacgatgttt  4800
cattacttaa gagcgcagga gtttgaacac ggcaagagcc gcattgctct cactaactcc  4860
gtgaatgaag ccctgctcaa tccgtcaagg gtgtacacat tctttagctc cgactatgtc  4920
aagaaagtga acaaagccac cgaagcggca atgttcctgg gatgggttga acaactggtc  4980
tacgacttca ccgacgagac ctctgaggtg agcacaacgg acaagattgc tgacatcact  5040
atcattatcc cgtatattgg acctgccttg aatattggca acatgctcta caaagacgat  5100
ttcgttggtg ccctgatctt cagcggtgcc gtgatcctgt tggagttcat tcctgaaatc  5160
gccatccctg tgctgggcac gttcgctctg gtctcataca ttgcgaataa ggtcttgacc  5220
gtgcagacaa tcgataatgc cctctccaaa cgtaacgaaa aatgggacga ggtctacaaa  5280
tacatcgtga ccaactggct ggcaaaggtt aacacccaaa ttgatctgat ccgtaagaaa  5340
atgaaggagg ctttggagaa ccaggctgaa gctactaaag ccattatcaa ctaccagtat  5400
aatcagtata cagaagagga aaagaataac atcaatttca acatcgatga cttgtcctca  5460
aagctgaacg agtccatcaa caaagctatg atcaacatca acaaattcct gaatcagtgc  5520
tccgtgtctt acctgatgaa ctctatgatc ccatacggtg tgaagcgcct ggaggacttc  5580
gatgccagcc tgaaagacgc actgctcaaa tacatttacg ataatcgcgg cactttgatt  5640
ggccaagttg accgtctgaa ggacaaggtt aacaatacct tgtcaaccga tatccccttt  5700
caactgtcca aatacgttga taaccagcgc ttgctctcta ctttcaccga atacattaac  5760
aacattatca atacatcaat tctcaacctg cgctatgagt ccaatcatct gatcgatctg  5820
tctcgttacg ccagcaagat caacattggc agcaaagtga acttcgatcc gattgacaag  5880
aaccaaatcc agttgttcaa cctcgaaagc tccaaaatcg aagtgatcct gaagaatgcc  5940
atcgtctaca actccatgta tgaaaatttc tcaacttcat tctggattag aatcccgaaa  6000
tacttcaact caatctctct gaataacgaa tacacgatca ttaactgtat ggagaataac  6060
tctggttgga aggtttcctt gaactatgga gaaattatct ggactctgca agatacgcaa  6120
gagatcaaac agcgtgtggt ctttaaatac agccagatga ttaacatctc tgactacatc  6180
aacagatgga tctttgtcac cattacaaac aatcgcctga ataactccaa aatctacatc  6240
aacggtcgtc tgatcgacca gaaacctatt tcaaacctcg gcaacattca tgcttccaat  6300
aacatcatgt ttaagttgga tggttgccgc gatacccacc gttacatctg gatcaagtat  6360
ttcaatctgt tcgacaaaga actcaatgag aaagagatca aagacttgta tgataatcag  6420
tcaaactccg gcattctgaa agacttctgg ggcgattacc tccagtacga taagccatat  6480
tacatgctga atctctatga ccctaacaaa tatgtggacg tgaacaatgt cggtatccgt  6540
ggctacatgt acctcaaagg accacgtggt agcgttatga caaccaacat ctacctgaat  6600
agctccttgt atcgcggtac gaagttcatt atcaagaagt acgcttcagg caacaaggac  6660
```

-continued

```
aacatcgtga ggaacaatga tcgcgtgtac atcaacgtcg tggtgaagaa taaggaatac   6720
cgcttggcga ccaacgcttc tcaggctgga gttgagaaga tcctgagcgc cttggagatc   6780
ccagacgttg gcaacctgag ccaagtggtt gtgatgaaaa gcaagaatga ccagggaatc   6840
accaacaaat gcaaaatgaa cctgcaagac aacaacggca atgacatcgg tttcatcggt   6900
ttccaccagt ttaacaatat tgcgaagctg gtcgccagca actggtacaa caggcagatt   6960
gagaggtcat cccgtacctt aggatgctct tgggaattta tccccgtgga cgatggttgg   7020
ggcgagagac ccctgggcgc aggttggtcc caccctcagt tcgagaagta atagttaata   7080
gataataata gctcgaggca tgcgagctcc ctcaggaggc ctacgtcgac gagctcacta   7140
gtcgcggccg ctttcgaatc tagagcctgc agtctcgagg catgcggtac caagcttgtc   7200
gagaagtact agaggatcat aatcagccat accacatttg tagaggtttt acttgcttta   7260
aaaaacctcc cacacctccc cctgaacctg aaacataaaa tgaatgcaat tgttgttgtt   7320
aacttgttta ttgcagctta taatggttac aaataaagca atagcatcac aaatttcaca   7380
aataaagcat ttttttcact gcattctagt tgtggtttgt ccaaactcat caatgtatct   7440
tatcatgtct ggatctgatc actgcttgag cctaggagat ccgaaccaga taagtgaaat   7500
ctagttccaa actattttgt catttttaat tttcgtatta gcttacgacg ctacacccag   7560
ttcccatcta ttttgtcact cttccctaaa taatccttaa aaactccatt tccacccctc   7620
ccagttccca actattttgt ccgcccacag cggggcattt ttcttcctgt tatgttttta   7680
atcaaacatc ctgccaactc catgtgacaa accgtcatct tcggctactt tttctctgtc   7740
acagaatgaa aatttttctg tcatctcttc gttattaatg tttgtaattg actgaatatc   7800
aacgcttatt tgcagcctga atggcgaatg g
```

This nucleotide sequence encodes the neurotoxin ΔLC-Peptide-BoNT/$A^{tev}$.

Another exemplary nucleic acid molecule of the present invention is set forth in GenBank Accession No. GQ855204 (SEQ ID NO:12), as follows:

```
gacgcgccct gtagcggcgc attaagcgcg gcgggtgtgg tggttacgcg cagcgtgacc    60
gctacacttg ccagcgccct agcgcccgct cctttcgctt tcttcccttc ctttctcgcc   120
acgttcgccg gctttccccg tcaagctcta aatcgggggc tccctttagg gttccgattt   180
agtgctttac ggcacctcga ccccaaaaaa cttgattagg gtgatggttc acgtagtggg   240
ccatcgccct gatagacggt ttttcgccct ttgacgttgg agtccacgtt ctttaatagt   300
ggactcttgt tccaaactgg aacaacactc aaccctatct cggtctattc ttttgattta   360
taagggattt tgccgatttc ggcctattgg ttaaaaaatg agctgattta acaaaaattt   420
aacgcgaatt ttaacaaaat attaacgttt acaatttcag gtggcacttt tcggggaaat   480
gtgcgcggaa cccctatttg tttatttttc taaatacatt caaatatgta tccgctcatg   540
agacaataac cctgataaat gcttcaataa tattgaaaaa ggaagagtat gagtattcaa   600
catttccgtg tcgcccttat tccctttttt gcggcatttt gccttcctgt ttttgctcac   660
ccagaaacgc tggtgaaagt aaaagatgct gaagatcagt tgggtgcacg agtgggttac   720
atcgaactgg atctcaacag cggtaagatc cttgagagtt ttcgccccga agaacgtttt   780
ccaatgatga gcacttttaa agttctgcta tgtggcgcgg tattatcccg tattgacgcc   840
gggcaagagc aactcggtcg ccgcatacac tattctcaga atgacttggt tgagtactca   900
ccagtcacag aaaagcatct tacggatggc atgacagtaa gagaattatg cagtgctgcc   960
```

-continued

```
ataaccatga gtgataacac tgcggccaac ttacttctga caacgatcgg aggaccgaag  1020
gagctaaccg cttttttgca caacatgggg gatcatgtaa ctcgccttga tcgttgggaa  1080
ccggagctga atgaagccat accaaacgac gagcgtgaca ccacgatgcc tgtagcaatg  1140
gcaacaacgt tgcgcaaact attaactggc gaactactta ctctagcttc ccggcaacaa  1200
ttaatagact ggatggaggc ggataaagtt gcaggaccac ttctgcgctc ggcccttccg  1260
gctggctggt ttattgctga taaatctgga gccggtgagc gtgggtctcg cggtatcatt  1320
gcagcactgg ggccagatgg taagccctcc cgtatcgtag ttatctacac gacggggagt  1380
caggcaacta tggatgaacg aaatagacag atcgctgaga taggtgcctc actgattaag  1440
cattggtaac tgtcagacca agtttactca tatatacttt agattgattt aaaacttcat  1500
ttttaattta aaaggatcta ggtgaagatc ctttttgata atctcatgac caaaatccct  1560
taacgtgagt tttcgttcca ctgagcgtca gaccccgtag aaaagatcaa aggatcttct  1620
tgagatcctt tttttctgcg cgtaatctgc tgcttgcaaa caaaaaaacc accgctacca  1680
gcggtggttt gtttgccgga tcaagagcta ccaactcttt ttccgaaggt aactggcttc  1740
agcagagcgc agataccaaa tactgtcctt ctagtgtagc cgtagttagg ccaccacttc  1800
aagaactctg tagcaccgcc tacatacctc gctctgctaa tcctgttacc agtggctgct  1860
gccagtggcg ataagtcgtg tcttaccggg ttggactcaa gacgatagtt accggataag  1920
gcgcagcggt cgggctgaac ggggggttcg tgcacacagc ccagcttgga gcgaacgacc  1980
tacaccgaac tgagatacct acagcgtgag cattgagaaa gcgccacgct tcccgaaggg  2040
agaaaggcgg acaggtatcc ggtaagcggc agggtcggaa caggagagcg cacgagggag  2100
cttccagggg gaaacgcctg gtatctttat agtcctgtcg ggtttcgcca cctctgactt  2160
gagcgtcgat ttttgtgatg ctcgtcaggg gggcggagcc tatggaaaaa cgccagcaac  2220
gcggcctttt tacggttcct ggccttttgc tggccttttg ctcacatgtt ctttcctgcg  2280
ttatcccctg attctgtgga taaccgtatt accgcctttg agtgagctga taccgctcgc  2340
cgcagccgaa cgaccgagcg cagcgagtca gtgagcgagg aagcggaaga gcgcctgatg  2400
cggtattttc tccttacgca tctgtgcggt atttcacacc gcagaccagc cgcgtaacct  2460
ggcaaaatcg gttacggttg agtaataaat ggatgccctg cgtaagcggg tgtgggcgga  2520
caataaagtc ttaaactgaa caaaatagat ctaaactatg acaataaagt cttaaactag  2580
acagaatagt tgtaaactga aatcagtcca gttatgctgt gaaaaagcat actggacttt  2640
tgttatggct aaagcaaact cttcattttc tgaagtgcaa attgcccgtc gtattaaaga  2700
ggggcgtggc caagggcatg gtaaagacta tattcgcggc gttgtgacaa tttaccgaac  2760
aactccgcgg ccgggaagcc gatctcggct tgaacgaatt gttaggtggc ggtacttggg  2820
tcgatatcaa agtgcatcac ttcttcccgt atgcccaact ttgtatagag agccactgcg  2880
ggatcgtcac cgtaatctgc ttgcacgtag atcacataag caccaagcgc gttggcctca  2940
tgcttgagga gattgatgag cgcggtggca atgccctgcc tccggtgctc gccggagact  3000
gcgagatcat agatatagat ctcactacgc ggctgctcaa acctgggcag aacgtaagcc  3060
gcgagagcgc caacaaccgc ttcttggtcg aaggcagcaa gcgcgatgaa tgtcttacta  3120
cggagcaagt tcccgaggta atcggagtcc ggctgatgtt gggagtaggt ggctacgtct  3180
ccgaactcac gaccgaaaag atcaagagca gcccgcatgg atttgacttg gtcagggccg  3240
agcctacatg tgcgaatgat gcccatactt gagccaccta actttgtttt agggcgactg  3300
ccctgctgcg taacatcgtt gctgctgcgt aacatcgttg ctgctccata acatcaaaca  3360
tcgacccacg gcgtaacgcg cttgctgctt ggatgcccga ggcatagact gtacaaaaaa  3420
```

-continued

```
acagtcataa caagccatga aaaccgccac tgcgccgtta ccaccgctgc gttcggtcaa  3480
ggttctggac cagttgcgtg agcgcatacg ctacttgcat tacagtttac gaaccgaaca  3540
ggcttatgtc aactgggttc gtgccttcat ccgtttccac ggtgtgcgtc acccggcaac  3600
cttgggcagc agcgaagtcg aggcatttct gtcctggctg gcgaacgagc gcaaggtttc  3660
ggtctccacg catcgtcagg cattggcggc cttgctgttc ttctacggca aggtgctgtg  3720
cacggatctg ccctggcttc aggagatcgg aagacctcgg ccgtcgcggc gcttgccggt  3780
ggtgctgacc ccggatgaag tggttcgcat cctcggtttt ctggaaggcg agcatcgttt  3840
gttcgcccag gactctagct atagttctag tggttggcta cgtatactcc ggaatattaa  3900
tagatcatgg agataattaa aatgataacc atctcgcaaa taaataagta ttttactgtt  3960
ttcgtaacag ttttgtaata aaaaaaccta taaatattcc ggattattca taccgtccca  4020
ccatcgggcg cggatcccgg tccgttcgaa ccagaactct ggaagcttaa ctcctaaaaa  4080
accgccacca tgaaattctt agtcaacgtt gcccttgttt ttatggtcgt atacatttct  4140
tacatctatg cggccgctca tcaccaccat catcaccatc accaccacac gcgtgaaaac  4200
ctgtattttc agggcgccgg tgactccctg tcttggctgc tccgtctgct caacgcgcgc  4260
ggtggagcta gcgtgagcaa gggcgccgag ctgttcaccg gcatcgtgcc catcctgatc  4320
gagctgaatg gcgatgtgaa tggccacaag ttcagcgtga gcggcgaggg cgagggcgat  4380
gccacctacg gcaagctgac cctgaagttc atctgcacca ccggcaagct gcctgtgccc  4440
tggcccaccc tggtgaccac cctgagctac ggcgtgcagt gcttctcacg ctaccccgat  4500
cacatgaagc agcacgactt cttcaagagc gccatgcctg agggctacat ccaggagcgc  4560
accatcttct tcgaggatga cggcaactac aagtcgcgcg ccgaggtgaa gttcgagggc  4620
gataccctgg tgaatcgcat cgagctgacc ggcaccgatt tcaaggagga tggcaacatc  4680
ctgggcaata agatggagta caactacaac gcccacaatg tgtacatcat gaccgacaag  4740
gccaagaatg gcatcaaggt gaacttcaag atccgccaca acatcgagga tggcagcgtg  4800
cagctggccg accactacca gcagaatacc cccatcggcg atggccctgt gctgctgccc  4860
gataaccact acctgtccac ccagagcgcc ctgtccaagg accccaacga gaagcgcgat  4920
cacatgatct acttcggctt cgtgaccgcc gccgccatca cccacggcat ggatgagctg  4980
tacaagggta ccaatggcaa cggtaacggt ggtaatctga gaaacaccaa cttggccgcc  5040
aacttcaacg gccaaaatac cgaaattaat aacatgaatt tcaccaaact gaagaacttt  5100
actggactgt tcgagttcta caagctgctc tgcgtgcgtg gcatcatcac ctcacatact  5160
cagtctctag accagggtgg cgagaacctg tacttccagg gtgctctgaa cgatctgtgt  5220
atcaaggtga ataactggga tctgttcttt agcccaagcg aggataactt cacgaacgat  5280
ctcaacaaag gtgaagagat cacgtctgat accaatatcg aagcggctga agagaatatc  5340
tccttggatc tcatccagca atattacctg acctttaact tcgataacga gcccgaaaac  5400
atctccatcg agaacctcag ctcagacatc attggtcagt tggagctgat gccaaacatt  5460
gaacgcttcc ccaacggcaa gaaatacgaa ctcgacaagt atacgatgtt tcattactta  5520
agagcgcagg agtttgaaca cggcaagagc cgcattgctc tcactaactc cgtgaatgaa  5580
gccctgctca atccgtcaag ggtgtacaca ttctttagct ccgactatgt caagaaagtg  5640
aacaaagcca ccgaagcggc aatgttcctg ggatgggttg aacaactggt ctacgacttc  5700
accgacgaga cctctgaggt gagcacaacg gacaagattg ctgacatcac tatcattatc  5760
ccgtatattg gacctgcctt gaatattggc aacatgctct acaaagacga tttcgttggt  5820
```

-continued

```
gccctgatct tcagcggtgc cgtgatcctg ttggagttca ttcctgaaat cgccatccct  5880
gtgctgggca cgttcgctct ggtctcatac attgcgaata aggtcttgac cgtgcagaca  5940
atcgataatg ccctctccaa acgtaacgaa aaatgggacg aggtctacaa atacatcgtg  6000
accaactggc tggcaaaggt taacacccaa attgatctga tccgtaagaa aatgaaggag  6060
gctttggaga accaggctga agctactaaa gccattatca actaccagta taatcagtat  6120
acagaagagg aaaagaataa catcaatttc aacatcgatg acttgtcctc aaagctgaac  6180
gagtccatca acaaagctat gatcaacatc aacaaattcc tgaatcagtg ctccgtgtct  6240
tacctgatga actctatgat cccatacggt gtgaagcgcc tggaggactt cgatgccagc  6300
ctgaaagacg cactgctcaa atacatttac gataatcgcg gcactttgat tggccaagtt  6360
gaccgtctga aggacaaggt taacaatacc ttgtcaaccg atatcccctt tcaactgtcc  6420
aaatacgttg ataaccagcg cttgctctct actttcaccg aatacattaa caacattatc  6480
aatacatcaa ttctcaacct gcgctatgag tccaatcatc tgatcgatct gtctcgttac  6540
gccagcaaga tcaacattgg cagcaaagtg aacttcgatc cgattgacaa gaaccaaatc  6600
cagttgttca acctcgaaag ctccaaaatc gaagtgatcc tgaagaatgc catcgtctac  6660
aactccatgt atgaaaattt ctcaacttca ttctggatta gaatcccgaa atacttcaac  6720
tcaatctctc tgaataacga atacacgatc attaactgta tggagaataa ctctggttgg  6780
aaggtttcct tgaactatgg agaaattatc tggactctgc aagatacgca agagatcaaa  6840
cagcgtgtgg tctttaaata cagccagatg attaacatct ctgactacat caacagatgg  6900
atctttgtca ccattacaaa caatcgcctg aataactcca aaatctacat caacggtcgt  6960
ctgatcgacc agaaacctat ttcaaacctc ggcaacattc atgcttccaa taacatcatg  7020
tttaagttgg atggttgccg cgatacccac cgttacatct ggatcaagta tttcaatctg  7080
ttcgacaaag aactcaatga gaaagagatc aaagacttgt atgataatca gtcaaactcc  7140
ggcattctga aagacttctg gggcgattac ctccagtacg ataagccata ttacatgctg  7200
aatctctatg accctaacaa atatgtggac gtgaacaatg tcggtatccg tggctacatg  7260
tacctcaaag gaccacgtgg tagcgttatg acaaccaaca tctacctgaa tagctccttg  7320
tatcgcggta cgaagttcat tatcaagaag tacgcttcag gcaacaagga caacatcgtg  7380
aggaacaatg atcgcgtgta catcaacgtc gtggtgaaga ataaggaata ccgcttggcg  7440
accaacgctt ctcaggctgg agttgagaag atcctgagcg ccttggagat cccagacgtt  7500
ggcaacctga gccaagtggt tgtgatgaaa agcaagaatg accagggaat caccaacaaa  7560
tgcaaaatga acctgcaaga caacaacggc aatgacatcg gtttcatcgg tttccaccag  7620
tttaacaata ttgcgaagct ggtcgccagc aactggtaca acaggcagat tgagaggtca  7680
tcccgtacct taggatgctc ttgggaattt atccccgtgg acgatggttg gggcgagaga  7740
cccctgggcg caggttggtc ccaccctcag ttcgagaagt aatagttaat agataataat  7800
agctcgaggc atgcgagctc cctcaggagg cctacgtcga cgagctcact agtcgcggcc  7860
gctttcgaat ctagagcctg cagtctcgag gcatgcggta ccaagcttgt cgagaagtac  7920
tagaggatca taatcagcca taccacattt gtagaggttt tacttgcttt aaaaaacctc  7980
ccacacctcc ccctgaacct gaaacataaa atgaatgcaa ttgttgttgt taacttgttt  8040
attgcagctt ataatggtta caaataaagc aatagcatca caaatttcac aaataaagca  8100
tttttttcac tgcattctag ttgtggtttg tccaaactca tcaatgtatc ttatcatgtc  8160
tggatctgat cactgcttga gcctaggaga tccgaaccag ataagtgaaa tctagttcca  8220
aactattttg tcatttttaa ttttcgtatt agcttacgac gctacaccca gttcccatct  8280
```

```
attttgtcac tcttccctaa ataatcctta aaaactccat ttccacccct cccagttccc    8340

aactattttg tccgcccaca gcggggcatt tttcttcctg ttatgttttt aatcaaacat    8400

cctgccaact ccatgtgaca aaccgtcatc ttcggctact ttttctctgt cacagaatga    8460

aaatttttct gtcatctctt cgttattaat gtttgtaatt gactgaatat caacgcttat    8520

ttgcagcctg aatggcgaat gg
```

This nucleotide sequence encodes the neurotoxin ΔLC-GFP-BoNT/A$^{tev}$.

Nucleic acid molecules of the present invention also include nucleic acid sequences that are at least 90%, 91%, 92%, 93%, 94%, 95%, 96%, 97%, 98%, 99% identical to the nucleic acid molecules of SEQ ID NOs:10-12 and 15.

Nucleic acid molecules of the present invention may encode the amino acid sequences of FIG. 1. In particular, the nucleic acid molecules of the present invention are modified from the wild type BoNT serotype sequences to have one or more characteristics shown in FIG. 1. Other modifications may include, without limitation, a mutation which renders the encoded propeptide resistant to low-specificity proteolysis, one or more silent mutations that inactivate putative internal DNA regulatory elements, and/or one or more unique restriction sites. Mature neurotoxin stability and yield may be optimized by site-directed mutation of residues within the intermediate region of the propeptide, thereby reducing the propeptides' susceptibility to non-specific proteolysis and poisoning of the host organism used for expression of the mature neurotoxin. Also, silent mutations are introduced into DNA regulatory elements that can affect RNA transcription or expression of the propeptides in the expression system of choice.

A nucleic acid molecule of the present invention may have a disabling mutation in a region encoding an active metalloprotease site of the propeptide.

A nucleic acid molecule of the present invention may also have a mutation in a region encoding the light chain region, such that the nucleic acid molecule encodes, in the light chain region, a non-native motif capable of inactivating light chain metalloprotease activity in a neuron intoxicated by wt *Clostridium botulinum* neurotoxin.

A nucleic acid molecule of the present invention may have a mutation encoding one or more of the following mutations in the neurotoxin: $E_{224}>A$, $Y_{366}>A$, $K_{438}>H$, $K_{440}>Q$, $K_{444}>Q$, and $K_{871}>N$.

A further aspect of the present invention relates to an expression system having a nucleic acid molecule encoding an isolated *Clostridium botulinum* neurotoxin propeptide of the present invention in a heterologous vector.

Yet another aspect of the present invention relates to a host cell having a heterologous nucleic acid molecule encoding an isolated *Clostridium botulinum* neurotoxin propeptide of the present invention.

Still another aspect of the present invention relates to a method of expressing a recombinant physiologically active *Clostridium botulinum* neurotoxin of the present invention. This method involves providing a nucleic acid construct having a nucleic acid molecule encoding an isolated *Clostridium botulinum* neurotoxin propeptide of the present invention. The nucleic acid construct has a heterologous promoter operably linked to the nucleic acid molecule and a 3' regulatory region operably linked to the nucleic acid molecule. The nucleic acid construct is then introduced into a host cell under conditions effective to express the physiologically active *Clostridium botulinum* neurotoxin.

In a preferred embodiment, the expressed neurotoxin is contacted with a highly specific protease under conditions effective to effect cleavage at the intermediate region. Preferably, the intermediate region of the *Clostridium botulinum* neurotoxin propeptide is not cleaved by proteases endogenous to the expression system or the host cell.

Expression of a *Botulinum* neurotoxin of the present invention can be carried out by introducing a nucleic acid molecule encoding a *Botulinum* neurotoxin propeptide into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted *Botulinum* neurotoxin propeptide-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the *Botulinum* neurotoxin propeptide-encoding sequence in a cell. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The *Botulinum* neurotoxin-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a *Botulinum* neurotoxin is inserted into a vector in the sense (i.e., 5→3') direction, such that the open reading frame is properly oriented for the expression of the encoded *Botulinum* neurotoxin propeptide under the control of a promoter of choice. Single or multiple nucleic acids may be ligated into an appropriate vector in this way, under the control of a suitable promoter, to prepare a nucleic acid construct.

Once the isolated nucleic acid molecule encoding the *Botulinum* neurotoxin propeptide has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like. Preferable host cells of the present invention include, but are not limited to, *Escherichia coli*, insect cells, and *Pichia pastoris* cells.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes"

which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In one embodiment of the present invention, the expressed neurotoxin propeptide is contacted with a highly specific protease (e.g., enterokinase or TEV sequence) under conditions effective to enable cleavage at the intermediate region of the propeptide of the present invention. By this means, the intermediate region is not cleaved by proteases endogenous to the host cell. The expressed neurotoxin propeptide has one or more disulfide bridges.

Another aspect of the present invention relates to an isolated, physiologically active *Clostridium botulinum* neurotoxin produced by cleaving an isolated *Clostridium botulinum* neurotoxin propeptide of the present invention. The propeptide is cleaved at the highly specific protease cleavage site. The light and heavy chain regions are linked by a disulfide bond.

The *Clostridium botulinum* neurotoxin of the present invention can be isolated at a yield or concentration of at least about 0.1 mg/L, at least about 0.5 mg/L, at least about 1 mg/L, at least about 5 mg/L, at least about 10 mg/L, about 10-20 mg/L, about 20-30 mg/L, or at least about 30 mg/L. One of the particular advantages of the propeptides of the present invention and the method of their expression described herein is that BoNT neurotoxins can be purified to a homogeneity using a two-stage, non-denaturing, and highly selective affinity purification, as described in greater detail infra.

As discussed supra, *Botulinum* neurotoxins are synthesized as single chain propeptides which are later activated by a specific proteolysis cleavage event, generating a dimer joined by a disulfide bond. These structural features can be illustrated using BoNT/A as an example, and are generally applicable to all *Clostridium botulinum* serotypes. The mature BoNT/A is composed of three functional domains of Mr ~50,000, where the catalytic function responsible for toxicity is confined to the light chain (residues 1-437), the translocation activity is associated with the N-terminal half of the heavy chain (residues 448-872), and cell binding is associated with its C-terminal half (residues 873-1,295) (Johnson, "Clostridial Toxins as Therapeutic Agents: Benefits of Nature's Most Toxic Proteins," *Annu. Rev. Microbiol.* 53:551-575 (1999); Montecucco et al., "Structure and Function of Tetanus and *Botulinum* Neurotoxins," *Q. Rev. Biophys.* 28:423-472 (1995), which are hereby incorporated by reference in their entirety).

Optimized expression and recovery of recombinant neurotoxins for BoNT serotypes in a native and physiologically active state is achieved by the introduction of one or more alterations to the nucleotide sequences encoding the BoNT propeptides, as discussed supra. These mutations are designed to maximize yield of recombinant *Botulinum* neurotoxin, while retaining the native toxins' structure and biological activity.

Isolated, full-length *Clostridium botulinum* neurotoxins of the present invention are physiologically active. This physiological activity includes, but is not limited to, toxin immunogenicity, trans- and intra-cellular trafficking, and cell recognition.

The mechanism of cellular binding and internalization of Clostridial toxins is still poorly understood. No specific receptor has been unambiguously identified, and the binding constants have not been characterized. The C-terminal portion of the heavy chain of all *Botulinum* neurotoxins binds to gangliosides (sialic acid-containing glycolipids), with a preference for gangliosides of the $G_{1b}$ series (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" *TIBS* 11:314-317 (1986); and Van Heyningen et al., "The Fixation of Tetanus Toxin by Ganglioside," *J. Gen. Microbiol.* 24:107-119 (1961), which are hereby incorporated by reference in their entirety). The sequence responsible for ganglioside binding has been identified for the structurally similar TeNT molecule, and is located within the 34 C-terminal amino acid residues of its heavy chain. BoNT/A, /B, /C, /E, and /F share a high degree of homology with TeNT in this region (Shapiro et al., "Identification of a Ganglioside Recognition Domain of Tetanus Toxin Using a Novel Ganglioside Photoaffinity Ligand," *J. Biol. Chem.* 272:30380-30386 (1997), which is hereby incorporated by reference in its entirety). Multiple types of evidence suggest the existence of at least one additional component involved in the binding of *Botulinum* neurotoxins to neuronal membranes (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" *TIBS* 11:314-317 (1986), which are hereby incorporated by reference in their entirety). In two reports (Nishiki et al., "The High-Affinity Binding of *Clostridium Botulinum* Type B Neurotoxin to Synaptotagmin II Associated with Gangliosides $G_{T1b}/G_{D1a}$," *FEBS Lett.* 378:253-257 (1996); Dong et al., "Synaptotagmins I and II Mediate Entry of *Botulinum* Neurotoxin B into Cells," *J. Cell Biol.* 162:1293-1303 (2003), which are hereby incorporated by reference in their entirety), synaptotagmins were identified as possible candidates for the auxiliary BoNT/B receptor, and synaptotagmins I and II were implicated as neuronal receptors for BoNT/G (Rummel et al., "Synaptotagmins I and II Act as Nerve Cell Receptors for *Botulinum* Neurotoxin G," *J. Biol. Chem.* 279:30865-30870 (2004), which is hereby incorporated by reference in its entirety). However, despite the structural similarity in the putative receptor-binding domain of *Botulinum* neurotoxins, other toxin subtypes show no affinity for synaptotagmins or synaptotagmin-related molecules. Lipid rafts (Herreros et al., "Lipid Rafts Act as Specialized Domains for Tetanus Toxin Binding and Internalization Into Neurons," *Mol. Biol. Cell* 12:2947-2960 (2001), which is hereby incorporated by reference in its entirety) have been implicated as a specialized domain involved in TeNT binding and internalization into neurons, but these domains are widely distributed on multiple cell types, and therefore cannot simply explain the high specificity of the toxins for neurons.

*Botulinum* neurotoxins are internalized through the presynaptic membrane by an energy-dependent mechanism (Montecucco et al., "Structure and Function of Tetanus and *Botulinum* Neurotoxins," *Q. Rev. Biophys.* 28:423-472 (1995); Matteoli et al., "Synaptic Vesicle Endocytosis Mediates the Entry of Tetanus Neurotoxin into Hippocampal Neurons," *Proc. Natl. Acad. Sci. USA* 93:13310-13315 (1996); and Mukherjee et al., "Endocytosis," *Physiol. Rev.* 77:759-803 (1997), which are hereby incorporated by reference in their entirety), and rapidly appear in vesicles where they are at least partially protected from degradation (Dolly et al., "Acceptors for *Botulinum* Neurotoxin Reside on Motor Nerve Terminals and Mediate Its Internalization," *Nature* 307:457-460 (1984); Critchley et al., "Fate of Tetanus Toxin Bound to the Surface of Primary Neurons in Culture: Evidence for Rapid Internalization," *J. Cell Biol.* 100:1499-1507 (1985), which are hereby incorporated by reference in their entirety).

The BoNT complex of light and heavy chains interacts with the endocytic vesicle membrane in a chaperone-like way, preventing aggregation and facilitating translocation of the light chain in a fashion similar to the protein conducting/translocating channels of smooth ER, mitochondria, and chloroplasts (Koriazova et al., "Translocation of *Botulinum* Neurotoxin Light Chain Protease Through the Heavy Chain Channel," *Nat. Struct. Biol.* 10:13-18 (2003), which is hereby incorporated by reference in its entirety). Acidification of the endosome is believed to induce pore formation, which allows translocation of the light chain to the cytosol upon reduction of the interchain disulfide bond (Hoch et al., "Channels Formed by *Botulinum*, Tetanus, and Diphtheria Toxins in Planar Lipid Bilayers: Relevance to Translocation of Proteins Across Membranes," *Proc. Natl. Acad. Sci. USA* 82:1692-1696 (1985), which is hereby incorporated by reference in its entirety). Within the cytosol, the light chain displays a zinc-endopeptidase activity specific for protein components of the synaptic vesicle exocytosis apparatus. TeNT and BoNT/B, /D, /F, and /G recognize VAMP/synaptobrevin. This integral protein of the synaptic vesicle membrane is cleaved at a single peptide bond, which differs for each neurotoxin. BoNT/A, /C, and /E recognize and cleave SNAP-25, a protein of the presynaptic membrane, at two different sites within the carboxyl terminus. BoNT/C also cleaves syntaxin, another protein of the nerve plasmalemma (Montecucco et al., "Structure and Function of Tetanus and *Botulinum* Neurotoxins," *Q. Rev. Biophys.* 28:423-472 (1995); Sutton et al., "Crystal Structure of a SNARE Complex Involved in Synaptic Exocytosis at 2.4 Å Resolution," *Nature* 395:347-353 (1998), which are hereby incorporated by reference in their entirety). The cleavage of any component of the synaptic release machinery results in inhibition of acetylcholine release, ultimately leading to neuromuscular paralysis.

The toxicity of *Botulinum* neurotoxins is a result of a multistep mechanism. From the circulation, BoNT targets the presynaptic membrane of neuromuscular junctions, where it is internalized to directly exert its toxic effect on the peripheral nervous system (Dolly et al., "Acceptors for *Botulinum* Neurotoxin Reside on Motor Nerve Terminals and Mediate Its Internalization," *Nature* 307 :457-460 (1984), which is hereby incorporated by reference in its entirety). Toxicity at the neuromuscular junction involves neuron binding; internalization into endocytic vesicles, similar to those involved in synaptic vesicle recycling; activation within an acidic compartment to the proteolytically active toxin which then penetrates into the neuronal cytoplasm; and target recognition and catalytic cleavage of substrates in the neuronal machinery for synaptic vesicle exocytosis.

*Clostridium botulinum* neurotoxins of the present invention are physiologically active, and may be either toxic or atoxic. Atoxic neurotoxins have a toxicity that is reduced from the wt BoNT by at least about 1000-fold. In certain exemplary embodiments, the $LD_{50}$ of an atoxic *Clostridium botulinum* neurotoxin of the present invention is between 1,000 and 150,000; between 50,000 and 150,000; between 75,000 and 150,000; between 100,000 and 150,000; between 1,000 and 100,000; between 50,000 and 100,000; between 75,000 and 100,000; 1,000; 25,000; 50,000; 75,000; 100,000; or 150,000-fold higher than the $LD_{50}$ of wt *Clostridium botulinum.*

The endopeptidase activity responsible for *Botulinum* neurotoxin toxicity is believed to be associated with the presence of a HExxHxxH (SEQ ID NO:1) motif in the light chain, characteristic of metalloproteases. Mutagenesis of BoNT/A light chain, followed by microinjection of the corresponding mRNA into presynaptic cholinergic neurons of *Aplysia californica*, allowed the minimal essential domain responsible for toxicity to be identified (Kurazono et al., "Minimal Essential Domains Specifying Toxicity of the Light Chains of Tetanus Toxin and *Botulinum* Neurotoxin Type A," *J. Biol. Chem.* 267:14721-14729 (1992), which is hereby incorporated by reference in its entirety). Site-directed mutagenesis of BoNT/A light chain pinpointed the amino acid residues involved in $Zn^{2+}$ coordination, and formation of the active metalloendoprotease core which cleaves SNAP-25 (Rigoni et al., "Site-Directed Mutagenesis Identifies Active-Site Residues of the Light Chain of *Botulinum* Neurotoxin Type A," *Biochem. Biophys. Res. Commun.* 288:1231-1237 (2001), which is hereby incorporated by reference in its entirety). The three-dimensional structures of *Botulinum* neurotoxins and their derivatives confirmed the mutagenesis results, and detailed the spatial organization of the protein domains. For the BoNT/A holotoxin, crystal structure was obtained to a resolution of 3.3 Å (Lacy et al., "Crystal Structure of *Botulinum* Neurotoxin Type A and Implications for Toxicity," *Nat. Struct. Biol.* 5:898-902 (1998), which is hereby incorporated by reference in its entirety). The BoNT/B holotoxin crystal structure was determined at 1.8 and 2.6 Å resolution (Swaminathan et al., "Structural Analysis of the Catalytic and Binding Sites of *Clostridium botulinum* Neurotoxin B," *Nat. Struct. Biol.* 7:693-699 (2000), which is hereby incorporated by reference in its entirety). Recently, a crystal structure for BoNT/E catalytic domain was determined to 2.1 Å resolution (Agarwal et al., "Structural Analysis of *Botulinum* Neurotoxin Type E Catalytic Domain and Its Mutant $Glu_{212}$>Gln Reveals the Pivotal Role of the $Glu_{212}$ Carboxylate in the Catalytic Pathway," *Biochemistry* 43:6637-6644 (2004), which is hereby incorporated by reference in its entirety). The later study provided multiple interesting structural details, and helps explain the complete loss of metalloendoproteolytic activity in the BoNT/E LC $E_{212}$>Q mutant. The availability of this detailed information on the relationship between the amino acid sequence and biological activities of Clostridial toxins enables the design of modified toxin genes with properties specifically altered for therapeutic goals.

Thus, the physiologically active and atoxic *Botulinum* neurotoxin of the present invention may have a disabling mutation in an active metalloprotease site. The physiologically active *Botulinum* neurotoxins of the present invention may also have a non-native motif (e.g., a SNARE motif) in the light chain region that is capable of inactivating light chain metalloprotease activity in a toxic *Botulinum* neurotoxin, as described in U.S. Patent Application Publication No. 2006/0204524 to Ichtchenko et al., which is hereby incorporated by reference in its entirety.

Exemplary *Clostridium botulinum* neurotoxins of the present invention have structures as shown in FIG. 1. Specifically, the neurotoxin may have a structure selected from BoNT/$Aad^{ek}$, BoNT/$Aad^{tev}$, ΔLC-Peptide-BoNT/$A^{tev}$, and ΔLC-GFP-BoNT/$A^{tev}$, or other such similar derivatives. Alternatively, neurotoxins of the present invention have an amino acid sequence that is at least 90%, 95%, 96%, 97%, 98%, or 99% identical to SEQ ID NOs:3-6 set forth below.

The full-length BoNT/$Aad^{ek}$ neurotoxin has an amino acid sequence of SEQ ID NO:3, as follows:

```
MKFLVNVALV FMVVYISYIY AAAHHHHHHH HHHTRENLYF QGAGDSLSWL LRLLNARGGA    60
SGPFVNKQFN YKDPVNGVDI AYIKIPNAGQ MQPVKAFKIH NKIWVIPERD TFTNPEEGDL   120
NPPPEAKQVP VSYYDSTYLS TDNEKDNYLK GVTKLFERIY STDLGRMLLT SIVRGIPFWG   180
GSTIDTELKV IDTNCINVIQ PDGSYRSEEL NLVIIGPSAD IIQFECKSFG HEVLNLTRNG   240
YGSTQYIRFS PDFTFGFEES LEVDTNPLLG AGKFATDPAV TLAHALIHAG HRLYGIAINP   300
NRVFKVNTNA YYEMSGLEVS FEELRTFGGH DAKFIDSLQE NEFRLYYYNK FKDIASTLNK   360
AKSIVGTTAS LQYMKNVFKE KYLLSEDTSG KFSVDKLKFD KLYKMLTEIY TEDNFVKFFK   420
VLNRKTALNF DKAVFKINIV PKVNYTIYDG FNLRNTNLAA NFNGQNTEIN NMNFTKLKNF   480
TGLFEFYKLL CVRGIITSHT QSLDQGYNDD DDKALNDLCI KVNNWDLFFS PSEDNFTNDL   540
NKGEEITSDT NIEAAEENIS LDLIQQYYLT FNFDNEPENI SIENLSSDII GQLELMPNIE   600
RFPNGKKYEL DKYTMFHYLR AQEFEHGKSR IALTNSVNEA LLNPSRVYTF FSSDYVKKVN   660
KATEAAMFLG WVEQLVYDFT DETSEVSTTD KIADITIIIP YIGPALNIGN MLYKDDFVGA   720
LIFSGAVILL EFIPEIAIPV LGTFALVSYI ANKVLTVQTI DNALSKRNEK WDEVYKYIVT   780
NWLAKVNTQI DLIRKKMKEA LENQAEATKA IINYQYNQYT EEEKNNINFN IDDLSSKLNE   840
SINKAMININ KFLNQCSVSY LMNSMIPYGV KRLEDFDASL KDALLKYIYD NRGTLIGQVD   900
RLKDKVNNTL STDIPFQLSK YVDNQRLLST FTEYINNIIN TSILNLRYES NHLIDLSRYA   960
SKINIGSKVN FDPIDKNQIQ LFNLESSKIE VILKNAIVYN SMYENFSTSF WIRIPKYFNS  1020
ISLNNEYTII NCMENNSGWK VSLNYGEIIW TLQDTQEIKQ RVVFKYSQMI NISDYINRWI  1080
FVTITNNRLN NSKIYINGRL IDQKPISNLG NIHASNNIMF KLDGCRDTHR YIWIKYFNLF  1140
DKELNEKEIK DLYDNQSNSG ILKDFWGDYL QYDKPYYMLN LYDPNKYVDV NNVGIRGYMY  1200
LKGPRGSVMT TNIYLNSSLY RGTKFIIKKY ASGNKDNIVR NNDRVYINVV VKNKEYRLAT  1260
NASQAGVEKI LSALEIPDVG NLSQVVVMKS KNDQGITNKC KMNLQDNNGN DIGFIGFHQF  1320
NNIAKLVASN WYNRQIERSS RTLGCSWEFI PVDDGWGERP LGAGWSHPQF EK
```

The full-length BoNT/Aad[tev] neurotoxin has an amino acid sequence of SEQ ID NO:4, as follows:

```
MKFLVNVALV FMVVYISYIY AAAHHHHHHH HHHTRENLYF QGAGDSLSWL LRLLNARGGA    60
SGPFVNKQFN YKDPVNGVDI AYIKIPNAGQ MQPVKAFKIH NKIWVIPERD TFTNPEEGDL   120
NPPPEAKQVP VSYYDSTYLS TDNEKDNYLK GVTKLFERIY STDLGRMLLT SIVRGIPFWG   180
GSTIDTELKV IDTNCINVIQ PDGSYRSEEL NLVIIGPSAD IIQFECKSFG HEVLNLTRNG   240
YGSTQYIRFS PDFTFGFEES LEVDTNPLLG AGKFATDPAV TLAHALIHAG HRLYGIAINP   300
NRVFKVNTNA YYEMSGLEVS FEELRTFGGH DAKFIDSLQE NEFRLYYYNK FKDIASTLNK   360
AKSIVGTTAS LQYMKNVFKE KYLLSEDTSG KFSVDKLKFD KLYKMLTEIY TEDNFVKFFK   420
VLNRKTALNF DKAVFKINIV PKVNYTIYDG FNLRNTNLAA NFNGQNTEIN NMNFTKLKNF   480
TGLFEFYKLL CVRGIITSHT QSLDQGGENL YFQGALNDLC IKVNNWDLFF SPSEDNFTND   540
LNKGEEITSD TNIEAAEENI SLDLIQQYYL TFNFDNEPEN ISIENLSSDI IGQLELMPNI   600
ERFPNGKKYE LDKYTMFHYL RAQEFEHGKS RIALTNSVNE ALLNPSRVYT FFSSDYVKKV   660
NKATEAAMFL GWVEQLVYDF TDETSEVSTT DKIADITIII PYIGPALNIG NMLYKDDFVG   720
ALIFSGAVIL LEFIPEIAIP VLGTFALVSY IANKVLTVQT IDNALSKRNE KWDEVYKYIV   780
TNWLAKVNTQ IDLIRKKMKE ALENQAEATK AIINYQYNQY TEEEKNNINF NIDDLSSKLN   840
ESINKAMINI NKFLNQCSVS YLMNSMIPYG VKRLEDFDAS LKDALLKYIY DNRGTLIGQV   900
```

-continued

```
DRLKDKVNNT LSTDIPFQLS KYVDNQRLLS TFTEYINNII NTSILNLRYE SNHLIDLSRY   960

ASKINIGSKV NFDPIDKNQI QLFNLESSKI EVILKNAIVY NSMYENFSTS FWIRIPKYFN  1020

SISLNNEYTI INCMENNSGW KVSLNYGEII WTLQDTQEIK QRVVFKYSQM INISDYINRW  1080

IFVTITNNRL NNSKIYINGR LIDQKPISNL GNIHASNNIM FKLDGCRDTH RYIWIKYFNL  1140

FDKELNEKEI KDLYDNQSNS GILKDFWGDY LQYDKPYYML NLYDPNKYVD VNNVGIRGYM  1200

YLKGPRGSVM TTNIYLNSSL YRGTKFIIKK YASGNKDNIV RNNDRVYINV VVKNKEYRLA  1260

TNASQAGVEK ILSALEIPDV GNLSQVVVMK SKNDQGITNK CKMNLQDNNG NDIGFIGFHQ  1320

FNNIAKLVAS NWYNRQIERS SRTLGCSWEF IPVDDGWGER PLGAGWSHPQ FEK
```

The full-length ΔLC-Peptide-BoNT/$A^{tev}$ neurotoxin has an amino acid sequence of SEQ ID NO:5, as follows:

```
MKFLVNVALV FMVVYISYIY AAAHHHHHHH HHHTRENLYF QGAGDSLSWL LRLLNARGGA   60

SGGTNGNGNG GNLRNTNLAA NFNGQNTEIN NMNFTKLKNF TGLFEFYKLL CVRGIITSHT  120

QSLDQGGENL YFQGALNDLC IKVNNWDLFF SPSEDNFTND LNKGEEITSD TNIEAAEENI  180

SLDLIQQYYL TFNFDNEPEN ISIENLSSDI IGQLELMPNI ERFPNGKKYE LDKYTMFHYL  240

RAQEFEHGKS RIALTNSVNE ALLNPSRVYT FFSSDYVKKV NKATEAAMFL GWVEQLVYDF  300

TDETSEVSTT DKIADITIII PYIGPALNIG NMLYKDDFVG ALIFSGAVIL LEFIPEIAIP  360

VLGTFALVSY IANKVLTVQT IDNALSKRNE KWDEVYKYIV TNWLAKVNTQ IDLIRKKMKE  420

ALENQAEATK AIINYQYNQY TEEEKNNINF NIDDLSSKLN ESINKAMINI NKFLNQCSVS  480

YLMNSMIPYG VKRLEDFDAS LKDALLKYIY DNRGTLIGQV DRLKDKVNNT LSTDIPFQLS  540

KYVDNQRLLS TFTEYINNII NTSILNLRYE SNHLIDLSRY ASKINIGSKV NFDPIDKNQI  600

QLFNLESSKI EVILKNAIVY NSMYENFSTS FWIRIPKYFN SISLNNEYTI INCMENNSGW  660

KVSLNYGEII WTLQDTQEIK QRVVFKYSQM INISDYINRW IFVTITNNRL NNSKIYINGR  720

LIDQKPISNL GNIHASNNIM FKLDGCRDTH RYIWIKYFNL FDKELNEKEI KDLYDNQSNS  780

GILKDFWGDY LQYDKPYYML NLYDPNKYVD VNNVGIRGYM YLKGPRGSVM TTNIYLNSSL  840

YRGTKFIIKK YASGNKDNIV RNNDRVYINV VVKNKEYRLA TNASQAGVEK ILSALEIPDV  900

GNLSQVVVMK SKNDQGITNK CKMNLQDNNG NDIGFIGFHQ FNNIAKLVAS NWYNRQIERS  960

SRTLGCSWEF IPVDDGWGER PLGAGWSHPQ FEK
```

The full-length ΔLC-GFP-BoNT/$A^{tev}$ neurotoxin has an amino acid sequence of SEQ ID NO:6, as follows:

```
MKFLVNVALV FMVVYISYIY AAAHHHHHHH HHHTRENLYF QGAGDSLSWL LRLLNARGGA   60

SVSKGAELFT GIVPILIELN GDVNGHKFSV SGEGEGDATY GKLTLKFICT TGKLPVPWPT  120

LVTTLSYGVQ CFSRYPDHMK QHDFFKSAMP EGYIQERTIF FEDDGNYKSR AEVKFEGDTL  180

VNRIELTGTD FKEDGNILGN KMEYNYNAHN VYIMTDKAKN GIKVNFKIRH NIEDGSVQLA  240

DHYQQNTPIG DGPVLLPDNH YLSTQSALSK DPNEKRDHMI YFGFVTAAAI THGMDELYKG  300

TNGNGNGGNL RNTNLAANFN GQNTEINNMN FTKLKNFTGL FEFYKLLCVR GIITSHTQSL  360

DQGGENLYFQ GALNDLCIKV NNWDLFFSPS EDNFTNDLNK GEEITSDTNI EAAEENISLD  420

LIQQYYLTFN FDNEPENISI ENLSSDIIGQ LELMPNIERF PNGKKYELDK YTMFHYLRAQ  480

EFEHGKSRIA LTNSVNEALL NPSRVYTFFS SDYVKKVNKA TEAAMFLGWV EQLVYDFTDE  540

TSEVSTTDKI ADITIIIPYI GPALNIGNML YKDDFVGALI FSGAVILLEF IPEIAIPVLG  600
```

-continued

```
TFALVSYIAN KVLTVQTIDN ALSKRNEKWD EVYKYIVTNW LAKVNTQIDL IRKKMKEALE   660

NQAEATKAII NYQYNQYTEE EKNNINFNID DLSSKLNESI NKAMININKF LNQCSVSYLM   720

NSMIPYGVKR LEDFDASLKD ALLKYIYDNR GTLIGQVDRL KDKVNNTLST DIPFQLSKYV   780

DNQRLLSTFT EYINNIINTS ILNLRYESNH LIDLSRYASK INIGSKVNFD PIDKNQIQLF   840

NLESSKIEVI LKNAIVYNSM YENFSTSFWI RIPKYFNSIS LNNEYTIINC MENNSGWKVS   900

LNYGEIIWTL QDTQEIKQRV VFKYSQMINI SDYINRWIFV TITNNRLNNS KIYINGRLID   960

QKPISNLGNI HASNNIMFKL DGCRDTHRYI WIKYFNLFDK ELNEKEIKDL YDNQSNSGIL  1020

KDFWGDYLQY DKPYYMLNLY DPNKYVDVNN VGIRGYMYLK GPRGSVMTTN IYLNSSLYRG  1080

TKFIIKKYAS GNKDNIVRNN DRVYINVVVK NKEYRLATNA SQAGVEKILS ALEIPDVGNL  1140

SQVVVMKSKN DQGITNKCKM NLQDNNGNDI GFIGFHQFNN IAKLVASNWY NRQIERSSRT  1200

LGCSWEFIPV DDGWGERPLG AGWSHPQFEK
```

Still another aspect of the present invention relates to a treatment method. This method involves providing an isolated *Clostridium botulinum* neurotoxin according to the present invention, where the light chain region and the heavy chain region are linked by a disulfide bond and the cargo comprises a therapeutic agent. The isolated *Clostridium botulinum* neurotoxin is administered to an individual in need of treatment under conditions effective to provide treatment to the individual.

Administration can be carried out orally, parenterally, for example, subcutaneously, intravenously, intramuscularly, intrarticularly, intraperitoneally, by intranasal instillation, or by application to mucous membranes, such as, that of the nose, throat, and bronchial tubes. The neurotoxin may be administered alone or with suitable pharmaceutical carriers, and can be in solid or liquid form such as, tablets, capsules, powders, solutions, suspensions, or emulsions.

The neurotoxin of the present invention may be orally administered, for example, with an inert diluent, or with an assimilable edible carrier, or may be enclosed in hard or soft shell capsules, or may be compressed into tablets, or may be incorporated directly with the food of the diet. For oral therapeutic administration, the neurotoxin (along with any cargo) may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The neurotoxin may also be administered parenterally. Solutions or suspensions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol, hyaluronan and its derivatives, or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The neurotoxin of the present invention may also be administered directly to the airways in the form of an aerosol. For use as aerosols, the neurotoxin of the present invention in solution or suspension may be packaged in a pressurized aerosol container together with suitable propellants, for example, hydrocarbon propellants like propane, butane, or isobutane with conventional adjuvants. The neurotoxin of the present invention also may be administered in a non-pressurized form such as in a nebulizer or atomizer.

In one embodiment, the neurotoxin of the present invention has a therapeutic agent as cargo, and the method involves treatment by the therapeutic agent. According to this embodiment, the *Botulinum* neurotoxin serves as a delivery vehicle for the therapeutic agent.

In another embodiment, the neurotoxin of the present invention has cargo other than a therapeutic agent and is administered to treat disorders amenable to treatment by *Botulinum* neurotoxins (either toxic or atoxic) including, for example, neuronal pathologies, such as tourettes syndrome (Porta et al., "Treatment of Phonic Tics in Patients with Tourette's Syndrome Using *Botulinum* Toxin Type A," *Neurol. Sci.* 24:420-423 (2004), which is hereby incorporated by reference in its entirety) and focal muscle spasticity or dystonias (MacKinnon et al., "Corticospinal Excitability Accompanying Ballistic Wrist Movements in Primary Dystonia," *Mov. Disord.* 19:273-284 (2004), which is hereby incorporated by reference in its entirety) including, but not limited to, treatment for cervical dystonia (Haussermann et al., "Long-Term Follow-Up of Cervical Dystonia Patients Treated with *Botulinum* Toxin A," *Mov. Disord.* 19:303-308 (2004), which is hereby incorporated by reference in its entirety), primary blepharospasm (Defazio et al., "Primary Blepharospasm: Diagnosis and Management," *Drugs* 64:237-244 (2004), which is hereby incorporated by reference in its entirety), hemifacial spasm, post-stroke (Bakheit, "Optimising the Methods of Evaluation of the Effectiveness of *Botulinum* Toxin Treatment of Post-Stroke Muscle Spasticity," *J. Neurol. Neurosurg. Psychiatry* 75:665-666 (2004), which is hereby incorporated by reference in its entirety), spasmodic dysphonia (Bender et al., "Speech Intelligibility in Severe Adductor Spasmodic Dysphonia," *J. Speech Lang. Hear Res.* 47:21-32 (2004), which is hereby incorporated by reference in its entirety), facial nerve disorders (Finn, "*Botulinum* Toxin Type A: Fine-Tuning Treatment of Facial Nerve Injury," *J. Drugs Dermatol.* 3:133-137 (2004), which is hereby incorporated by reference in its entirety), and Rasmussen syndrome (Lozsadi et al., "*Botulinum* Toxin A Improves Involuntary Limb Movements in Rasmussen Syndrome," *Neurology* 62:1233-1234 (2004), which is hereby incorporated by reference in its entirety). Other neurologic treatments include treatment for amputation pain (Kern et al., "Effects of *Botulinum* Toxin Type B on Stump Pain and Involuntary Movements of the Stump," *Am. J. Phys. Med. Rehabil.* 83:396-399 (2004), which is hereby incorporated by reference in its entirety), voice tremor (Adler et al., "*Botulinum* Toxin Type A for Treating Voice Tremor," *Arch. Neurol.* 61:1416-1420 (2004), which is hereby incorporated by reference in its entirety), crocodile tear syndrome (Kyrmizakis et al., "The Use of *Botulinum* Toxin Type A in the Treatment of Frey and Crocodile Tears Syndrome," *J. Oral Maxillofac. Surg.* 62:840-844 (2004), which is hereby incorporated by reference in its entirety), marginal mandibular nerve paralysis, and pain control (Cui et al., "Subcutaneous Administration of *Botulinum* Toxin A Reduces Formalin-Induced Pain," *Pain* 107:125-133 (2004), which is hereby incorporated by reference in its entirety) including, but not limited to, pain after mastectomy (Layeeque et al., "*Botulinum* Toxin Infiltration for Pain Control After Mastectomy and Expander Reconstruction," *Ann. Surg.* 240:608-613 (2004), which is hereby incorporated by reference in its entirety) and chest pain of esophageal origin (Schumulson et al., "Current and Future Treatment of Chest Pain of Presumed Esophageal Origin," *Gastroenterol. Clin. North Am.* 33:93-105 (2004), which is hereby incorporated by reference in its entirety). Another neurologic treatment amenable to the methods of the present invention is headache (Blumenfeld et al., "*Botulinum* Neurotoxin for the Treatment of Migraine and Other Primary Headache Disorders," *Dermatol. Clin.* 22:167-175 (2004), which is hereby incorporated by reference in its entirety).

The methods of the present invention are also suitable for treatment of cerebral palsy (Balkrishnan et al., "Longitudinal Examination of Health Outcomes Associated with *Botulinum* Toxin Use in Children with Cerebral Palsy," *J. Surg. Orthop. Adv.* 13:76-80 (2004); Berweck et al., "Use of *Botulinum* Toxin in Pediatric Spasticity (Cerebral Palsy)," *Mov. Disord.* 19:S162-S167 (2004); Pidcock, "The Emerging Role of Therapeutic *Botulinum* Toxin in the Treatment of Cerebral Palsy," *J. Pediatr.* 145:S33-S35 (2004), which are hereby incorporated by reference in their entirety), hip adductor muscle dysfunction in multiple sclerosis (Wissel et al., "*Botulinum* Toxin Treatment of Hip Adductor Spasticity in Multiple Sclerosis," *Wien Klin Wochesnchr* 4:20-24 (2001), which is hereby incorporated by reference in its entirety), neurogenic pain and inflammation, including arthritis, iatrogenic parotid sialocele (Capaccio et al., "Diagnosis and Therapeutic Management of Iatrogenic Parotid Sialocele," *Ann. Otol. Rhinol. Laryngol.* 113:562-564 (2004), which is hereby incorporated by reference in its entirety), and chronic TMJ displacement (Aquilina et al., "Reduction of a Chronic Bilateral Temporomandibular Joint Dislocation with Intermaxillary Fixation and *Botulinum* Toxin A," *Br. J. Oral Maxillofac. Surg.* 42:272-273 (2004), which is hereby incorporated by reference in its entirety). Other conditions that can be treated by local controlled delivery of pharmaceutically active toxin include intra-articular administration for the treatment of arthritic conditions (Mahowald et al., "Long Term Effects of Intra-Articular BoNT A for Refractory Joint Pain," *Annual Meeting of the American College of Rheumatology* (2004), which is hereby incorporated by reference in its entirety), and local administration for the treatment of joint contracture (Russman et al., "Cerebral Palsy: A Rational Approach to a Treatment Protocol, and the Role of *Botulinum* Toxin in Treatment," *Muscle Nerve Suppl.* 6:S181-S193 (1997); Pucinelli et al., "Botulinic Toxin for the Rehabilitation of Osteoarthritis Fixed-Flexion Knee Deformity," *Annual Meeting of the Osteoartritis Research Society International* (2004), which are hereby incorporated by reference in their entirety). The methods of the present invention are also suitable for the treatment of pain associated with various conditions characterized by the sensitization of nociceptors and their associated clinical syndromes, as described in Bach-Rojecky et al., "Antinociceptive Effect of *Botulinum* Toxin Type A In Rat Model of Carrageenan and Capsaicin Induced Pain," *Croat. Med. J.* 46:201-208 (2005); Aoki, "Evidence for Antinociceptive Activity of *Botulinum* Toxin Type A in Pain Management," *Headache* 43 Suppl 1:S9-15 (2003); Kramer et al., "*Botulinum* Toxin A Reduces Neurogenic Flare But Has Almost No Effect on Pain and Hyperalgesia in Human Skin," *J. Neurol.* 250:188-193 (2003); Blersch et al., "*Botulinum* Toxin A and the Cutaneous Nociception in Humans: A Prospective, Double-Blind, Placebo-Controlled, Randomized Study," *J. Neurol. Sci.* 205:59-63 (2002), which are hereby incorporated by reference in their entirety.

In one embodiment, accumation of atoxic *Botulinum* neurotoxins of the present invention at particular sites (e.g., in neuronal cells in periarticular tissues of joints) may be effective in treating disorders described herein (e.g., arthritis and chronic musculoskeletal pain syndromes, and other disorders associated with the central pain pathway). Accumulation may include accumulation of the light chain in neuronal cytosol.

The methods and products of the present invention may be customized to optimize therapeutic properties (see e.g., Chaddock et al., "Retargeted Clostridial Endopeptidases: Inhibition of Nociceptive Neurotransmitter Release In vitro, and Antinociceptive Activity in In vivo Models of Pain," *Mov. Disord.* 8:S42-S47 (2004); Finn, "*Botulinum* Toxin Type A: Fine-Tuning Treatment of Facial Nerve Injury," *J. Drugs Dermatol.* 3:133-137 (2004); Eleopra et al., "Different Types of *Botulinum* Toxin In Humans," *Mov. Disord.* 8:S53-S59 (2004); Flynn, "Myobloc," *Dermatol. Clin.* 22:207-211 (2004); and Sampaio et al., "Clinical Comparability of Marketed Formulations of *Botulinum* Toxin," *Mov. Disord.* 8:S129-S136 (2004), which are hereby incorporated by reference in their entirety).

A further aspect of the present invention is directed to a method of detecting *Clostridium botulinum* neurotoxin trafficking either for mechanistic studies or for imaging specific sites of high neuronal activity. This method involves expressing a recombinant physiologically active *Clostridium botulinum* neurotoxin according to the methods of the present invention, where a fluorophore is coupled to the neurotoxin, and detecting trafficking of the neurotoxin by detecting one or more locations of the fluorophore.

This method of the present invention can be carried out in vivo or in vitro.

Detecting location of a fluorophore or other imaging modality can be carried out using methods well-known in the art. For example, detection devices are known that are capable of receiving fluorescent emissions and generating a response to be examined by an operator. Suitable detectors include, without limitation, charge coupled devices (CCDs), photomultiplier tubes (PMTS), avalanche photodiodes (APDs), and photodiodes that contain a semiconductor material such as Si, InGaAs, extended InGaAs, Ge, HgCdTe, PbS, PbSe, or GaAs to convert optical photons into electrical current. CCD can produce an image in extremely dim light, and its resolution (i.e., sharpness or data density) does not degrade in low light. Other imaging procedures suitable for detection may include CAT scan, PET scan, and MRI.

Another aspect of the present invention relates to a method of detecting levels of neuronal activity. This method involves providing the isolated *Clostridium botulinum* neurotoxin of the present invention and administering the neurotoxin to an individual or a tissue sample. The method further involves detecting location of the neurotoxin, where detection of the neurotoxin at a specific site in the individual or tissue sample indicates an increased level of activity of neurons at that site.

EXAMPLES

The following examples are provided to illustrate embodiments of the present invention but are by no means intended to limit its scope.

Example 1

Creation of the Construct Encoding BoNT/Aad$^{ek}$ in pLitmus Vector

Modification of pLitmus28i by Replacement of the Existent Polylinker with a Custom-Built Polylinker A vector with a custom polylinker derived from Litmus 28i (New England Biolabs, Cat. #N3528S, 2823 b.p.) was used for subcloning the full-length BoNT/Aad$^{ek}$. This derivative of Litmus 28i (pLitmus28C1) was created by restriction digestion of Litmus 28i with Bgl II and Aat II followed by dephosphorylation. Annealed phosphorylated oligonucleotides C1-1S and C1-1A (Table 1) were ligated into digested Litmus 28i, resulting in the intermediate vector, pLitmus28C1INT (2842 b.p.). Vector pLitmus28C1INT was digested with Kas I and Stu I and dephosphorylated. Annealed phosphorylated oligonucleotides C1-2S and C1-2A were ligated into digested pLitmus28C1INT, resulting in the vector pLitmus28C1 (2890 b.p.). The sequence of this vector was deposited in GenBank under accession number GQ855199, and has a sequence of SEQ ID NO:13, as follows:

```
gttaactacg tcaggtggca cttttcgggg aaatgtgcgc ggaaccccta tttgtttatt    60
tttctaaata cattcaaata tgtatccgct catgagacaa taaccctgat aaatgcttca   120
ataatattga aaaaggaaga gtatgagtat tcaacatttc cgtgtcgccc ttattccctt   180
ttttgcggca ttttgccttc ctgtttttgc tcacccagaa acgctggtga aagtaaaaga   240
tgctgaagat cagttgggtg cacgagtggg ttacatcgaa ctggatctca acagcggtaa   300
gatccttgag agttttcgcc ccgaagaacg ttctccaatg atgagcactt ttaaagttct   360
gctatgtggc gcggtattat cccgtgttga cgccgggcaa gagcaactcg gtcgccgcat   420
acactattct cagaatgact tggttgagta ctcaccagtc acagaaaagc atcttacgga   480
tggcatgaca gtaagagaat tatgcagtgc tgccataacc atgagtgata acactgcggc   540
caacttactt ctgacaacga tcggaggacc gaaggagcta accgcttttt tgcacaacat   600
gggggatcat gtaactcgcc ttgatcgttg ggaaccggag ctgaatgaag ccataccaaa   660
cgacgagcgt gacaccacga tgcctgtagc aatggcaaca acgttgcgca aactattaac   720
tggcgaacta cttactctag cttcccggca acaattaata gactggatgg aggcggataa   780
agttgcagga ccacttctgc gctcggccct tccggctggc tggtttattg ctgataaatc   840
tggagccggt gagcgtgggt ctcgcggtat cattgcagca ctggggccag atggtaagcc   900
ctcccgtatc gtagttatct acacgacggg gagtcaggca actatggatg aacgaaatag   960
acagatcgct gagataggtg cctcactgat taagcattgg taactgtcag accaagttta  1020
ctcatatata ctttagattg atttaccccg gttgataatc agaaaagccc caaaaacagg  1080
aagattgtat aagcaaatat ttaaattgta aacgttaata ttttgttaaa attcgcgtta  1140
aatttttgtt aaatcagctc attttttaac caataggccg aaatcggcaa aatcccttat  1200
```

-continued

```
aaatcaaaag aatagcccga gatagggttg agtgttgttc cagtttggaa caagagtcca  1260
ctattaaaga acgtggactc caacgtcaaa gggcgaaaaa ccgtctatca gggcgatggc  1320
ccactacgtg aaccatcacc caaatcaagt tttttggggt cgaggtgccg taaagcacta  1380
aatcggaacc ctaaagggag cccccgattt agagcttgac ggggaaagcg aacgtggcga  1440
gaaaggaagg gaagaaagcg aaaggagcgg gcgctagggc gctggcaagt gtagcggtca  1500
cgctgcgcgt aaccaccaca cccgccgcgc ttaatgcgcc gctacagggc gcgtaaaagg  1560
atctaggtga agatcctttt tgataatctc atgaccaaaa tcccttaacg tgagttttcg  1620
ttccactgag cgtcagaccc cgtagaaaag atcaaaggat cttcttgaga tccttttttt  1680
ctgcgcgtaa tctgctgctt gcaaacaaaa aaaccaccgc taccagcggt ggtttgtttg  1740
ccggatcaag agctaccaac tctttttccg aaggtaactg gcttcagcag agcgcagata  1800
ccaaatactg ttcttctagt gtagccgtag ttaggccacc acttcaagaa ctctgtagca  1860
ccgcctacat acctcgctct gctaatcctg ttaccagtgg ctgctgccag tggcgataag  1920
tcgtgtctta ccgggttgga ctcaagacga tagttaccgg ataaggcgca gcggtcgggc  1980
tgaacggggg gttcgtgcac acagcccagc ttggagcgaa cgacctacac cgaactgaga  2040
tacctacagc gtgagctatg agaaagcgcc acgcttcccg aagggagaaa ggcggacagg  2100
tatccggtaa gcggcagggt cggaacagga gagcgcacga gggagcttcc agggggaaac  2160
gcctggtatc tttatagtcc tgtcgggttt cgccacctct gacttgagcg tcgatttttg  2220
tgatgctcgt caggggggcg gagcctatgg aaaaacgcca gcaacgcggc ctttttacgg  2280
ttcctggcct tttgctggcc ttttgctcac atgtaatgtg agttagctca ctcattaggc  2340
accccaggct ttacacttta tgcttccggc tcgtatgttg tgtggaattg tgagcggata  2400
acaatttcac acaggaaaca gctatgacca tgattacgcc aagctacgta atacgactca  2460
ctatagggca gatctgaaga cataagtcgg tccgttcgaa ccagaactct ggaagcttga  2520
cgcggccgct atccatggca cacgcgttca gctagcttag gcgcctatgc gcgctaaccg  2580
cggtcactta agtatgatat ctctctgcag ttacccgggc atgacgtcta tatgcatatt  2640
ctcgaggcat gcgagctccc tcaggaggcc tatagtgagt cgtattacgg actggccgtc  2700
gttttacaac gtcgtgactg ggaaaaccct ggcgttaccc aacttaatcg ccttgcagca  2760
catccccctt tcgccagctg gcgtaatagc gaagaggccc gcaccgatcg cccttcccaa  2820
cagttgcgca gcctgaatgg cgaatggcgc ttcgcttggt aataaagccc gcttcggcgg  2880
gcttttttt
```

TABLE 1

Oligonucleotides Used for Cloning Experiments

| Abbreviation | Length | Sequence |
|---|---|---|
| C1-1S | 103 b. | 5'-pGAT CTG AAG ACA TAA GTC GGT CCG TTC GAA CCA GAA CTC TGG AAG CTT GAC GCG GCC GCT ATC CAT GGC ACA CGC GTT CAG CTA GCT TAG GCG CCT ATG ACG T-3' (SEQ ID NO: 16) |
| C1-1A | 95 b. | 5'-pCAT AGG CGC CTA AGC TAG CTG AAC GCG TGT GCC ATG GAT AGC GGC CGC GTC AAG CTT CCA GAG TTC TGG TTC GAA CGG ACC GAC TTA TGT CTT CA-3'(SEQ ID NO: 17) |
| C1-2S | 108 b. | 5'-pGCG CCT ATG CGC GCT AAC CGC GGT CAC TTA AGT ATG ATA TCT CTC TGC AGT TAC CCG GGC ATG ACG TCT ATA TGC ATA TTC TCG AGG CAT GCG AGC TCC CTC AGG AGG-3'(SEQ ID NO: 18) |

TABLE 1-continued

| Oligonucleotides Used for Cloning Experiments | | |
|---|---|---|
| Abbreviation | Length | Sequence |
| C1-2A | 104 b. | 5'-pCCT CCT GAG GGA GCT CGC ATG CCT CGA GAA TAT GCA TAT AGA CGT CAT GCC CGG GTA ACT GCA GAG AGA TAT CAT ACT TAA GTG ACC GCG GTT AGC GCG CAT AG-3' (SEQ ID NO: 19) |
| CP1S | 88 b. | 5'-pAGC TTA ACT CCT AAA AAA CCG CCA CCA TGA AAT TCT TAG TCA ACG TTG CCC TTG TTT TTA TGG TCG TAT ACA TTT CTT ACA TCT ATG C-3'(SEQ ID NO: 20) |
| CP1A | 88 b. | 5'-pGGC CGC ATA GAT GTA AGA AAT GTA TAC GAC CAT AAA AAC AAG GGC AAC GTT GAC TAA GAA TTT CAT GGT GGC GGT TTT TTA GGA GTT A-3'(SEQ ID NO: 21) |
| CP2S | 38 b. | 5'-pGGC CGC TCA TCA CCA CCA TCA TCA CCA TCA CCA CCA CA-3'(SEQ ID NO: 22) |
| CP2A | 38 b. | 5'-pCGC GTG TGG TGG TGA TGG TGA TGA TGG TGG TGA TGA GC-3'(SEQ ID NO: 23) |
| CP3S | 78 b. | 5'-pCGC GTG AAA ACC TGT ATT TTC AGG GCG CCG GTG ACT CCC TGT CTT GGC TGC TCC GTC TGC TCA ACG CGC GCG GTG GCG-3'(SEQ ID NO: 24) |
| CP3A | 78 b. | 5'-pCTA GCG CCA CCG CGC GCG TTG AGC AGA CGG AGC AGC CAA GAC AGG GAG TCA CCG GCG CCC TGA AAA TAC AGG TTT TCA-3'(SEQ ID NO: 25) |
| CP4S | 45 b. | 5'-pAGC TTA CCA TGG GTC ATC ACC ACC ATC ATC ACC ATC ACC ACC ACA-3'(SEQ ID NO: 26) |
| CP4A | 45 b. | 5'-pCGC GTG TGG TGG TGA TGG TGA TGA TGG TGG TGA TGA CCC ATG GTA-3'(SEQ ID NO: 27) |
| CP5S | 45 b. | 5'-pAGC TTA CGC TGC TCC ATC ACC ACC ATC ATC ACC ATC ACC ACC ACA-3'(SEQ ID NO: 28) |
| CP5A | 45 b. | 5'-pCGC GTG TGG TGG TGA TGG TGA TGA TGG TGG TGA TGG AGC ATG CTA-3'(SEQ ID NO: 29) |
| CP6 | 10 b. | 5'-pTAC CCT AGG G-3'(SEQ ID NO: 30) |
| CP7S | 31 b. | 5'-TCA TGC TAG CGT GAG CAA GGG CGC CGA GCT G-3' (SEQ ID NO: 31) |
| CP7A | 32 b. | 5'-TAT AGG TAC CCT TGT ACA GCT CAT CCA TGC CG-3' (SEQ ID NO: 32) |

Cloning of BoNT/Aad$^{ek}$ into pLitmus28C1

In the first cloning step, pLitmus28C1 was digested with Hind III and Not I and dephosphorylated. Annealed phosphorylated oligonucleotides CP1S and CP1A were ligated into digested pLitmus28C1, resulting in vector pLitSB3A1 (2968 b.p.). Vector pLitSB3A1 carried several unique 5'-restriction sites, including Bgl II, Bbs I, Rsr II, and BstB I, to be used for the subsequent subcloning of the full-length construct into expression vectors. This polylinker was followed by the enhancer sequence AACTCCTAAAAAACCGCCACC (SEQ ID NO:33), followed by the honeybee mellitin signal peptide sequence.

In the next step, pLitSB3A1 was digested with Not I and Mlu I and dephosphorylated. Annealed phosphorylated oligonucleotides CP2S and CP2A were ligated into digested pLitSB3A1, resulting in vector pLitSB3A2 (2987 b.p.), which carried the sequence encoding a 10-His affinity tag downstream of the sequence encoding the honeybee mellitin signal peptide. Next, pLitSB3A2 was digested with Mlu I and Nhe I and dephosphorylated. Annealed phosphorylated oligonucleotides CP3S and CP3A were ligated into digested pLitSB3A2, resulting in vector pLitSB3A3 (3056 b.p.), which carried the sequence encoding the tobacco etch virus (TEV) protease cleavage site, followed by the sequence encoding S6 peptide tag downstream of the sequence encoding the 10-His affinity tag.

In the next three steps the synthetic DNA of the full-length BoNT/Aad$^{ek}$ with the sequence optimized for expression in two hosts, *S. frugiperda* and *E. coli*, was consecutively built into the pLitSB3A3 vector. The synthetic gene for full-length BoNT/Aad$^{ek}$ was synthesized in the form of three contiguous DNA segments, each supplied by the vendor (Genscript) as DNA subcloned in the pUC57 vector. Numbers in the text below correspond to amino acid numbering in wt BoNT/A. First, a 1347 b.p. DNA fragment encoding the sequence $P_2$-$L_{442}$ was isolated from pUC57-BAad-1 by restriction digest with BssH II and Afl II and subcloned into pLitSB3A3 (which had been digested with the same set of restriction enzymes and dephosphorylated) to generate the 4355 b.p. vector, pLitSB3A4. Then, a 1233 b.p. DNA fragment encoding the sequence $D_{443}$-$I_{849}$ was isolated from pUC57-BAad-2 by digest with Xba I and EcoR V and subcloned in pLitSB3A4 (digested with the same set of restriction enzymes and dephosphorylated) to generate the 5570 b.p. vector, pLitSB3A5. Finally, a 1401 b.p. DNA fragment encoding the sequence $P_{850}$-$L_{1296}$ followed by a sequence encoding a short linker, the StrepTag II sequence, WSHPQFEK (SEQ ID NO:34), and a triplet of termination codons in three reading frames was isolated from pUC57-BAad-3 by digest with EcoRV and Xho I, and subcloned into pLitSB3A5 (digested with the same set of restriction enzymes and dephosphorylated) to generate the 6925 b.p. vector, pLitSB3A. The sequence of pLitSB3A has been deposited into GenBank under accession number GQ855200, and has a sequence of SEQ ID NO:14, as follows:

```
gttaactacg tcaggtggca cttttcgggg aaatgtgcgc ggaaccccta tttgtttatt    60
tttctaaata cattcaaata tgtatccgct catgagacaa taaccctgat aaatgcttca   120
ataatattga aaaaggaaga gtatgagtat tcaacatttc cgtgtcgccc ttattccctt   180
ttttgcggca ttttgccttc ctgtttttgc tcacccagaa acgctggtga aagtaaaaga   240
tgctgaagat cagttgggtg cacgagtggg ttacatcgaa ctggatctca acagcggtaa   300
gatccttgag agttttcgcc ccgaagaacg ttctccaatg atgagcactt ttaaagttct   360
gctatgtggc gcggtattat cccgtgttga cgccgggcaa gagcaactcg gtcgccgcat   420
acactattct cagaatgact tggttgagta ctcaccagtc acagaaaagc atcttacgga   480
tggcatgaca gtaagagaat tatgcagtgc tgccataacc atgagtgata acactgcggc   540
caacttactt ctgacaacga tcggaggacc gaaggagcta accgcttttt tgcacaacat   600
gggggatcat gtaactcgcc ttgatcgttg ggaaccggag ctgaatgaag ccataccaaa   660
cgacgagcgt gacaccacga tgcctgtagc aatggcaaca acgttgcgca aactattaac   720
tggcgaacta cttactctag cttcccggca acaattaata gactggatgg aggcggataa   780
agttgcagga ccacttctgc gctcggccct tccggctggc tggtttattg ctgataaatc   840
tggagccggt gagcgtgggt ctcgcggtat cattgcagca ctggggccag atggtaagcc   900
ctcccgtatc gtagttatct acacgacggg gagtcaggca actatggatg aacgaaatag   960
acagatcgct gagataggtg cctcactgat taagcattgg taactgtcag accaagttta  1020
ctcatatata ctttagattg atttaccccg gttgataatc agaaaagccc caaaaacagg  1080
aagattgtat aagcaaatat ttaaattgta aacgttaata ttttgttaaa attcgcgtta  1140
aatttttgtt aaatcagctc attttttaac caataggccg aaatcggcaa aatcccttat  1200
aaatcaaaag aatagcccga gatagggttg agtgttgttc cagtttggaa caagagtcca  1260
ctattaaaga acgtggactc caacgtcaaa gggcgaaaaa ccgtctatca gggcgatggc  1320
ccactacgtg aaccatcacc caaatcaagt tttttggggt cgaggtgccg taaagcacta  1380
aatcggaacc ctaaagggag cccccgattt agagcttgac ggggaaagcg aacgtggcga  1440
gaaaggaagg gaagaaagcg aaaggagcgg gcgctagggc gctggcaagt gtagcggtca  1500
cgctgcgcgt aaccaccaca cccgccgcgc ttaatgcgcc gctacagggc gcgtaaaagg  1560
atctaggtga agatcctttt tgataatctc atgaccaaaa tcccttaacg tgagttttcg  1620
ttccactgag cgtcagaccc cgtagaaaag atcaaaggat cttcttgaga tccttttttt  1680
ctgcgcgtaa tctgctgctt gcaaacaaaa aaaccaccgc taccagcggt ggtttgtttg  1740
ccggatcaag agctaccaac tctttttccg aaggtaactg gcttcagcag agcgcagata  1800
ccaaatactg ttcttctagt gtagccgtag ttaggccacc acttcaagaa ctctgtagca  1860
ccgcctacat acctcgctct gctaatcctg ttaccagtgg ctgctgccag tggcgataag  1920
tcgtgtctta ccgggttgga ctcaagacga tagttaccgg ataaggcgca gcggtcgggc  1980
tgaacggggg gttcgtgcac acagcccagc ttggagcgaa cgacctacac cgaactgaga  2040
tacctacagc gtgagctatg agaaagcgcc acgcttcccg aagggagaaa ggcggacagg  2100
tatccggtaa gcggcagggt cggaacagga gagcgcacga gggagcttcc agggggaaac  2160
gcctggtatc tttatagtcc tgtcgggttt cgccacctct gacttgagcg tcgatttttg  2220
```

-continued

```
tgatgctcgt caggggggcg gagcctatgg aaaaacgcca gcaacgcggc ctttttacgg 2280
ttcctggcct tttgctggcc ttttgctcac atgtaatgtg agttagctca ctcattaggc 2340
accccaggct ttacacttta tgcttccggc tcgtatgttg tgtggaattg tgagcggata 2400
acaatttcac acaggaaaca gctatgacca tgattacgcc aagctacgta atacgactca 2460
ctatagggca gatctgaaga cataagtcgg tccgttcgaa ccagaactct ggaagcttaa 2520
ctcctaaaaa accgccacca tgaaattctt agtcaacgtt gcccttgttt ttatggtcgt 2580
atacatttct tacatctatg cggccgctca tcaccaccat catcaccatc accaccacac 2640
gcgtgaaaac ctgtattttc agggcgccgg tgactccctg tcttggctgc tccgtctgct 2700
caacgcgcgc ggtggagcta gcggcccgtt cgttaacaaa caatttaact acaaggatcc 2760
tgtcaatggt gtggacattg cctatattaa gatcccgaat gcgggtcaga tgcaacccgt 2820
gaaagcattc aagatccaca acaaaatctg ggtcatccct gaacgtgaca ctttcacaaa 2880
ccctgaagag ggcgacctca accctccccc agaagccaaa caggttccgg tgtcttacta 2940
cgatagcacg tacttgtcca ccgataacga gaaggacaac tacctgaagg gagtgaccaa 3000
gttgtttgag aggatctact ctaccgatct cggacgtatg ctgctcacga gcattgtgcg 3060
cggtatccca ttctggggcg gttcaaccat tgatacagaa ctgaaagtca ttgacactaa 3120
ttgtatcaac gttattcaac cagatggcag ctaccgttcc gaggaattga acttggtcat 3180
cattggtcca tccgcagaca tcattcagtt tgaatgcaaa tccttcggtc acgaagtgct 3240
caacctgacg cgcaacggtt acggctccac ccagtacatc cgtttcagcc ctgatttcac 3300
atttggcttc gaggaaagcc tggaggttga caccaacccg ctcctgggtg ctggcaagtt 3360
tgcaaccgat cccgcggtga ctctcgctca tgctctgatc cacgccggac accgcctcta 3420
tggcatcgct atcaatccga accgcgtgtt caaagtgaat acgaacgcct actatgagat 3480
gagcggtctg gaggtttcct ttgaggaact gagaaccttc ggcggtcacg atgccaagtt 3540
catcgacagc ttgcaggaaa atgagtttcg cctgtactat tacaacaagt ttaaagacat 3600
cgcttccaca ttgaacaaag ccaagtcaat cgtgggtacg acagcttcat tgcagtatat 3660
gaagaatgtt ttcaaggaga aatacttgct gtcagaggat acctctggca agttctctgt 3720
ggacaaactg aaattcgaca aactgtacaa gatgctgacc gagatttata cggaagataa 3780
ctttgtgaaa ttcttcaaag tcctcaacag gaaaactgct ctgaactttg acaaggctgt 3840
gttcaagatc aacatcgtcc ccaaagttaa ctacacaatc tatgatggat tcaatctgag 3900
aaacaccaac ttggccgcca acttcaacgg ccaaaatacc gaaattaata acatgaattt 3960
caccaaactg aagaacttta ctggactgtt cgagttctac aagctgctct gcgtgcgtgg 4020
catcatcacc tcacatactc agtctctaga ccagggttat aacgacgatg acgataaagc 4080
tctgaacgat ctgtgtatca aggtgaataa ctgggatctg ttctttagcc caagcgagga 4140
taacttcacg aacgatctca acaaaggtga agagatcacg tctgatacca atatcgaagc 4200
ggctgaagag aatatctcct tggatctcat ccagcaatat tacctgacct ttaacttcga 4260
taacgagccc gaaaacatct ccatcgagaa cctcagctca gacatcattg gtcagttgga 4320
gctgatgcca aacattgaac gcttccccaa cggcaagaaa tacgaactcg acaagtatac 4380
gatgtttcat tacttaagag cgcaggagtt tgaacacggc aagagccgca ttgctctcac 4440
taactccgtg aatgaagccc tgctcaatcc gtcaagggtg tacacattct ttagctccga 4500
ctatgtcaag aaagtgaaca aagccaccga agcggcaatg ttcctgggat gggttgaaca 4560
actggtctac gacttcaccg acgagacctc tgaggtgagc acaacggaca agattgctga 4620
catcactatc attatcccgt atattggacc tgccttgaat attggcaaca tgctctacaa 4680
```

-continued agacgatttc gttggtgccc tgatcttcag cggtgccgtg atcctgttgg agttcattcc 4740
tgaaatcgcc atccctgtgc tgggcacgtt cgctctggtc tcatacattg cgaataaggt 4800
cttgaccgtg cagacaatcg ataatgccct ctccaaacgt aacgaaaaat gggacgaggt 4860
ctacaaatac atcgtgacca actggctggc aaaggttaac acccaaattg atctgatccg 4920
taagaaaatg aaggaggctt tggagaacca ggctgaagct actaaagcca ttatcaacta 4980
ccagtataat cagtatacag aagaggaaaa gaataacatc aatttcaaca tcgatgactt 5040
gtcctcaaag ctgaacgagt ccatcaacaa agctatgatc aacatcaaca aattcctgaa 5100
tcagtgctcc gtgtcttacc tgatgaactc tatgatccca tacggtgtga agcgcctgga 5160
ggacttcgat gccagcctga aagacgcact gctcaaatac atttacgata atcgcggcac 5220
tttgattggc caagttgacc gtctgaagga caaggttaac aataccttgt caaccgatat 5280
cccctttcaa ctgtccaaat acgttgataa ccagcgcttg ctctctactt tcaccgaata 5340
cattaacaac attatcaata catcaattct caacctgcgc tatgagtcca atcatctgat 5400
cgatctgtct cgttacgcca gcaagatcaa cattggcagc aaagtgaact tcgatccgat 5460
tgacaagaac caaatccagt tgttcaacct cgaaagctcc aaaatcgaag tgatcctgaa 5520
gaatgccatc gtctacaact ccatgtatga aaatttctca acttcattct ggattagaat 5580
cccgaaatac ttcaactcaa tctctctgaa taacgaatac acgatcatta actgtatgga 5640
gaataactct ggttggaagg tttccttgaa ctatggagaa attatctgga ctctgcaaga 5700
tacgcaagag atcaaacagc gtgtggtctt taaatacagc cagatgatta acatctctga 5760
ctacatcaac agatggatct ttgtcaccat tacaaacaat cgcctgaata actccaaaat 5820
ctacatcaac ggtcgtctga tcgaccagaa acctatttca aacctcggca acattcatgc 5880
ttccaataac atcatgttta agttggatgg ttgccgcgat acccaccgtt acatctggat 5940
caagtatttc aatctgttcg acaaagaact caatgagaaa gagatcaaag acttgtatga 6000
taatcagtca aactccggca ttctgaaaga cttctggggc gattacctcc agtacgataa 6060
gccatattac atgctgaatc tctatgaccc taacaaatat gtggacgtga acaatgtcgg 6120
tatccgtggc tacatgtacc tcaaaggacc acgtggtagc gttatgacaa ccaacatcta 6180
cctgaatagc tccttgtatc gcggtacgaa gttcattatc aagaagtacg cttcaggcaa 6240
caaggacaac atcgtgagga acaatgatcg cgtgtacatc aacgtcgtgg tgaagaataa 6300
ggaataccgc ttggcgacca acgcttctca ggctggagtt gagaagatcc tgagcgcctt 6360
ggagatccca gacgttggca acctgagcca agtggttgtg atgaaaagca agaatgacca 6420
gggaatcacc aacaaatgca aaatgaacct gcaagacaac aacggcaatg acatcggttt 6480
catcggtttc caccagttta acaatattgc gaagctggtc gccagcaact ggtacaacag 6540
gcagattgag aggtcatccc gtaccttagg atgctcttgg gaatttatcc ccgtggacga 6600
tggttggggc gagagacccc tgggcgcagg ttggtcccac cctcagttcg agaagtaata 6660
gttaatagat aataatagct cgaggcatgc gagctccctc aggaggatag tgagtcgtat 6720
tacggactgg ccgtcgtttt acaacgtcgt gactgggaaa accctggcgt tacccaactt 6780
aatcgccttg cagcacatcc ccctttcgcc agctggcgta atagcgaaga ggcccgcacc 6840
gatcgccctt cccaacagtt gcgcagcctg aatggcgaat ggcgcttcgc ttggtaataa 6900
agcccgcttc ggcgggcttt ttttt

Example 2

Creation of Vectors for Protein Expression in *E. coli* pET-19b-Based Construct

Vector pLitSB3A was linearized by digestion with Hind III and Mlu I and dephosporylated. The 6799 b.p. DNA fragment was isolated from an agarose gel and purified. Synthetic phosphorylated oligonucleotides CP4S and CP4A were annealed and ligated into the isolated vector DNA to generate the vector pLitB3A1 (6844 b.p.). Vector pLitB3A1 was digested with Nco I and Xho I and the 4078 b.p. DNA fragment was isolated and purified from an agarose gel. This fragment was ligated into expression vector pET-19b (Novagen, Cat. #69677, 5717 b.p.), that had been digested with Nco I and Xho I and dephosphorylated, generating the 9721 b.p. vector pET19B3A.

pETcoco2-Based Construct

Vector pLitSB3A was linearized by digestion with Hind III and Mlu I and dephosphorylated. The 6799 b.p. DNA fragment was isolated from an agarose gel and purified. Synthetic phosphorylated oligonucleotides CP5S and CP5A were annealed and ligated into the isolated vector DNA to generate the vector pLitB3A2 (6844 b.p.). Vector pLitB3A2 was digested with Xho I and treated with CpG methyltransferase (M. SssI, New England Biolabs, Cat. #M0226). After completion of methylation, the enzyme was inactivated and removed by phenol/chloroform extraction, followed by DNA precipitation with ethanol. DNA was treated with Klenow fragment of DNA polymerase I (New England Biolabs, Cat. #M021) to fill in 5' overhangs generated by Xho I cleavage, and ligated. Ligated DNA was digested with Pvu I and dephosphorylated. Annealed phosphorylated synthetic oligonucleotide CP 6 was ligated into Pvu I digested vector to generate pLitB3A3 (6858 b.p.). This vector was transformed, amplified, and propagated in NEB 10-beta *E. coli* strain (New England Biolabs, Cat. #C3020K). Following propagation, plasmid DNA was isolated and digested with restriction endonucleases Sph I and Avr II. The 4081 b.p. DNA fragment was isolated from an agarose gel, purified, and ligated into the vector pETcoco2 (Novagen, Cat. #71148-3, 12417 b.p.) (that had been treated with the same set of restriction endonucleases and dephosphorylated) to generate the expression vector pETcocoB3A (16263 b.p.).

Example 3

Creation of Vectors for Protein Expression in Baculovirus

Construct for Expression of BoNT/Aad$^{ek}$

The plasmid pLitSB3A was digested with the restriction endonucleases Rsr II and Xho I. The 4190 b.p. DNA fragment, encoding full-length BoNT/Aad$^{ek}$, was isolated from an agarose gel, purified, and ligated into the baculovirus transposition vector, pFastBac1™ (Invitrogen, Cat. #10360-014, 4776 b.p.) (which had been digested with Rsr II and XhoI and dephosphorylated) to generate the 8968 b.p. vector pFB1SB3AEK. The DNA sequence of pFB1SB3AEK with annotations has been deposited to GenBank under accession number GQ855201 (SEQ ID NO:15). Features of the 1372 aa protein, translated from the open reading frame of the insert DNA (BoNT/Aad$^{ek}$), are shown in FIG. 1.

Construct for Expression of BoNT/Aad$^{tev}$

In this construct, DNA encoding the enterokinase cleavage site positioned between LC and HC was replaced with a sequence encoding a second TEV cleavage site. The 348 b.p. fragment containing the enterokinase cleavage site was excised from pFB1SB3AEK by digestion with Xba I and Afl II. The linearized vector was dephosphorylated and a 351 b.p. Xba I/Afl II DNA fragment excised from the plasmid pUC57-TEV (GenScript) was ligated into the vector to generate the 8971 b.p. vector pFB1SB3ATEV. The DNA sequence of pFB1SB3ATEV, along with annotations, has been deposited to GenBank under accession number GQ855202 (SEQ ID NO:10). Features of the 1373 aa protein, translated from the open reading frame of the insert DNA (BoNT/Aad$^{tev}$), are shown in FIG. 1.

Construct for Expression of ΔLC-Peptide-BoNT/A$^{tev}$

Vector pFB1SB3ATEV was linearized by digestion with BssH II and Xba I and dephosphorylated. The 7631 b.p. dephosphorylated vector was isolated from an agarose gel and purified. A DNA fragment containing the sequence encoding the ΔLC-peptide was obtained in the form of synthetic DNA cloned into pUC57 (pUC57-Pept), supplied by the manufacturer (GenScript). pUC 57-Pept was digested with BssH II and Xba I and the 200 b.p. DNA fragment was isolated from an agarose gel, purified, and ligated into the linearized pFB1SB3ATEV, resulting in the 7831 b.p. vector, pFB1SPepB2ATEV. The DNA sequence of pFB1SPepB2ATEV, along with annotations, have been deposited in GenBank under accession number GQ855203 (SEQ ID NO:11). Features of the 993 aa protein, translated from the open reading frame of the insert DNA (ΔLC-Peptide-BoNT/A$^{tev}$), are shown in FIG. 1.

Construct for Expression of ΔLC-GFP-BoNT/A$^{tev}$

DNA encoding the GFP sequence was obtained by PCR amplification from plasmid pAcGFP1-C2 (Clontech, Cat. #632481, 4722 b.p.) using primers CP7S and CP7A (Table 1) and PrimeSTAR HS DNA polymerase (Takara, Cat. #TAK R010A) in a 50 μl reaction mixture in a GeneAmp PCR system 9700 (PE/Applied Biosystems). The reaction buffer and conditions were set according to the protocol provided by Takara. The PCR product was digested with restriction endonucleases Nhe I and Acc65 I, and the 700 b.p. digested DNA was isolated from an agarose gel and purified. Vector pFB1SPepB2ATEV was digested with Nhe I and under digested (short incubation time and small amount of the restriction endonuclease) with Acc65 I. The 7822 b.p. DNA fragment was isolated from an agarose gel, purified, and dephosphorylated. The purified GFP PCR product and the linearized pFB1SPepB2ATEV were ligated, resulting in the 7822 b.p. vector pFB1SGFPB2ATEV. The DNA sequence of pFB1SGFPB2ATEV, along with annotations, has been deposited to GenBank under accession number GQ855204 (SEQ ID NO:12). Features of the 1230 aa protein, translated from the open reading frame of the insert DNA (ΔLC-GFP-BoNT/A$^{tev}$), are shown in FIG. 1.

Custom synthetic oligonucleotides were obtained from Sigma-Aldrich. *E. coli* strain TOP10, used for plasmid transformation and amplification, was purchased in a form of electrocompetent cells from Invitrogen (Cat. #C404052), except as specified otherwise. Restriction endonucleases, T4 DNA ligase, and arctic shrimp alkaline phosphatase were purchased from New England Biolabs. All DNA fragments isolated from agarose gels after enzymatic treatment were purified with Qiaex II DNA extraction kit (Qiagen, Cat. #20051). DNA sequences of all final constructs were obtained using overlapping sets of primers at the DNA sequencing facility at NYU's Skirball Institute of Biomolecular Medicine. The sequencing data obtained proved constructs to be free of unexpected mutations.

Example 4

Protein Expression and Purification—*E. coli* Experiments

Electrocompetent *E. coli* strain JM109 (DE3) (Promega, Cat. #P9801) was transformed with pET19B3A plasmid according to an established protocol. A single colony isolated from a Luria-Bertani (LB) plate containing carbenicillin (100 μg/ml) was inoculated into 10 ml of LB medium containing carbenicillin and grown overnight with agitation (250 rpm) at 37° C. An aliquot (2 ml) of the culture was transferred to 200 ml of fresh LB medium with the addition of carbenicillin (100 μg/ml), and the cells were grown further at 37° C. with agitation to reach an $OD_{600}$ of approximately 0.5 (about 4 hours). The suspension was rapidly cooled to approximately 25° C. in an ice bath, and isopropyl-β-D-thiogalactoside (IPTG) was added to a final concentration of 1 mM. Induction was allowed to proceed for 12 hours at 25° C. Aliquots were collected at 3, 6, and 12 hours after IPTG induction and cells were harvested by centrifugation at 6000 g for 15 min at 4° C. The cells were resuspended at 4° C. in BugBuster protein extraction reagent (Novagen, Cat. #70584) and lysed with the addition of Lysonase™ bioprocessing reagent (lysozyme and benzonase, Novagen, Cat. #71230-4) in the presence of protease inhibitor cocktail without EDTA (Pierce, Cat. #78430) by triturating the suspension until signs of high viscosity disappeared (approximately 30 minutes), The BugBuster lysate was cleared by centrifugation at 35,000 g for 15 minutes, 4° C., distributed in 0.5 ml aliquots and stored at −80° C. The residual pellet was resuspended at room temperature in 6 M urea, 25 mM Tris-HCl, pH 8.0. Cleared urea solubilizate was collected by centrifugation at 35,000 g for 15 minutes at room temperature, distributed in 0.5 ml aliquots, and stored at −80° C. Aliquots of BugBuster and urea lysates were batch incubated with TALON® affinity resin (Clontech, Cat. #63506) at 4° C. for 30 minutes. TALON® beads were sequentially washed with 100 mM NaCl, 25 mM Tris HCl-pH8.0 and protein was eluted by resuspension of the beads in 1× SDS PAGE loading buffer with β-mercaptoethanol (Bio-Rad, Cat. #161-0710). BugBuster and urea lysates, as well as eluates of these lysates obtained from Talon® resin, were loaded on a 10.5-14% Criterion SDS PAGE gel (Bio-Rad, Cat. #345-0106) and separated. Proteins were transferred to nitrocellulose membranes (Bio-Rad, Cat. #162-0117) and probed with polyclonal antibodies against BoNT/A holotoxin (Pol001, raised against BoNT/A holotoxoid (Staten Serum Institut, Denmark)). As a positive control, m BoNT/A was loaded on the gel, and JM109 (DE3) transformed with the empty vector was used as the negative control. When the results were analyzed by elecrophoresis and Western blotting, it was unexpectedly found that toxin of the proper molecular weight and immunoreactivity could not be produced.

pETcocoB3A was transformed into competent *E. coli* Rosetta-gami B (DE3) cells (Novagen, Cat. #71136-3) according to the manufacturer's protocol. A single bacterial colony, picked from an LB agar plate, was grown in (i) LB medium with 100 μg/ml carbenicillin, 15 μg/ml kanamycin, 12 μg/ml tetracycline, and 34 μg/ml chloramphenicol, and (ii) LB medium with 0.01% L-arabinose, 100 μg/ml carbenicillin, 15 μg/ml kanamycin, 12 μg/ml tetracycline, and 34 μg/ml chloramphenicol for 16 hours at 37° C. An aliquot of overnight cultures (1:100 v/v) were transferred to fresh LB media supplemented with antibiotics, with and without addition of L-arabinose. The cells were grown at 37° C. with agitation to reach $OD_{600}$ of approximately 0.4 (about 9 hours). The suspensions were rapidly cooled to approximately 25° C. in an ice bath, and IPTG was added to a final concentration of 0.5 mM. The cultures were incubated with agitation for 12 hours at 25° C. Aliquots were collected at 3, 6, and 12 hours after IPTG induction and cells were harvested by centrifugation at 6000 g for 15 min at 4° C. Protein extraction, sample preparation, SDS PAGE, and Western blotting were performed as described above. When the results were analyzed by elecrophoresis and Western blotting, it was unexpectedly found that toxin of the proper molecular weight and immunoreactivity could not be produced.

Example 5

Baculovirus Experiments

Generating Recombinant Bacmids pFastBac™ constructs were used for transposition of the cloned DNA into the shuttle vector (bacmid). Approximately 1 ng of plasmid DNA was used to transform MAX Efficiency® DH10Bac™ *E. coli* (Invitrogen, Cat. #10361-012) using a heat-shock method according to the manufacturer's protocol (Invitrogen, BactoBac® baculovirus expression system). Colonies were grown on LB agar plates supplemented with 50 μg/ml kanamycin, 7 μg/ml gentamycin, 10 μg/ml tetracycline, 100 μg/ml Bluo-Gal, and 40 μg/ml IPTG, for 48 hours for full color development. For each construct, two white colonies were picked and re-grown for 24 hours at 37° C. in 50 ml LB medium supplemented with antibiotics. The recombinant bacmids were isolated and purified from harvested cells using a QIAGEN Large-Construct Kit (Cat. #12462), according to the manufacturer's protocol. The DNA concentration was measured with a NanoDrop spectrophotometer and adjusted to 0.5 mg/ml with TE buffer. The yield of the bacmid DNA was approximately 1 μg/ml of starting LB culture. Transposition of the cloned genes into recombinant bacmids was confirmed by PCR with bacmid as a template and sets of primers specific for each cloned construct.

Example 6

Transfecting Insect Cells and Collecting Baculoviral Stock for Protein Expression Sf9 insect cells, grown in shaker flasks in serum-free Sf-900 II medium (Invitrogen, Cat. #10902-096) were plated in 6-well (35 mm) culture plates at a density of $1\times10^6$ cells per well. Plates were incubated at 28° C. in a humidified incubator until cells adhered to the surface (approximately 1 hour). Two (2) μg of bacmid DNA (0.5 mg/ml) was diluted with 100 μl unsupplemented Grace's insect cell medium (Invitrogen, Cat. #11595-030) in a 15-ml sterile polystyrene tube. In a separate tube, 7 μl of CELLFECTIN® reagent (Invitrogen, Cat. #10362-010) was also diluted with 100 μl of unsupplemented Grace's medium. Diluted bacmid DNA and CELLFECTN® were combined and incubated at room temperature for 40 minutes. While DNA:lipid complexes were incubating, the medium was aspirated from the adherent Sf9 cells, cells were washed with unsupplemented Grace's medium, and 2 ml of fresh Grace's medium was added to each well. At the end of the 40 minute incubation, 800 μl of unsupplemented Grace's medium was added to the DNA-CELLFECTIN® mixture, the medium covering the cells was aspirated, and 1 ml of the DNA-CELLFECTIN® mixture was gently added to the adherent Sf9 cells. Cells were incubated at 28° C. for 5 hours, after which the DNA-lipid complexes were aspirated and 2 ml of fresh Sf-900 II serum-free medium was added to the cells and incubation was continued. P1 low-titer baculoviral stock (2 ml of growth medium) was collected 72 hours after transfection.

To generate P2 high-titer stock, 1 ml of P1 stock was added to 25 ml of Sf9 grown in Sf-900 II medium in a shaker flask. Cell density at the time of infection was approximately $1.5\times10^6$ cells/ml. Cells were incubated for 72 hours at 28° C. in a humidified incubator. Cells were removed from high titer P2 stock by centrifugation at 1000 g. The titer of the P2 stock was measured by viral plaque assay (Invitrogen, BAC-TOBAC® baculovirus expression system). P2 titers for the constructs were approximately $1\text{-}2\times10^8$ pfu/ml. P2 stock was used to infect Sf9 cells for expression of the proteins of interest.

Example 7

Protein Expression, Purification, and Processing

Sf9 cells grown to a density of approximately $1.5\times10^6$ cells/ml in a shaker flask in Sf-900 II serum-free medium were infected with recombinant P2 baculovirus stock. For each recombinant protein-expression vector, the optimal multiplicity of infection (MOI) and time after infection for harvesting was determined empirically. For BoNT/Aad$^{ek}$ and BoNT/Aad$^{tev}$, these conditions were MOI approximately 0.1 and 60 hours; for ΔLC-Peptide-BoNT/A$^{tev}$ and ΔLC-GFP -BoNT/A$^{tev}$, the conditions were MOI approximately 0.5 and 72 hours. At the time of harvest, medium was separated from the cells by centrifugation at 1000 g, filtered through a Whatman GF/F filter (Schleicher&Schuell, Cat. #1825090), concentrated approximately 3 fold on a Millipore Prep/Scale TFF cartridge (Cat. #CDUF002LT), and dialyzed against TALON® resin chromatography loading buffer (500 mM NaCl, 25 mM TrisHCl, 5 mM imidazole, pH 8.0). For ΔLC-Peptide-BoNT/A$^{tev}$ and ΔLC -GFP-BoNT/A$^{tev}$, 0.3% Triton X-100 was added to the medium prior to concentration. Dialyzed supernatant was loaded on TALON® resin (Clontech, Cat. #63506) pre-equilibrated with the loading buffer. After loading, resin was washed with 10 volumes of loading buffer, 20 volumes of wash buffer (500 mM NaCl, 25 mM TrisHCl, 20 mM imidazole, pH 8.0), and protein was eluted with 5 volumes of elution buffer (500 mM NaCl, 25 mM TrisHCl, 200 mM imidazole, pH 8.0). For ΔLC -Peptide-BoNT/A$^{tev}$ and ΔLC-GFP-BoNT/A$^{tev}$ derivatives, chromatography was slightly modified by inclusion of 1% TRITON® X-100 in the loading buffer. For these derivatives, after loading and column wash with 10 volumes of loading buffer, the column was washed with 10 volumes of 20 mM imidazole wash buffer with 1% TRITON® X-100 followed by washing with 10 volumes of 20 mM imidazole wash buffer without detergent. Protein was eluted with 5 volumes of elution buffer containing 0.2% n-octyl-β-D-glucopyranoside (USB, Cat. #29836-26-8). Eluted proteins were dialyzed against 100 mM NaCl, 25 mM TrisHCl buffer, pH 8.0, either without (BoNT/Aad$^{ek}$ and BoNT/Aad$^{tev}$), or with (ΔLC-Peptide-BoNT/A$^{tev}$ and ΔLC -GFP-BoNT/A$^{tev}$) 0.2% n-octyl-β-D-glucopyranoside, and concentrated using Millipore Amicon Ultra 30,000 MWCO centrifugal filter units (Cat. #UFC803024) to a final total protein concentration of approximately 10 mg/ml. Dialyzed and concentrated fractions were loaded on StrepTactin superflow agarose (Novagen, Cat. #71592) pre-equlibrated with 100 mM NaCl, 25 mM TrisHCl buffer, pH 8.0 with or without 0.2% n-octyl-β-D-glucopyranoside, and washed with the same buffer. Bound protein was eluted with 3 mM D-desthiobiotin (Novagen, Cat. #71610). Fractions containing pure protein were combined, dialyzed, and concentrated using Amicon Ultra centrifugal filter units.

Processing of BoNT/Aad$^{ek}$

The 10-His tag was removed from recombinant protein using AcTEV protease (Invitrogen, Cat. #12575-015). The protein was incubated with AcTEV protease (1 unit of enzyme per 1 μg of protein) at 30° C. for 6 hours in digestion buffer (50 mM NaCl, 0.5 mM EDTA, 3 mM glutathione, 0.3 mM oxidized glutathione, pH 8.0). Completion of the cleavage was confirmed by Western blotting with anti-His monoclonal antibodies (Santa Cruz, H-3 His probe, Cat #sc-8036 HRP). The AcTEV and potentially under-digested protein were removed from the reaction mixture by TALON RESIN® chromatography. De-tagged protein was collected in the flow-through fractions, which were analyzed, combined, dialyzed against low-salt buffer, and concentrated using Amicon Ultra centrifugal filter units. Propeptide was converted to the heterodimer by treatment with recombinant enterokinase (rEK, Novagen, Cat. #71537-3). The protein was incubated with Tag-off high activity rEK (0.007 units of enzyme per 1 μg of the protein) at 16° C. for 16 hours in digestion buffer (50 mM NaCl, 20 mM TrisHCl, 2 mM $CaCl_2$, pH 7.8). Approximately 95% of the protein was processed to heterodimer by this treatment as assessed by Coomassie-stained SDS-PAGE under reducing conditions. The rEK was removed from the reaction mixture by Tag-off cleavage capture kit (Novagen, Cat. #71540-3), according to the manufacturer's protocol. Protein was dialyzed against buffer (100 mM NaCl, 40 mM sodium phosphate, 40% glycerol, pH 7.2) and concentrated using Amicon Ultra filtration units.

Processing of BoNT/A ad$^{tel}$, ΔLC-Peptide-BoNT/A$^{tev}$, and ΔLC-GFP-BoNT/A$^{tev}$ N-terminally placed 10-His tag removal and propeptide cleavage were performed simultaneously, according to the protocol described for BoNT/Aac$^{ek}$ above. ΔLC-Peptide-BoNT/A$^{tev}$ and ΔLC-GFP-BoNT/A$^{tev}$ required the presence of 0.2% n-octyl-β-D-glucopyranoside during the cleavage. The detergent was removed after cleavage by dialysis and concentration on Amicon Ultra filtration units.

Example 8

Enzymatic Labeling of BoNT/Aad$^{ek}$

All expressed proteins incorporated S6 peptide GDSLSWLLRLLN (SEQ ID NO:2) (Zhou et al., "Genetically Encoded Short Peptide Tags for Orthogonal Protein Labeling by Sfp and AcpS Phosphopantetheinyl Transferases," *ACS Chem. Biol.* 2(5):337-346 (2007), which is hereby incorporated by reference in its entirety) at the N-terminus of the smaller subunit of the heterodimer The pET29 vector with cloned C-terminally His6-tagged Sfp phosphopantetheinyl transferase from *B. subtilis* was kindly provided by Dr. Jun Yin (University of Chicago). Recombinant Sfp phosphopantetheinyl transferase was expressed in *E. coli* strain BL21 (DE3) (Novagen, Cat. #69450) and purified according to the protocol. CoA 547 was purchased from Covalys (Cat. #SV124) or from New England Biolabs (Cat. #S9349S). Prior to enzymatic labeling, the fluorescent substrate was dissolved in DMSO to a final concentration of 1 mM. Aliquots of this solution were used as a stock for further dilution in aqueous buffer-based labeling preparations. The labeling reaction was optimized and performed according to the following protocol: The molar ratio of labeled protein: Sfp phosphopantetheinyl transferase: CoA 547 was 4:1:5. A pilot reaction was performed by assembling approximately 18 μg of processed BoNT/Aad$^{ek}$ in a 30 μl reaction mixture containing 1× unsupplemented Grace's insect cell culture medium (prepared from the dry medium, Invitrogen, Cat. #11300-

043), 5 mM $MgCl_2$, mixture of short peptides used to suppress the background labeling and consisting of 150 μM Neurokinin A (Peninsula Laboratories, Cat. #7359), 75 mM Substance P (Peninsula Laboratories, Cat. #7451), 2 mM poly-L -lysine hydrobromide (MW 500-2000) (Sigma, Cat. #P8954), 1 μM Sfp phosphopantetheinyl transferase and 5 μM CoA 547, pH 7.0. Fluorescent substrate was added as the final component and the reaction mixture was incubated for 15 minutes at 30° C. For visualization after labeling, the reaction was stopped by the addition of 2× Laemmli SDS loading buffer followed by SDS PAGE, transfer of the proteins to a nitrocellulose membrane, and scanning on a Typhoon scanner. For the preparative isolation of labeled proteins, after the 15 minute incubation, 10 volumes of TALON® resin loading buffer (500 mM NaCl, 25 mM TrisHCl, pH 8.0) was added to the reaction mix and the resulting solution was passed through TALON® chelating resin. Flow through fractions and three additional washes (each corresponding to the column volume) were combined and immediately concentrated using Amicon ultrafiltration units. Concentrated protein was dialyzed against glycerol-phosphate buffer (100 mM NaCl, 40 mM sodium phosphate, 40% glycerol, pH 7.2). All procedures that involved fluorescent substrate or labeled protein were performed in the dark.

Example 9

Structural Analysis of BoNT/Aad$^{ek}$ and Fluorescently Labeled BoNT/Aad$^{ek}$ Edman Degradation BoNT/Aad$^{ek}$ LC and HC, separated under reducing conditions on 10-14% Criterion SDS PAGE (Bio-Rad), were transferred to a PVDF membrane (Bio-Rad, Cat. #162-0182) and stained with Bio-Safe Coomassie BB G-250 (Bio-Rad, Cat. #161-0786). Proteins were subjected to sequencing on an ABI 494-HT Procise Edman Sequencer at the Molecular Structure Facility at UC Davis.

In-Gel Tryptic Digestion

Gel bands were destained until clear using 30% acetonitrile in 25 mM ammonium bicarbonate. The gel slices were then cut into smaller pieces, approximately 1 $mm^3$ in size, and placed in a Speed Vac vacuum centrifuge for complete dehydration. After dehydration, 25 μl of 0.1% RapiGest SF (Waters, Milford, Mass.) was added and the samples were incubated at 37° C. for 10 min. All remaining supernatant fluid was discarded and the samples were placed in a Speed Vac vacuum centrifuge for complete dehydration. Then 10 ng/μl sequencing grade trypsin (Promega Corporation, Madison, Wis.) in 50 mM ammonium bicarbonate was added to each sample and they were left to digest overnight at 37° C. Samples were extracted stepwise using acetonitrile, 1% formic acid, and acetonitrile again. Samples were vortexed at 800 rpm between steps and supernatant fluids were transferred to 0.5 ml Eppendorf tubes. Then 10 μl of 10% TFA was added to each extract followed by incubation at 37° C. for 10 min. Samples were then dried in the vacuum centrifuge until approximately 3 μl of extract remained.

MALDI-TOF Analysis of BoNT/Aad$^{ek}$ Tryptic Digest

Samples were desalted using C18 ZipTips (Millipore, Billerica, Mass.) and eluted with 50% acetonitrile, 0.1% formic acid after which 1 μl of sample was combined with 1 μl of alpha-cyano-4-hydroxycinnamic acid (Agilent Technologies, Santa Clara, Calif.). Sample (1 μl) was then spotted on a Bruker 384 steel target frame (Billerica, Mass.) and allowed to air dry at room temperature. Samples were analyzed using a Bruker Autoflex MALDI-TOF mass spectrometer in positive ion reflectron mode under standard operating conditions.

HPLC-Q-TOF MS/MS Analysis

A Q-TOF Premier mass spectrometer (Waters, Milford, Mass.) equipped with a Waters nano-ESI source coupled directly to a Nano-Acquity UPLC system (Waters) equipped with a 100 μm×15 cm reverse phase column (BEH C18, Waters) was used for all LC-MS/MS analyses. Samples were directly loaded on the column using 0.1% formic acid at a flow rate of 0.8 μl/min for 20 min and eluted by a gradient of 1-40% acetonitrile in 0.1% formic acid over 40 min.

Samples for quantitation were analyzed by the mass spectrometer in TOF-MS mode while samples for identification by MS/MS were analyzed in DDA (data-dependent acquisition) mode. The mass range for all survey scans was 300-1400 m/z. Mascot software (version 2.2.1, Matrix Science, London, U.K.) was used for database searching and spectral interpretation.

Example 10

Expression, Purification, and Processing of BoNT/Aad$^{ek}$

The full-length BoNT/A ad (atoxic derivatives) DNA and proteins were generated under biosafety level 2 containment (project approved by CDC on Feb. 7, 2006 for the registered entity C20060207-0419).

To improve the yield of the recombinant protein, the DNA sequence encoding the full-length construct was optimized for expression in both and Sf9 insect cells and *E. coli* and synthesized de novo, as explained in supra.

A four amino acid insert, DDDD (SEQ ID NO:44), was introduced between amino acid residues $N_{447}$ and $K_{448}$ in the first construct, BoNT/Aad$^{ek}$, to create a site recognized and cleaved by enterokinase (FIG. 1).

*E. coli* Experiments

The BoNT/Aad$^{ek}$ insert was initially created in a non-expression vector derived from the Litmus 28i plasmid and named pLitSB3A. The insert DNA contains a 5' enhancer sequence placed upstream of the initiation codon and signal peptide, both of which are used exclusively for protein expression in the baculovirus system. To generate a vector suitable for *E. coli* expression, the DNA sequence encoding full-length BoNT/Aad$^{ek}$ was isolated from pLitSB3A and subcloned downstream of the T7lac promoter into expression vector pET 19. The resulting vector was transformed into *E. coli* strain JM109 (DE3), followed by growth of the transformed culture, IPTG induction, harvesting, lysis, SDS PAGE, and Western blotting with BoNT/A polyclonal antibodies. Under the conditions tested, BoNT/A-specific immunoreactivity in the processed samples was unable to be detected.

Next, expression of BoNT/Aad$^{ek}$ was tested in a different expression vector and different *E. coli* strain. DNA encoding full-length BoNT/Aad$^{ek}$ was isolated from pLitSB3A and subcloned downstream of T7lac promoter in the expression vector pETcoco2. The pETcoco system combines the advantages of T7 promoter-driven protein expression with the ability to control plasmid copy number. The pETcoco vectors are normally maintained at one copy per cell. In the single-copy state pETcoco clones are extremely stable, which is especially important for target genes toxic to the host. Copy number can be amplified to 20-50 copies per cell by the addition of L-arabinose to the culture medium. In λDE3 lysogenic hosts carrying pETcoco vectors expression of the target gene can be increased by as much as 2,500-fold over background when IPTG is added to the culture media. The expression construct was transformed into *E. coli* Rosetta-gami B (DE3) competent cells and was grown in LB media with carbenicillin, kanamycin, tetracycline, and chloramphenicol. Carbenicillin was added to maintain propagation of the cells carrying the pETcoco-based bla marker, kanamycin and tetracycline were added to select for thioredoxin (irxB) and glutathione reductase (gor) mutations, thus improving the chances for proper disulfide bond formation in the *E. coil* cytoplasm (Derman et al., "Mutations that Allow Disulfide Bond Formation In the Cytoplasm of *Escherichia coli*," *Science* 262 (5140):1744-1747 (1993); Prinz et al., "The Role of the Thioredoxin and Glutaredoxin Pathways in Reducing Protein Disulfide Bonds In the *Escherichia coli* Cytoplasm," *J. Biol. Chem.* 272(25):15661-15667 (1997), which are hereby incorporated by reference in their entirety). Chloramphenicol was added to the medium to maintain helper plasmids that provide tRNAs for rare codons, thereby increasing the expression of proteins encoded by DNA with codons non-canonical for *E. coli*. Multiple conditions were tested to optimize expression of the BoNT/Aad$^{ek}$. Cultures were grown with and without L-arabinose in the media, and different IPTG concentrations were evaluated for induction. Incubation temperatures and times were also optimized for expression. Optimal conditions were as follows: *E. coli* cultures were incubated overnight in the presence of L-arabinose at 37° C. until reaching an $OD_{600}$ of approximately 0.4. The temperature of the bacterial suspension was then lowered to 25° C. over 30 minutes, and IPTG was added to a final concentration 0.5 mM. After induction, culture growth was allowed to continue on a shaker incubator at 25° C. for twelve more hours. The bacterial pellet was harvested by centrifugation, lysed with BugBuster lysis reagent in the presence of benzonase, lysozyme, and a cocktail of protease inhibitors, The lysate was cleared by centrifugation and purified by incubation with a TALON® affinity resin. The supernatant and eluate from the TALON® beads were run on SDS PAGE and analyzed by Western blot with polyclonal antibodies raised against the full-length BoNT/A holotoxin. Rosetta-gami B (DE3), transformed with the empty vector was used as the negative control. The expressed protein was partially soluble, immunoreactive to the polyclonal BoNT/A antibodies, and could be purified using the metal affinity tag. However, the molecular weight of the recombinant propeptide expressed was significantly lower than that of the native full-length BoNT/A propeptide. Extensive proteolysis was observed with all purification and expression protocols tested, even when the derivative was expressed with the single-copy plasmid. This instability may be related to the systems available in *E. coli* for post-translational processing of proteins, with improper folding and disulfide bonding making the recombinant protein susceptible to degradation.

Baculovirus Expression

The insert for expression of BoNT/Aadek was isolated from pLitSB3A and subcloned into the donor vector pFastBacl under control of the polyhedrin promoter. A 21 b.p. cis-DNA sequence AACTCCTAAAAAACCGCCACC (SEQ ID NO:35) that was shown to increase the expression levels of exogenous genes in baculovirus-infected insect cells (Sano et al., "Enhancement of Protein Expression In Insect Cells by a Lobster Tropomyosin cDNA Leader Sequence," *FEBS Lett.* 532(1-2):143-146 (2002), which is hereby incorporated by reference in its entirety) was positioned in front of the first methionine, upstream of DNA encoding the honeybee mellitin signal peptide MKFLVNVALVFMVVYISYIYAA (SEQ ID NO:36). The signal peptide is needed for transport of the expressed protein into the culture medium and is removed by processing during intracellular trafficking and secretion (von Heijne, "Signals for Protein Targeting Into and Across Membranes," *Subcell. Biochem.* 22:1-19 (1994), which is hereby incorporated by reference in its entirety). For the purpose of protein purification, an N-terminal 10-His tag and C-terminal Strep-tag II were also present in the construct. The generation of recombinant baculovirus and insect cell procedures are detailed supra. The expressed propeptide was detected in the secreted medium with polyclonal antibodies raised against BoNT/A holotoxin. The mobility of the protein band was similar to the mobility of the unprocessed form of wt BoNT/A. After optimization of expression, the BoNT/Aad$^{ek}$ propeptide was highly enriched to virtual homogeneity from Sf-900 II medium in two steps: metal chelate affinity resin (FIG. 2A), followed by StrepTactin affinity chromatography (FIG. 2B).

The purified protein was then processed to the heterodimer by cleavage with recombinant enterokinase. In the pilot reaction shown in FIGS. 3A-B, the optimal enzyme/protein ratio for the cleavage was determined However, it was also noted that an excess of enterokinase led to non-specific protein degradation (FIG. 3B, lanes 4-7). This degradation could be attributed either to secondary activity of the enterokinase, or to contaminants in the commercially available enterokinase preparations. The bulk of the expressed BoNT/Aad$^{ek}$ propeptide was processed with 0.007 units of enzyme per microgram of protein for 12 hours at 16° C., and resulted in ~95% completion of cleavage without visible degradation of light and heavy chains in the processed BoNT/Aad$^{ek}$ heterodimer. Recombinant enterokinase was removed from the reaction mixture by incubation with Tag-off cleavage capture kit (Novagen).

To facilitate removal of the 10-His tag from the BoNT/Aad$^{ek}$ propeptide, a TEV protease recognition sequence was introduced downstream of the metal chelate affinity tag in the expressed protein. Due to the small size (19 aa) of the peptide released as a result of the cleavage, the shift in BoNT/Aad$^{ek}$ propeptide mobility and the degree of the enzymatic cleavage were not evident on the Coomassie-stained gels. To examine and optimize conditions for TEV digest, a time course pilot reaction was conducted. Samples of BoNT/Aad$^{ek}$ without addition of the enzyme were used as a control. Aliquots from the reaction mixture were taken at times ranging from 1 to 6 hours, separated by SDS PAGE, transferred to nitrocellulose membrane, and probed with anti His-tag monoclonal antibody. The results are shown in FIG. 4. Incubation of one microgram of the BoNT/A1ad$^{ek}$ with one unit of the AcTEV protease at 30° C. for 6 hours led to almost complete removal of the His tag from the propeptide (FIG. 4, lane 10). The mobility of the propeptide band on SDS PAGE before and after the cleavage did not indicate any apparent non-specific proteolytic activity associated with AcTEV. The AcTEV protease was removed from the reaction mixture by affinity chromatography on TALON® resin.

Some recombinant proteins expressed in a secreted form in the baculovirus system can be excessively glycosylated (Sydow et al., "Overexpression of a Functional NMDA Receptor Subunit (NMDAR1) In Baculovirus-Infected Trichoplusia In Insect Cells," *Brain Res. Mol. Brain. Res.* 41(1-2):228-240 (1996); Pechan et al., "Heterologous Expression of Maize (*Zea mays* L.) Mirl Cysteine Proteinase in Eukaryotic and Prokaryotic Expression Systems," *Protein Expr. Purif.* 34(1): 134-141 (2004), which are hereby incorporated by reference in their entirety). To rule out the presence of this post-translational modification, the mobility of the expressed, processed, and denatured BoNT/Aad$^{ek}$ after treatment with Endo-α-N-acetylgalactosaminidase and PNGaseF (New England Biolabs, Cat #P0733S, P0704S) was compared with untreated samples. No difference in mobility of treated versus untreated samples were detected by SDS PAGE.

The 12 aa S6 peptide tag placed downstream of the 10-His sequence and upstream of the N-terminus of the LC was incorporated as a target for Sfp phosphopantetheinyl transferase in BoNT/Aad$^{ek}$ and the other derivatives described herein. Sfp phosphopantetheinyl transferase catalyzes incorporation of small -molecule-CoA-based cargo to a specific serine residue within the S6 tag (Zhou et al., "Genetically Encoded Short Peptide Tags for Orthogonal Protein Labeling by Sfp and AcpS Phosphopantetheinyl Transferases," *ACS Chem. Biol.* 2(5):337-346 (2007), which is hereby incorporated by reference in its entirety). As a prototypic cargo molecule, and to create a molecular probe to study BoNT/A trafficking, a commercially available fluorescent conjugate of CoA (CoA547, New England Biolabs) suitable for standard TAMRA and Cy3 microscopy emission filter sets was used for BoNT/Aad$^{ek}$ labeling.

A vector expressing recombinant C-terminally 6-His-tagged Sfp phosphopantetheinyl transferase from *B. subtilis* was expressed in *E. coli*, purified, and concentrated according to the cited procedure (Yin et al., "Site-Specific Protein Labeling by Sfp Phosphopantetheinyl Transferase," *Nat. Protoc.* 1(1):280-285 (2006), which is hereby incorporated by reference in its entirety). The original report, and New England Biolabs protocols, described conditions used for in vitro labeling of recombinant proteins expressed on the cell surface, i.e., when complex mixtures of various biopolymers are present in the reaction. It was noted that under conditions tested, an increase of the CoA substrate concentration usually resulted in a higher background and did not necessarily increase the signal to background ratio. The addition of fetal calf serum or 0.5% BSA to the reaction mixture reduced the background staining.

During optimization of this site-specific BoNT/Aad$^{ek}$ labeling in vitro, background staining was also noticed. To minimize the background, and to avoid introducing contaminating proteins such as BSA into the labeling reaction, BSA was replaced by a mixture of short peptides that were subsequently removed by dialysis and ultrafiltration. The fluorescent derivative of the BoNT/Aad$^{ek}$ heterodimer was synthesized under physiological conditions, as described supra. The results of the enzymatic labeling are shown in FIGS. 5A-B. In FIGS. 5A-B, labeled and unlabeled samples of BoNT/Aad$^{ek}$ were separated on SDS PAGE and either stained with Coomassie, or transferred to a nitrocellulose membrane and scanned using a 532/580 nm excitation/emission filter set. Under the tested conditions, 7 ng of the fluorescently labeled BoNT/Aad$^{ek}$ light chain were visualized, an amount otherwise undetectable on Coomassie-stained gels. The recombinant Sfp phosphopantetheinyl transferase was removed from the reaction mixture by affinity chromatography on TALON® resin; the excess of CoA 547 and other low molecular weight components were removed by dialysis and ultrafiltration.

N-Terminal Sequencing of BoNT/Aad$^{ek}$

BoNT/Aad$^{ek}$ LC and HC, separated under reducing conditions on 10-14% Criterion SDS PAGE (Bio-Rad), were transferred to PVDF membrane (Bio-Rad, Cat. #162-0182) and stained with Bio-Safe Coomassie BB G-250 (Bio-Rad, Cat. #161-0786). The proteins were subject to sequencing on an ABI 494-HT Procise Edman Sequencer at the Molecular Structure Facility at UC Davis. N-terminal sequencing of LC identified the first six amino acids as GAGDSL (SEQ ID NO:37), and for the HC as ALNDLC (SEQ ID NO:38), which confirmed the predicted sequences of the protein N-termini.

Mass Spectrometric Analysis of BoNT/Aad$^{ek}$ and CoA547-BoNT/Aad$^{ek}$

FIG. 6 shows an ESI Q-TOF MS/MS spectrum confirming the identity of the intact tryptic peptide from the C-terminus of BoNT/Aad$^{ek}$ light chain, and confirming the sequence of the predicted enterokinase cleavage site in the loop between LC and HC.

FIGS. 7A-C show MALDI-TOF MS (FIG. 7B) and ESI Q-TOF MS/MS (FIG. 7C) spectra of a tryptic peptide of sequence LLCVR (SEQ ID NO:39) from the BoNT/Aad$^{ek}$ light chain linked via a disulfide bridge to a tryptic peptide of sequence ALNDLCIK (SEQ ID NO:40) from the BoNT/Aad$^{ek}$ heavy chain. The peptide of observed m/z 1489.84 was detected in the MALDI-TOF mass spectrum of the non-reduced toxin (FIG. 7B), which closely matches the predicted m/z of the singly charged monoisotopic dipeptide ion of 1489.82. The peptides are absent from the MALDI-TOF MS spectrum of a tryptic digest of the reduced BoNT/Aad$^{ek}$ light chain (FIG. 7A). The sequence of the peptide was confirmed by the MS/MS spectrum (FIG. 7C), and the peptide representing the heavy chain was identified by Mascot database searching when including the mass of the disulfide bonded light chain peptide.

After enzymatic labeling of BoNT/Aad$^{ek}$ light chain by Sfp phosphopantetheinyl transferase with CoA 547, three separate in-gel tryptic digests were analyzed by LC-MS in duplicate, and compared to the LC-MS spectra of digests of protein incubated with enzyme without CoA 547 to estimate the labeling efficiency of the reaction. Because the labeled N-terminal peptide was not observed by mass spectrometry, reduction of the amount of unlabeled peptide was used to estimate labeling efficiency. Mean ion intensity of the unmodified N-terminal peptide, after normalization to the total ion intensity of all observed tryptic peptides from each respective protein, was reduced by 69±6% compared to the intensity of the unmodified peptide.

Example 11

Expression, Purification, and Processing of BoNT/Aad$^{tev}$

The BoNT/Aad$^{tev}$ construct is very similar to the BoNT/Aad$^{ek}$ construct, but enables the heterodimer-forming cleavage step and removal of the 10-His tag to be performed during a single processing step with TEV protease. The design of this construct for expression in the baculovirus system is provided in detail supra. The generation of baculovirus stock and the procedure for Sf9 infection and culture growth was similar to BoNT/Aad$^{ek}$, as described supra. The propeptide was purified using the 2-step affinity chromatography procedure, and yielded approximately 30 mg per liter of insect cell culture. Removal of the 10-His tag and processing of the propeptide were performed simultaneously by incubating 1 μg of the BoNT/Aad$^{tev}$ propeptide with 2 units of AcTEV protease at 30° C. for 6 hours. Processed peptide was separated from AcTEV protease by affinity chromatography on TALON® resin and collected in flow-through fractions. Loss of protein during this procedure was ~5%. FIGS. 8A-C show the purified protein separated by SDS PAGE under reducing and non-reducing conditions.

Example 12

Expression, Purification, and Processing of ΔLC-Peptide -BoNT/A$^{tev}$ and ΔLC-GFP-BoNT/A$^{tev}$ The ΔLC constructs were developed to evaluate the role of the LC peptide in BoNT-mediated delivery to the neuronal cytosol, and the limits on cargo that can be targeted using HC-mediated mechanisms. The design of constructs for expression in the baculovirus system is provided in detail supra. The generation of baculovirus stock and the procedure for Sf9 infection and culture growth was similar to the previous two constructs, except for differences in MOI and incubation time after infection, which were approximately 0.5 and 72 hours, respectively. The propeptides were purified using 2-step affinity chromatography, as described supra. With both ΔLC derivatives, precipitation was noted during the concentration step. To prevent protein precipitation, prior to the concentration step, TRITON® X-100 was added to filtered medium. TRITON® X-100 was present throughout the TALON® chromatography procedure, and was replaced with dialyzable n-octyl-β-D-glucopyranoside for StrepTactin affinity chromatography. Removal of the 10-His tag and processing of the propeptides were performed simultaneously by incubating 1 μg of the propeptides with 2 units of AcTEV protease at 30° C. for 6 hours in the presence of 0.2% n-octyl-β-D-glucopyranoside, which was removed by dialysis and ultrafiltration after the cleavage. Processed peptides were separated from AcTEV protease by affinity chromatography on TALON® resin and collected in flow-through fractions. The yield of ΔLC-Peptide-BoNT/$A^{tev}$ constituted approximately 2 mg per liter and ΔLC-GFP-BoNT/$A^{tev}$ 1 mg per liter of insect cell culture medium. FIGS. 8A-C show the purified proteins separated by SDS PAGE under reducing and non-reducing conditions.

Example 13

Discussion of BoNT/A Derivatives that Retain Wild Type Features Required for Native Trafficking Botulinum neurotoxin type A (BoNT/A) is the most toxic protein known, with $LD_{50}$ values for mice of <1 pg/g. The consequent high risk associated with handling large amounts of this toxin have hindered the study of BoNT/A absorption and trafficking in vitro and in vivo. High toxicity has also prevented use of quantities of toxin that can be detected using standard protein protocols. Potential solutions to this challenge include studying the protein domains expressed as separate entities, or studying atoxic versions of the full-length toxin, as, for example, variants carrying point mutations that eliminate protein toxicity associated with light chain metalloprotease. Because BoNTs are large (150 kDa), multi-domain, disulfide-bonded heterodimers, with mutual stabilization of the protein domains through multiple hydrogen bonds and hydrophobic interactions, it is challenging to produce recombinant BoNTs that retain all of the structural features and trafficking properties of native BoNTs. Factors affecting the success of protein expression include the design of the expression construct and the choice of expression system. When domains are expressed separately, they can be denatured, poorly soluble (Ahmed et al., "Light Chain of Botulinum A Neurotoxin Expressed As an Inclusion Body From a Synthetic Gene Is Catalytically and Functionally Active," *J. Protein Chem.* 19(6):475-487 (2000); Zhou et al., "Cloning, High-Level Expression, Single-Step Purification, and Binding Activity of His6-Tagged Recombinant Type B Botulinum Neurotoxin Heavy Chain Transmembrane and Binding Domain," *Protein Expr. Purif.* 34(1):8-16 (2004); Lacy et al., "Recombinant Expression and Purification of the Botulinum Neurotoxin Type A Translocation Domain," *Protein Expr. Purif.* 11(2):195-200 (1997), which are hereby incorporated by reference in their entirety), or unstable (Baldwin et al., "The C-Terminus of Botulinum Neurotoxin Type A Light Chain Contributes to Solubility, Catalysis, and Stability," *Protein Expr. Purif.* 37(1):187-195 (2004), which is hereby incorporated by reference in its entirety). BoNTs are also unusually sensitive to mechanical factors, and mild agitation has been reported to denature the native toxin structure (Toth et al., "Extreme Sensitivity of Botulinum Neurotoxin Domains Towards Mild Agitation," *J. Pharm. Sci.* 98(9): 3302-3311 (2009), which is hereby incorporated by reference in its entirety). Even when the isolated domains are soluble and properly folded, their functionality in comparison with full-length native toxin is limited.

For these reasons, expression of mutated, atoxic forms of the full-length botulinum neurotoxin A was pursued. The mature wt BoNT/A is a heterodimer formed between light (LC) and heavy (HC) chains, connected via a disulfide bridge; a second, intrachain disulfide bridge is also present at the C-terminus of the toxin's receptor-binding domain (Krieglstein et al., "Covalent Structure of Botulinum Neurotoxin Type A: Location of Sulfhydryl Groups, and Disulfide Bridges and Identification of C-Termini of Light and Heavy Chains," *J. Protein Chem.* 13(1):49-57 (1994), which is hereby incorporated by reference in its entirety). An endogenous clostridial protease is involved in processing of wt BoNT/A propeptide to the mature form. The cleavage occurs at a basic amino acid residue in the loop between LC and HC. The recombinant BoNT/A derivatives described herein were expressed as single chain propeptides and were subsequently enzymatically processed to form LC-HC heterodimers, as in wt BoNT/A. However, the specificity of the cleavage was increased by introducing a more complex sequence (>5 aa) into the loop between LC and HC as a protease recognition site.

In prior work (U.S. Patent Application Publication No. 2006/0204524 to Ichtchenko et al.; Ichtchenko et al., "Full-Length *Clostridium botulinum* Serotype A Derivatives with Native Structure and Properties," *Neurotox. Res.* 9:234 (2006), which are hereby incorporated by reference in their entirety) expression of several full-length BoNT/A derivatives was described. The DNA construct encoding the first of these was generated by consecutive subcloning of two phosphorylated linkers and five DNA fragments obtained from PCR reactions performed on genomic DNA isolated from *Clostridium botulinum* A1 Hall strain. Although this derivative was not able to be expressed in *E. coli*, the baculovirus system enabled its expression in a secreted form that could be readily purified from the culture medium without harsh processing. The major problems encountered in earlier baculovirus work were related to low yield of the protein after purification (approximately 0.35 mg per liter of insect cell culture medium) and the inability to establish a single step purification procedure based on the original 6-His tag incorporated at the N-terminus of the construct for this purpose. Either because of insufficient length, or partial burial of the tag in the globule of the light chain, protein was eluted from the $Ni^{2+}$ affinity resin in 40 mM imidazole along with multiple major contaminants. As a solution, a 4-step conventional/affinity chromatography protocol was established. The complexity of the protocol contributed to the low yield of the final product. These results were considered when designing and synthesizing the constructs described herein.

The BoNT/A ad constructs reported here represent full length botulinum neurotoxin type A carrying two mutations, $E_{224}$>A and $Y_{366}$>A, introduced in the light chain. Both original amino acids, $E_{224}$ and $Y_{366}$, are conserved among different botulinum neurotoxin serotypes and are part of the catalytic core of the light chain metalloprotease responsible for cleavage of the substrate. The light chain in mutated full-length BoNT/A ad lacks the ability to cleave SNAP 25 (Rigoni et al., "Site-Directed Mutagenesis Identifies Active-Site Residues of the Light Chain of Botulinum Neurotoxin Type A," *Biochem. Biophys. Res. Commun.* 288(5):1231-1237 (2001); Zhou et al., "Expression and Purification of the Light Chain of Botulinum Neurotoxin A: A Single Mutation Abolishes Its Cleavage of SNAP-25 and Neurotoxicity After Reconstitution With the Heavy Chain," *Biochemistry* 34(46): 15175-15181 (1995); Li et al., "Probing the Mechanistic Role of Glutamate Residue In the Zinc-Binding Motif of Type A Botulinum Neurotoxin Light Chain," *Biochemistry* 39(9): 2399-2405 (2000), which are hereby incorporated by reference in their entirety). It was also shown that mutation of $E_{224}$ and $Y_{366}$ did not change the secondary structure, topography of aromatic amino residues, $Zn^{2+}$ content, or substrate binding ability of the LC metalloprotease (Li et al., "Probing the Mechanistic Role of Glutamate Residue In the Zinc-Binding Motif of Type A Botulinum Neurotoxin Light Chain," *Biochemistry* 39(9):2399-2405 (2000), which is hereby incorporated by reference in its entirety). Several popular expression systems, including *E. coli* and *Pichia pastoris*, show high bias against clostridial AT-rich DNA, resulting in slow growth (Baldwin et al., "The C-Terminus of Botulinum Neurotoxin Type A Light Chain Contributes to Solubility, Catalysis, and Stability," *Protein Expr. Purif.* 37(1):187-195 (2004), which is hereby incorporated by reference in its entirety), premature termination of protein synthesis, or initiation of irrelevant translation from an alternative reading frame (Lacy et al., "Recombinant Expression and Purification of the Botulinum Neurotoxin Type A Translocation Domain," *Protein Expr. Purif.* 11(2):195-200 (1997), which is hereby incorporated by reference in its entirety). Similar problems were observed in attempts to express protein in *E. coli*, and the initial attempts in the baculovirus expression system resulted in low protein yields. Typically, the use of *E. coli* strains supplemented with rare tRNAs, silent mutagenesis of the native clostridial DNA, or codon-optimized synthetic DNA are used in attempts to resolve this problem (Ahmed et al., "Light Chain of Botulinum A Neurotoxin Expressed As an Inclusion Body From a Synthetic Gene Is Catalytically and Functionally Active," *J. Protein Chem.* 19(6):475-487 (2000); Sutton et al., "Preparation of Specifically Activatable Endopeptidase Derivatives of *Clostridium botulinum* Toxins Type A, B, and C and Their Applications," *Protein Expr. Purif.* 40(1):31-41 (2005), which are hereby incorporated by reference in their entirety). Here, a fully synthetic DNA sequence was created de novo, encoding full-length constructs that were optimized for expression in both Sf9 insect cells and *E. coli*, as explained supra. A 7 aa spacer sequence was introduced, to separate the N-terminus of the light chain domain from the upstream sequence. In the constructs described here the length of the metal affinity tag was increased from 6 to 10 histidine residues, which significantly improved the intended single step affinity purification using non-denaturing conditions.

The constructs described herein additionally contain an 8 aa StrepTag II added at their C-termini to improve the selectivity of purification. While the addition of extra amino acids to the C-terminus of the clostridial neurotoxins causes some concern for interference with the protein binding to its cognate receptors, recent data obtained from X-ray studies of a StrepTag II C-terminally fused BoNT/B in complex with its receptors showed that the amino acid sequence of this tag is spatially separated from the receptor-binding epitopes of BoNT/B (Jin et al., "Botulinum Neurotoxin B Recognizes Its Protein Receptor With High Affinity and Specificity," *Nature* 444(7122):1092-1095 (2006), which is hereby incorporated by reference in its entirety). Therefore, it was decided to use this tag in the design of the neurotoxins described herein. The benefit of having both N- and C-terminally tagged protein is to allow separation of the full-length protein from N- or C-terminally truncated products generated adventitiously in the host expression system.

In early structural studies of BoNT/A isolated from *Clostridium botulinum*, it was shown that an endogenous protease, or trypsin, can cleave BoNT/A propeptide at $K_{444}$, followed by cleavage at $K_{448}$, which generates the tetrapeptide $G_{445}YNK_{448}$ (SEQ ID NO:41) which is released as a cleavage product (DasGupta et al., "Botulinum Neurotoxin Type A: Sequence of Amino Acids at the N-Terminus and Around the Nicking Site," *Biochimie* 72(9):661-664 (1990), which is hereby incorporated by reference in its entirety). In subsequent work, $K_{438}$ was identified as the C-terminus of the mature LC, generated by the excision of the 10 amino acid peptide, $T_{439}KSLDKGYNK_{448}$ (SEQ ID NO:42) from the wt BoNT/A precursor (Krieglstein et al., "Covalent Structure of Botulinum Neurotoxin Type A: Location of Sulfhydryl Groups, and Disulfide Bridges and Identification of C-Termini of Light and Heavy Chains," *J. Protein Chem.* 13(1):49-57 (1994), which is hereby incorporated by reference in its entirety). The most C-terminal amino acid of the light chain visible in the published X-ray structure of the BoNT/A holotoxin is $R_{432}$ (Lacy et al., "Crystal Structure of Botulinum Neurotoxin Type A and Implications for Toxicity," *Nat. Struct. Biol.* 5(10):898-902 (1998), which is hereby incorporated by reference in its entirety). There is thus a discrepancy between the native form of the light chain, extending to position 438, and the form seen in the crystal structure, extending only to position 432. This discrepancy, which could influence BoNT properties, could arise because the C-terminal residues beyond $R_{432}$ of the light chain in crystal are present, but are too flexible to generate distinct electron density on X-ray. Alternatively, a trypsin-like protease may have cleaved the LC-HC propeptide at $R_{432}$ so that this fragment is not actually present in the crystal structure. It was rationalized that the constructs described herein should not be shortened by the length of the peptide loop excised from wt BoNT/A precursor because this might influence the 3D structural constraints on this region, but should rather be made resistant to trypsin-like proteases. Therefore, mutations $K_{438}$>H, $K_{440}$>Q, and $K_{444}$>Q were introduced into the constructs described herein to render the propeptide derivatives resistant to proteolytic cleavage by trypsin-like proteases and to yield uniformly processed LC C-termini in the heterodimers. Trypsin treatment of wt BoNT/A can also lead to cleavage of its receptor-binding $HC_C$ domain, and complete loss of toxicity (Shone et al., "Inactivation of *Clostridium botulinum* Type A Neurotoxin by Trypsin and Purification of Two Tryptic Fragments, Proteolytic Action Near the COOH-Terminus of the Heavy Subunit Destroys Toxin-Binding Activity," *Eur. J. Biochem.* 151(1):75-82 (1985), which is hereby incorporated by reference in its entirety). Therefore, the mutation $1(_{871}$>N at the $HC_N$-$HC_c$ junction was introduced into the constructs described herein, rendering the HC insensitive to this type of non-specific cleavage as well (Chaddock et al., "Expression and Purification of Catalytically Active, Non-Toxic Endopeptidase Derivatives of *Clostridium botulinum* Toxin Type A," *Protein Expr. Purif.* 25(2):219-228 (2002); Shone et al., "Inactivation of *Clostridium botulinum* Type A Neurotoxin by Trypsin and Purification of Two Tryptic Fragments, Proteolytic Action Near the COOH-Terminus of the Heavy Subunit Destroys Toxin-Binding Activity," *Eur. J. Biochem.* 151 (1):75-82 (1985), which are hereby incorporated by reference in their entirety).

The biological activity of botulinum neurotoxins requires proper folding and disulfide bonding of the protein during post-translational processing. There are 9 cysteine residues in wt BoNT/A, five of which carry free sulfhydryl groups and 4 of which are involved in formation of two disulfide bridges (Krieglstein et al., "Covalent Structure of Botulinum Neurotoxin Type A: Location of Sulfhydryl Groups, and Disulfide Bridges and Identification of C-Termini of Light and Heavy Chains," *J. Protein Chem.* 13(1):49-57 (1994), which is hereby incorporated by reference in its entirety). Expression of individual BoNT/A domains with endogenous cysteines in the reduced state has been reported to contribute to formation of protein aggregates (Baldwin et al., "The C-Terminus of Botulinum Neurotoxin Type A Light Chain Contributes to Solubility, Catalysis, and Stability," *Protein Expr. Purif.* 37(1):187-195 (2004); Lacy et al., "Recombinant Expression and Purification of the Botulinum Neurotoxin Type A Translocation Domain," *Protein Expr. Purif.* 11(2):195-200 (1997), which are hereby incorporated by reference in their entirety). The use of maltose-binding protein as a fusion partner for expression of LC-$HC_N$ clostridial polypeptides in *E. coli* has been beneficial for formation of S—S bonds in *E. coli*-based expression systems, albeit the nature of the bond(s) formed was not confirmed (Sutton et al., "Preparation of Specifically Activatable Endopeptidase Derivatives of *Clostridium botulinum* Toxins Type A, B, and C and Their Applications," *Protein Expr. Purif.* 40(1):31-41 (2005), which is hereby incorporated by reference in its entirety). Maltose-binding protein probably not only contributes to solubility of the fusion polypeptides, but rather acts as a chaperone, promoting partial export of the fusion protein into the oxidizing environment of the periplasm. A recent review describes a variety of methods to optimize expression of cysteine-containing proteins in *E. coli* (de Marco, "Strategies for Successful Recombinant Expression of Disulfide Bond-Dependent Proteins In *Escherichia coli*," *Microb. Cell. Fact.* 8:26 (2009), which is hereby incorporated by reference in its entirety). The currently available reports of soluble, properly folded, and biologically active, full-length clostridial polypeptides expressed in *E. coli* did not utilize strains that contain any of these specialized features required for proper post-translational modifications (Rummel et al., "Two Carbohydrate Binding Sites in the $HC_c$-Domain of Tetanus Neurotoxin Are Required for Toxicity," *J. Mol. Biol.* 326(3):835-847 (2003); Rummel et al., "The $HC_C$-Domain of Botulinum Neurotoxins A and B Exhibits a Singular Ganglioside Binding Site Displaying Serotype Specific Carbohydrate Interaction," *Mol. Microbiol.* 51(3):631-643 (2004); Rummel et al., "Synaptotagmins I and II Act as Nerve Cell Receptors for Botulinum Neurotoxin G," *J. Biol. Chem.* 279(29):30865-30870 (2004); Bade et al., "Botulinum Neurotoxin Type D Enables Cytosolic Delivery of Enzymatically Active Cargo Proteins to Neurons Via Unfolded Translocation Intermediates," *J. Neurochem.* 91(6):1461-1472 (2004); Li et al., "Recombinant Forms of Tetanus Toxin Engineered for Examining and Exploiting Neuronal Trafficking Pathways," *J. Biol. Chem.* 276(33):31394-31401 (2001), which are hereby incorporated by reference in their entirety). Attempts to obtain full-length BoNT/$Aad^{ek}$ in two different strains of *E. coli* have not been successful. However, efforts with the baculovirus expression system have been successful on multiple levels, as described herein.

Four distinct BoNT/A derivatives were expressed and characterized using the baculovirus system. The first derivative, BoNT/$Aad^{ek}$, represents the substantially intact BoNT/A, with two mutations, $E_{224}$>A and $Y_{366}$>A, introduced to inactivate the toxin protease, and thereby render the derivative atoxic, and with an enterokinase site for processing the expressed propeptide into the heterodimer This derivative was expressed as a soluble single chain protein secreted into insect cell culture medium, and was purified to homogeneity by chromatography on metal affinity resin and StrepTactin column, yielding 30 milligrams per liter of culture medium. The propeptide was treated with AcTEV protease to remove the N-terminal 10-His tag, and was treated with enterokinase to produce the LC-HC heterodimer The structural authenticity of the expressed protein was confirmed by Western blotting with BoNT/A polyclonal antibodies and by Edman degradation of LC and HC. MALDI-TOF and ESI-Q-TOF LC-MS/MS analysis of LC tryptic digests confirmed uniformity of the enterokinase cleavage at the LC-HC junction through identification of the predicted C-terminal peptide of the LC (FIGS. 7A-C). The presence of the disulfide bridge formed between $Cys_{430}$ and $Cys_{454}$ (aa numbers are from the sequence of wt BoNT/A) in the expressed protein was confirmed by MALDI-TOF and ESI-Q-TOF LC-MS/MS analysis through identification of the S—S linked dipeptide in tryptic digests of processed BoNT/$Aad^{ek}$ heterodimer (FIG. 6).

The second derivative, BoNT/$Aad^{tev}$ is similar to BoNT/$Aad^{ek}$ but replaces the enterokinase site between LC and HC with a TEV recognition sequence. This avoids non-specific cleavage associated with excess enterokinase, and reduces the number of steps required for protein processing. This derivative was also expressed as a soluble single chain protein secreted into insect cell culture medium, and was purified to virtual homogeneity by chromatography on metal affinity resin and StrepTactin column, yielding 30 milligrams per liter of culture medium. The propeptide was further processed with AcTEV protease to simultaneously remove the N-terminal 10-His tag and to generate the LC-HC heterodimer. The structural authenticity of the expressed heterodimer, and formation of the S—S bridge between LC and HC in this derivative, were confirmed by reduced and unreduced SDS PAGE and Western blotting (FIGS. 8A-C).

In the third derivative, ΔLC-Peptide-BoNT/$A^{tev}$, the entire catalytic domain ($P_2$-$F_{390}$) of the light chain was removed, leaving a 54 aa LC segment ($N_{391}$-$G_{445}$) that forms the disulfide bridge and otherwise interacts with the $HC_N$. Two TEV protease cleavage sites in this derivative allowed simultaneous removal of the N-terminal 10-His tag and processing of the precursor to generate the ΔLC-HC heterodimer. This derivative was expressed as a soluble single chain protein secreted into insect cell culture medium, but was found to have a tendency to precipitate during concentration prior to the first affinity chromatography. To prevent precipitation, TRITON® X-100 was added to the medium during concentration and was maintained throughout processing. The protein was eluted from TALON® resin and purified further on a StrepTactin column in the presence of n-octyl-β-D-glucopyranoside. After processing with AcTEV protease to generate the ΔLC-HC heterodimer and remove the 10-His affinity tag, it became possible to remove detergent because the solubility of the processed heterodimer increased markedly. Yield of the protein was 2 milligrams per liter of culture medium. The purified AcTEV-processed protein migrated as ~110 kDa band on SDS PAGE in the absence of reducing agent and, as expected in the presence of β-mercaptoethanol, separated as LC-remnant and HC with apparent mobilities of 10 and 100 kDa, respectively. Western blotting performed with polyclonal antibodies raised against BoNT/A holotoxin confirmed the structural identity of the ΔLC-Peptide-BoNT/$A^{tev}$ heavy chain, but did not detect the truncated LC (FIGS. 8A-C).

The fourth derivative, ΔLC-GFP-BoNT/$A^{tev}$, originates from the third derivative by insertion of green fluorescent protein (GFP) into the sequence of the short LC remnant peptide at its N-terminus. It likewise includes the 54 aa LC segment ($N_{391}$-$G_{445}$) that forms the disulfide bridge and otherwise interacts with the $HC_N$. Two TEV protease cleavage sites in this derivative allow simultaneous removal of the N-terminal 10-His tag and processing of the precursor to the LC-HC heterodimer. Aggregation of this protein during concentration prior to chromatography also required use of a combination of detergents and the purification scheme described supra for ΔLC-Peptide-BoNT/$A^{tev}$. Yield of the protein was 1 milligram per liter of culture medium. The purified AcTEV-processed protein migrated as ~140 kDa band on SDS PAGE in the absence of reducing agent and, as expected in the presence of β-mercaptoethanol, migrated as independent ΔLC-GFP and HC with apparent mobilities of 40 and 100 kDa, respectively. Western blotting performed with polyclonal antibodies raised against BoNT/A holotoxin and monoclonal antibody against GFP confirmed the structural identity of ΔLC-GFP -BoNT/$A^{tev}$ light and heavy chains (FIGS. 8A-C).

The relatively low yield and aggregation of derivatives three and four, where the majority of the LC has been removed, is attributed to conformational instability and spatial tension in the expressed propeptides. The published X-ray structure of BoNT/A holotoxin (Lacy et al., "Crystal Structure of Botulinum Neurotoxin Type A and Implications for Toxicity," *Nat. Struct. Biol.* 5(10):898-902 (1998), which is hereby incorporated by reference in its entirety) suggests that the N-terminal portion of the $N_{391}$-$G_{445}$ sequence is a flexible loop and not part of the distinct protein fold. It was hypothesized that deletion of the entire LC catalytic domain exposes hydrophobic areas of the propeptide that cannot optimally collapse due to the constraints imposed by the tethering of the loop on both ends, and that AcTEV cleavage relieves this constraint by untethering one end so that the propeptide can collapse into a more soluble conformation.

During early pilot stages using natural genes instead of the synthetic genes reported here, to evaluate the utility of the baculovirus expression system and the physiological activity of the designed constructs, a full-length BoNT/A derivative without any introduced mutations that would inactivate the LC metalloprotease was expressed. When the non-mutated derivative was tested in vitro and in vivo, it demonstrated toxicity and absorption kinetics comparable to that of the native toxin. The expressed toxic derivative was tested in mouse phrenic nerve-hemidiaphragm preparations. Exocytosis was evoked by stimulation of the nerve trunk (0.2 Hz), and the muscle twitch was monitored. When added at a concentration of ~$1\times10^{-11}$ M, the toxic derivative produced blockage of transmission in 167±17 min (n=4), comparable to pharmaceutical preparations of BoNT/A. To insure that the blockade was attributed to a botulinum toxin-type action, the derivative was pre-incubated (room temperature, 60 min) with rabbit antiserum raised against the carboxy-terminal half of the native BoNT/A heavy chain (i.e., receptor-binding domain). When these experiments (n=3) were performed in the presence of this polyclonal BoNT/A antiserum, there was no onset of paralysis throughout the duration of the experiment (approximately 400 minutes of tissue monitoring) (U.S. Patent Application Publication No. 2006/0204524 to Ichtchenko et al.; Ichtchenko et al., "Full-Length *Clostridium botulinum* Serotype A Derivatives with Native Structure and Properties," *Neurotox. Res.* 9:234 (2006), which are hereby incorporated by reference in their entirety).

According to one embodiment, the recombinant BoNT/A derivatives described herein carry an S6 tag in their N-terminal region. Specific conditions for in vitro CoA-fluorophore labeling were optimized and shown for BoNT/$Aad^{ek}$. Prior studies using fluorescent-labeled BoNTs to evaluate either LC trafficking in neurons or BoNT/A uptake by epithelial or neuronal cells have primarily relied on two methods: (i) transient expression following transfection with LC sequences tagged with a fluorescent marker (e.g., GFP) (Oyler et al., "Trafficking and Post-Translational Modifications of BoNT Light Chains Within Cells," *Abstracts of the 5th International Conference on Basic and Theraupeutic Aspects of Botulinum and Tetanus Toxins*, Denver, Colo. 24 (2005); Fernandez-Salas et al., "Plasma Membrane Localization Signals In the Light Chain of Botulinum Neurotoxin," *Proc. Natl. Acad. Sci.* (*USA*) 101(9):3208-3213 (2004); Fernandez-Salas et al., "Is the Light Chain Subcellular Localization an Important Factor In Botulinum Toxin Duration of Action?" *Mov. Disord.* 19(Suppl 8):S23-S34 (2004), which are hereby incorporated by reference in their entirety), or (ii) attachment of fluorescent tags to LC-HC BoNT heterodimers using chemical methods (Verderio et al., "Internalization and Proteolytic Action of Botulinum Toxins in CNS Neurons and Astrocytes," *J. Neurochem.* 73(1):372-379 (1999); Lalli et al., "Functional Characterisation of Tetanus and Botulinum Neurotoxins Binding Domains," *J. Cell. Sci.* 112(Pt 16):2715-2724 (1999); Grumelli et al., "Internalization and Mechanism of Action of Clostridial Toxins In Neurons," *Neurotoxicology* 26(5):761-767 (2005); Ahsan et al., "Visualization of Binding and Transcytosis of Botulinum Toxin by Human Intestinal Epithelial Cells," *J. Pharmacol. Exp. Ther.* 315(3):1028-1035 (2005), which are hereby incorporated by reference in their entirety). The transient expression system provides important information on LC interactions after the recombinant protein accumulates in neurons, but cannot be used to explore the normal trafficking route that delivers LC to the neuronal cytoplasm. The chemical method for attaching probes is limited by the lack of selective fluorophore attachment (e.g., both LC and HC will be modified), and the inevitable formation of complex mixtures (unlabeled, singly, and multiply labeled species). The latter problem makes it particularly difficult to confidently attribute behavior of fluorescently labeled BoNT molecules as being representative of native trafficking and biological activity; the most intensely fluorescently labeled molecules could produce the most intense signal despite potentially being the least related to native trafficking, while a small population of unmodified molecules could be responsible for any observed biological activity. One study showed that a protein with relatively simple spatial organization, such as ~50 kDa glutathione S-transferase (GST), can lose 90% of its activity as a result of chemical labeling, while targeted enzymatic incorporation of a fluorescent probe into GST completely preserved its biological function (Taki et al., "Transglutaminase-Mediated N- and C-Terminal Fluorescein Labeling of a Protein Can Support the Native Activity of the Modified Protein," *Protein Eng. Des. Sel.* 17(2):119-126 (2004), which is hereby incorporated by reference in its entirety). In the original work describing the design and selection of the S6 tag for site-selective enzymatic attachment of fluorophores to recombinant proteins, the ligand-binding properties of two enzymatically labeled proteins, EGF and transferrin receptors, were tested. The data confirmed that site-specific labeling of the expressed receptors with CoA-fluorophore did not interfere with physiological binding or recycling of either EGF or transferrin (Zhou et al., "Genetically Encoded Short Peptide Tags for Orthogonal Protein Labeling by Sfp and AcpS Phosphopantetheinyl Transferases," *ACS Chem. Biol.* 2(5):337-346 (2007); Yin et al., "Site-Specific Protein Labeling by Sfp Phosphopantetheinyl Transferase," *Nat. Protoc.* 1(1):280-285 (2006); Zhou et al., "An Eight Residue Fragment of an Acyl Carrier Protein Suffices for Post-Translational Introduction of Fluorescent Pantetheinyl Arms In Protein Modification In vitro and In vivo," *J. Am. Chem. Soc.* 130(30):9925-9930 (2008), which are hereby incorporated by reference in their entirety).

One aspect of the present invention provides experimental evidence demonstrating enzymatic site-specific fluorescent labeling of a recombinant full-length BoNT/A derivative, with the fluorophore attached to a specific site located on the N-terminal peptide, designed as such to minimally interfere with native BoNT structure. Interestingly, the ability to incorporate CoA 547 into recombinant protein also indirectly confirms the sorting mechanism through which these derivatives are secreted into insect culture medium. Sfp phosphopantetheinyl transferase is a ubiquitous enzyme that is present in the cytoplasm of insect cells, and would therefore be expected to attach endogenous CoA to the BoNT derivatives described herein if they were not secreted into the culture medium and thereby separated from the endogenous phosphopantetheinyl transferase in the insect cell cytoplasm. The unmodified serine residue within the S6 tag identified by Edman degradation confirms that the recombinant protein undergoes a sorting mechanism that protects it from enzymatic action of the endogenous cytoplasmic Sfp phosphopantetheinyl transferase in the Sf9 cell expression host. According to mass spectrometric analysis of CoA547-modified versus non-modified derivative, the fluorescent marker was attached to approximately 69±6% of the BoNT/$Aad^{ek}$ added to the enzymatic labeling reaction mixture. With the existing commercially available derivatives, such as CoA-biotin (New England Biolabs, Cat. #S9351S), it is possible to achieve 100% probe incorporation by streptavidin affinity enrichment. The chemistry behind coupling of various moieties to CoA has been described (Yin et al., "Site-Specific Protein Labeling by Sfp Phosphopantetheinyl Transferase," *Nat. Protoc.* 1(1):280-285 (2006), which is hereby incorporated by reference in its entirety) and can provide almost unlimited opportunities in terms of coupling small molecules, bioactive peptides, and peptidomimetics to the atoxic BoNT/A derivatives described herein, exemplifying a versatile platform for targeting diverse therapeutic agents to the neuronal cytoplasm.

Three previously mentioned reports describe expression and purification of recombinant, atoxic, full-length BoNT derivatives, with point mutations to the LC active site (Kiyatkin et al., "Induction of an Immune Response by Oral Administration of Recombinant Botulinum Toxin," *Infect. Immun.* 65:4586-4591 (1997); Pier et al., "Recombinant Holotoxoid Vaccine Against Botulism," *Infect. Immun.* 76(1):437-442 (2008); Webb et al., "Production of Catalytically Inactive BoNT/A1 Holoprotein and Comparison With BoNT/A1 Subunit Vaccines Against Toxin Subtypes A1, A2, and A3," *Vaccine* 27(33):4490-4497 (2009), which are hereby incorporated by reference in their entirety). All three of these recombinant holotoxoids were developed with the specific intention of producing a recombinant BoNT vaccine, rather than with the intention of developing probes for BoNT trafficking studies, or delivery vehicles that can target the neuronal cytosol. The recombinant metalloprotease-inactivated BoNT/C reported by Kiyatkin et al., "Induction of an Immune Response by Oral Administration of Recombinant Botulinum Toxin," *Infect. Immun.* 65:4586-4591 (1997), which is hereby incorporated by reference in its entirety, was non-toxic at doses up to 10 μg per mouse. BoNT/$A^{RYM}$ described by Pier et al., "Recombinant Holotoxoid Vaccine Against Botulism," *Infect. Immun.* 76(1):437-442 (2008), which is hereby incorporated by reference in its entirety showed no apparent toxicity up to doses of 1 μg per mouse, and ciBoNT/A HP described by Webb et al., "Production of Catalytically Inactive BoNT/A1 Holoprotein and Comparison With BoNT/A1 Subunit Vaccines Against Toxin Subtypes A1, A2, and A3," *Vaccine* 27(33):4490-4497 (2009), which is hereby incorporated by reference in its entirety, was non-toxic at doses up to 50 μg per mouse, indicating that the respective holotoxoids can elicit immunity at the non-toxic doses mentioned supra. Although data on toxicity at higher doses was not included in these reports, the relative absence of toxicity in different vaccine candidates might be considered somewhat surprising if in fact the recombinant proteins follow the native BoNT targeting pathway. BoNT/A LC mutated in its active site has been shown in crystallographic studies to still be capable of binding its substrate SNAP-25 (Breidenbach et al., "Substrate Recognition Strategy for Botulinum Neurotoxin Serotype A," *Nature* 432:925-929 (2004), which is hereby incorporated by reference in its entirety), and if delivered to neurons at high doses might be expected to bind and potentially interfere with the exocytotic machinery at high doses. Secondly, HCs delivered to the endosomal compartment of motor neurons might be expected to retain their pore-forming capability in the acidic endosomal environment, and likewise potentially disrupt physiologic neuronal activity (Shone et al., "A 50-kDa Fragment From the NH2-Terminus of the Heavy Subunit of *Clostridium botulinum* Type A Neurotoxin Forms Channels In Lipid Vesicles," *Eur. J. Biochem.* 167(1):175-180 (1987), which is hereby incorporated by reference in its entirety). Since the mutated LC does not disable the apparatus for its own endocytosis, these recombinant holotoxoids should accumulate in neurons when administered at high concentrations, and might be expected to have some effect on neuronal function. It should be noted in this context that immunogenic activity can be retained in the absence of structural features required for native BoNT trafficking. Thus, although it is clear that these recombinant holotoxoids are effective vaccine candidates and that their low toxicity may provide the acceptable therapeutic index required, the data presented do not address the question of whether the recombinant holotoxoids follow the native BoNT trafficking pathway, and therefore do not currently support their potential utility for BoNT trafficking studies, or as delivery vehicles that can target the neuronal cytosol.

The above data demonstrate that the baculovirus expression system, used in conjunction with synthetic gene constructs described herein, enables production of a series of atoxic, full-length, and truncated BoNT derivatives that preserve important structural features of native BoNT. The derivatives can be recovered from culture media as soluble disulfide-bonded heterodimers, and can be purified to homogeneity using two-stage, non-denaturing, and highly selective affinity purification. The ability to recover the expressed derivatives as soluble proteins obviates the need to recover insoluble expressed derivatives from inclusion bodies using denaturing conditions. Retaining native BoNT structure during harsh solubilization and purification steps is challenging. Renaturation is equally challenging, because of the large, complex, disulfide-bonded structure of BoNTs. Attempts to restore disulfide bonding in recombinant BoNT/A $HC_C$ domain expressed in P. pastoris, which is only ⅓ of the full-length molecule, illustrate the difficulty of achieving physiologically relevant protein folding during recombinant protein expression (Bouvier et al., "Identifying and Modulating Disulfide Formation In the Biopharmaceutical Production of a Recombinant Protein Vaccine Candidate," *J. Biotechnol.* 103(3):257-271 (2003), which is hereby incorporated by reference in its entirety). Another recent publication highlights vulnerability of botulinum neurotoxins to rapid and irreversible denaturation during handling, as even mild agitation was shown to alter the secondary structure of HCs and LCs from diverse BoNT serotypes (Toth et al., "Extreme Sensitivity of Botulinum Neurotoxin Domains Towards Mild Agitation," *J. Pharm. Sci.* 98(9):3302-3311 (2009), which is hereby incorporated by reference in its entirety). The sensitivity of BoNT/A to isolation and purification conditions is also reflected in the wide batch-to-batch variability observed during pharmaceutical BoNT/A production from clostridial cultures in terms of BoNT/A specific activity units per mg of therapeutic protein preparation. Because the expression and purification methodology employed in the present invention circumvents all types of denaturing conditions, the expressed BoNT derivatives described herein have been designed to retain native BoNT structure to a greater extent than methods requiring exposure to harsh reagents.

Example 14

BoNT/Aad$^{ek}$ is Non-Toxic to Neuronal Cultures and Can Effectively Compete with wt BoNT/A To confirm that BoNT/A ad is non-toxic, but otherwise has characteristics similar to wt BoNT/A, primary rat spinal cord cells were exposed to as much as 500 nM BoNT/A ad. In particular, these primary rat spinal cord neurons were used to determine whether BoNT/Aad$^{ek}$ itself has any observable effects on cultured neuronal cells, and whether it has the ability to compete with, or otherwise antagonize, the effects of wt BoNT/A on the neuronal cultures. This assay can detect toxicity of femtomolar amounts of wt BoNT/A (measured by SNAP 25 cleavage) (Pellett et al., "A Neuronal Cell-based Botulinum Neurotoxin Assay for Highly Sensitive and Specific Detection of Neutralizing Serum Antibodies," *FEBS Lett* 581(25): 4803-08 (2007); Pellett et al., "Comparison of the Primary Rat Spinal Cord Cell (RSC) Assay and the Mouse Bioassay for Botulinum Neurotoxin Type A Potency Determination," *J. Pharmacol. Toxicol. Methods* 61(3):304-310 (2010), which are hereby incorporated by reference in their entirety), yet incubation of cells with 500 nM BoNT/A ad resulted in no detectable BoNT-specific proteolytic activity (FIG. 10). In other words, exposure of cells to as much as 500 nM BoNT/Aad$^{ek}$ did not result in detectable cleavage of intracellular SNAP 25, the target of the wt toxin.

Structural and partial functional identity of wt BoNT/A and BoNT/A ad was further confirmed by the dose-dependent ability of BoNT/A ad to block SNAP 25 cleavage by wt BoNT/A (FIG. 10). In this competition assay, pre-incubation of the primary rat spinal cord cells with 500 nM BoNT/Aad$^{ek}$ blocked intracellular SNAP 25 cleavage induced by 0.5 nM wt BoNT/A.

Example 15

Toxicity Studies of BoNT/Aad$^{ek}$

To examine toxicity in vivo, the $LD_{50}$ of BoNT/A ad was determined by mouse bioassay, and was approximately 50 μg/kg intraperitoneally, which is about 100,000-fold higher than the $LD_{50}$ of wt BoNT/A.

The wt BoNT/A is targeted to the neuromuscular junction where it cleaves SNAP 25 and causes neuromuscular paralysis by disabling the machinery of regulated exocytosis. Specificity of BoNT/A ad binding to the presynaptic sites at the neuromuscular junction ("NMJ") was confirmed by immunocytochemical analysis of triangularis sterni nerve-muscle preparations after in vivo injection of mice (FIGS. 11A-C). These results indicate that residual toxicity of BoNT/A ad is associated with NMJ-specific accumulation.

Next, it was determined if the light chain of BoNT/A ad undergoes translocation to the neuronal cytosol. Rat hippocampal neuronal cultures (Vicario, "Long-term Culture of Hippocampal Neurons," in *Current Protocols in Neuroscience Suppl.* 26: 3.2.1.-3.2.13 (John Wiley & Sons, Inc. 2004), which is hereby incorporated by reference in its entirety) were exposed to BoNT/A ad, and analyzed by immunostaining using an antibody, MAb F1-40, which is a well characterized BoNT/A L-chain specific antibody (Stanker et al., "Development and Partial Characterization of High-affinity Monoclonal Antibodies for Botulinum Toxin Type A and Their Use in Analysis of Milk by Sandwich ELISA," J. *Immunol. Methods* 336 (1):1-8 (2008); Scotcher et al., "Epitope Characterization and Variable Region Sequence of F1-40, a High-Affinity Monoclonal Antibody to Botulinum Neurotoxin Type a (Hall strain)" *PLoS One* 4 (3):e4924 (2009), which are hereby incorporated by reference in their entirety) with high specificity, sensitivity, and reproducibility in immunocytochemistry.

Immunostaining of neurons with three different treatment and chase regimens of BoNT/A ad is shown in FIG. 12. BoNT/A ad uptake could be visualized when neuronal cultures were exposed to BoNT/A ad for 30-90 minutes at 37° C. as an extracellular punctuate pattern (FIG. 12, Columns B and D, Row 1), representing the active synaptic contacts and points of BoNT/A ad entry at the axon termini. This staining gradually disappears during the chase (FIG. 12, Column D, Rows 2 and 3), due to continuous intracellular uptake of the extracellular BoNT/A ad and absence of additional recombinant protein in the medium. When cells are chased for 90 min after incubation with BoNT/A ad (FIG. 12, Row 3), most of the LC ad staining is concentrated intracellularly, adjacent to the plasma membrane and co-localized with SNAP 25. This type of staining has never been shown for wt BoNT/A because the amount of wt LC delivered to the neuronal cytoplasm is exceedingly low (below the level for visualization). The immunostaining of the neurons shown in Row 3 of FIG. 12 is consistent with earlier reports where LC/A-GFP constructs were expressed in neuronal and nonneuronal cultures. The pattern of the LC/A-GFP distribution after transfection shows that intrinsic properties of LC/A contributed to accumulation of LC/A-GFP on the inner leaflet of the neuronal plasma membrane after expression (Fernández-Salas et al., "Is the Light Chain Subcellular Localization an Important Factor in Botulinum Toxin Duration of Action?" *Mov. Disord.,* 19, Suppl 8: 23-34 (2004); Wang et al., "Novel Chimeras of Botulinum Neurotoxins A and E Unveil Contributions From the Binding, Translocation, and Protease Domains to Their Functional Characteristics" *J. Biol. Chem.* 283(25): 16993-17002 (2008); Tsai et al., "Targeting Botulinum Neurotoxin Persistence by the Ubiquitin-proteasome System," *Proc. Natl. Acad. Sci. USA.,* 107 (38):16554-16559 (2010), which are hereby incorporated by reference in their entirety).

It was then directly examined whether LC ad interacted with SNAP 25 in the cytosol of neuronal cells exposed to BoNT/A ad. As shown in FIGS. 13A and 13B, the ~52 kDa band corresponding to LC ad was co-precipitated with an anti-SNAP 25 antibody. Neither SNAP 25 nor LC ad were detected in a control experiment with BHK fibroblasts treated with BoNT/A ad under the same conditions. If LC ad binds SNAP 25 in the neuronal cytoplasm without cleaving it, then binding could lead to sequestration of SNAP 25 from the tripartite complex and disruption of neuronal activity. This would suggest that the toxicity of BoNT/A ad at high doses was a result of increased LC ad accumulation in the neuronal cytosol due to unlimited internalization—a feature beneficial for neuronal delivery of a wide range of therapeutic moieties. Therefore, it was examined whether exocytosis was affected by exposure of neuronal cells to BoNT/A ad.

Rat hippocampal neurons were pre-loaded under depolarizing conditions with FM 143 dye. When 100-500 nM BoNT/A ad was added to the depolarizing medium, an inhibition of exocytosis (fusion of FM-143 labeled synaptic vesicles with plasma membrane) occurred in a dose-dependent manner. Similar results were obtained for wt BoNT/A, albeit the testing was performed with picomolar concentrations of the toxin. Finally, the absorption profile of a BoNT derivative modified through enzymatic lipidation was assessed (FIGS. 14A-B). Lipidation should result in rapid binding to cell membranes, thereby reducing diffusion. The ΔLC-GFPBoNT/A derivative is readily taken up by neuronal cells due to the presence of BoNT/A heavy chain which binds to the neuron-specific SV2 receptor. In non-neuronal cells, however, which are deficient in SV2 (such as COS7 or BHK), there is no specific binding. For lipidation, the ΔLCGFP-BoNT/A derivative was labeled enzymatically with palmitoyl-CoA. Non-neuronal COS7 cells were used to assess lipid-mediated binding in the absence of receptor-meditated binding.

Incubation of COS7 cells for various times with ΔLC-GFP-BoNT/A did not produce any visible pattern of protein uptake. In comparison, when the palmitoylated derivative of ΔLC-GFPBoNT/A was added to the cells, within 5 minutes the staining of plasma membrane was evident. Longer incubation with palmitoylated ΔLC-GFPBoNT/A resulted in intracellular uptake of the protein consistent with endosome/lysosome internalization similar to other studies with lapidated GFP derivatives (Antos et al., "Lipid Modification of Proteins Through Sortase-Catalyzed Transpeptidation," *J. Am. Chem. Soc.* 130 (48):16338-16343 (2008), which is hereby incorporated by reference in its entirety).

Prophetic Example 16

Formation of BoNT/Aad Derivatives to which Lipid Moieties Have Been Selectively Incorporated at the S6 Cargo Site, with the Purpose of Improved Targeting of BoNT Action, and Minimizing Unintended Diffusion and Pharmacologic Action at Unintended Sites BoNT/Aad, atoxic derivative retains the essential wild type toxin features required for native trafficking, but has been rendered atoxic through the introduction of metalloprotease-inactivating mutations in the light chain of BoNT/A. To produce a pharmaceutically active BoNT/A derivative, the inactivating point mutaions can be restored to their native sequence. Both such toxic and atoxic derivatives carry an S6 peptide tag upstream of the linker sequence adjacent to the N-terminus of the light chain, which allows site-specific enzymatic attachment of various molecules for potential use in therapeutic intervention.

Here, a method is described to selectively incorporate lipid moieties into recombinant BoNT/A derivatives by enzymatic coupling to a cargo attachment peptide (e.g., the S6 peptide tag), in order to restrict the diffusion of the protein adduct from the site of injection. The goal of this project is to test a novel approach for precisely localizing the pharmaceutical action of lipidated BoNT/Aad within the targeted neuromuscular junction at the site of injection, thereby preventing effects associated with unintended dispersal and spread of the toxin beyond the site of application.

To accomplish this, the derivative will be additionally modified to contain a sequence specifically cleaved by the BACE-1 enzyme (B-secretase) specifically localized to the surface of neurons, inserted between the spacer sequence and S6 cargo attachment site. This enables the BoNT/A derivative to be specifically released from its attachment at the external surface of the plasma membrane of neurons, and thereby to improve localization of its pharmacologic action to neurons at the site of application. As an example, lipidated ΔLC-GFP-BoNT/A ad, described above, can be used to study the association of the protein with cells through the lipid tail and/or through receptor-mediated endocytosis via the HC of BoNT/A ad. To study the fate of the internalized protein (light chain) after translocation from an endocytic comparment to the cytoplasmic comparment of neurons, see infra, lipidated BoNT/A ad derivatives will be used, because the ΔLC-GFP-BoNT/A ad derivative will remain stuck in the endocytic compartment due to the rigidity of the GFP portion of ΔLC-GFP-BoNT/A ad.

Expression and purification of atoxic BoNT/A derivative with cleavage recognition sequence positioned between the S6 tag and the spacer sequence upstream of the N-terminus of BoNT/Aad will be performed as described supra. Removal of the 10-His purification tag and processing of BoNT/Aad single chain propeptide to heterodimer will be performed with TEV protease, as described supra.

Labeling of BoNT/Aad with palmitoyl-CoA will be performed with recombinant Sfp phosphopantetheinyl transferase from B. subtilis as described supra. Yield of palmitoylated BoNT/Aad will be evaluated by mass-spectral analysis. Purification of palmitoylated protein from unmodified BoNT/Aad will be performed by fractionation with Triton X-114 with modification: Instead of ion exchange chromatography, either affinity chromatography on StrepTactin agarose or hydrophobic chromatography on octyl-sepharose will be used.

The length and type of lipid moiety attached to the protein not only contributes to protein diffusibility and kinetics of absorption, but to the route of internalization and fate of internalized proteins in vitro (Antos et al., "Lipid Modification of Proteins Through Sortase-Catalyzed Transpeptidation," *J. Am. Chem. Soc.* 130 (48):16338-16343 (2008), which is hereby incorporated by reference in its entirety). Therefore, in addition to generating palmitoylated, aliphatic (C-16) adduct of BoNT/A ad derivative, an adduct will be created with a longer aliphatic chain (C -22) and an adduct will be created where cholesterol will be used as a lipid moiety. These adducts will be obtained by modifying purified BoNT/A ad protein (Band et al., "Recombinant Derivatives of Botulinum Neurotoxin A Engineered for Trafficking Studies and Neuronal Delivery," *Protein Expr. Purif.* 71(1):62-73 (2010), which is hereby incorporated by reference in its entirety) through Sfp phosphopantetheinyl transferase labeling (Zhou et al., "Genetically Encoded Short Peptide Tags for Orthogonal Protein Labeling by Sfp and AcpS Phosphopantetheinyl Transferases," *ACS Chem. Biol.* 2 (5):337-346 (2007), which is hereby incorporated by reference in its entirety) with lipidated CoA precursors. The precursors will include commercially available (palmitoyl-CoA, C-16, Sigma-Aldrich) and synthesized (C-22 aliphatic -CoA or cholesterol-CoA, Irvine Chemistry Laboratory) compounds.

A test will be done to compare the diffusion pattern and effects of local and systemic distribution of BoNT/Aad and palmitoylated BoNT/A ad (or other lipidated BoNT/A ad noted above) with targeted solubility after injection into mouse hindlimb muscle.

It is expected that limited diffusion of palmitoylated BoNT/Aad from the site of injection will be observed, in comparison with unpalmitoylated derivative, as has been described for other in vitro lipidated proteins.

Mice will be used as an animal model, because their small muscle size increases the sensitivity of immunoassays. Swiss-Webster adult male CD1 mice weighing ~30 g will be used for injection. Mice will be housed in groups of six and food and water will be provided ad libitum. Mice will be maintained on a 12-h light/dark photoperiod for 4 days before the start of experiments. All work with animals will be performed by personnel trained in the safe and humane use of laboratory animals according to existing and pending animal protocols.

Animals (time-pregnant rats) are used as a source for producing adherent cultures of primary rat hippocampal neurons, embryonic spinal cord cells (BACE1-positive), and fetal myoblast cultures (BACE1-negative) as a models for the type of cells encountered after administration of the derivatives in vivo. Live mice will also be used to test toxicity, diffusion, and systemic distribution of pairs of nonlipidated/lipidated BoNT/A ad variants in order to identify a lead candidate for future development of the pharmacologically active recombinant version of BoNT/A, obtained by reversion of the inactivating mutations. Primary cell cultures: Rat embryonic hippocampal neurons and spinal cord cells represent the widely in vitro used system to dissect physiological mechanism of BoNT/A trafficking and internalization. Live timed-pregnant rats will be used as a source of the primary neuronal cultures. Though established immortalized cell lines are available with some neuron-like features, their exclusive use for studies of BoNT/A ad derivatives trafficking is undesirable due to the up/down regulation and mutations in multiple gene products involved in the BoNT pathway. The requirement for primary neuronal culture for these types of studies is widely recognized as the standard approach. All work with animals will be performed by personnel trained in the safe and humane use of laboratory animals according to existing and pending animal protocols.

For in vitro studies, while adherent cultures of primary rat hippocampal neurons (Vicario-Abejon, "Long-term Culture of Hippocampal Neurons," in *Current Protocols in Neuroscience*, Suppl. 26, 3.2.1.-3.2.13 (John Wiley & Sons, Inc., 2004), which is hereby incorporated by reference in its entirety), embryonic spinal cord cells (Pellett et al., "A Neuronal Cell-based Botulinum Neurotoxin Assay for Highly Sensitive and Specific Detection of Neutralizing Serum Antibodies," *FEBS Lett.*, 581 (25):4803-4808 (2007); Pellett et al. "Comparison of the Primary Rat Spinal Cord Cell (RSC) Assay and the Mouse Bioassay for Botulinum Neurotoxin Type A Potency Determinatio," *J. Pharmacol. Toxicol. Methods* 61(3):304-310 (2010), which are hereby incorporated by reference in their entirety) (BACE1-positive), and fetal myoblast cultures (Pin et al., "Embryonic and Fetal Rat Myoblasts Express Different Phenotypes Following Differentiation in vitro," *Dev. Genet.* 14 (5):356-368 (1993); Pin et al., "Embryonic and Fetal Rat Myoblasts Form Different Muscle Fiber Types in an Ectopic in vivo Environment," *Dev. Dyn.* 224 (3):253-266 (2002), which are hereby incorporated by reference in their entirety) (BACE1-negative) will be used as models of the most abundant nerve and muscle tissue at the site of injection in vivo, some assays will rely on use of neuronal cell lines (such as PC 12 or Neuro 2A, BACE1-positive) or non-neuronal cell lines (such as COS7 or BHK, BACE1-negative) in suspension cultures.

The first step will be to measure protein association with the cell membrane and to assess resistance to diffusion. To measure relative ability to associate with cells, lipidated and nonlipidated ΔLC-GFP-BoNT/A derivatives will be added to cells suspended in serum-free medium, and the extent to which the presence of the lipid tail and differences in the lipid moiety contribute to binding of the proteins to cells will be quantified. Membrane binding kinetics will be measured by comparing fluorescence of the medium vs. fluorescence of the cells as described (Antos et al., "Lipid Modification of Proteins Through Sortase-Catalyzed Transpeptidation," *J. Am. Chem. Soc.* 130 (48):16338-16343 (2008), which is hereby incorporated by reference in its entirety). It is expected that the majority of lipidated ΔLC-GFPBoNT/A derivatives will be rapidly and effectively bound by all cells through insertion of the lipid moiety into the plasma membrane.

Diffusibility will be measured in monolayers of cells grown on a nitrocellulose matrix. ΔLC-GFPBoNT/A or/and BoNT/A ad derivatives will be added in millicell inserts (Millipore) positioned in the center of the growth circle. The diffusibility of the proteins will be directly measured by visualizing and quantifying the diameter of green fluorescence and its intensity relative to the diameter of the insert (0% diffusibility) and the diameter of the plate (100% diffusibility) as described (Flaumenhaft et al., "Heparin and Heparan Sulfate Increase the Radius of Diffusion and Action of Basic Fibroblast Growth Factor," *J. Cell. Biol.*, 111 (4):1651-1659 (1994), which is hereby incorporated by reference in its entirety). Those lipidated BoNT derivatives that exhibit a ≥90% reduction in diffusibility compared to their nonlipidated counterparts will be selected for further characterization.

Possible cytotoxic effects of the BoNT/A ad and lipidated BoNT/A ad will be determined, as described in Francis et al., "Enhancement of Diphtheria Toxin Potency by Replacement of the Receptor Binding Domain with Tetanus Toxin C-fragment: a Potential Vector for Delivering Heterologous Proteins to Neurons," *J. Neurochem.* 74 (6):2528-2536 (2000), which is hereby incorporated by reference in its entirety. The cytotoxicity will be evaluated over a concentration range from 1 to 500 nM. Cultures will also be observed microscopically for signs of toxicity up to 96 hours post-exposure. Cultures exposed to wt BoNT/A and untreated cells will be included as controls.

Comparison of protein uptake in neuronal and non-neuronal cultures will also be conducted. An attractive feature of the lipidated BoNT derivatives is the possibility of their efficient uptake and degradation by non-neuronal cells, which would abet removal of excess toxin. It is known that the type of lipid tail affects protein internalization. Antos et al., "Lipid Modification of Proteins Through Sortase-Catalyzed Transpeptidation," *J. Am. Chem. Soc.* 130 (48):16338-16343 (2008), which is hereby incorporated by reference in its entirety. To ensure lysosomal targeting of the lipidated BoNT/A ad in non-neuronal cells, internalization patterns of different lipidated BoNT/A derivatives will be compared using (a) immunocytochemical staining and (b) subcellular fractionation of the treated cells, followed by Western blotting. The rate of uptake relative to nonlipidated BoNT/A ad will be calculated. The internalization of the proteins by cells in culture will be assessed at different time points by two methods: first, by comparison of the intensity of LC ad signal on Western blot with antibodies against LC, and second, by LC ad association with specific cellular markers, such as SNAP 25 (cytoplasmic target for LC ad binding), Rab5/EEA1

(early endosome marker), Rab7 (late endosome marker), or LAMP1 (lysosomal marker) as described in de Araujo et al., "Isolation of Endocytic Organelles by Density Gradient Centrifugation," *Methods Mol. Biol.* 424:317-33 (2008); Huber et al., "Organelle Proteomics: Implications for Subcellular Fractionation in Proteomics," *Circ. Res.* 92:962-968 (2003); Lemichez et al., "Membrane Translocation of Diphtheria Toxin Fragment A Exploits Early to Late Endosome Trafficking Machinery," *Mol. Microbiol.* 23:445-457 (1997); and Ratts et al., "The Cytosolic Entry of Diphtheria Toxin Catalytic Domain Requires a Host Cell Cytosolic Translocation Factor Complex," *J. Cell Biol.* 160:1139-1150 (2003), which are hereby incorporated by reference in their entirety.

Additional evidence of LC ad presence in the neuronal cytoplasm will be performed by co-immunoprecipitation from cultures with anti-SNAP 25 antibodies, as described in Example 15 (FIGS. 13A-C). As many as 3 pairs of nonlipidated/lipidated BoNT constructs will be tested. Those that exhibit, relative to BoNT/A ad, a 90% reduction in diffusibility and a 10-fold increased rate of absorption by cells in culture, and which are targeted to a lysosomal degradation pathway in non-neuronal cells but to physiological LC ad translocation to the cytoplasm in neuronal cells, will be tested further.

The experimental outcome of the studies related to BoNT/A diffusion from the site of injection are not expected to be in agreement with common perceptions based on the principle that larger proteins diffuse more slowly through an identical aqueous medium compared with smaller proteins. According to this principle, it would be predicted that BoNTs of greater size or molecular weight will be less likely to diffuse outside the target tissue compared with those of smaller size. Thus, in this view, BOTOX®, composed of uniform 900 kDa complexes, should be less likely to diffuse outside the target tissue compared with DYSPORT® (a heterogeneous mixture of 500-900 kDa complex sizes) or XEOMIN® (pure 150 kDa toxin). In multiple studies it was found that BoNT/A injected intramuscularly exhibited some diffusion to muscles adjacent to the site of injection, and when the same amount of active neurotoxin was used, regardless of manufacturer or average MW, the observed effect was indistinguishable. However, the volume of injection and the total amount of injected protein are factors affecting both local and systemic spread of the toxin. Therefore, for the planned experiments, the same amount of either palmitoylated or non-palmitoylated BoNT/Aad will be used for injection.

The BoNT/Aad and palmitoylated BoNT/Aad protein concentration will be determined by the BCA-protein assay kit (Pierce), equalized and reconstituted with 0.9% sodium chloride to a final concentration 0.4 mg/ml. Before injection, mice will be anesthetized. The injection volume will be 25 μl. The protein will be injected in the tibialis anterior muscle in one hindlimb while carrier alone (control) will be injected in the contralateral muscle.

The extent of diffusion of BoNT/Aad versus palmitoylated BoNT/Aad will be evaluated by examining the direct pattern of protein immunostaining and by the effect of BoNT on muscles located at different distances from the site of injection. In particular, sections of the soleus muscle, which is close to the injected tibialis anterior muscle, the gastrocnemius muscle, which is next to the soleus, and the even more distant quadriceps femoris muscle, located in a rostral position, will be evaluated.

Lethal doses of BoNT/A released to circulation cause death from respiratory arrest resulting from neuromuscular paralysis produced by accumulation of toxin in the phrenic nerve. Therefore, potential dispersal of the toxin through the circulation following injection into tibialis anterior muscle will be assessed by immunostaining of the diaphragm with antibodies against BoNT/A holotoxin.

According to a previous study, the most notable changes in diffusion of the toxin from the site of injection occurred within 1-48 hours after injection. Therefore, the immunostaining pattern of BoNT/Aad diffusion will be studied after injection within this time frame.

The expression of N-CAM in mouse hindlimb muscles at different times following injection will be used as a readout of the effect generated by BoNT/Aad. N-CAM can be detected with high sensitivity and spatial resolution by histological and Western blot analyses. N-CAM is present on the surface of embryonic myotubes, but it is lost as development proceeds. N-CAM is nearly absent from adult muscle, but muscle denervation induces the reappearance of N-CAM. Paralysis of skeletal muscle by BoNT/A is sufficient to activate N-CAM expression. However, the action of the toxin, stemming from accumulation of its light chain in the cytosol of affected neurons, causes significantly delayed reappearance of N-CAM relative to a rapidly changed BoNT/A diffusion pattern. N-CAM is usually detected within 5-30 days after injection. This same time frame will be used.

Immunostaining will be performed 1, 2, 6, 12 hours, and one and two days after injection (for direct BoNT/A immunodetection) and 2, 7, 14, 30, and 60 days after injection (for N-CAM immunostaining). Tibialis anterior, soleus, gastrocnemius, and quadriceps femoris muscles will be dissected from both hindlimbs of the mice and frozen in isopentane precooled in liquid nitrogen. Preparation of mouse diaphragm will be performed in situ. Muscle cryosections (10 μm) will be probed with polyclonal antibodies against BoNT/A holotoxin (Staten Serum Institut, Denmark) diluted 1:1000, or polyclonal antibodies to N-CAM (Chemicon) diluted 1:500 in blocking solution. Goat anti-rabbit IgG conjugated to Alexa-555 (Invitrogen) diluted 1:200 in blocking solution will be used for detection. Alexa-488 alpha-bungarotoxin will be used for counterstaining of NMJ. Images will be collected using a confocal microscope.

The presence of BoNT/Aad and the expression level of N-CAM in different muscles after injection with either form of BoNT/Aad will also be assessed quantitatively by Western blot analysis. The resulting data will be normalized using tubulin as a loading standard and will be plotted as intensity units relative to the basal value of the non-injected muscle.

After dissection, tissue lysates will be prepared for analysis by Western blot. Samples will be loaded (10 μg/lane) on 4%-12% Tris-HCl polyacrylamide gels (Bio-Rad) and subjected to electrophoresis. The proteins will be transferred to nitrocellulose membranes (Bio-Rad), and probed either with polyclonal antibodies against BoNT/A holotoxin (Staten Serum Institut, Denmark) diluted 1:5000 or polyclonal antibodies to N-CAM (Chemicon) diluted 1:300 in TBST supplemented with 5% nonfat milk. Membranes will also be probed with anti-tubulin monoclonal antibody (1:1,000, Sigma Aldrich), which will serve as an internal standard for protein quantification. Densitometric analysis will be performed using Typhoon image analysis software (GE Healthcare).

The immunostaining panels and bars on quantification plots will be representative of several sections/protein extract preparations (n=4-6) made from each of the different injected animals (n=4). Descriptive statistics of means and standard deviations (±SD) will be calculated. The t-test will be used post-hoc to determine significance of differences.

Another preferred way to analyze the diffusion of pairs of nonlipidated/lipidated BoNT/A ad variants is to examine the presence of the protein by ELISA. The double sandwhich ELISA for wt BoNT/A is more sensitive that direct immunostaining and is preferable. The local diffusion of BoNT/A ad will be evaluated by assessing presence of BoNT by immunoreactivity in three distal muscle groups: the soleus muscle, which is close to the injected tibialis anterior muscle, the gastrocnemius muscle, which is distal to the soleus, and the more distal quadriceps femoris muscle, located in a rostral position. The percent reduction in diffusibility will be calculated both by distance (muscle group) and by quantity (ELISA signal).

For evaluation of systemic spread of BoNT, the immunoreactivity will be tested by ELISA in phrenic nerve preparations (the phrenic nerve is known to be a target of wt BoNT/A in circulation), the tibialis anterior muscle of the other (noninjected) limb, and in serum. Samples for ELISA will be prepared as described in Whelchel et al., "Molecular Targets of Botulinum Toxin at the Mammalian Neuromuscular Junction," *Mov. Disord.* 19, Suppl 8: S7-S16 (2004), which is hereby incorporated in its entirety. The most notable changes in diffusion of wt toxin from the site of injection occur within 1-48 hours after injection (Tang-Liu et al., "Intramuscular Injection of $^{125}$I-botulinum Neurotoxin-complex Versus $^{125}$I-Botulinum-free Neurotoxin: Time Course of Tissue Distribution," *Toxicon* 42 (5): 461-469 (2003), which is hereby incorporated by reference in its entirety). Therefore, tissue will be collected for analysis at six time points 1-48 hours after injection. The results will be normalized against tissue from animals injected with vehicle only.

Percent reduction in systemic exposure will be calculated from ELISA data as rate of appearance and quantity in phrenic nerve and serum. 5 mice are expected to be used per time point, as was used previously (Carli et al., "Assay of Diffusion of Different Botulinum Neurotoxin Type A Formulations Injected in the Mouse Leg," *Muscle Nerve* 40 (3): 374-380 (2009), which is hereby incorporated by reference in its entirety).

With the control group, the projected number of animals for the pair of lipidated/nonlipidated BoNT/A ad derivatives will be 120. Descriptive statistics of means and standard deviations (±SD) will be calculated. The t-test will be used post-hoc to determine significance of differences. Limited diffusion of lipidated BoNT/A ad is expected from the site of injection in comparison with nonlipidated derivatives, as has been described for other in vitro lipidated proteins (Antos et al., "Lipid Modification of Proteins Through Sortase-Catalyzed Transpeptidation," *J. Am. Chem. Soc.* 130 (48):16338-16343 (2008); Grogan et al., "Synthesis of Lipidated Green Fluorescent Protein and its Incorporation in Supported Lipid Bilayers," *J. Am. Chem. Soc.* 127 (41), 14383-14387 (2005), which are hereby incorporated by reference in their entirety).

This experiment will investigate a novel approach for precisely localizing the pharmaceutical action of botulinum neurotoxin A (BoNT/A) (e.g., BOTOX®, DYSPORT®) within the targeted neuromuscular junction at the site of injection, thereby preventing effects associated with unintended dispersal and spread of the toxin beyond the site of entry. BoNT/A therapy has a good safety record, which depends partly on the toxin's ability to remain relatively localized at the site of injection. The ability of the toxin to spread from the site of the injection to distant sites is a consequence of the fact that the toxin is soluble in aqueous solution and can be transported from the site of injection through the circulation or diffused locally to nearby tissue. Safety concerns are likely to become more important as increasing BoNT/A doses are used to treat conditions such as cerebral palsy or spasticity. In this regard, symptoms of generalized weakness have been described in BoNT-treated patients. These concerns are clearly valid, since therapeutic use of BoNT resulted in 28 deaths between 1989 and 2003, while the number of therapeutic applications of the toxin is rapidly increasing.

The low toxicity of BoNT/Aad makes it an ideal candidate for trafficking studies, because the amount of protein used in vivo can provide reliable and direct immunodetection, a goal which has never been accomplished using wt BoNT/A because of its extremely high toxicity. In addition, the ability to selectively incorporate lipidated moieties into recombinant BoNT/Aad by enzymatic coupling can restrict the diffusion of the protein adduct from the site of injection. Both of these properties—low toxicity and the ability to enzymatically modify the recombinant protein will be used to advantage.

It is anticipated that palmitoylated BoNT/Aad will be targeted for insertion into the plasma membrane of cells proximal to the injection site. Thus, palmitoylated BoNT/Aad will be excluded from the circulation immediately after injection, and its capacity for systemic dispersal will be minimal An additional important modification of the expressed BoNT/Aad will be a 13 amino acid sequence, SEISY↓EVEFRWKK (SEQ ID NO:43), which will be positioned between the cargo attachment peptide squence and the spacer sequence upstream of the N-terminus of the recombinant protein. This peptide provides the specific substrate sequence for BACE1, an aspartic acid membrane-bound protease involved in the pathology of Alzheimer's disease, and which is predominantly expressed in cells of neural origin. Among non-neuronal cells at the site of injection, the internalization of palmitoylated BoNT/Aad should result in non-specific uptake of the recombinant palmitoylated protein. In neurons, in contrast, because of the presence of BACE1 on the cell surface, recombinant BoNT/Aad should be cleaved, releasing soluble dichain BoNT/Aad in the proximity of synaptic contact. Released recombinant BoNT/Aad should enter the cell via the normal, heavy chain-mediated, double receptor mechanism of internalization followed by translocation of the light chain into the neuronal cytosol.

Prior to incorporation of the canonical BACE1 recognition sequence into existing BoNT/A ad constructs (as mentioned above), a cell-based FRET assay will be used along with a variety of commercially available FRET-based BACE1 substrates (Sigma, Invitrogen, Siena Biotech, etc.) (Gruninger-Leitch et al., "Substrate and Inhibitor Profile of BACE (beta-secretase) and Comparison with Other Mammalian Aspartic Proteases," *J. Biol. Chem.*, 277 (7):4687-4693 (2002), which is hereby incorporated by reference in its entirety) to optimize the BACE1 recognition sequence for the greatest cleavage efficiency in neuronal cells and minimal/absent cleavage in non-neuronal cells. The amino acid sequence of the substrate that best fits these criteria will be incorporated in BoNT/A ad as an alternative to the canonical sequence. To estimate the efficiency of BACE1-mediated cleavage after internalization of lipidated BoNT/A ad, adducts will also be used in which the lipid moiety is C13-labeled. Three BoNT/A ad constructs will be used to compare the relative yield of LC ad internalized through BoNT/A-receptor mediated endocytosis, which should result in LC ad translocation into the cytoplasm: non-lipidated BoNT/A ad, lipidated BoNT/A ad, and lipidated BACE1-BoNT/A ad. Cytosolic fractions from neuronal cultures exposed to all three types of proteins will be prepared by digitonin solubilization, as described in Example 15 (FIGS. 13A-C). LC ad from these fractions will be co-immunoprecipitated with anti-SNAP 25 antibodies, separated on SDS PAGE and the resulting Western blot will be probed with anti-LC MAb F1-40 as described (FIGS. 13A-C). It is expected that there will be comparable signals from LC ad from the cultures treated with BoNT/A ad and lipidated BACE1-BoNT/A ad, but minimal or no signal from lipidated BoNT/A ad, which should remain anchored to the membrane. It is also expected that LC ad from the fraction obtained after treatment with lipidated BACE1-BoNT/A ad will lack the radioactive lipid moiety as a consequence of BACE1-mediated cleavage.

This project is intended to complete preliminary steps in the pre-clinical development of a non-diffusible botulinum neurotoxin A formulation with targeted solubility, which is intended as a therapeutic for neurological disorders.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. An isolated *Clostridium botulinum* neurotoxin propeptide comprising:

a light chain region;

a heavy chain region, wherein the light and heavy chain regions are linked by a disulfide bond;

an intermediate region connecting the light and heavy chain regions and comprising a highly specific protease cleavage site, wherein said highly specific protease cleavage site has three or more specific adjacent amino acid residues that are recognized by the highly specific protease in order to enable cleavage; and a cargo attachment peptide sequence to enable site-specific attachment of cargo, wherein the cargo attachment peptide sequence is positioned upstream of the light chain region and is separated from the N-terminus of the light chain region by an amino acid spacer sequence.

2. The propeptide according to claim 1, wherein the *Clostridium botulinum* is serotype A.

3. The propetide according to claim 1, wherein the cargo attachment peptide sequence comprises an S6 peptide sequence of SEQ ID NO:2.

4. The propeptide according to claim 1 further comprising:

a signal peptide coupled to the cargo attachment peptide sequence, wherein the signal peptide is suitable to permit secretion of the neurotoxin propeptide from a eukaryotic cell to a medium.

5. The propeptide according to claim 4 further comprising:

a 10-His affinity tag positioned between and connecting the signal peptide to the cargo attachment peptide sequence.

6. The propeptide according to claim 5 further comprising:

a TEV recognition sequence positioned between and connecting the 10-His affinity tag to the cargo attachment peptide.

7. The propeptide according to claim 5 further comprising:

an 8 amino acid StrepTag II connected to the propeptide at the C-terminus.

8. The propeptide according to claim 1, wherein the highly specific protease cleavage site is selected from an enterokinase cleavage site and a TEV recognition sequence.

9. The propeptide according to claim 1, wherein the light and heavy chain regions are not truncated.

10. The propeptide according to claim 1, wherein the entire catalytic domain of the light chain region has been removed.

11. The propeptide according to claim 10 further comprising:

a fluorophore connected to the N-terminus of the light chain region.

12. The propeptide according to claim 1, wherein the cargo is selected from the group consisting of lipid moieties, therapeutic agents, marker molecules, and targeting agents.

13. The propeptide according to claim 12, wherein the cargo is a lipid moiety selected from the group consisting of fatty acids, neutral lipids, phospholipids, and complex lipids.

14. The propeptide according to claim 12, wherein the cargo is a lipid moiety selected from the group consisting of palmitoyl-CoA, C-22 aliphatic CoA, and cholesterol CoA.

15. The propeptide acoding to claim 12, further comprising a neuron-specific protease cleavage site positioned between the N-terminus of the light chain region and the cargo.

16. The propeptide according to claim 1, wherein the amino acid spacer sequence comprises at least 7 amino acid residues.

17. An isolated, physiologically active *Clostridium botulinum* neurotoxin produced by cleaving the propeptide according to claim 1 at the highly specific protease cleavage site, wherein the light chain region and the heavy chain region are linked by a disulfide bond.

18. The isolated *Clostridium botulinum* neurotoxin according to claim 17, wherein the *Clostridium botulinum* is serotype A.

19. The isolated *Clostridium botulinum* neurotoxin according to claim 17 further comprising:

a signal peptide coupled to the cargo attachment peptide sequence, wherein the signal peptide is suitable to permit secretion of the neurotoxin from a eukaryotic cell to a medium.

20. The isolated *Clostridium botulinum* neurotoxin according to claim 19 further comprising:

a 10-His affinity tag positioned between and connecting the signal peptide to the cargo attachment peptide sequence.

21. The isolated *Clostridium botulinum* neurotoxin according to claim 20 further comprising:

a TEV recognition sequence positioned between and connecting the 10-His affinity tag to the cargo attachment peptide sequence.

22. The isolated *Clostridium botulinum* neurotoxin according to claim 17 further comprising:

an 8 amino acid StrepTag II connected to the neurotoxin at the C-terminus.

23. The isolated *Clostridum botulinum* neurotoxin according to claim 18 further comprising:

$E_{224}$>A and $Y_{366}$>A mutations.

24. The isolated *Clostridum botulinum* neurotoxin according to claim 18 further comprising:

one or more mutations in the light chain region selected from $K_{438}$>H, $K_{440}$>Q, and $K_{444}$>Q.

25. The isolated *Clostridium botulinum* neurotoxin according to claim 18 further comprising:

a $K_{871}$>N mutation in the heavy chain region.

26. The isolated *Clostridium botulinum* neurotoxin according to claim 17, wherein the light and heavy chain regions are not truncated.

27. The isolated *Clostridium botulinum* neurotoxin according to claim 17, wherein the entire catalytic domain of the light chain region has been removed.

28. The isolated *Clostridium botulinum* neurotoxin according to claim 27 further comprising:

a fluorophore connected to the N-terminus of the light chain region.

29. The isolated *Clostridium botulinum* neurotoxin according to claim 17, wherein the cargo is selected from the group consisting of lipid moieties, therapeutic agents, marker molecules, and targeting agents.

30. The isolated *Clostridium botulinum* neurotoxin according to claim 17, wherein the neurotoxin is atoxic.

31. The isolated *Clostridium botulinum* neurotoxin according to claim 18, having a structure selected from BoNT/$Aad^{ek}$, BoNT/$Aad^{tev}$, ΔLC-Peptide-BoNT/$A^{tev}$, and ΔLC-GFP-BoNT/$A^{tev}$.

32. The isolated *Clostridium botulinum* neurotoxin according to claim 17, wherein the cargo attachment peptide sequence comprises at least 7 amino acid residues.

33. The isolated *Clostridium botulinum* neurotoxin according to claim 17, wherein the neurotoxin (a) has an $LD_{50}$ that is at least 75,000-fold higher than the $LD_{50}$ of wild-type *Clostridium botulinum* neurotoxin and/or (b) accumulates within neuronal cytosol in higher amounts than wild type *Clostridium botulinum* neurotoxin.

34. The propeptide according to claim 1, wherein the propeptide has an amino acid sequence selected from the group consisting of SEQ ID NO:3, SEQ ID NO:4, SEQ ID NO:5, and SEQ ID NO:6.

* * * * *

UNITED STATES PATENT AND TRADEMARK OFFICE

CERTIFICATE OF CORRECTION

PATENT NO. : 8,980,284 B2
APPLICATION NO. : 13/013518
DATED : March 17, 2015
INVENTOR(S) : Konstantin Ichtchenko and Philip A. Band It is certified that error appears in the above-identified patent and that said Letters Patent is hereby corrected as shown below:

In the claims

In claim 3, col. 192, line 65, delete "propetide" and insert in its place --propeptide--.

Signed and Sealed this
Twenty-third Day of February, 2016

Michelle K. Lee
*Director of the United States Patent and Trademark Office*